US006969711B2

(12) United States Patent
Shibuya et al.

(10) Patent No.: US 6,969,711 B2
(45) Date of Patent: Nov. 29, 2005

(54) CYCLIC DIAMINE COMPOUNDS AND MEDICINE CONTAINING THE SAME

(75) Inventors: Kimiyuki Shibuya, Saitama (JP); Katsumi Kawamine, Saitama (JP); Yukihiro Sato, Tokyo (JP); Toru Miura, Tokyo (JP); Chiyoka Ozaki, Tokyo (JP); Toshiyuki Edano, Saitama (JP); Mitsuteru Hirata, Saitama (JP); Tadaaki Ohgiya, Saitama (JP)

(73) Assignee: Kowa Company, Ltd., Aichi (JP)

( * ) Notice: Subject to any disclaimer, the term of this patent is extended or adjusted under 35 U.S.C. 154(b) by 271 days.

(21) Appl. No.: 10/371,234

(22) Filed: Feb. 20, 2003

(65) Prior Publication Data

US 2004/0038987 A1 Feb. 26, 2004

Related U.S. Application Data

(63) Continuation-in-part of application No. 09/424,417, filed on Mar. 30, 2000, now abandoned, which is a continuation of application No. PCT/JP98/02300, filed on May 26, 1998.

(30) Foreign Application Priority Data

May 26, 1997 (JP) .............................. 9-149892

(51) Int. Cl.[7] .................... C07D 403/12; C07D 417/12; C07D 498/04; A61K 31/454; A61P 9/10
(52) U.S. Cl. ............. 514/218; 514/253.04; 514/254.02; 514/254.06; 540/575; 544/362; 544/369; 544/370
(58) Field of Search ................................ 514/218, 253, 514/254.02, 254.06; 540/575; 544/362, 369, 370

(56) References Cited

FOREIGN PATENT DOCUMENTS

| EP | 0 372 445 | 6/1990 |
|---|---|---|
| EP | 0 807 627 | 11/1997 |
| WO | WO 92/07825 | 5/1992 |
| WO | WO 98/42680 | 10/1998 |
| WO | WO 99/25712 | 5/1999 |

OTHER PUBLICATIONS

Grant, David J.W., "University of Minnesota– Twin Cities Campus College of Pharmacy, Annual Report," 1999.
Ulrich, Joachim, "Kirk–Othmer Encyclopedia of Chemical Technology", John Wilet & Sons, 2002.
West, Anthony R., Solid State Chemistry and its Applications, Wiley, New York, 1988, pp. 358–365.
Brown, Michael S. et al., "Lipoprotein Metabolism In The Macrophage: Implications for Cholesterol Deposition In Atherosclerosis," Ann. Review Biochem., 1983, vol. 52, pp. 223–261.
Ross, Russell, "The pathogenesis of atherosclerosis: a perspective for the 1990s," Nature, vol. 362, 1993, pp. 801–809.
Bocan, Thomas M.A. et al., "Comparison of CI–976, an ACAT Inhibitor, and Selected Lipid–Lowering Agents for Antiatherosclerotic Activity in Iliac–Femoral and Thoracic Aortic Lesions," Arteriosclerosis and Thrombosis, vol. 11, No. 6, 1991, pp. 1830–1843.
O'Brien, Patrick M. et al., "ACAT Inhibitors: A Potential New Approach to the Treatment of Hypercholesterolaemia and Atherosclerosis," Therapeutic Patents, vol. 2, No. 4, 1992, pp. 507–526.

(Continued)

*Primary Examiner*—James O. Wilson
*Assistant Examiner*—Thomas C. McKenzie
(74) *Attorney, Agent, or Firm*—Peter F. Corless; John B. Alexander; Edwards & Angell, LLP

(57) ABSTRACT

The present invention offers novel cyclic diamine compounds and a pharmaceutical composition containing the same.

The present invention relates to a compound represented by the formula (I) or salt(s) or solvate(s) thereof.

$$\text{(I)}$$

(In the formula, is an optionally substituted divalent residue of benzene, pyridine, cyclohexane or naphthalene or is a vinylene group where
   Ar is an optionally substituted aryl group;
   X is —NH—, oxygen atom or sulfur atom;
   Y is —NR$_1$—, oxygen atom, sulfur atom, sulfoxide or sulfone;
   Z is a single bond or —NR$_2$—;
   R$_1$ is hydrogen atom, optionally substituted lower alkyl group, optionally substituted aryl group or optionally substituted silyl lower alkyl group;
   R$_2$ is hydrogen atom, optionally substituted lower alkyl group, optionally substituted aryl group or optionally substituted silyl lower alkyl group;
   l is an integer of from 0 to 15;
   m is an integer of 2 or 3; and
   n is an integer of from 0 to 3).

The compound of the present invention is useful as a pharmaceutical composition, particuarly as an inhibitor of acyl coenzyme A cholesterol acyltransferase (ACAT).

7 Claims, No Drawings

OTHER PUBLICATIONS

Iiskovic Dargo R., "ACAT Inhibitor: Potential Anti–atherosclerotic Agents," Current Medicinal Chemistry, 1994, pp. 204–225.

Scandinavian Simvastatin Survival Group, "Randomizes trial of cholesterol lowering in 4444 patient with coronary heart disease: the Scandinavian Simvastatin Survival Study (4S)," The Lancet, vol. 344, 1994, pp. 1383–1389.

CYCLIC DIAMINE COMPOUNDS AND MEDICINE CONTAINING THE SAME

CROSS-REFERENCE TO RELATED APPLICATION(S)

This application is a continuation in part of U.S. patent application Ser. No. 09/424,417, filed on Mar. 30, 2000, now abandoned, which is a con of PCT/JP98/02300 May, 26, 1998.

TECHNICAL FIELD

The present invention relates to azole compounds having novel cyclic diamine structure and pharmaceutical compositions containing the same. More particularly, the present invention relates to a compound represented by the following formula (I), salt(s) or solvate(s) thereof and also to a pharmaceutical composition consisting of the same.

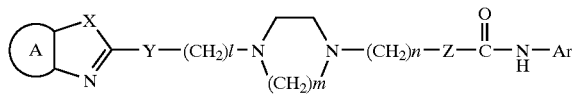

(In the formula,

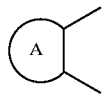

is an optionally substituted divalent residue of benzene, pyridine, cyclohexane or naphthalene or is a group

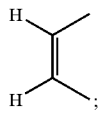

wherein
Ar is an optionally substituted aryl group;
X is —NH—, oxygen atom or sulfur atom;
Y is —$NR_1$—, oxygen atom, sulfur atom, sulfoxide or sulfone;
Z is a single bond or —$NR_2$—;
$R_1$ is hydrogen atom, optionally substituted lower alkyl group, optionally substituted aryl group or optionally substituted silyl lower alkyl group;
$R_2$ is hydrogen atom, optionally substituted lower alkyl group, optionally substituted aryl group or optionally substituted silyl lower alkyl group;
l is an integer of from 0 to 15;
m is an integer of 2 or 3; and
n is an integer of from 0 to 3).

BACKGROUND ART

In recent years, as a result of an increase in persons of advanced age and also of changes in daily eating habits to the food of European and American style containing high calories and high cholesterol due to upgrade of the standard of living, there has been a rapid increase in hyperlipemia and arteriosclerotic diseases caused thereby and that is one of the social problems. The pharmacotherapy for hyperlipemia and arteriosclerosis up to now has mostly given its priority to reduce the lipid content in blood which is a cause thereof and has not been a therapy where arteriosclerotic focus per se is a target.

Acyl coenzyme A cholesterol acyltransferase (ACAT) is an enzyme which catalyzes the synthesis of cholesterol ester from cholesterol and plays an important role in metabolism and absorption in digestive organs of cholesterol. It is believed that inhibition of ACAT enzyme which esterifies free cholesterol in epithelial cells of small intestine results in inhibition of absorption of cholesterol from intestinal tract, that inhibition of production of cholesterol ester in liver due to ACAT inhibition suppresses the secretion of very low-density lipoprotein (VLDL) from liver into blood and that, as a result thereof, a decrease in cholesterol in blood is resulted. Many of ACAT inhibitors until now have been those which act the ACAT enzyme in small intestine and liver whereby a decrease in cholesterol in blood is expected as antihyperlipemic agents.

For example, 2,2-dimethyl-N-(2,4,6-trimethoxyphenyl) dodecanamide and N'-(2,4-difluorophenyl)-N-[5-(4,5-diphenyl-1H-imidazol-2-yl thio)pentyl]-N-heptylurea are described as ACAT inhibitors in the U.S. Pat. No. 4,716,175 and the European Patent No. 372,445, respectively. However, many ACAT inhibitors up to now give a priority on lowering of cholesterol in blood as antihyperlipemic agents and, due to administration in large doses for achieving the action, many side effects such as intestinal bleeding, intestinal disturbance, diarrhea and hepatic disturbance occurred which made their clinical development difficult.

Incidentally, arteriosclerosis is a lesion characterized by thickening of intima and accumulation of lipid in blood vessel and, according to the recent studies, suppression of foaming of macrophage playing a central role in formation of arteriosclerotic lesion is expected to achieve an involution of arteriosclerotic lesion itself. Foam cells (cholesterol ester is stored in the cells as fat droplets) derived from macrophage are in focus of pultaceous arteriosclerosis and it has been said that this foaming of macrophage is closely related to the progress of the focus. It is also reported that the ACAT activity on the blood vessel wall of focus site of arteriosclerosis is high and the cholesterol is accumulated on the blood vessel wall (Gillies, P. J., et al.: Exp. Mole. Pathol., 44, 329–339(1986)).

Inhibition of esterification of cholesterol by an ACAT inhibitor produces free cholesterol in cells and this is then taken out by a high-density lipoprotein (HDL) followed by being transmitted to liver (reverse transmission) to be metabolized and, accordingly, suppression of accumulation of cholesterol at the focus site is expected. It is believed that, as a result thereof, a direct antiarteriosclerotic action is achieved. It is reported that there are two types of ACAT—one is present in small intestine and another is present on blood vessel wall (Kinnunen, P. M., et al.: Biochemistry, 27, 7344–7350(1988)) although many investigations on ACAT inhibitors until now have been conducted using enzymes which are those of a type existing in small intestine and liver (Tomoda, H., et al: J. Antibiotics, 47, 148–153(1994)). Having an idea that the drug which selectively inhibits the ACAT enzyme of a type existing in blood vessel wall can be a therapeutic agent for arteriosclerosis having less side effect, the present inventors have conducted synthesis and investigation on such an inhibitor, found that the compounds represented by the following formula. (A) selectively inhibit the ACAT enzyme and filed patent applications (refer to the specifications of the Japanese Patent Applications Hei-09/88660 and Hei-09/90146).

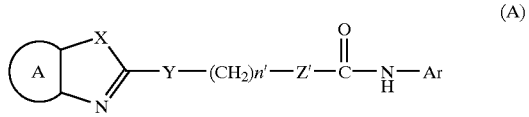 (A)

[In the formula, A, Ar, X and Y have the same meanings as those defined for the above-mentioned formula (I) of the present invention; Z' is Z or —CR$_4$'R$_5$'—Z— (where Z has the same meaning as that defined for the above-mentioned formula (I) of the present invention and R$_4$' and R$_5$' are same or different and are hydrogen atom, lower alkyl group or lower alkoxy group); and n' is an integer of from 0 to 15.]

However, those compounds are highly liposoluble and, therefore, they have disadvantages that oral absorption is not good and that duration in serum is short.

Accordingly, there has been a demand for developing the compounds where oral absorption is improved and a high drug concentration in serum is maintained for long time.

DISCLOSURE OF THE INVENTION

In order to achieve the above object, the present inventors have continued the investigation and have found that azole compounds where a cyclic diamine structure is introduced into a molecule are highly soluble in water and exhibit an excellent biological activity. Therefore, to be more specific, the present invention has been accomplished as a result of a finding that the compound represented by the following formula (I) or salt(s) or solvate(s) thereof has an excellent ACAT inhibitory action and also an excellent solubility.

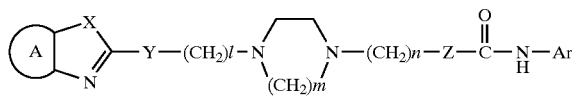 (I)

(In the formula,

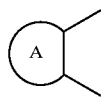

is an optionally substituted divalent residue of benzene, pyridine, cyclohexane or naphthalene or is a group

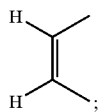

wherein

Ar is an optionally substituted aryl group;

X is —NH—, oxygen atom or sulfur atom;

Y is —NR$_1$—, oxygen atom, sulfur atom, sulfoxide or sulfone;

Z is a single bond or —NR$_2$—;

R$_1$ is hydrogen atom, optionally substituted lower alkyl group, optionally substituted aryl group or optionally substituted silyl lower alkyl group;

R$_2$ is hydrogen atom, optionally substituted lower alkyl group, optionally substituted aryl group or optionally substituted silyl lower alkyl group;

l is an integer of from 1 to 15;

m is an integer of 2 or 3; and n is an integer of from 1 to 3).

More specifically, the formula,

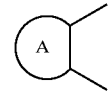

is a divalent residue of benzene, pyridine, cyclohexane or naphthalene each of which may be substituted with from one to four group(s) selected from W1:

Ar is an aryl group which may be substituted with group(s) selected from W5;

R$_1$ is hydrogen atom, lower alkyl group which may be substituted with group(s) selected from W2, aryl group which may be substituted with group(s) selected from W5 or silyl lower alkyl group which may be substituted with group(s) selected from W4;

R$_2$ is hydrogen atom, lower alkyl group which may be substituted with group(s) selected from W2, aryl group which may be substituted with group(s) selected from W5 or silyl lower alkyl group which may be substituted with group(s) selected from W4;

W1 is lower alkyl group which may be substituted with group(s) selected from W2, lower alkoxy group which may be substituted with group(s) selected from W2, lower alkylcarbonyl group which may be substituted with group(s) selected from W2, lower alkylthio group, lower alkylsulfinyl group, lower alkylsulfonyl group, halogen atom, hydroxyl group, carboxyl group, alkoxycarbonyl group, phosphoric acid group, cyano group, nitro group, sulfonamide group, amino group which may be substituted with group(s) selected from W3, aminoalkyl group which may be substituted with group(s) selected from W3, silyl lower alkyl group which may be substituted with group(s) selected from W4 or heterocyclic residue; and alkylenedioxy group;

W2 is hydroxyl group, lower alkoxy group, lower alkylthio group, lower alkoxycarbonyl group, lower alkylcarbonyloxy group, aryl group, halogen atom, amino group, nitro group, hydroxy lower alkoxy group, lower alkoxy lower alkoxy group, lower alkoxycarbonyl lower alkoxy group and halogenated lower alkoxy group;

W3 is lower alkyl group, aryl group which may be substituted with lower alkyl group or lower alkoxy group and an aralkyl group which may be substituted with lower alkyl group or lower alkoxy group;

W4 is lower alkyl group, aryl groups and an aralkyl group;

W5 is lower alkyl group which may be substituted with group(s) selected from W2, lower alkoxy group which may be substituted with group(s) selected from W2, lower alkylthio group which may be substituted with group(s) selected from W2, lower alkylsulfinyl group which may be substituted with group(s) selected from W2, lower alkylsulfonyl group which may be substituted with group(s) selected from W2, lower alkylsulfonyloxy group which may be substituted with group(s) selected from W2, hydroxy lower alkylthio group, lower alkylcarbonyl group which may be substituted with group(s) selected from W2, lower alkylcarbonyloxy group which may be substituted with group(s) selected from W2, halogen atom, hydroxyl group, nitro group, phosphoric acid group, di-(lower alkoxy)-phosphoryloxy group, sulfonamide group, amino group which may be substituted with group(s) selected from W3, pyranosyloxy group and alkylenedioxy group.

The present inventors have found that those azole compounds having intramolecular cyclic diamine structure have organ-selective ACAT inhibitory action and an inhibiting action to intracellular cholesterol transportation and also that they are the compounds where oral absorption is improved and high drug concentration in serum can be maintained for long time. Those compounds of the present invention are particularly useful as antihyperlipemic agents having an excellent cholesterol-lowering action in blood and also as preventive and therapeutic agents for arteriosclerosis, and so on having an suppressing action to foaming of macrophage.

Accordingly, the present invention offers the compounds represented by the above formula (I) and salt(s) or solvate(s) thereof.

The present invention further offers a pharmaceutical composition consisting of therapeutically effective amount of one or more of the compounds represented by the above formula (I) or salt(s) or solvate(s) thereof and a pharmaceutically acceptable carrier.

The present invention furthermore offers an ACAT inhibitor, an agent for inhibiting the transportation of intracellular cholesterol, an agent for lowering the cholesterol in blood or an agent for suppressing the foaming of macrophage containing the compound represented by the above formula (I) or salt(s) or solvate(s) thereof and a pharmaceutically acceptable carrier. Thus, the present invention offers a pharmaceutical composition for therapy and prevention, an agent for therapy and prevention and a method for therapy and prevention of the diseases such as hyperlipemia, arteriosclerosis, cervical and cerebral arteriosclerosis, cerebrovascular disorder, ischemic cardiopathy, coronary arteriosclerosis, nephrosclerosis, arteriosclerotic nephrosclerosis, arteriocapillary sclerotic nephrosclerosis, malignant nephrosclerosis, ischemic entheropathy, acute occlusion of mesenteric vessel, chronic mesenteric angina, ischemic colitis, aortic aneurysm and arteriosclerosis obliterans (ASO).

Among the compounds of the present invention represented by the above formula (I), more preferred compounds are those represented by the following formula (II) or salt(s) or solvate(s) thereof.

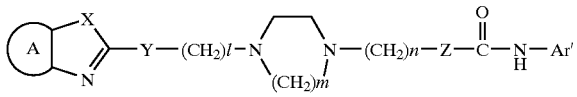

(II)

(In the formula,

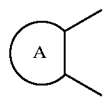

is an optionally substituted divalent residue of benzene, pyridine, cyclohexane or naphthalene or is a group

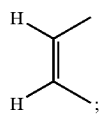

wherein
X is —NH—, oxygen atom or sulfur atom;
Y is —NR$_1$—, oxygen atom, sulfur atom, sulfoxide or sulfone;
Z is a single bond or —NR$_2$—;

Ar' is phenyl, pyridyl or pyrimidyl group which may be substituted with from one to four group(s) selected from optionally-substituted lower alkyl group, optionally substituted lower alkoxy group, lower alkylthio group, lower alkylsulfinyl group, lower alkylsulfonyl group, lower alkylsulfonyloxy group, optionally substituted lower acyl group, halogen atom, hydroxyl group, optionally substituted lower acyloxy group, nitro group, phosphoric acid group, di-(lower alkoxy)-phosphoryloxy group, sulfonamide group, optionally substituted amino group and alkylenedioxy group;
R$_1$ is hydrogen atom, optionally substituted lower alkyl group, optionally substituted aryl group or optionally substituted silyl lower alkyl group;
R$_2$ is hydrogen atom, optionally substituted lower alkyl group, optionally substituted aryl group or optionally substituted silyl lower alkyl group;
l is an integer of from 1 to 15;
m is an integer of 2 or 3; and
n is an integer of from 1 to 3).
More specifically, the formula,

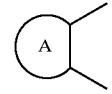

is a divalent residue of benzene, pyridine, cyclohexane or naphthalene each of which may be substituted with from one to four group(s) selected from W1.
Ar' is phenyl, pyridyl or pyrimidyl group which may be substituted with from one to four group(s) selected from lower alkyl group which may be substituted with group(s) selected from W2, lower alkoxy group which may be substituted with group(s) selected from W2, lower alkylthio group, lower alkylsulfinyl group, lower alkylsulfonyl group, lower alkylsulfonyloxy group, hydroxy lower alkylthio group, lower alkylcarbonyl group which may be substituted with group(s) selected from W2, halogen atom, hydroxyl group, lower alkylcarbonyloxy group which may be substituted with group(s) selected from W2, nitro group, phosphoric acid group, di-(lower alkoxy)-phosphoryloxy group, sulfonamide group, amino group which may be substituted with group(s) selected from W3, pyranosyloxy group and alkylenedioxy group;
R$_1$ is hydrogen atom, lower alkyl group which may be substituted with group(s) selected from W2, aryl group which may be substituted with group(s) selected from W5 or silyl lower alkyl group which may be substituted with group(s) selected from W4;
R$_2$ is hydrogen atom, lower alkyl group which may be substituted with group(s) selected from W2, aryl group which may be substituted with group(s) selected from W5, or silyl lower alkyl group which may be substituted with group(s) selected from W4;
W1 is lower alkyl group which may be substituted with group(s) selected from W2, lower alkoxy group which may be substituted with group(s) selected from W2, lower alkylcarbonyl group which may be substituted with group(s) selected from W2, lower alkylthio group, lower alkylsulfinyl group, lower alkylsulfonyl group, halogen atom, hydroxyl group, carboxyl group, alkoxycarbonyl group, phosphoric acid group, cyano group, nitro group, sulfonamide group, amino group which may be substituted with group(s) selected from W3, aminoalkyl group which may be substituted with group(s) selected from W3, silyl lower alkyl group which may be substituted with group(s) selected from W4 or heterocyclic residue; and alkylenedioxy group;

W2 is hydroxyl group, lower alkoxy group, lower alkylthio group, lower alkoxycarbonyl group, lower alkylcarbonyloxy group, aryl group, halogen atom, amino group, nitro group, hydroxy lower alkoxy group, lower alkoxy lower alkoxy group, lower alkoxycarbonyl lower alkoxy group and halogenated lower alkoxy group;

W3 is lower alkyl group, aryl group which may be substituted with lower alkyl group or lower alkoxy group and an aralkyl group which may be substituted with lower alkyl group or lower alkoxy group;

W4 is lower alkyl group, aryl groups and an aralkyl group;

W5 is lower alkyl group which may be substituted with group(s) selected from W2, lower alkoxy group which may be substituted with group(s) selected from W2, lower alkylthio group which may be substituted with group(s) selected from W2, lower alkylsulfinyl group which may be substituted with group(s) selected from W2, lower alkylsulfonyl group which may be substituted with group(s) selected from W2, lower alkylsulfonyloxy group which may be substituted with group(s) selected from W2, lower alkylcarbonyl group which may be substituted with group(s) selected from W2, lower alkylcarbonyloxy group, halogen atom, hydroxyl group, nitro group, phosphoric acid group, di-(lower alkoxy)-phosphoryloxy group, sulfonamide group, amino group which may be substituted with group(s) selected from W3 and alkylenedioxy group.

More preferred compounds among the compounds of the present invention represented by the above formula (I) are those represented by the following formula (III) or salt(s) or solvate(s) thereof.

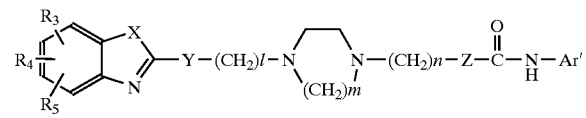

(III)

(In the formula,

X is —NH—, oxygen atom or sulfur atom;

Y is —NR$_1$—, oxygen atom, sulfur atom, sulfoxide or sulfone;

Z is a single bond or —NR$_2$—;

Ar' is phenyl, pyridyl or pyrimidyl group which may be substituted with from one to four group(s) selected from optionally-substituted lower alkyl group, optionally substituted lower alkoxy group, lower alkylthio group, lower alkylsulfinyl group, lower alkylsulfonyl group, lower alkylsulfonyloxy group, optionally substituted lower acyl group, halogen atom, hydroxyl group, optionally substituted lower acyloxy group, nitro group, phosphoric acid group, di-(lower alkoxy)-phosphoryloxy group, sulfonamide group, optionally substituted amino group and alkylenedioxy group;

R$_1$ is hydrogen atom, optionally substituted lower alkyl group, optionally substituted aryl group or optionally substituted silyl lower alkyl group;

R$_2$ is hydrogen atom, optionally substituted lower alkyl group, optionally substituted aryl group or optionally substituted silyl lower alkyl group;

R$_3$, R$_4$ and R$_5$ are same or different and are hydrogen atom, optionally substituted lower alkyl group, optionally substituted lower alkoxy group, optionally substituted lower acyl group, lower alkylthio group, lower alkylsulfinyl group, lower alkylsulfonyl group, halogen atom, hydroxyl group, carboxyl group, alkoxycarbonyl group, hydroxyalkyl group, phosphoric acid group, cyano group, nitro group, sulfonamide group, optionally substituted amino group, optionally substituted aminoalkyl group, optionally substituted silyl lower alkyl group or heterocyclic residue; or any of two of R$_3$, R$_4$ and R$_5$ form an alkylenedioxy group together;

l is an integer of from 1 to 15;

m is an integer of 2 or 3; and n is an integer of from 1 to 3).

More specifically, Ar' is phenyl, pyridyl or pyrimidyl group which may be substituted with from one to four group(s) selected from lower alkyl group which may be substituted with group(s) selected from W2, lower alkoxy group which may be substituted with group(s) selected from W2, lower alkylthio group, lower alkylsulfinyl group, lower alkylsulfonyl group, lower alkylsulfonyloxy group, hydroxy lower alkylthio-group, lower alkylcarbonyl group which may be substituted with group(s) selected from W2, halogen atom, hydroxyl group, lower alkylcarbonyloxy group which may be substituted with group(s) selected from W2, nitro group, phosphoric acid group, di-(lower alkoxy)-phosphoryloxy group, sulfonamide group, amino group which may be substituted with group(s) selected from W3, pyranosyloxy group and alkylenedioxy group;

R$_1$ is hydrogen atom, lower alkyl group which may be substituted with group(s) selected from W2, aryl group which may be substituted with group(s) selected from W5, or silyl lower alkyl group which may be substituted with group(s) selected from W4;

R$_2$ is hydrogen atom, lower alkyl group which may be substituted with group(s) selected from W2, aryl group which may be substituted with group(s) selected from W5, or silyl lower alkyl group which may be substituted with group(s) selected from W4;

R$_3$, R$_4$ and R$_5$ are same or different and are hydrogen atom, lower alkyl group which may be substituted with group(s) selected from W2, lower alkoxy group which may be substituted with group(s) selected from W2, lower alkylcarbonyl group which may be substituted with group(s) selected from W2, lower alkylthio group, lower alkylsulfinyl group, lower alkylsulfonyl group, halogen atom, hydroxyl group, carboxyl group, alkoxycarbonyl group, phosphoric acid group, cyano group, nitro group, sulfonamide group, amino group which may be substituted with group(s) selected from W3, aminoalkyl group which may be substituted with group(s) selected from W3, silyl lower alkyl group which may be substituted with group(s) selected from W4, or heterocyclic residue; or any of two of R$_3$, R$_4$ and R$_5$ form an alkylenedioxy group together;

W2 is hydroxyl group, lower alkoxy group, lower alkylthio group, lower alkoxycarbonyl group, lower alkylcarbonyloxy group, aryl group, halogen atom, amino group, nitro group, hydroxy lower alkoxy group, lower alkoxy lower alkoxy group, lower alkoxycarbonyl lower alkoxy group and halogenated lower alkoxy group;

W3 is lower alkyl group, aryl group which may be substituted with lower alkyl group or lower alkoxy group and an aralkyl group which may be substituted with lower alkyl group or lower alkoxy group;

W4 is lower alkyl group, aryl groups and an aralkyl group;

W5 is lower alkyl group which may be substituted with group(s) selected from W2, lower alkoxy group which may be substituted with group(s) selected from W2, lower alkylthio group which may be substituted with group(s) selected from W2, lower alkylsulfinyl group which may be substituted with group(s) selected from W2, lower alkylsulfonyl group which may be substituted with group(s) selected from W2, lower alkylsulfonyloxy group which may be substituted with group(s) selected from W2, lower alkylcarbonyl group which may be substituted with group(s) selected from W2, lower alkylcarbonyloxy group, halogen atom, hydroxyl group, nitro group, phosphoric acid group, di-(lower alkoxy)-phosphoryloxy group, sulfonamide group, amino group which may be substituted with group(s) selected from W3 and alkylenedioxy group;

Additional more preferred compounds are those represented by the following formula (IV) or salt(s) or solvate(s) thereof.

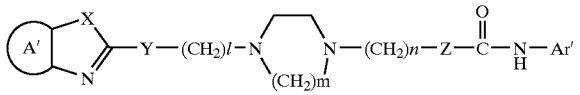

(IV)

(In the formula,

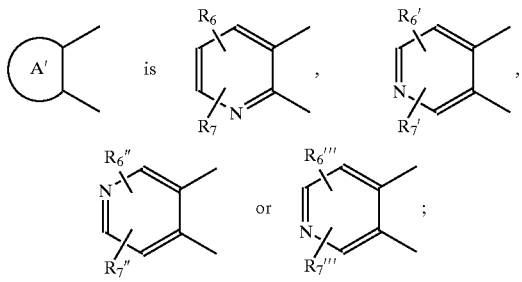

X is —NH—, oxygen atom or sulfur atom;
Y is —NR$_1$—, oxygen atom, sulfur atom, sulfoxide or sulfone;
Z is a single bond or —NR$_2$—;
Ar' is phenyl, pyridyl or pyrimidyl group which may be substituted with from one to four group(s) selected from optionally substituted lower alkyl group, optionally substituted lower alkoxy group, lower alkylthio group, lower alkylsulfinyl group, lower alkylsulfonyl group, lower alkylsulfonyloxy group, optionally substituted lower acyl group, halogen atom, hydroxyl group, optionally substituted lower acyloxy group, nitro group, phosphoric acid group, di-(lower alkoxy)-phosphoryloxy group, sulfonamide group, optionally substituted amino group and alkylenedioxy group;
R$_1$ is hydrogen atom, optionally substituted lower alkyl group, optionally substituted aryl group or optionally substituted silyl lower alkyl group;
R$_2$ is hydrogen atom, optionally substituted lower alkyl group, optionally substituted aryl group or optionally substituted silyl lower alkyl group;
R$_6$, R$_7$, R$_6$', R$_7$', R$_6$", R$_7$", R$_6$'" and R$_7$'" are same or different and are hydrogen atom, optionally substituted lower alkyl group, optionally substituted lower alkoxy group, halogen atom, hydroxyl group, carboxyl group, alkoxycarbonyl group, hydroxyalkyl group, phophoric acid group, sulfonamide group, optionally substituted amino group, optionally substituted aminoalkyl group, optionally substituted silyl lower alkyl group or heterocyclic residue; or any two of R$_6$, R$_7$, R$_6$', R$_7$', R$_6$", R$_7$", R$_6$'" and R$_7$'" may form an alkylenedioxy group;
l is an integer of from 1 to 15;
m is an integer of 2 or 3; and
n is an integer of from 1 to 3).
More specifically, Ar' is phenyl, pyridyl or pyrimidyl group which may be substituted with from one to four group(s) selected from lower alkyl group which may be substituted with group(s) selected from W2, lower alkoxy group which may be substituted with group(s) selected from W2, lower alkylthio group, lower alkylsulfinyl group, lower alkylsulfonyl group, lower alkylsulfonyloxy group, hydroxyl lower alkylthio group, lower alkylcarbonyl group which may be substituted with group(s) selected from W2, halogen atom, hydroxyl group, lower alkylcarbonyloxy group which may be substituted with group(s) selected from W2, nitro group, phosphoric acid group, di-(lower alkoxy)-phosphoryloxy group, sulfonamide group, amino group which may be substituted with group(s) selected from W3, pyranosyloxy group and alkylenedioxy group;
R$_1$ is hydrogen atom, lower alkyl group which may be substituted with group(s) selected from W2, aryl group which maybe substituted with group(s) selected from W5, or silyl lower alkyl group which may be substituted with group(s) selected from W4;
R$_2$ is hydrogen atom, lower alkyl group which may be substituted with group(s) selected from W2, aryl group which may be substituted with group(s) selected from W5, or silyl lower alkyl group which may be substituted with group(s) selected from W4;
R$_6$, R$_7$, R$_6$', R$_7$', R$_6$", R$_7$", R$_6$'" and R$_7$ '" are same or different and are hydrogen atom, lower alkyl group which may be substituted with group(s) selected from W2, lower alkoxy group which may be substituted with group(s) selected from W2, halogen atom, hydroxyl group, carboxyl group, alkoxycarbonyl group, phosphoric acid group, sulfonamide group, amino group which may be substituted with group(s) selected from W3, aminoalkyl group which may be substituted with group(s) selected from W3, silyl lower alkyl group which may be substituted with group(s) selected from W4, or heterocyclic residue; or any two of R$_6$, R$_7$, R$_6$', R$_7$', R$_6$", R$_7$", R$_6$'" and R$_7$'" may form an alkylenedioxy group;
W2 is hydroxyl group, lower alkoxy group, lower alkylthio group, lower alkoxycarbonyl group, lower alkylcarbonyloxy group, aryl group, halogen atom, amino group, nitrogroup, hydroxy lower alkoxy group, lower alkoxy lower alkoxy group, lower alkoxycarbonyl lower alkoxy group and halogenated lower alkoxy group;
W3 is lower alkyl group, aryl group which may be substituted with lower alkyl group or lower alkoxy group and an aralkyl group which may be substituted with lower alkyl group or lower alkoxy group;
W4 is lower alkyl group, aryl groups and an aralkyl group;
W5 is lower alkyl group which may be substituted with group(s) selected from W2, lower alkoxy group which may be substituted with group(s) selected from W2, lower alkylthio group which may be substituted with group(s) selected from W2, lower alkylsulfinyl group which may be substituted with group(s) selected from W2, lower alkylsulfonyl group which may be substituted with group(s) selected from W2, lower alkylsulfonyloxy group which may be substituted with group(s) selected from W2, lower alkylcarbonyl group which may be substituted with group(s) selected from W2, lower alkylcarbonyloxy group, halogen atom, hydroxyl group, nitro group, phosphoric acid group, di-(lower alkoxy)-phosphoryloxy group, sulfonamide group, amino group which may be substituted with group(s) selected from W3 and alkylenedioxy group.

Consequently, the present invention relates to a pharmaceutical composition containing the compound which is represented by the above-mentioned formula (I), (II), (III) or (IV) or salt(s) or solvate(s) thereof. To be more specific, the present invention relates to a pharmaceutical composition containing an effective amount of one or more of the compounds which are represented by the above-mentioned formula (I), (II), (III) or (IV) or salt(s) or solvate(s) thereof and a pharmaceutically acceptable carrier. The pharmaceutical composition of the present invention can be used as an ACAT inhibitor, an agent for inhibiting the transportation of intracellular cholesterol, an agent for lowering the cholesterol in blood or an agent for suppressing the foaming of macrophage and can be used as an agent for therapy and prevention of the diseases such as hyperlipemia, arteriosclerosis, cervical and cerebral arteriosclerosis, cerebrovascular disorder, ischemic cardiopathy, coronary arteriosclerosis, nephrosclerosis, arteriosclerotic nephrosclerosis, arteriocapillary sclerotic nephrosclerosis, malignant nephrosclerosis, ischemic entheropathy, acute occlusion of mesenteric vessel, chronic mesenteric angina, ischemic colitis, aortic aneurysm and arteriosclerosis obliterans (ASO).

The present invention further relates to the use of the compound represented by the above-mentioned formula (I), (II), (III) or (IV) or salt(s) or solvate(s) thereof for the preparation of an ACAT inhibitor, an agent for inhibiting the transportation of intracellular cholesterol, an agent for lowering the cholesterol in blood or an agent for suppressing the foaming of macrophage. To be more specific, the present invention relates to the above-mentioned use where the ACAT inhibitor, the agent for inhibiting the transportation of intracellular cholesterol, the agent for lowering the cholesterol in blood or the agent for suppressing the foaming of macrophage is an agent for therapy and prevention of the diseases such as hyperlipemia, arteriosclerosis, cervical and cerebral arteriosclerosis, cerebrovascular disorder, ischemic cardiopathy, coronary arteriosclerosis, nephrosclerosis, arteriosclerotic nephrosclerosis, arteriocapillary sclerotic nephrosclerosis, malignant nephrosclerosis, ischemic entheropathy, acute occlusion of mesenteric vessel, chronic mesenteric angina, ischemic colitis, aortic aneurysm and arteriosclerosis obliterans (ASO).

The present invention still further relates to a method for therapy or prevention of the diseases such as hyperlipemia, arteriosclerosis, cervical and cerebral arteriosclerosis, cerebrovascular disorder, ischemic cardiopathy, coronary arteriosclerosis, nephrosclerosis, arteriosclerotic nephrosclerosis, arteriocapillary sclerotic nephrosclerosis, malignant nephrosclerosis, ischemic entheropathy, acute occlusion of mesenteric vessel, chronic mesenteric angina, ischemic colitis, aortic aneurysm and arteriosclerosis obliterans (ASO) by administering an effective amount of one or more of the compounds which are represented by the above-mentioned formula (I), (II), (III) or (IV) or salt(s) or solvate(s) thereof to the patient suffering from those diseases. The present invention still furthermore relates to a method for the therapy and prevention of the above-mentioned diseases by administering an effective amount of one or more of the compounds of the above-mentioned formula (I), (II), (III) or (IV) or salt(s) or solvate(s) thereof to the above-mentioned patient as an ACAT inhibitor, an agent for inhibiting the transportation of intracellular cholesterol, an agent for lowering the cholesterol in blood or an agent for suppressing the foaming of macrophage.

When

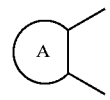

in the above-mentioned formula (I) is optionally substituted divalent residue of benzene, pyridine, cyclohexane or naphthalene, a fused ring system is formed together with the adjacent nitrogen atom and an atom represented by a substituent X as well as carbon atom on the ring. Further, when the group is the following formula,

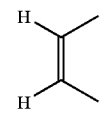

a monocyclic azole is formed.

These divalent residues of benzene, pyridine, cyclohexane or naphthalene may be unsubstituted or may be substituted with from 1 to 3 or, preferably, from 1 to 2 substituent (s). Among those, a divalent residue of benzene or pyridine is preferred.

Among the divalent residues of benzene, a group represented by the following formula is preferred.

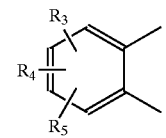

(In the formula, $R_3$, $R_4$ and $R_5$ are same or different and are hydrogen atom, optionally substituted lower alkyl, optionally substituted lower alkoxy, optionally substituted lower acyl, lower alkylthio, lower alkylsulfinyl, lower alkylsulfonyl, halogen atom, hydroxyl group, carboxyl group, alkoxycarbonyl group, hydroxyalkyl group, phosphoric acid group, cyano group, nitro group, sulfonamide group, optionally substituted amino group, optionally substituted aminoalkyl group, optionally substituted silyl lower alkyl group or heterocyclic residue; or any of two of $R_3$, $R_4$ and $R_5$ form an alkylenedioxy group together.)

With respect to the divalent residue of pyridine, a group represented by the following formula is preferred depending upon the selection of the divalent residue of pyridine and upon the connecting position to the adjacent azole ring.

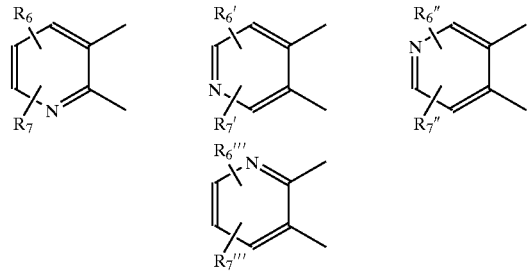

(In the formulae, $R_6$, $R_7$, $R_6'$, $R_7'$, $R_6''$, $R_7''$, $R_6'''$ and $R_7'''$ are same or different and are hydrogen atom, optionally substituted lower alkyl group, optionally substituted lower alkoxy group, halogen atom, hydroxyl group, carboxyl group, alkoxycarbonyl group, hydroxyalkyl group, phophoric acid group, sulfonamide group, optionally substituted amino group, optionally substituted aminoalkyl group, optionally substituted silyl lower alkyl group or heterocyclic residue; or any two of $R_6$, $R_7$, $R_6'$, $R_7'$, $R_6''$, $R_7''$, $R_6'''$ and $R_7'''$ may form an alkylenedioxy group.)

The groups used in each of the formulae of the present invention will be further illustrated as hereunder.

"Aryl group" is a group having six-membered aromatic hydrocarbon group or a group having from five- to seven-membered heterocyclic group which may have substituent containing from one to three oxygen atom(s), nitrogen atom(s) or sulfur atom(s) as heteroatom(s) and its examples are phenyl group, naphthyl group, biphenyl group, pyridyl group, furyl group, thienyl group, imidazolyl group and pyrimidyl group. Examples of preferred aryl group are phenyl group, pyridyl group and pyrimidyl group.

The aryl group may be substituted with functional group (s) which will not affect the property of the compound of the present invention. Examples of the substituent for the aryl group are optionally substituted lower alkyl group, optionally substituted lower alkoxy group, optionally substituted lower alkylthio group, optionally substituted lower alkylsulfinyl group, optionally substituted lower alkylsulfonyl group, optionally substituted lower alkylsulfonyloxy group, optionally substituted lower acyl group, optionally substituted lower acyloxy, halogen atom, hydroxyl group, nitro group, phosphoric acid group, di-(lower alkoxy)-phosphoryloxy group, sulfonamide group, amino group, substituted amino group, pyranosyloxy group and alkylenedioxy group. Examples of the particularly preferred group are lower alkyl group, lower alkoxy lower alkoxy group, lower alkoxycarbonyl lower alkoxy group, lower alkylthio group, lower alkylsulfinyl group, lower alkylsulfonyl group, lower alkylsulfonyloxy group, lower acyl group, halogen atom, hydroxyl group, nitro group, phosphoric acid group, sulfonamide group, amino group, substituted amino group and alkylenedioxy group. The aryl group may have 1–4, preferably 1–3 or, more preferably, 1–2 of such substituent(s).

"Aralkyl group" is a group having 7–20 carbons or preferably, 7–20 carbons such as benzyl group and phenethyl group.

"Lower alkyl group" is preferably a straight chain or a branched chain having 1–8 or, preferably, 1–6 carbon atom(s) and its particularly preferred examples are methyl group, ethyl group, n-propyl group, isopropyl group, n-butyl group, isobutyl group, tert-butyl group, n-pentyl group and n-hexyl group.

"Alkyl group" is preferably a straight chain or a branched chain having 1–15, preferably 1–8 or, more preferably, 1–6 carbon atom(s) and its particularly preferred examples are methyl group, ethyl group, n-propyl group, isopropyl group, n-butyl group, isobutyl group, tert-butyl group, n-pentyl group, n-hexyl group, n-octyl group and n-nonyl group.

"Lower alkoxy group" is preferably an alkoxy group comprising the above-mentioned lower alkyl group and its examples are methoxy group, ethoxy group and n-propoxy group.

"Alkylenedioxy group" has an alkylene group of a straight chain or a branched chain having 1–8, preferably 1–6 or, more preferably, 1–3 carbon atom(s) and its examples are methylenedioxy group, ethylenedioxy group and dimethylmethylenedioxy group.

"Lower alkylthio group" is preferably an alkylthio group comprising the above-mentioned lower alkyl group and its examples are methylthio group, ethylthio group, n-propylthio group and isopropylthio group.

"Lower alkylsulfinyl group" is preferably an alkylsulfinyl group comprising the above-mentioned lower alkyl group and its examples are methylsulfinyl group, ethylsulfinyl group, n-propylsulfinyl group and isopropylsulfinyl group.

"Lower alkylsulfonyl group" is preferably an alkylsulfonyl group comprising the above-mentioned lower alkyl group and its examples are methylsulfonyl group, ethylsulfonyl group, n-propylsulfonyl group and isopropylsulfonyl group.

"Lower alkylsulfonyloxy group" is preferably an alkylsulfonyloxy group comprising the above-mentioned lower alkyl group and its examples are methylsulfonyloxy group, ethylsulfonyloxy group, n-propylsulfonyloxy group and isopropylsulfonyloxy group.

"Lower acyl group" is preferably an alkylcarbonyl group comprising the above-mentioned lower alkyl group and its examples are acetyl group, ethylcarbonyl group, n-propylcarbonyl group and isopropylcarbonyl group.

"Lower acyloxy group" is preferably an alkylcarbonyloxy group comprising the above-mentioned lower alkyl group and its examples are acetyloxy group, ethylcarbonyloxy group, n-propylcarbonyloxy group and isopropylcarbonyloxy group.

"Lower alkoxycarbonyl group" is preferably a group where oxycarbonyl group is bonded to the above-mentioned lower alkyl group and its examples are methoxycarbonyl group, ethoxycarbonyl group and tert-butoxycarbonyl group.

"Di-(lower alkoxy)-phosphoryloxy group" is preferably a di-(lower alkoxy)-phosphoryloxy group comprising the above-mentioned lower alkyl group and its examples are dimethoxyphosphoryloxy group, diethoxyphosphoryloxy group, di-n-propylphosphoryloxy group and di-isopropylphosphoryloxy group.

Examples of "pyranosyloxy group" are glucopyranosyloxy group, galactopyranosyloxy group and mannopyranosyloxy group.

Hydrogen atom of the lower alkyl moiety or alkyl moiety in those groups may be substituted with other substituent if necessary and examples of such a substituent are hydroxyl group, lower alkoxy group, lower alkylthio group, lower alkoxycarbonyl group, lower acyloxy group, aryl group, halogen atom, amino group and nitro group upon substitution with such a substituent, the substituent may be only one or the substitution may be conducted by two or more substituents. Examples of the group having substituent are hydroxyalkyl group, hydroxy lower alkoxy group, lower alkoxy lower alkoxy group, lower alkoxy lower alkyl group, lower alkoxycarbonyl lower alkoxy group, lower alkoxycarbonyl lower alkyl group, halogenated lower alkoxy group, halogenated lower alkyl group and amino lower alkyl group.

Preferred examples of halogen atom are fluorine atom, chlorine atom, bromine atom and iodine atom.

The lower alkyl group in the optionally substituted silyl lower alkyl group is the above-mentioned lower alkyl group and examples of the substituent for the silyl group are the above-mentioned lower alkyl and aryl groups and an aralkyl group having 7–20 carbons or, preferably, 7–12 carbons such as benzyl group and phenethyl group. Trimethylsilylmethyl group and dimethylphenylsilylmethyl group are exemplified.

The optionally substituted amino group may be a free amino group or an amino group which is substituted with one or two substituent(s). Preferred substituent for the amino group are above-mentioned lower alkyl group; the above-mentioned aryl group such as phenyl group and naphthyl group; and an aralkyl group having 7–20 carbons or, preferably, 7–12 carbons such as benzyl group and phenethyl group. Those aromatic ring may be further substituted with the above-mentioned lower alkyl group, lower alkoxy group, and so on Furthermore, the two substituents of the amino group may form a five- to seven-membered ring together with the nitrogen atom of the amino group. One or more carbon atom(s) in the ring may be substituted with oxygen atom, sulfur atom or nitrogen atom. Examples of such an amino group forming a ring are morpholino group, piperazino group and pyrrolidino group. Those rings may be further substituted with other substituent(s).

The alkyl group in the optionally substituted aminoalkyl group is the above-mentioned alkyl group and the amino group therein is the above-mentioned substituted or unsubstituted amino group.

The heterocyclic residue is a residue of a saturated or unsaturated five to seven-membered heterocyclic group containing one to four oxygen atom(s), nitrogen atom(s) or sulfur atom(s) as heteroatom(s) and its example is a tetrazolyl group. Such a heterocyclic residue may have one or more substituent(s) and examples of the substituent are those which were mentioned as the substituents for the above-mentioned alkyl group.

l in the formula (I) is an integer of from 0 to 15, preferably from 1 to 15, more preferably from 1 to 10 or, still more preferably, from 2 to 5 while n is an integer of from 0 to 3 or, preferably, from 1 to 3.

Examples of the acid addition salt(s) of the compound (I) of the present invention are inorganic acid salt(s) such as hydrochloride, sulfate, nitrate and phosphate and organic acid salt(s) such as methanesulfonate, maleate, fumarate and citrate.

The solvate(s) is a product where the solvent used during preparation, purification, and so on such as water and alcohol is added and there is no particular limitation therefor so far as that does not badly affect the ACAT inhibitory action, and so on. Hydrate is preferred as the solvate(s).

BEST MODE FOR CONDUCTING THE INVENTION

The compound (I) may be manufactured by various known methods and there is no particular limitation therefor. For example, the compound may be manufactured in accordance with the following reaction steps.

1. Preparation of the Compound Where Z is a Single Bond.

(1) An amide derivative represented by the formula (VII) is obtained when an arylamine represented by the formula (V) is made to react, in accordance with the following reaction formulae, with a carboxylic acid represented by the formula (VI) or a reactive derivative thereof such as an acid halide. When the resulting compound represented by the formula (VII) is made to react with a cyclic diamine compound represented by the formula (VIII), a primary alcohol derivative represented by the formula (IX) is obtained. The resulting alcohol is subjected to mesylation, tosylation, and soon and then the resulting reactive derivative (X) is made to react with a compound represented by the formula (XI) whereupon the desired compound (I') wherein Z is a single bond is manufactured.

The above reaction routes are shown by the following chemical reaction formulae.

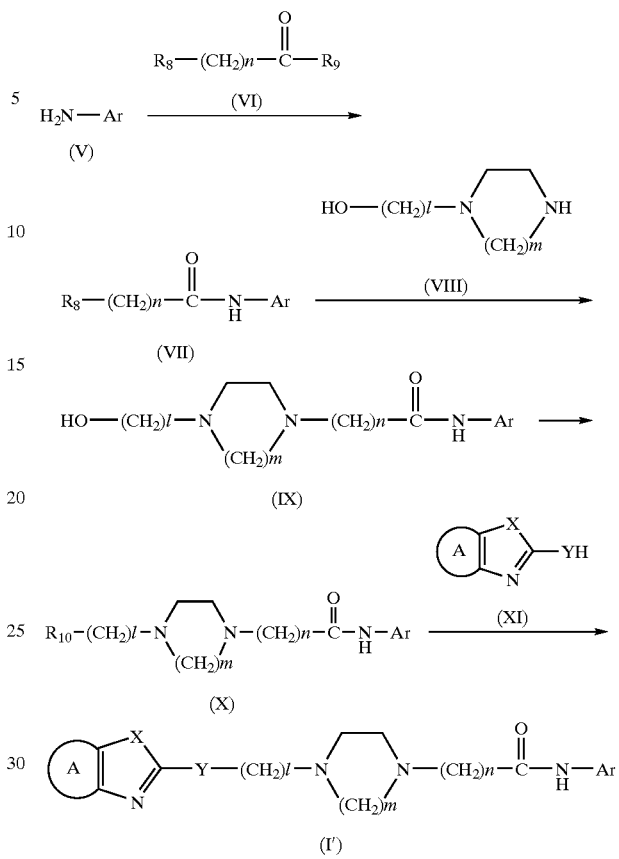

(In the formulae, $R_8$ and $R_{10}$ are leaving groups; and $R_9$ is a residue of a reactive derivative of hydroxyl group or carboxyl group.)

Methods which are used for common peptide synthesis may be applied to the reaction of the compound (V) with the compound (VI). Preferred examples of the leaving group $R_8$ in the formula (VI) are halogen atoms such as chlorine atom and bromine atom while those of the residue of the reactive derivative of carboxyl group represented by $R_9$ are acid anhydride residues such as anhydrides of mesylic acid, tosylic acid, acetic acid and pivalic acid. In conducting this reaction, both compounds are made to react, for example, in the presence of a condensing agent whereupon the desired compound is prepared. With regard to a condensing agent, 1-(3'-dimethylaminopropyl)-3-ethyl-carbodimide (WSC), 1,3-dicyclohexylcarbodiimide (DCC), or the like, for example, may be used either solely or jointly together with 1-hydroxybenzotriazole (HOBt), N-hydroxysuccinimide (HOSu), or the like. There is no particular limitation for the solvent and, for example, dimethylformamide, methylene chloride, chloroform, tetrahydrofuran (THF) and toluene may be used either solely or jointly.

The reaction condition may vary depending upon the materials used but, usually, it is completed when the reaction is conducted at 0–100° C. or, preferably, at around room temperature for 1–30 hours or, preferably, 10–20 hours. When a carboxylic acid halide having a high reactivity is used as the compound (VI), it is possible, for example, that the compound (V) is made to react by a common method with the compound (VI) in the presence of a base such as triethylamine, 4-dimethylaminopyridine or N-methylmorpholine.

The reaction of the compound (VII) obtained in the above method with the compound (VIII) may be conducted in a solvent in the presence or absence of a base. With regard to a solvent, the above-mentioned one may be used while, with regard to a base, inorganic bases such as alkali metal hydroxide such as sodium hydroxide and potassium hydroxide; alkali metal carbonates such as sodium carbonate and potassium carbonate; alkali metal bicarbonate such as sodium bicarbonate and potassium bicarbonate; organic bases such as pyridine, triethylamine, N,N-diisopropylethylamine, N-methylmorpholine and N,N-dimethylaniline; and the like may be used.

When the resulting compound (IX) is subjected, for example, to sulfonylating reaction such as mesylation or tosylation, a compound (X) is obtained. Common methods may be used for the sulfonylating reaction but a method using, for example, an agent for producing sulfonate such as methanesulfonyl chloride, methanesulfonic acid anhydride, methanesulfonyl fluoride, benzenesulfonyl chloride and p-toluenesulfonyl chloride is preferred. When the compound (IX) is made to react with the agent for producing sulfonate in a solvent in the presence or absence of a base, the compound (X) is prepared. Examples of the solvent are tetrahydrofuran, methylene chloride and chloroform while those of the base are those which were mentioned already.

Reaction of the compound (X) prepared by the above method with a compound (XI) may be conducted by a similar method as mentioned in the above second step.

(2) Alternatively, after the secondary amino group of the compound (VIII) is protected with a group $R_{11}$, a compound (XII) wherein hydroxyl group of the compound represented by the formula (VIII) is substituted with a leaving group such as a sulfonyl group is made to react with a compound represented by the formula (XI) to provide a compound represented by the formula (XIII). The protective group of the compound represented by the formula (XIII) is deprotected, and when the resulting compound (XIII') is made to react with a compound represented by the formula (VII), a desired compound (I') where Z is a single bond is obtained.

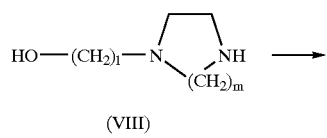

(VIII)

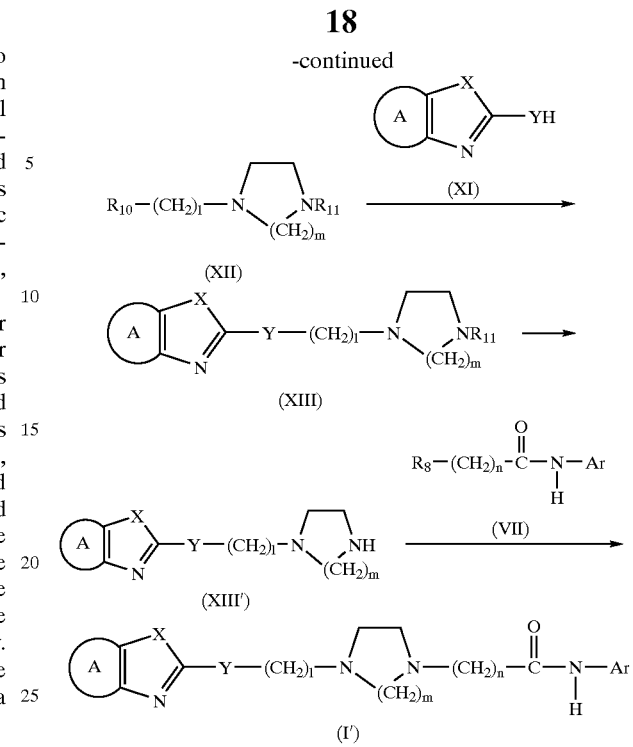

(In the formulae, $R_8$ and $R_{10}$ are leaving groups, and $R_{11}$ is a protective group for amino group.)

The third step in the above-mentioned (1) may be applied to a step for the preparation of the compound (XII) from the compound (VIII).

The reaction of the resulting compound (XII) with the compound (XI) may be conducted by a similar method as in the final step of the above (1).

The reaction of the resulting compound (XIII') with the compound (VII) may be conducted by a similar method as in the second step of the above-mentioned (1)

2. Preparation of the Compound Where Z is a Single Bond and n is 2.

The compound (I'') where Z is a single bond and n is 2 may be manufactured according to the reactions as shown in the following formulae.

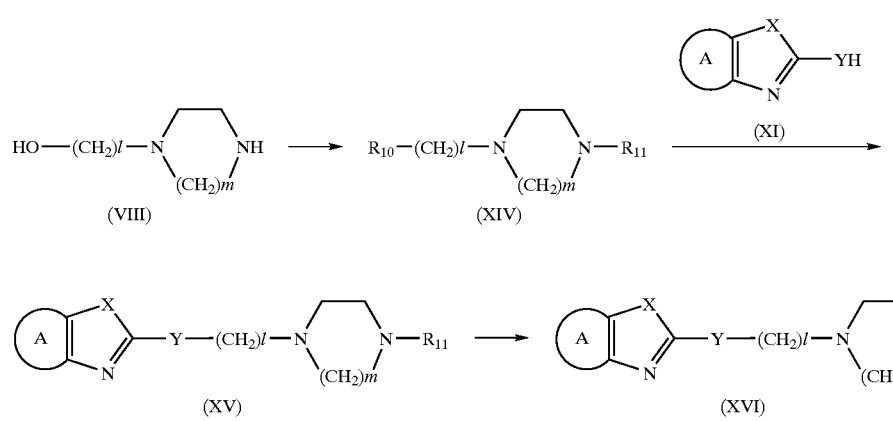

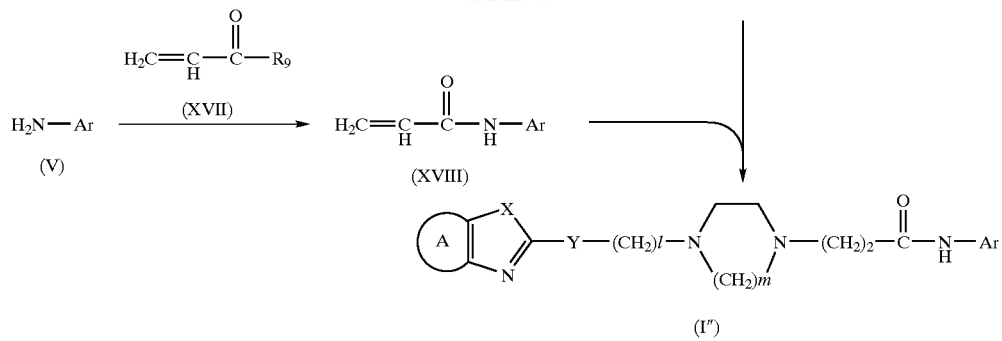

(In the formulae, $R_9$ is a residue of a reactive derivative of carboxyl group or hydroxyl group; $R_{10}$ is a leaving group; and $R_{11}$ is a protective group for amino group.)

After the secondary amine of the compound (VIII) is protected with a group $R_{11}$, the hydroxyl group is substituted with a leaving group such as a sulfonyl group whereupon the compound (XIV) is obtained. With regard to a protective group for amino group, tert-butoxycarbonyl group is preferred. When a method similar to that for the fourth step in (1) in the above-mentioned 1 is applied to the resulting N-protected compound, a compound (XV) is obtained and, when that is deprotected using, for example, an acid, a compound (XVI) is obtained.

On the other hand, when the compound (V) is made to react with the compound (XVII) or a reactive derivative of carboxylic acid, the compound (XVIII) is obtained. This reaction may be conducted in a similar manner as in the reaction for the first step of (1) of the above-mentioned 1.

When the resulting compound (XVI) and compound (XVIII) are subjected to a Michael reaction in a solvent, the desired compound (I″) is obtained. With regard to a solvent, alcohols such as methanol, ethanol and propanol as well as N,N-dimethylformamide, pyridine, and so on may be used either solely or jointly. The reaction condition may vary depending upon the materials used but, usually, the reaction is conducted at 0–100° C. or, preferably, at around the boiling point of the solvent for 1–100 hours or, preferably, 24–72 hours whereupon the desired product can be obtained in a good yield.

3. Method for the Preparation of a Compound (I‴) where Z is a group —$NR_2$—.

The compound represented by the formula (I) where Z is a group —$NR_2$— may be manufactured by various methods such as by the method as shown in the following reaction formulae.

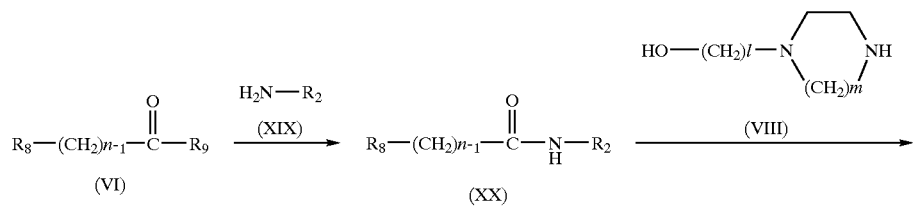

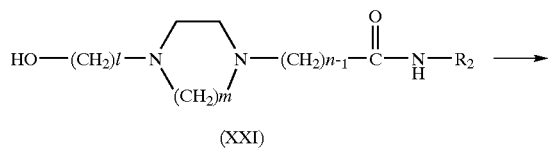

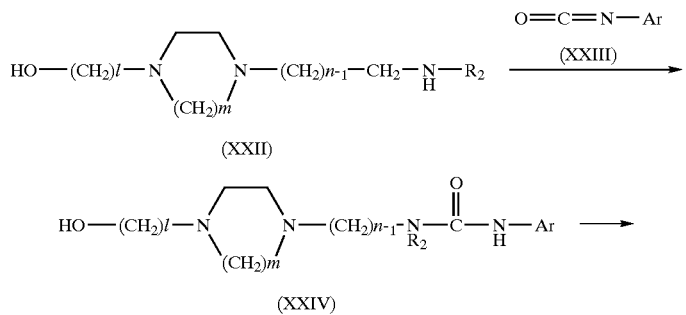

-continued

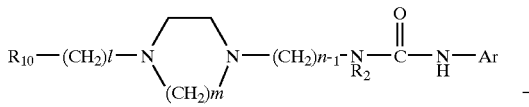 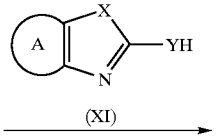

(XXV)     (XI)

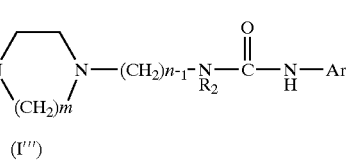

(I''')

(In the formulae, $R_9$ is a residue of a reactive derivative of carboxyl group or hydroxyl group; $R_8$ is a leaving group; and $R_{10}$ is a leaving group.)

When the compound represented by the formula (XIX) is made to react with a carboxylic acid represented by the formula (VI) or a reactive derivative thereof such as an acid halide, an amide derivative represented by the formula (XX) is obtained. The reaction may be conducted in a similar manner as in the first step of (1) of the above-mentioned 1.

When an amide compound represented by the formula (XX) is made to react with a cyclic diamine-alcohol compound represented by the formula (VIII), an amide derivative represented by the formula (XXI) is obtained. The reaction may be conducted in a solvent in the presence or absence of a base. With regard to the solvent, N,N-dimethylformamide (DMF), acetonitrile, and so on are particularly preferred. With regard to the base, the use of inorganic bases such as alkali metal hydroxides such as sodium hydroxide and potassium hydroxide; alkali metal carbonates such as sodium carbonate and potassium carbonate; alkali metal bicarbonates such as sodium bicarbonate and potassium bicarbonate; and so on is preferred.

When the resulting compound (XXI) is reduced, a compound represented by the formula (XXII) is obtained.

The reaction may be conducted by the use of a hydrogenating reducing agent in a solvent. Examples of the applicable solvent are tetrahydrofuran, ether and toluene while examples of the applicable reducing agent are lithium aluminum hydride, aluminum hydride and sodium aluminum bis(2-methoxyethoxy)hydride.

When the resulting amide compound (XXII) is made to react with an isocyan derivative represented by the formula (XXIII), an urea derivative represented by the formula (XXIV) is obtained. The desired compound (XXIV) is obtained when both compounds are made to react in a solvent at 0–100° C. or, preferably, at around room temperature for several minutes to several hours. Examples of the applicable solvent are tetrahydrofuran, ether, hexane, methylene chloride, chloroform, carbon tetrachloride, toluene, N,N-dimethylformamide and acetonitrile.

When the hydroxyl group of the resulting urea derivative represented by the formula (XXIV) is sulfonated and the compound (XXV) obtained thereby is made to react with a compound represented by the formula (XI), the desired compound (I''') where Z is —$NR_2$— is obtained. Methods similar to that for the third step and the fourth step of (1) of the above-mentioned 1 can be applied to the reaction.

4. Methods for the Preparation of the Compound (I) Having Substituent(s) on Ar by Other Methods.

Besides the above-mentioned methods, there is a method where the main skeleton of the compound of the present invention is manufactured and then each substituent at the side of azole or of aryl group is manufactured. Known methods may be used for producing those substituents and some of them will be exemplified hereunder.

(1) Method for the preparation of a compound having N-lower alkylamino group on Ar.

Among the compound (I), that having N-lower alkylamino group on Ar can be manufactured as follows. Thus, a nitro group of the compound (I) having a nitro group on Ar is reduced and the resulting amine compound is subjected to an N-lower alkylation.

Reduction of nitro group can be conducted by a hydrogenation in an inert solvent such as ethyl acetate or ethanol using palladium-carbon or Raney nickel as a catalyst. Alternatively, reduction using metal such as zinc, tin or iron in an acidic medium such as acetic acid or hydrochloric acid is also able to convert nitro group to amino group.

N-Lower alkylation of the amine compound can be conducted by the reaction of the amine compound with lower alkyl sulfate, lower alkyl halide, and so on in a solvent in the presence of a base and each of the resulting N-mono and dialkyl compounds can be isolated from a resulting mixture thereof. Especially in the case of a compound having N,N-dimethylamino group, it can be prepared by subjecting the amino compound to Clarke-Eschweiler reaction. Thus, the amino compound is made to react with formaldehyde, the resulting Schiff's base is reduced, and the resulting N-monomethylamino compound is further made to react with formaldehyde followed by reducing to provide a compound having N,N-dimethylamino group.

Examples of the base which is applicable for the N-lower alkylation are alkali metal bicarbonate such as sodium bicarbonate and potassium bicarbonate; alkali metal carbonates such as sodium carbonate and potassium carbonate; alkali metal hydroxides such as sodium hydroxide and potassium hydroxide; metal hydrides such as sodium hydride; alkali metal alkoxides such as sodium ethoxide and potassium butoxide; and organic bases such as pyridine, triethylamine, N,N-diisopropyl ethylamine, N-methylmorpholine and N,N-dimethylaniline.

With regard to a solvent, acetone, dimethyl sulfoxide, N,N-dimethylformamide, tetrahydrofuran and a mixed solvent thereof are preferred. The reaction is completed for 0.1–20 hours at 20–150° C. or, preferably, for 1–5 hours at 50–130° C.

With regard to the solvent used in Clarke-Eschweiler reaction, acetonitrile, N,N-dimethylformamide, formic acid, acetic acid and a mixed solvent thereof are preferred. With regard to a reducing agent, formic acid which acts as a solvent as well may be used or sodium cyanoborohydride may be used in an acidic solvent.

(2) Method for the preparation of a compound having lower alkylthio group on Ar.

Among the compound (I), that which has lower alkylthio group on Ar can be manufactured by diazotizing a compound (I) having amino group on Ar followed by subjecting to a reaction with di-lower alkyl disulfide or lower thioalkoxide. To be more specific, the corresponding amine compound is diazotized with amyl-nitrite or the like in a solution of di-lower alkyl disulfide followed by decomposing by heating (Japanese Laid-Open Patent Publication Hei-10/025,281) or the amine compound is diazotized with sodium nitrite in an acidic solution followed by heating in an aqueous solution of sodium lower thioalkoxide.

(3) Method for the preparation of a compound having lower acyloxy group, lower alkoxy group, lower alkylsulfonyloxy group or di-lower alkoxyphosphoryloxy group on Ar.

The compounds (I) having lower acyloxy group, lower alkoxy group, lower alkylsulfonyloxy group or di-lower alkoxyphosphoryloxy group on Ar can be manufactured as follows. Thus, the corresponding amine compound in the compound (I) is diazotized, heated in an aqueous solution to convert to hydroxyl compound and the compound is then subjected to lower acylation, lower alkylation, lower alkylsulfonylation or di-lower alkoxyphosphorylation.

Hydroxy compound can be manufactured by diazotizing the corresponding amine compound in a diluted sulfuric acid solution with sodium nitrite followed by pouring the aqueous solution of the resulting diazonium salt(s) into boiling water and by decomposing by heating.

Lower acyloxy compound can be manufactured by the reaction of the corresponding hydroxy compound with acid halide, acid anhydride, and so on in a solvent in the presence of a base. To be more specific, it can be manufactured by the reaction of a hydroxy compound with acetyl chloride in a pyridine solvent.

Lower alkoxy compound can be manufactured by the reaction of the corresponding hydroxy compound with lower alkyl sulfate, lower alkyl halide, and so on in a solvent in the presence of abase. To be more specific, it can be manufactured by the reaction of a hydroxy compound with sodium hydride in a dimethylformamide solvent followed by subjecting to a reaction with lower alkyl halide. Alternatively, it can be manufactured by the reaction of a hydroxy compound with diazomethane, trimethylsilyl diazomethane, and so on in a solvent in the presence of a base as well.

Lower alkylsulfonyloxy compound can be manufactured by the reaction of the corresponding hydroxy compound with lower alkyl sulfonic acid halide, lower alkyl sulfonic acid anhydride, and so on in a solvent in the presence of a base. To be more specific, it can be manufactured by the reaction of a hydroxy compound with methanesulfonyl chloride in a solvent in the presence of triethylamine.

Di-lower alkoxyphosphoryloxy compound can be manufactured by the reaction of the corresponding hydroxy compound with di-lower alkyl phosphoric acid halide in a solvent in the presence of a base. To be more specific, it can be manufactured by the reaction of a hydroxy compound with sodium hydride in a dimethylformamide solvent followed by subjecting to a reaction with dialkylphosphoric acid chloride.

(4) Method for the preparation of a compound having hydroxyl group and nitro group on Ar.

The compound (I) having hydroxyl group and nitro group on Ar can be manufactured by the reaction of a hydroxy compound with nitric acid or acetyl nitrate in an inert solvent. To be more specific, it can be manufactured by the reaction of a hydroxy compound in an acetonitrile solvent with acetyl nitrate.

Intermediates and desired compounds obtained in the above reactions can be, if necessary, isolated and purified by means of purifying methods which have been commonly used in organic synthetic chemistry such as filtration, extraction, washing, drying, concentration, recrystallization and various chromatographic means. With regard to intermediates, they may be subjected to the next reaction without particular purification.

The resulting compound (I) can be made into an acid addition salt(s)by a common method. It can also be prepared as solvate(s) with a solvent for the reaction or for the recrystallization, especially as a hydrate or an alcoholate.

Specific examples of the compounds obtained by the above-mentioned methods are shown in Tables 1–26.

In case of a compound forming hydrate, a desired acid, for example, inorganic acid such as sulfuric acid or organic acid, is added to an aqueous solution, the compound represented by the formula (I) is dissolved by heating in the solution, and the resulting solution is cooled to obtain the crystals of the acid salt hydrate of the formula (I).

In case of a compound forming alcohol solvate, the compound represented by the formula (I) is dissolved by heating in lower alcohol, such as methanol, ethanol, and etc., and the resulting solution is cooled to obtain the crystals of the alcohol solvate of the formula (I).

TABLE 1

| Ex. No. | A | X | Y | Z | l | m | n | Ar |
|---|---|---|---|---|---|---|---|---|
| 1 | (phenyl, methyl-substituted) | O | S | *1 | 2 | 2 | 1 | 2,6-di-i-Pr-phenyl |
| 2 | " | S | S | *1 | 2 | 2 | 1 | " |
| 3 | " | NH | S | *1 | 2 | 2 | 1 | " |
| 4 | MeOOC-(phenyl, methyl-substituted) | O | S | *1 | 2 | 2 | 1 | " |
| 5 | (phenyl with COOMe, methyl) | O | S | *1 | 2 | 2 | 1 | " |
| 6 | (pyridyl, methyl-substituted) | O | S | *1 | 2 | 2 | 1 | " |
| 7 | (phenyl, methyl-substituted) | O | S | *1 | 3 | 2 | 1 | " |
| 8 | " | S | S | *1 | 3 | 2 | 1 | " |

TABLE 1-continued
| Ex. No. | A | X | Y | Z | l | m | n | Ar |
|---|---|---|---|---|---|---|---|---|
| 9 | " | NH | S | *1 | 3 | 2 | 1 | " |
| 10 |  | O | S | *1 | 3 | 2 | 1 | " |
| 11 | 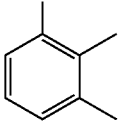 | O | S | *1 | 3 | 2 | 1 | " |
| 12 | 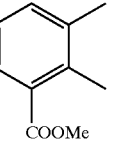 | O | S | *1 | 3 | 2 | 1 | " |
| 13 |  | O | S | *1 | 3 | 3 | 1 | " |
| 14 | 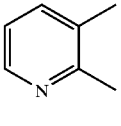 | O | S | *1 | 3 | 3 | 1 | " |
TABLE 2
| Ex. No. | A | X | Y | Z | l | m | n | Ar |
|---|---|---|---|---|---|---|---|---|
| 15 | 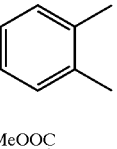 | O | S | *1 | 3 | 3 | 1 | 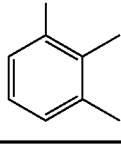 |
| 16 |  | O | S | N(CH$_2$)$_6$CH$_3$ | 2 | 2 | 2 | " |
| 17 | 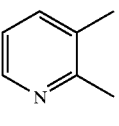 | O | S | N(CH$_2$)$_6$CH$_3$ | 2 | 2 | 2 | " |
| 18 | 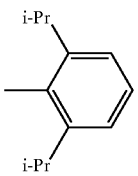 | O | S | N(CH$_2$)$_6$CH$_3$ | 2 | 2 | 2 | " |
| 19 | 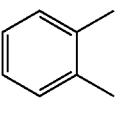 | O | S | N(CH$_2$)$_6$CH$_3$ | 3 | 2 | 2 | " |

TABLE 2-continued

| Ex. No. | A | X | Y | Z | l | m | n | Ar |
|---|---|---|---|---|---|---|---|---|
| 20 | MeOOC-substituted benzene (2,3-dimethyl) | O | S | N(CH$_2$)$_6$CH$_3$ | 3 | 2 | 2 | " |
| 21 | 2,3-dimethylpyridine | O | S | N(CH$_2$)$_6$CH$_3$ | 3 | 2 | 2 | " |
| 22 | o-xylene | O | S | *1 | 2 | 2 | 2 | " |
| 23 | o-xylene | O | S | *1 | 3 | 2 | 2 | " |
| 24 | o-xylene | O | S | *1 | 2 | 2 | 1 | MeS, Me-substituted pyridine with MeS |
| 25 | 2,3-dimethylpyridine | O | S | *1 | 2 | 2 | 1 | " |
| 26 | MeOOC-substituted benzene (2,3-dimethyl) | O | S | *1 | 2 | 2 | 1 | " |
| 27 | o-xylene | O | S | *1 | 2 | 2 | 2 | " |

*1 Single Bond

TABLE 3

| Ex.No. | A | X | Y | Z | l | m | n | Ar |
|---|---|---|---|---|---|---|---|---|
| 28 | o-xylene | O | S | *1 | 3 | 2 | 1 | MeS, Me-substituted pyridine with MeS |

TABLE 3-continued

| Ex.No. | A | X | Y | Z | l | m | n | Ar |
|---|---|---|---|---|---|---|---|---|
| 29 | pyridine (2,3-diyl) | O | S | *1 | 3 | 2 | 1 | " |
| 30 | MeOOC-benzene (2,3-diyl) | O | S | *1 | 3 | 2 | 1 | " |
| 31 | benzene (1,2-diyl) | S | S | *1 | 2 | 2 | 1 | " |
| 32 | benzene (1,2-diyl) | NH | S | *1 | 2 | 2 | 1 | " |
| 33 | pyridine (2,3-diyl) | O | S | *1 | 3 | 2 | 2 | " |
| 34 | benzene (1,2-diyl) | O | S | *1 | 2 | 2 | 1 | 4-(ethylthio)-2-(ethylthio)-3,6-dimethylpyridine |
| 35 | MeOOC-benzene (2,3-diyl) | O | S | *1 | 2 | 2 | 1 | " |

*1 Single Bond

TABLE 4
| Ex. No. | A  | X | Y | Z | l | m | n | Ar |
|---|---|---|---|---|---|---|---|---|
| 36 | 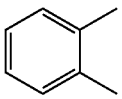 | O | S | *1 | 2 | 2 | 1 | 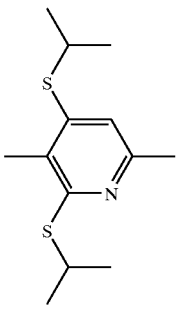 |
| 37 | 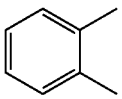 | NH | S | *1 | 2 | 2 | 1 | " |
| 38 | 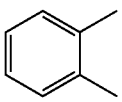 | S | S | *1 | 2 | 2 | 1 | " |
| 39 | 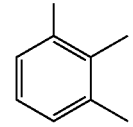 | O | S | *1 | 2 | 2 | 1 | " |
| 40 | 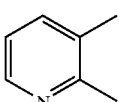 | O | S | *1 | 2 | 2 | 1 | " |
*1 Single Bond
TABLE 5
| Ex. No. | A  | X | Y | Z | l | m | n | Ar |
|---|---|---|---|---|---|---|---|---|
| 41 | 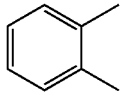 | O | S | *1 | 3 | 2 | 1 | 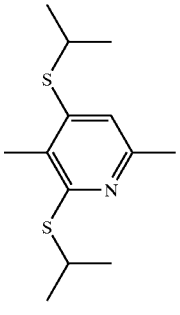 |
| 42 | 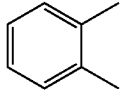 | O | S | *1 | 2 | 2 | 1 | 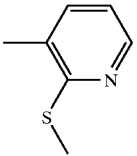 |

TABLE 5-continued
| Ex. No. | A | X | Y | Z | l | m | n | Ar |
|---|---|---|---|---|---|---|---|---|
| 43 |  | O | S | *1 | 2 | 2 | 1 | 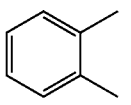 |
| 44 | 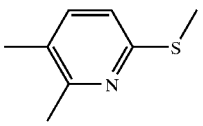 | O | S | *1 | 2 | 2 | 1 | 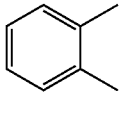 |
| 45 | 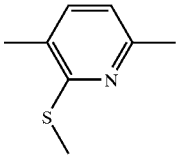 | O | S | *1 | 2 | 2 | 1 | 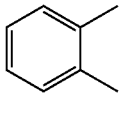 |
*1 Single Bond
TABLE 6
| Ex. No. | A | X | Y | Z | l | m | n | Ar |
|---|---|---|---|---|---|---|---|---|
| 46 | 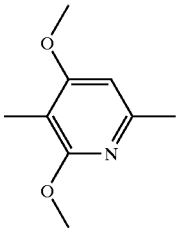 | O | S | *1 | 2 | 2 | 1 |  |
| 47 | 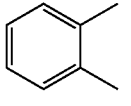 | O | S | *1 | 2 | 2 | 1 | 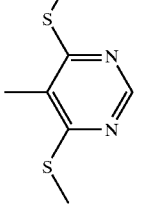 |
| 48 | 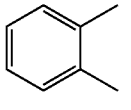 | O | S | *1 | 2 | 2 | 1 | 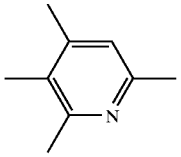 |

TABLE 6-continued

| Ex. No. | A | X | Y | Z | l | m | n | Ar |
|---|---|---|---|---|---|---|---|---|
| 49 | benzene (o-) | NH | S | *1 | 2 | 2 | 1 | " |
| 50 | benzene (o-) | S | S | *1 | 2 | 2 | 1 | " |

*1 Single Bond

TABLE 7

| Ex. No. | A | X | Y | Z | l | m | n | Ar |
|---|---|---|---|---|---|---|---|---|
| 51 | MeOOC-benzene | O | S | *1 | 2 | 2 | 1 | 2,4,6-triisopropylphenyl |
| 52 | pyridine | O | S | *1 | 2 | 2 | 1 | " |
| 53 | benzene (o-) | O | S | *1 | 3 | 2 | 1 | " |
| 54 | benzene (o-) | NH | S | *1 | 3 | 2 | 1 | " |
| 55 | benzene (o-) | S | S | *1 | 3 | 2 | 1 | " |

*1 Single Bond

TABLE 8

| Ex. No. | A | X | Y | Z | l | m | n | Ar |
|---|---|---|---|---|---|---|---|---|
| 56 | MeOOC-substituted benzene (2,3-disubstituted) | O | S | *1 | 3 | 2 | 1 | 2,4,6-triisopropylphenyl |
| 57 | 2,3-disubstituted pyridine | O | S | *1 | 3 | 2 | 1 | " |
| 58 | 1,2-disubstituted benzene | O | S | *1 | 2 | 2 | 1 | 2,3-diisopropyl-4-nitro substituted phenyl (with NO₂) |
| 59 | 1,2-disubstituted benzene | O | S | *1 | 2 | 2 | 1 | 2,3-diisopropyl-4-(N(CH₃)₂) phenyl |
| 60 | 1,2-disubstituted benzene | O | S | *1 | 2 | 2 | 1 | 2,3-diisopropyl-4-(SMe) phenyl |

*1 Single Bond

TABLE 9

| Ex. No. | A | X | Y | Z | l | m | n | Ar |
|---|---|---|---|---|---|---|---|---|
| 61 | benzene | O | S | *1 | 2 | 2 | 1 | 2,3-diisopropyl-phenol derivative with OH |
| 62 | benzene | O | S | *1 | 2 | 2 | 1 | aryl with OMs |
| 63 | benzene | O | S | *1 | 2 | 2 | 1 | aryl with OAc |
| 64 | benzene | O | S | *1 | 2 | 2 | 1 | aryl with OMe |
| 65 | benzene | O | S | *1 | 2 | 2 | 1 | aryl with O-CH$_2$CH$_2$-O-Et |

*1 Single Bond

TABLE 10

| Ex. No. | A | X | Y | Z | l | m | n | Ar |
|---|---|---|---|---|---|---|---|---|
| 66 | benzene (o-disub) | O | S | *1 | 2 | 2 | 1 | 3,5-diisopropyl-4-methyl-2-nitro-6-hydroxyphenyl (2,4-diisopropyl-3-methyl-6-nitrophenol) |
| 67 | benzene (o-disub) | O | S | *1 | 3 | 2 | 1 | 2,4-diisopropyl-3-methyl-6-nitrophenyl |
| 68 | benzene (o-disub) | O | S | *1 | 3 | 2 | 1 | 2,4-diisopropyl-3-methyl-6-(methylthio)phenyl |
| 69 | benzene (o-disub) | O | S | *1 | 3 | 2 | 1 | 2,4-diisopropyl-3-methyl-6-hydroxyphenyl |
| 70 | benzene (o-disub) | O | S | *1 | 3 | 2 | 1 | 2,4-diisopropyl-3-methyl-6-methoxyphenyl |

*1 Single Bond

TABLE 11

| Ex. No. | ⟨A⟩ | X | Y | Z | l | m | n | Ar |
|---|---|---|---|---|---|---|---|---|
| 71 | benzene (o-) | O | S | *1 | 3 | 2 | 1 | 2,6-diisopropyl-3-methyl-4-(2-ethoxyethoxy)phenyl |
| 72 | benzene (o-) | O | S | *1 | 2 | 2 | 1 | 3,5-diisopropyl-4-methyl-phenol |
| 73 | benzene (o-) | O | S | *1 | 2 | 2 | 1 | 3,5-diisopropyl-4-methylphenyl acetate |
| 74 | benzene (o-) | O | S | *1 | 2 | 2 | 1 | 3,5-diisopropyl-4-methylphenyl methanesulfonate |
| 75 | benzene (o-) | O | S | *1 | 2 | 2 | 1 | 3,5-diisopropyl-4-methyl-methoxyphenyl |

*1 Single Bond

TABLE 12

| Ex. No. | A (with substituents) | X | Y | Z | l | m | n | Ar |
|---|---|---|---|---|---|---|---|---|
| 76 | benzene (ortho-disubstituted) | O | S | *1 | 2 | 2 | 1 | 3,5-diisopropyl-4-methylphenyl–O–P(=O)(OEt)(OEt) |
| 77 | benzene (ortho-disubstituted) | O | S | *1 | 2 | 2 | 1 | 3,5-diisopropyl-4-methylphenyl–O–CH₂–C(=O)–O–Et (ethyl (3,5-diisopropyl-4-methylphenoxy)acetate) |
| 78 | benzene (ortho-disubstituted) | O | S | *1 | 2 | 2 | 1 | 3,5-diisopropyl-4-methylphenyl–O–CH₂CH₂–O–Et |
| 79 | benzene (ortho-disubstituted) | O | S | —NH— | 2 | 2 | 2 | 2,6-diisopropyl-3-methylphenyl |
| 80 | benzene (ortho-disubstituted) | NH | S | —NH— | 2 | 2 | 2 | " |

*1 Single Bond

TABLE 13

| Ex. No. | A | X | Y | Z | l | m | n | Ar |
|---|---|---|---|---|---|---|---|---|
| 81 | (benzene) | S | S | —NH— | 2 | 2 | 2 | 2,6-diisopropyl-phenyl (methyl substituted) |
| 82 | MeOOC-benzene | O | S | —NH— | 2 | 2 | 2 | " |
| 83 | pyridine | O | S | —NH— | 2 | 2 | 2 | " |
| 84 | (benzene) | O | S | *1 | 2 | 2 | 3 | " |
| 85 | CF$_3$-benzene | O | S | *1 | 2 | 2 | 1 | " |

*1 Single Bond

TABLE 14

| Ex. No. | A | X | Y | Z | l | m | n | Ar |
|---|---|---|---|---|---|---|---|---|
| 86 | CF$_3$-benzene | O | S | *1 | 2 | 2 | 1 | 3,5-diisopropyl-4-methoxy-methylphenyl |
| 87 | " | O | S | *1 | 2 | 2 | 1 | 2,6-diisopropyl-3-nitro-methylphenyl |

TABLE 14-continued
| Ex. No. | A | X | Y | Z | l | m | n | Ar |
|---|---|---|---|---|---|---|---|---|
| 88 | " | O | S | *1 | 2 | 2 | 1 | 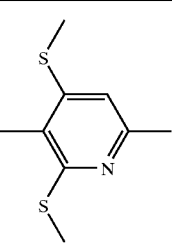 |
| 89 | " | O | S | *1 | 2 | 2 | 1 | 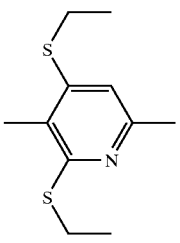 |
| 90 | " | O | S | *1 | 2 | 2 | 1 | 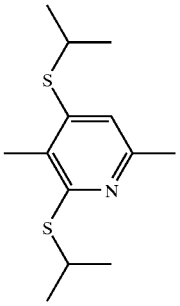 |
*1 Single Bond
TABLE 15
| Ex. No. | A | X | Y | Z | l | m | n | Ar |
|---|---|---|---|---|---|---|---|---|
| 91 | 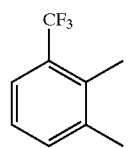 | O | S | *1 | 3 | 3 | 1 | 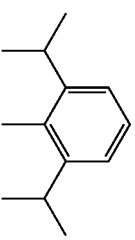 |
| 92 | 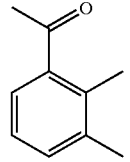 | O | S | *1 | 2 | 2 | 1 | " |

TABLE 15-continued
| Ex. No. | 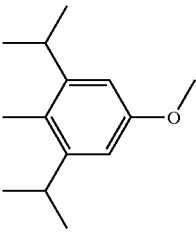 | X | Y | Z | l | m | n | Ar |
|---|---|---|---|---|---|---|---|---|
| 93 | " | O | S | *1 | 2 | 2 | 1 | 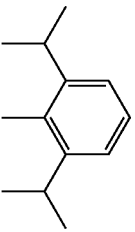 |
| 94 | " | O | S | *1 | 3 | 3 | 1 | 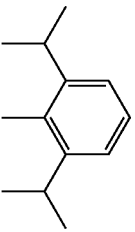 |
| 95 | 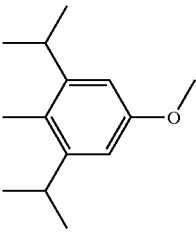 | O | S | *1 | 2 | 2 | 1 | " |
*1 Single Bond
TABLE 16
| Ex. No. | 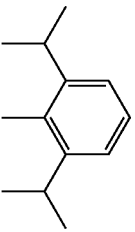 | X | Y | Z | l | m | n | Ar |
|---|---|---|---|---|---|---|---|---|
| 96 | 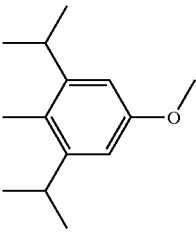 | O | S | *1 | 2 | 2 | 1 | 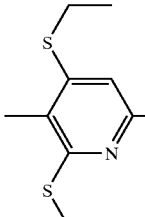 |
| 97 | 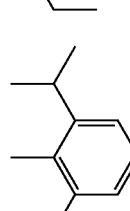 | O | S | *1 | 2 | 2 | 1 | 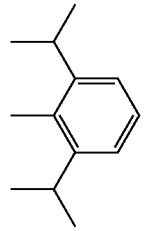 |

TABLE 16-continued
| Ex. No. | A | X | Y | Z | l | m | n | Ar |
|---|---|---|---|---|---|---|---|---|
| 98 |  | O | S | *1 | 2 | 2 | 1 | " |
| 99 | 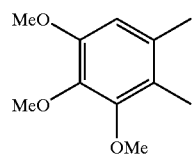 | O | S | *1 | 2 | 2 | 1 | " |
| 100 | 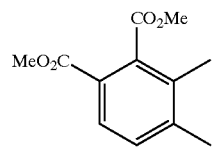 | O | S | *1 | 2 | 2 | 1 | " |
*1 Single Bond
TABLE 17
| Ex. No. | A | X | Y | Z | l | m | n | Ar |
|---|---|---|---|---|---|---|---|---|
| 101 | 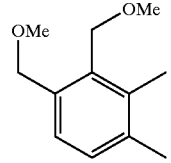 | O | S | *1 | 2 | 2 | 1 |  |
| 102 | 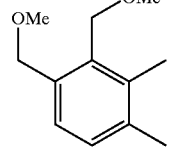 | O | S | *1 | 2 | 2 | 1 | 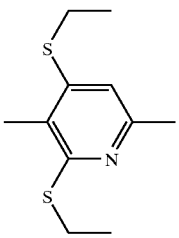 |
| 103 | 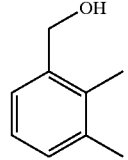 | O | S | *1 | 2 | 2 | 1 | " |

TABLE 17-continued
| Ex. No. | A | X | Y | Z | l | m | n | Ar |
|---|---|---|---|---|---|---|---|---|
| 104 |  (NO₂, dimethylphenyl) | O | S | *1 | 2 | 2 | 1 | " |
| 105 | " | O | S | *1 | 2 | 2 | 1 | 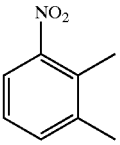 |
*1 Single Bond
TABLE 18
| Ex. No. | A | X | Y | Z | l | m | n | Ar |
|---|---|---|---|---|---|---|---|---|
| 106 | 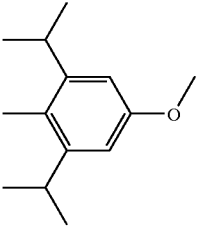 (NO₂, dimethylphenyl) | O | S | *1 | 2 | 2 | 1 |  |
| 107 | " | O | S | *1 | 2 | 2 | 1 | 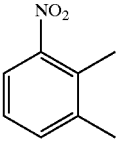 |
| 108 | " | O | S | *1 | 2 | 2 | 1 | 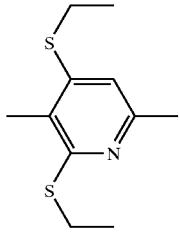 |

TABLE 18-continued

| Ex. No. | A | X | Y | Z | l | m | n | Ar |
|---|---|---|---|---|---|---|---|---|
| 109 | 5-Cl, 2,3,4-triMe, 6-iPr-phenyl | O | S | *1 | 2 | 2 | 1 | 4,6-bis(ethylthio)-3,5-dimethylpyridin-2-yl (shown structure) |
| 110 | " | O | S | *1 | 3 | 2 | 1 | 4-methoxy-2,3-diisopropyl-6-methylphenyl |

*1 Single Bond

TABLE 19

| Ex. No. | A | X | Y | Z | l | m | n | Ar |
|---|---|---|---|---|---|---|---|---|
| 111 | 2-CF₃, 3,6-diMe-phenyl | O | S | *1 | 3 | 2 | 1 | 4-methoxy-2,3-diisopropyl-6-methylphenyl |
| 112 | 2-SMe, 3,6-diMe-phenyl | O | S | *1 | 2 | 2 | 1 | 2,6-diisopropyl-3-methylphenyl |
| 113 | 2-SO₂Me, 3,6-diMe-phenyl | O | S | *1 | 2 | 2 | 1 | " |

*1 Single Bond

TABLE 20

| Ex. No. | A | X | Y | Z | l | m | n | Ar |
|---|---|---|---|---|---|---|---|---|
| 114 | 3-CF₃, 2-methylphenyl | O | S | *1 | 2 | 2 | 1 | 3,4-dimethyl-5-isopropyl-... 4-OH-3,5-diisopropyl-... |
| 115 | 3-CF₃, 2-methylphenyl | O | S | N(CH₂)₆CH₃ | 2 | 2 | 2 | 4-OH-3,5-diisopropyl-4-methyl phenyl |
| 116 | 5-Cl, 2-isopropyl-3,4-dimethylphenyl | O | S | N(CH₂)₆CH₃ | 2 | 2 | 2 | 4-OH-3,5-diisopropyl-4-methyl phenyl |
| 117 | 5-Cl, 2-isopropyl-3,4-dimethylphenyl | O | S | *1 | 3 | 2 | 1 | 2-isopropyl-3-methyl-4-(2-ethoxyethoxy)... |
| 118 | 2,3-dimethylphenyl | O | S | *1 | 3 | 2 | 1 | 4-OH-3,5-diisopropyl-4-methyl phenyl |
| 119 | 2,3-dimethylphenyl | O | S | *1 | 3 | 2 | 1 | 4-OMe-3,5-diisopropyl-4-methyl phenyl |

TABLE 20-continued

| Ex. No. | A | X | Y | Z | l | m | n | Ar |
|---|---|---|---|---|---|---|---|---|
| 120 | (o-phenylene) | O | S | *1 | 3 | 2 | 1 | 3,5-diisopropyl-4-methylphenyl-O-CH₂CH₂-O-Et |

*1 Single Bond

TABLE 21

| Ex. No. | A | X | Y | Z | l | m | n | Ar |
|---|---|---|---|---|---|---|---|---|
| 121 | 2,3-dimethyl-SOMe-phenyl | O | S | *1 | 2 | 2 | 1 | 2,6-diisopropyl-3-methylphenyl |
| 122 | 2,3-dimethyl-4-isopropylphenyl | O | S | *1 | 2 | 2 | 1 | 2,6-diisopropyl-3-methylphenyl |
| 123 | (o-phenylene) | O | S | N(CH₂)₆CH₃ | 3 | 2 | 2 | 3,5-dimethyl-2,4-bis(MeS)pyridin-yl |
| 124 | (o-phenylene) | O | S | N(CH₂)₆CH₃ | 2 | 2 | 2 | 3,5-dimethyl-2,4-bis(EtS)pyridin-yl |
| 125 | (o-phenylene) | S | S | N(CH₂)₆CH₃ | 2 | 2 | 2 | 3,5-dimethyl-2,4-bis(EtS)pyridin-yl |

TABLE 21-continued

| Ex. No. | A | X | Y | Z | l | m | n | Ar |
|---|---|---|---|---|---|---|---|---|
| 126 | benzene (1,2-disubstituted) | NH | S | N(CH₂)₆CH₃ | 2 | 2 | 2 | 2,6-bis(ethylthio)pyridin-3-yl (3-methyl, 4-EtS, 2,6-EtS on pyridine) |
| 127 | pyridine (2,3-disubstituted) | O | S | *1 | 2 | 2 | 1 | 2,6-bis(ethylthio)pyridin-3-yl (3-methyl, 4-EtS, 2,6-EtS on pyridine) |

*1 Single Bond

TABLE 22

| Ex. No. | A | X | Y | Z | l | m | n | Ar |
|---|---|---|---|---|---|---|---|---|
| 128 | benzene (1,2-disubstituted) | O | S | *1 | 2 | 2 | 1 | 2,6-diisopropyl-3-methyl-N-(methylsulfonyl)anilino phenyl |
| 129 | 3-(trifluoromethyl)benzene (1,2-disubstituted) | O | S | *1 | 2 | 2 | 1 | 2,6-diisopropyl-3-methyl-N-(methylsulfonyl)anilino phenyl |
| 130 | 3-(trifluoromethyl)benzene (1,2-disubstituted) | O | S | *1 | 2 | 2 | 1 | 2,6-diisopropyl-3-methyl-4-hydroxyphenyl |

TABLE 22-continued

| Ex. No. | A | X | Y | Z | l | m | n | Ar |
|---|---|---|---|---|---|---|---|---|
| 131 | benzene (1,2-disubstituted) | O | S | *1 | 2 | 2 | 1 | 4-(MeS)-3,6-dimethylpyridin-2-yl-S-CH2CH2OH |
| 132 | pyridine (2,3-disubstituted) | O | S | *1 | 2 | 2 | 1 | 4-(MeS)-3,6-dimethylpyridin-2-yl-S-CH2CH2OH |
| 133 | benzene (1,2-disubstituted) | O | S | *1 | 2 | 2 | 1 | 3,5-diisopropyl-4-methylphenyl-O-(tetrahydropyran-2-yl with 3,4,5-triOH and 6-CH2OH) |

*1 Single Bond

TABLE 23
| Ex. No. |  (A) | X | Y | Z | l | m | n | Ar |
|---|---|---|---|---|---|---|---|---|
| 134 | 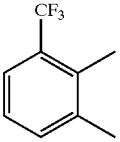 | O | S | *1 | 2 | 2 | 1 | 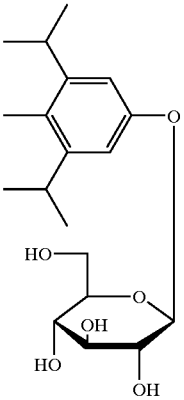 |
| 135 | 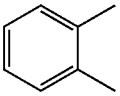 | O | S | *1 | 2 | 2 | 1 | 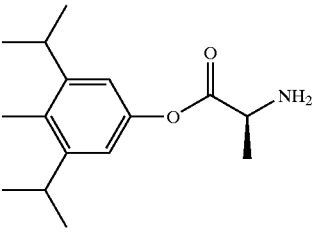 |
| 136 | 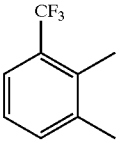 | O | S | *1 | 2 | 2 | 1 | 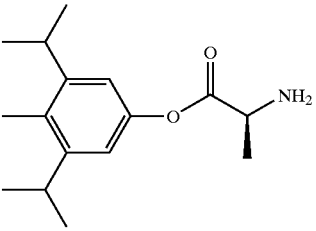 |
| 137 | 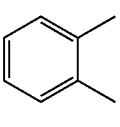 | O | S | N(CH$_2$)$_6$CH$_3$ | 2 | 2 | 2 | 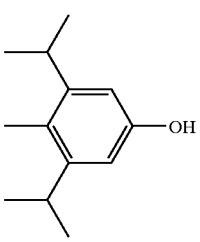 |
| 138 | 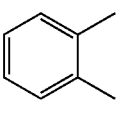 | O | S | N(CH$_2$)$_6$CH$_3$ | 2 | 2 | 2 | 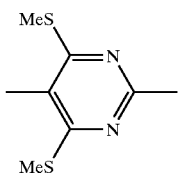 |

TABLE 23-continued

| Ex. No. | A | X | Y | Z | l | m | n | Ar |
|---|---|---|---|---|---|---|---|---|
| 139 | 2,3-pyridyl | O | S | N(CH$_2$)$_6$CH$_3$ | 2 | 2 | 2 | 3,5-diisopropyl-4-methylphenol |

*1 Single Bond

TABLE 24

| Ex. No. | A | X | Y | Z | l | m | n | Ar |
|---|---|---|---|---|---|---|---|---|
| 140 | 3-CF$_3$-2-methylphenyl | O | S | *1 | 2 | 2 | 1 | 3,5-diisopropyl-4-methylbenzyl alcohol |
| 141 | 3-Cl-2-methyl-5-CF$_3$-phenyl | NH | S | *1 | 2 | 2 | 1 | 2,6-diisopropyl-3-methylphenyl |
| 142 | 3-isopropyl-5-Cl-2,4-dimethylphenyl | O | S | *1 | 2 | 2 | 1 | 3,5-diisopropyl-4-methylphenol |
| 143 | 2-methylphenyl | NH | S | *1 | 2 | 2 | 1 | 4-MeS-3,6-dimethyl-2-(methylsulfinyl)pyridyl |

TABLE 24-continued
| Ex. No. | A | X | Y | Z | l | m | n | Ar |
|---|---|---|---|---|---|---|---|---|
| 144 |  | NH | S | *1 | 2 | 2 | 1 | 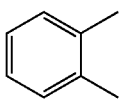 |
| 145 | 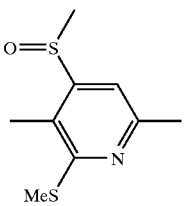 | NH | S | *1 | 2 | 2 | 1 | 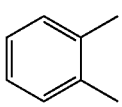 |
| 146 | 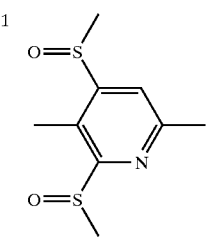 | NH | SO$_2$ | *1 | 2 | 2 | 1 | 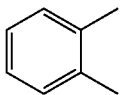 |
*1 Single Bond
TABLE 25
| Ex. No. | A | X | Y | Z | l | m | n | Ar |
|---|---|---|---|---|---|---|---|---|
| 147 | 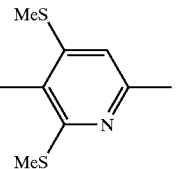 | NH | SO | *1 | 2 | 2 | 1 |  |
| 148 | 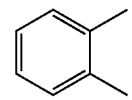 | NH | SO | *1 | 2 | 2 | 1 | 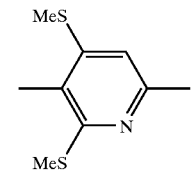 |
| 149 | 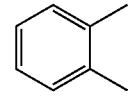 | NH | S | *1 | 2 | 2 | 1 | 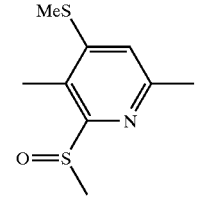 |

TABLE 25-continued

| Ex. No. | A | X | Y | Z | l | m | n | Ar |
|---|---|---|---|---|---|---|---|---|
| 150 | 4-(benzyloxy)-2-methylphenyl | NH | S | *1 | 2 | 2 | 1 | 2,4-bis(methylthio)-3-methylpyridin-... |
| 151 | 4-hydroxy-2-methylphenyl | NH | S | *1 | 2 | 2 | 1 | 2,4-bis(methylthio)-3-methylpyridin-... |
| 152 | 4-methoxy-2-methylphenyl | NH | S | *1 | 2 | 2 | 1 | 2,4-bis(methylthio)-3-methylpyridin-... |
| 153 | 2-methylphenyl | NH | O | *1 | 2 | 2 | 1 | 2,4-bis(methylthio)-3-methylpyridin-... |

*1 Single Bond

TABLE 26

| Ex. No. | A | X | Y | Z | l | m | n | Ar |
|---|---|---|---|---|---|---|---|---|
| 154 | 2-methylphenyl | NH | O | *1 | 2 | 2 | 1 | 2,6-diisopropylphenyl |
| 155 | 2-methylphenyl | O | S | *1 | 2 | 2 | 1 | 2,6-diisopropyl-3-fluorophenyl |

TABLE 26-continued

| Ex. No. | A | X | Y | Z | l | m | n | Ar |
|---|---|---|---|---|---|---|---|---|
| 156 | (2-methylphenyl) | NH | S | *1 | 2 | 2 | 1 | 2,6-diisopropyl-4-hydroxyphenyl |
| 157 | (3-trifluoromethyl-2-methylphenyl) | O | S | *1 | 2 | 2 | 1 | 2,6-diisopropyl-4-(methylsulfonyloxy)phenyl |
| 158 | (2-methylphenyl) | NH | S | *1 | 2 | 2 | 1 | 2,6-diisopropyl-4-(methylsulfonyloxy)phenyl |

*1 Single Bond

The compounds of the present invention represented by the formula (I) have an ACAT inhibitory action and/or intracellular cholesterol transportation inhibiting action and are useful in a medical field as therapeutic agents for hyperlipemia and for arteriosclerosis. Particularly since the compounds of the present invention show an action of selectively inhibiting the ACAT enzyme of a type existing on blood vessel wall, they have less side effect as compared with nonselective ACAT inhibitors and, further since they are soluble in water, they are expected to have improved oral absorption and are preferred as effective ingredients of pharmaceuticals.

A pharmaceutical composition of the present invention contains the compound represented by the formula (I) or acid addition salt(s) or solvate(s) thereof as an effective ingredient and the effective ingredient can be made into a dosage form such as tablets, capsules, granules, powder, injection and suppositories either as it is or together with other pharmaceutically acceptable fillers, binders, diluents, and so on.

Those preparations can be manufactured by a known method. For example, in the preparation of a preparation for oral administration, it can be manufactured by formulating the compound of the formula (I) by means of an appropriate compounding with fillers such as mannitol and lactose; binders such as sodium carboxymethyl cellulose and hydroxypropyl cellulose; disintegrating agents such as crystalline cellulose and calcium carboxymethyl cellulose; lubricants such as talc and magnesium stearate; fluidization improving agents such as light silicic acid anhydride; and so on The pharmaceutical composition of the present invention can be administered by means of either oral administration or parenteral administration.

Dose of the pharmaceutical composition of the present invention varies depending upon body weight, age, sex, symptom, and so on of the patient and, usually in the case of adults, it is preferred that 1–100 mg/day or, preferably, 5–200 mg/day as a compound represented by the formula (I) is administered once to three times a day.

ACAT inhibitory action, and so on of the compounds of the present invention represented by the formula (I) were tested by the following experimental examples.

Experimental Example 1

ACAT Inhibitory Action.

Microsome was prepared by a conventional method from stethartery of rabbits fed for eight weeks with a 1% cholesterol feed and was suspended in a 0.15M phosphate buffer (pH, 7.4) to provide an enzyme solution. An enzyme solution derived from small intestine was prepared from small intestine or rabbits fed with normal feed. Measurement of ACAT inhibitory activity was conducted by modifying a method of J. G. Hider (J. Lipid Res., 24, 1127–1134, 1983). Thus, 2 µl of a test compound dissolved in dimethyl sulfoxide (DMSO) was added to 88 µl of a 15M phosphate buffer (pH, 7.4) containing $^{14}$C-oleoyl-CoA (40 µM, 60,000 dpm) and bovine serum albumin (2.4 mg/ml) and incubated at 37° C. for five minutes. An enzyme solution (10 µl) was added to this liquid and made to react at 37° C. for five minutes (or three minutes in the case of small intestine), the reaction was stopped by adding 3 ml of chloroform/methanol (2/1) and 0.5 ml of 0.04N hydrochloric acid and lipid was extracted therefrom. The solvent layer was concentrated to dryness, the residue was dissolved in hexane and the solution was spotted on a TLC plate (manufactured by Merck) followed by developing with hexane: ether:acetic acid (75:25:1). Radioactivity of the resulting cholesterol ester fraction was measured by a BAS 2000 (manufactured by Fuji Photo Film) and $IC_{50}$ values were determined from a comparative calculation with the control to which only DMSO was added. The result is shown in Table 27.

TABLE 27

| Compound (Ex. No.) | Enzyme from A* $IC_{50}$ ($\mu$M) | Enzyme from B* $IC_{50}$ ($\mu$M) | $IC_{50}$ (B)/ $IC_{50}$ (A) |
|---|---|---|---|
| 1 | 0.024 | 0.045 | 1.9 |
| 2 | 0.021 | 0.045 | 2.1 |
| 3 | 0.011 | 0.051 | 4.6 |
| 5 | 0.056 | 0.13 | 2.3 |
| 6 | 0.11 | 0.32 | 2.9 |
| 7 | 0.019 | 0.039 | 2.1 |
| 10 | 0.035 | 0.039 | 1.1 |
| 25 | 0.12 | 0.21 | 1.8 |
| 75 | 0.038 | 0.21 | 5.5 |
| 78 | 0.040 | 0.21 | 5.3 |
| 85 | 0.012 | 0.059 | 4.9 |
| Control 1 | 0.45 | 0.87 | 1.9 |
| Control 2 | 0.047 | 0.13 | 2.8 |
| Control 3 | 0.034 | 0.056 | 1.7 |
| Control 4 | 0.026 | 0.037 | 1.4 |
| Control 5** | 0.004 | 0.021 | 4.8 |

*In table, "A" means the blood vessel wall, and "B" means the small intestine.
**The compound of Control 5 is corresponding to one disclosed in Example 8 of Japanese Patent Application No. 9-88660.

Experimental Example 2

ACAT Inhibitory Action (Anti-Foaming Action) in J774 Cells and HepG2 Cells.

J774 cells or HepG2 cells were planted on a 24-well plate and incubated at 37° C. for 24 hours in a 5% $CO_2$ incubator using DMEM or MEM culture liquid (each containing 10% of fetal calf serum) for J774 cells or HepG cells, respectively. The medium was exchanged with 0.5 ml of each culture liquid containing 10 $\mu$g/ml of 25-OH cholesterol and sample followed by incubating for 18 hours more. The medium was removed and, after washing with PBS twice, extraction was conducted with 1.5 ml of hexane: isopropanol (3:2) followed by concentrating to dryness. The extract was dissolved in 0.2 ml of isopropanol containing 10% of 10% Triton X-100 and total cholesterol (TC) and free cholesterol (FC) were determined by a Cholesterol E Test Wako (Wako Pure Chemicals) and a Free Cholesterol ETest Wako (Wako Pure Chemicals), respectively. Residue of the cells after extraction was solubilized with 0.25 ml of 2N NaOH at 30° C. for 30 minutes and amount of protein was determined by means of a BCA Protein Assay Reagent (Pierce). From the difference between TC and FC, amount of cholesterol ester per protein was calculated and then $IC_{50}$ was determined by means of a comparative calculation with the control. The result is shown in Table 28.

TABLE 28

| Compound (Ex. No.) | Enzyme (J774) $IC_{50}$ ($\mu$M) | Enzyme (HepG2) $IC_{50}$ ($\mu$M) | $IC_{50}$ (HepG2)/ $IC_{50}$ (J774) |
|---|---|---|---|
| 1 | 0.051 | 0.067 | 5.1 |
| 2 | 0.20 | 2.25 | 11.3. |
| 3 | 0.28 | 9.19 | 32.8 |
| 5 | 0.10 | 1.45 | 14.5 |
| 10 | 0.27 | 4.9 | 18.2 |
| 25 | 0.1 | >9.6 | >96 |
| 75 | 0.10 | >10 | >100 |
| 78 | 0.014 | 0.82 | 58.6 |
| 85 | 0.019 | >1 | >53 |
| Control 1 | 0.56 | 5.3 | 9.5 |
| Control 2 | 0.58 | 1.1 | 1.9 |
| Control 3 | 0.32 | 1.3 | 4.1 |
| Control 4 | 0.12 | 0.75 | 6.3 |
| Control 5 | 0.007 | 0.61 | 87.1 |

Result of the test by the same manner for the following compounds as controls in those tests is given in Tables 27 and 28 as well.

Control compound (1): 5-[2-(2-(4-Fluorophenyl)ethyl)-3-(1-methyl-1H-imidazol-2-yl)-2H-1-benzopyran-6-yl]oxy-2,2-dimethyl-N-(2,6-diisopropylphenyl)-pentanamide (compound mentioned in WO92/09582);

Control compound (2): (+)-(S)-2-[5-(3,5-Dimethyl-pyrazol-1-yl)pentasulfinyl]-4,5-diphenylimidazole (compound mentioned in European Patent No. 523941);

Control compound (3): N-(2,2,5,5-Tetramethyl-1,3-dioxan-4-ylcarbonyl)-β-alanine 2(S)-[N'-(2,2-dimethyl-propyl-N'-nonylureido)-1(S)-cyclohexyl ester (compound mentioned in European Patent No. 421441);

Control compound (4): [5-(4,5-Diphenyl-1H-imidazol-2-ylthio)pentyl]-N-heptyl-2-benzoxazolamine (compound mentioned in WO93/23392); and Control compound (5): 6-(Benzoxazol-2-ylthio)-N-(2,6-diisopropylphenyl)nonanamide (compound mentioned in Example 8 of Japanese Patent Application Hei-09/88660).

Experimental Example 3

Disintegration Test.

Compounds of the present invention and the compounds mentioned in the previously-filed Japanese Patent Applications Hei-09/88660 (hereinafter, referred to as "A") and Hei-09/90146 (hereinafter, referred to as "B") as controls were suspended in a liquid No. 1 for disintegration test regulated by the Japanese Pharmacopoeia, shaken for two hours, allowed to stand at room temperature for one hour and filtered through a membrane filter of 0.45 $\mu$m. Absorbance of a mixture of this filtrate with methanol in the same amounts was measured and, from the previously-determined $\epsilon_{1\% \ 1cm}$ values, solubility was calculated. The result is shown in Table 29.

As the control compounds (5)–(8), the following compounds mentioned in the above A and B were used.

Control compound (5): 6-(Benzoxazol-2-ylthio)-N-(2,6-diisopropylphenyl)nonanamide (compound mentioned in Example 8 of A);

Control compound (6): 6-(Benzoxazol-2-ylthio)-N-(2,6-diisopropylphenyl)hexanamide (compound mentioned in Example 5 of A);

Control compound (7): 6-[5-(N,N-Dimethylaminomethyl)-benzoxazol-2-ylthio]-N-(2,6-diisopropylphenyl)hexanamide (compound mentioned in Example 37 of B); and Control compound (8): 6-[5-(N,N-Dimethylamino)-benzoxazol-2-ylthio]-N-(2,6-diisopropylphenyl)hexanamide (compound mentioned in Example 38 of B).

TABLE 29

| Compound | Solubility | pH |
|---|---|---|
| Ex. 1 | 14 mg/ml | 1.2 |
| Ex. 6 | 35 mg/ml | 1.2 |
| Ex. 13 | 7.4 mg/ml | 1.2 |
| Ex. 24 | 17 mg/ml | 1.2 |
| Control 5 | 0.05 μg/ml | 1.2 |
| Control 6 | 0.05 μg/ml | 1.2 |
| Control 7 | 360~400 μg/ml | 1.2 |
| Control 8 | 170~180 μg/ml | 1.2 |

EXAMPLES

Compounds of the present invention will be specifically mentioned as hereunder although the present invention is not limited to those specific examples.

Example 1

Preparation of 2-[4-[2-(benzoxazol-2-ylthio)ethyl]-piperazin-1-yl]-N-(2,6-diisopropylphenyl)acetamide:

Potassium carbonate (2.35 g, 17 mmol) was added to a solution of 1-(2-hydroxyethyl)piperazine (2.21 g, 17 mmol) and 2-bromo-N-(2,6-diisopropylphenyl)acetamide (synthesized by a method mentioned in Example 1 of Japanese Patent Application Hei-08/158,743) (5.07 g, 17 mmol) in DMF (30 ml) and stirred at 80° C. for 2 hours. The reaction solution was diluted with water and extracted with ethyl acetate. The organic layer was successively washed with water and a saturated sodium chloride solution and dried over anhydrous sodium sulfate and the solvent was evaporated therefrom.

The resulting residue was purified by a silica gel column chromatography (100 g of silica gel; developing solvent, ammonia-saturated methanol:chloroform=1:20) and the resulting crystals were recrystallized from acetone-hexane to provide 4.72 g (yield 80%) of N-(2,6-diisopropylphenyl)-2-[4-(2-hydroxyethyl)piperazin-1-yl]acetamide as colorless crystals.

To a solution of this alcohol (300 mg, 0.86 mmol) in THF (5 ml) were added triethylamine (172 mg, 1.7 mmol) and 4-dimethylaminopyridine (10 mg, 0.09 mmol), then methanesulfonyl chloride (115 mg, 1.0 mmol) was dropped there into with ice-cooling and stirring, and the mixture was stirred for 40 minutes. After that, triethylamine (172 mg, 1.7 mmol) was further added thereto, then methanesulfonyl chloride (115 mg, 1.0 mmol) was dropped thereinto with ice-cooling and stirring, and the mixture was stirred for 20 minutes. The reaction solution was diluted with water and extracted with ethyl acetate. The organic layer was washed with water, an aqueous solution of sodium bicarbonate and a saturated sodium chloride solution successively and dried over anhydrous sodium sulfate, and the solvent was evaporated therefrom. The resulting residue was dissolved in DMF (7 ml), then 2-mercaptobenzooxazole (130 mg, 0.86 mmol), potassium carbonate (180 mg, 1.3 mmol) and 18-crown-6 (21 mg, 0.08 mmol) were added thereto, and the mixture was stirred at 80° C. for 1 hour. The reaction solution was diluted with water and extracted with ethyl acetate. The organic layer was washed with water and a saturated sodium chloride solution successively and dried over anhydrous sodium sulfate and the solvent was evaporated therefrom. The residue was purified by a silica gel column chromatography (40 g of silica gel; developing solvent, hexane:acetone= 5:1~10:3) and the resulting crystals were recrystallized from acetone-hexane to provide 326 mg (yield 79%) of the desired compound as colorless needles.

Melting point: 161–163° C. IR (KBr) cm$^{-1}$: 3318, 3290, 2961, 1664, 1495. 1H-NMR (CDCl$_3$) δ: 1.21 (12H, d, J=7.1 Hz), 2.57–2.80 (8H, m), 2.84 (2H, t, J=7.1 Hz), 3.02 (2H, sept, J=7.1 Hz), 3.22 (2H, s), 3.49 (2H, t, J=7.1 Hz), 7.18 (1H, d, J=8.3 Hz), 7.19 (1H, d, J=6.8 Hz), 7.21–7.33 (3H, m), 7.43 (1H, m), 7.59 (1H, m), 8.61 (1H, br s).

EIMS m/z (relative intensity): 480 (M$^+$), 97 (100). Elementary analysis as C$_{27}$H$_{36}$N$_4$O$_2$S Calculated: C, 67.47; H, 7.55; N, 11.66; S, 6.67. Found: C, 67.47; H, 7.52, N, 11.58; S, 6.65.

Example 2

Preparation of 2-[4-[2-(benzothiazol-2-ylthio)ethyl]-piperazin-1-yl]-N-(2,6-diisopropylphenyl)acetamide:

The same reaction and treatment as in Example 1 were conducted using 2-mercaptobenzothiazole instead of 2-mercaptobenzooxazole to provide the desired compound as colorless needles.

Melting point: 170–171° C. IR (KBr) cm$^{-1}$: 3435, 3311, 3281, 2961, 1666, 1500. 1H-NMR (d$_6$-DMSO) δ: 1.14 (12H, d, J=7.1 Hz), 2.58–2.66 (8H, m), 2.77–2.82 (2H, m), 3.06 (2H, sept, J=7.1 Hz), 3.12 (2H, s), 3.50 (2H, t, J=7.0 Hz), 7.11 (1H, d, J=8.5 Hz), 7.11 (1H, d, J=6.6 Hz), 7.21 (1H, dd, J=8.5, 6.6 Hz), 7.31 (1H, td, J=7.3, 1.2 Hz), 7.42 (1H, td, J=7.3, 1.2 Hz), 7.80 (1H, ddd, J=7.3, 1.2, 0.7 Hz), 7.90 (1H, ddd, J=7.3, 1.2, 0.7 Hz), 8.74 (1H, br s). EIMS m/z (relative intensity): 496 (M$^+$), 111 (100).

Elementary analysis as C$_{27}$H$_{36}$N$_4$OS$_2$ Calculated: C, 65.29; H, 7.30; N, 11.28; S, 13.04. Found: C, 65.28; H, 7.42, N, 11.13; S, 12.91.

Example 3

Preparation of 2-[4-[2-(benzimidazol-2-ylthio)ethyl]-piperazin-1-yl]-N-(2,6-diisopropylphenyl)acetamide:

The same reaction and treatment as in Example 1 were conducted using 2-mercaptobenzimidazole instead of 2-mercaptobenzooxazole to provide the desired compound as colorless needles.

Melting point: 207° C.(d) R (KBr) cm$^{-1}$: 3432, 3282, 2961, 1662, 1500. 1H-NMR (d$_6$-DMSO) δ: 1.14 (12H, d, J=6.8 Hz), 2.57–2.65 (8H, m), 2.73–2.78 (2H, m),3.05 (2H, sept, J=6.8 Hz), 3.12 (2H, s), 3.40 (2H, t, J=7.0 Hz), 7.07 (2H, dd, J=5.9, 3.2 Hz), 7.11 (1H, d, J=8.6 Hz), 7.11 (1H, d, J=6.6 Hz), 7.31 (1H, dd, J=8.6, 6.6 Hz), 7.40 (2H, dd, J=5.9, 3.2 Hz), 8.74 (1H, br s).

EIMS m/z (relative intensity): 479 (M$^+$), 316 (100). Elementary analysis as C$_{27}$H$_{37}$N$_5$OS Calculated: C, 67.61; H, 7.77; N, 14.60; S, 6.68. Found: C, 67.46; H, 7.91, N, 14.39; S, 6.62.

Example 4

Preparation of 2-[4-[2-(7-methoxycarbonylbenzoxazol-2-ylthio)ethyl]-piperazin-1-yl]-N-(2,6diisopropylphenyl) acetamide:

The same reaction and treatment as in Example 1 were conducted using 2-mercapto-7-methoxycarbonylbenzoxazole instead of 2-mercaptobenzooxazole to provide the desired compound as colorless crystals.

Melting point: 159–161° C. IR (KBr) cm$^{-1}$: 3436, 3291, 2959, 1729, 1657. 1H-NMR (CDCl$_3$) δ: 1.21 (12H, d, J=6.8 Hz), 2.63–2.76 (8H, m), 2.86 (2H, t, J=6.8 Hz),3.00 (2H, sept, J=6.8 Hz), 3.21 (2H, s), 3.51 (2H, t, J=6.8 Hz), 4.00 (3H, s), 7.18 (1H, d, J=8.3 Hz), 7.18 (1H, d, J=7.1 Hz),7.29

(1H, dd, J=8.3, 7.1 Hz), 7.35 (1H, t, J=7.8 Hz), 7.77 (1H, dd, J=7.8, 1.2 Hz), 7.88 (1H, dd, J=7.8, 1.2 Hz), 8.60 (1H, br s).

EIMS m/z (relative intensity): 538 (M$^+$), 317 (100). Elementary analysis as $C_{29}H_{38}N_4O_4S$ Calculated: C, 64.66; H, 7.11; N, 10.40; S, 5.95. Found: C, 64.65; H, 7.12, N, 10.27; S, 5.95.

Example 5

Preparation of 2-[4-[2-(4-methoxycarbonylbenzoxazol-2-ylthio)ethyl]-piperazin-1-yl]-N-(2,6-diisopropylphenyl)acetamide:

The same reaction and treatment as in Example 1 were conducted using 2-mercapto-4-methoxycarbonylbenzoxazole instead of 2-mercaptobenzooxazole to provide the desired compound as colorless crystals.

Melting point: 173–175° C. IR (KBr) cm$^{-1}$: 3428, 3278, 2960, 1710, 1663. 1H-NMR (CDCl$_3$) δ: 1.21 (12H, d, J=6.8 Hz), 2.63–2.76 (8H, m), 2.86 (2H, t, J=6.8 Hz), 3.00 (2H, sept, J=6.8 Hz), 3.22 (2H, s), 3.58 (2H, t, J=6.8 Hz), 3.99 (3H, s), 7.18 (1H, d, J=8.1 Hz), 7.18 (1H, d, J=6.8 Hz), 7.29 (1H, dd, J=8.1, 6.8 Hz), 7.30 (1H, t, J=8.1 Hz), 7.62 (1H, dd, J=8.1, 1.0 Hz), 7.94 (1H, dd, J=8.1, 1.0 Hz), 8.61 (1H, br s).

EIMS m/z (relative intensity): 538 (M$^+$), 317 (100). Elementary analysis as $C_{29}H_{38}N_4O_4S$ Calculated: C, 64.66; H, 7.11; N, 10.40; S, 5.95. Found: C, 64.63; H, 7.24, N, 10.34; S, 5.91.

Example 6

Preparation of 2-[4-[2-(oxazolo[4,5-b]pyridine-2-ylthio)ethyl]-piperazin-1-yl]-N-(2,6-diisopropylphenyl)acetamide:

The same reaction and treatment as in Example 1 were conducted using 2-mercaptooxazolo[4,5-b]pyridine instead of 2-mercaptobenzooxazole to provide the desired compound as colorless needles.

Melting point: 153–154° C. IR (KBr) cm$^{-1}$: 3433, 3318, 3293, 2961, 1667. 1H-NMR (CDCl$_3$) δ: 1.21 (12H, d, J=6.9 Hz), 2.64–2.77 (8H, m), 2.87 (2H, t, J=6.8 Hz), 3.00 (2H, sept, J=6.9 Hz), 3.22 (2H, s), 3.56 (2H, t, J=6.8 Hz), 7.18 (1H, d, J=8.6 Hz), 7.18 (1H, d, J=6.6 Hz), 7.18 (1H, dd, J=8.1, 4.9 Hz), 7.29 (1H, dd, J=8.6, 6.6 Hz), 7.70 (1H, dd, J=8.1, 1.5 Hz), 8.45 (1H, dd, J=4.9, 1.5 Hz), 8.60 (1H, br s).

EIMS m/z (relative intensity): 481 (M$^+$), 126 (100). Elementary analysis as $C_{26}H_{35}N_1O_2S$ Calculated: C, 64.84; H, 7.32; N, 14.54; S, 6.66. Found: C, 64.84; H, 7.42, N, 14.33; S, 6.65.

Example 7

Preparation of 2-[4-[3-(benzoxazol-2-ylthio)propyl]-piperazin-1-yl]-N-(2,6-diisopropylphenyl)acetamide:

Potassium carbonate (0.76 g, 5.5 mmol) was added to a solution of 1-(3-hydroxypropyl)piperazine (0.71 g, 5.0 mmol) and 2-bromo-N-(2,6-diisopropylphenyl)acetamide (1.49 g, 5.0 mmol) in DMF (10 ml) and the mixture was stirred at 80° C. for 2 hours. The reaction solution was diluted with water and extracted with ethylacetate. The organic layer was successively washed with water and a saturated sodium chloride solution and dried over anhydrous sodium sulfate and the solvent was evaporated therefrom.

The resulting residue was purified by a silica gel column chromatography (30 g of silica gel; developing solvent, ammonia-saturated methanol:chloroform=1:20) and the resulting crystals were recrystallized from ethyl acetate-chloroform to provide 1.13 g (yield 63%) of 2-[4-(3-hydroxypropyl)piperazin-1-yl]-N-(2,6-diisopropylphenyl) acetamide as colorless crystals.

To a solution of this alcohol (444 mg, 1.22 mmol) in THF (10 ml) were added triethylamine (185 mg, 1.83 mmol) and 4-dimethylaminopyridine (14 mg, 0.06 mmol), then methanesulfonyl chloride (167 mg, 1.46 mmol) was dropped thereinto with ice-cooling and stirring, and the mixture was stirred for 40 minutes. After that, triethylamine (185 mg, 1.83 mmol) was further added thereto, then methanesulfonyl chloride (167 mg, 1.46 mmol) was dropped thereinto with ice-cooling and stirring and the mixture was stirred for 30 minutes. The reaction solution was diluted with water and extracted with ethyl acetate. The organic layer was successively washed with water, an aqueous solution of sodium bicarbonate and a saturated sodium chloride solution and dried over anhydrous sodium sulfate and the solvent was evaporated therefrom. The resulting residue was dissolved in DMF (7 ml), then 2-mercaptobenzooxazole (151 mg, 1.0 mmol), potassium carbonate (166 mg, 1.2 mmol) and 18-crown-6 (13 mg, 0.05 mmol) were added thereto, and the mixture was stirred at 80° C. for 1 hour. The reaction solution was diluted with water and extracted with ethyl acetate. The organic layer was washed with water and a saturated sodium chloride solution successively and dried over anhydrous sodium sulfate and the solvent was evaporated therefrom.

The residue was purified by a silica gel column chromatography (40 g of silica gel; developing solvent, hexane:acetone=5:1~10:3) and the resulting crystals were recrystallized from acetone-hexane to provide 321 mg (yield 60%) of the desired product as colorless crystals.

Melting point: 123–125° C. IR (KBr) cm$^{-1}$: 3317, 2959, 1663, 1499, 1129. 1H-NMR (CDCl$_3$) δ: 1.21 (12H, d, J=6.8 Hz), 2.04 (2H, quint J=6.8 Hz), 2.46–2.80 (8H, m), 2.54 (2H, t, J=6.8 Hz), 3.00 (2H, sept, J=6.8 Hz), 3.22 (2H, s), 3.37 (2H, t, J=6.8 Hz), 7.18 (1H, d, J=8.1 Hz), 7.18 (1H, d, J=6.8 Hz), 7.20–7.32 (3H, m), 7.43 (1H, m), 7.59 (1H, m), 8.62 (1H, br s).

EIMS m/z (relative intensity): 494 (M$^+$), 290 (100). Elementary analysis as $C_{28}H_{38}N_4O_2S$ Calculated: C, 67.98; H, 7.74; N, 11.33; S, 6.48. Found: C, 67.84; H, 7.78; N, 11.22; S, 6.43.

Example 8

Preparation of 2-[4-[3-(benzothiazol-2-ylthio)propyl]piperazin-1-yl]-N-(2,6-diisopropylphenyl)acetamide:

The same reaction and treatment as in Example 7 were conducted using 2-mercaptobenzothiazole instead of 2-mercaptobenzooxazole to provide the desired compound as colorless needles.

Melting point: 113–115° C. IR (KBr) cm$^{-1}$: 3436, 3299, 2962, 1661, 1502. 1H-NMR (CDCl$_3$) δ: 1.21 (12H, d, J=6.8 Hz), 2.03 (2H, quint, J=7.1 Hz), 2.51–2.58 (6H, m), 2.73–2.77 (4H, m), 3.01 (2H, sept, J=6.8 Hz), 3.22 (2H, s), 3.41 (2H, t, J=7.1 Hz), 7.18 (1H, d, J=8.3 Hz), 7.18 (1H, d, J=6.8 Hz), 7.29 (1H, dd, J=8.3, 6.8 Hz), 7.29 (1H, td, J=7.8, 1.2 Hz), 7.41 (1H, td, J=7.8, 1.2 Hz), 7.76 (1H, dd, J=7.8, 1.2 Hz), 7.85 (1H, dd, J=7.8, 1.2 Hz), 8.63 (1H, br s).

EIMS m/z (relative intensity): 510 (M$^+$), 139 (100). Elementary analysis as $C_{28}H_{38}N_4OS_2$ Calculated: C, 65.85; H, 7.50; N, 10.97; S, 12.55. Found: C, 65.76; H, 7.59, N, 10.78; S, 12.49.

Example 9

Preparation of 2-[4-[3-(benzimidazole-2-ylthio)phenyl]piperazin-1-yl]-N-(2,6-diisopropylphenyl)acetamide:

The same reaction and treatment as in Example 7 were conducted using 2-mercaptobenzimidazole instead of 2-mercaptobenzooxazole to provide the desired compound as colorless needles.

Melting point: 123–125° C. IR (KBr) cm$^{-1}$: 3429, 3273, 2961, 1659, 1506. 1H-NMR (d$_6$-DMSO) δ: 1.13 (12H, d, J=6.8 Hz), 1.90 (2H, quint, J=6.8 Hz), 2.40–2.52 (6H, m), 2.61–2.65 (4H, m), 3.05 (2H, sept, J=6.8 Hz), 3.12 (2H, s), 3.29 (2H, t, J=6.8 Hz), 7.06–7.10 (2H, m) 7.12 (2H, d, J=7.6 Hz), 7.22 (1H, t, J=7.6 Hz), 7.38–7.42 (2H, m), 8.76 (1H, br s).

EIMS m/z (relative intensity): 493 (M$^+$), 139 (100).

Example 10

Preparation of 2-[4-[3-(7-methoxycarbonylbenzoxazol-2-ylthio)propyl]piperazin-1-yl]-N-(2,6-diisopropylphenyl)acetamide:

The same reaction and treatment as in Example 7 were conducted using 2-mercapto-7-methoxycarbonylbenzoxazole instead of 2-mercaptobenzooxazole to provide the desired compound as colorless crystals.

Melting point: 135–136° C. IR (KBr) cm$^{-1}$: 3429, 3340, 2961, 1720, 1663. 1H-NMR (CDCl$_3$) δ: 1.21 (12H, d, J=6.8 Hz), 2.07 (2H, quint, J=7.0 Hz), 2.52–2.57 (6H, m), 2.73–2.76 (4H, m), 3.01 (2H, sept, J=6.8 Hz), 3.22 (2H, s), 3.40 (2H, t, J=7.0 Hz), 4.00 (3H, s), 7.18 (1H, d, J=8.3 Hz), 7.18 (1H, d, J=7.1 Hz), 7.29 (1H, dd, J=8.3, 7.1 Hz), 7.35 (1H, t, J=7.8 Hz), 7.77 (1H, dd, J=7.8, 1.2 Hz), 7.88 (1H, dd, J=7.8, 1.2 Hz), 8.63 (1H, br s).

EIMS m/z (relative intensity): 552 (M$^+$, 100). Elementary analysis as C$_{30}$H$_{40}$N$_4$O$_4$S Calculated: C, 65.19; H, 7.29; N, 10.14; S, 5.80. Found: C, 65.31; H, 7.57; N, 10.02; S, 5.78.

Example 11

Preparation of 2-[4-[3-(4-methoxycarbonylbenzoxazol-2-ylthio)propyl]piperazin-1-yl]-N-(2,6-diisopropylphenyl)acetamide:

The same reaction and treatment as in Example 7 were conducted using 2-mercapto-4-methoxycarbonylbenzoxazole instead of 2-mercaptobenzooxazole to provide the desired compound as faint orange crystals.

Melting point: 132–133° C. IR (KBr) cm$^{-1}$: 3422, 3239, 2958, 1717, 1660. 1H-NMR (CDCl$_3$) δ: 1.21 (12H, d, J=6.8 Hz), 2.06 (2H, quint, J=7.0 Hz), 2.52–2.57 (6H, m), 2.74–2.77 (4H, m), 3.01 (2H, sept, J=6.8 Hz), 3.23 (2H, s), 3.45 (2H, t, J=7.0 Hz), 4.00 (3H, s), 7.18 (1H, d, J=8.1 Hz), 7.19 (1H, d, J=6.8 Hz), 7.29 (1H, dd, J=8.1, 6.8 Hz), 7.30 (1H, t, J=7.8 Hz), 7.62 (1H, dd, J=7.8, 1.0 Hz), 7.94 (1H, dd, J=7.8, 1.0 Hz), 8.64 (1H, br s).

EIMS m/z (relative intensity): 552 (M$^+$, 100). Elementary analysis as C$_{30}$H$_{40}$N$_4$O$_4$S Calculated: C, 65.19; H, 7.29; N, 10.14; S, 5.80. Found: C, 65.18; H, 7.39; N, 9.90; S, 5.84.

Example 12

Preparation of 2-[4-[3-(oxazolo[4,5-b]pyridine-2-ylthio)propyl]piperazin-1-yl]-N-(2,6-diisopropylphenyl)acetamide:

The same reaction and treatment as in Example 7 were conducted using 2-mercaptooxazolo[4,5-b]pyridine instead of 2-mercaptobenzooxazole to provide the desired compound as colorless needles.

Melting point: 125–127° C. IR (KBr) cm$^{-1}$: 3431, 3241, 2959, 1664, 1496. 1H-NMR (CDCl$_3$) δ: 1.21 (12H, d, J=6.8 Hz), 2.09 (2H, quint, J=7.2 Hz), 2.52–2.59 (6H, m), 2.73–2.77 (4H, m), 3.01 (2H, sept, J=6.8 Hz), 3.22 (2H, s), 3.44 (2H, t, J=7.2 Hz), 7.18 (1H, d, J=8.3 Hz) 7.18 (1H, d, J=6.6 Hz), 7.18 (1H, dd, J=8.1, 5.1 Hz), 7.29 (1H, dd, J=8.3, 6.6 Hz), 7.69 (1H, dd, J=8.1, 1.5 Hz), 8.45 (1H, dd, J=5.1, 1.5 Hz), 8.63 (1H, br s).

EIMS m/z (relative intensity): 495 (M$^+$), 302 (100). Elementary analysis as C$_{27}$H$_{37}$N$_5$O$_2$S Calculated: C, 65.42; H, 7.52; N, 14.13; S, 6.47. Found: C, 65.57; H, 7.63, N, 13.84; S, 6.38.

Example 13

Preparation of 2-[4-[3-(benzoxazol-2-ylthio)propyl]-homopiperazin-1-yl]-N-(2,6-diisopropylphenyl)acetamide:

To a solution of 3-hydroxypropyl-1-homopiperazine (158 mg, 1 mmol) in acetonitrile (5 ml) were added potassium carbonate (152 mg, 1.1 mmol) and 2-bromo-N-(2,6-diisopropylphenyl)acetamide (298 mg, 1 mmol) and the mixture was stirred at room temperature for 3 hours. The reaction solution was concentrated and the residue was extracted with ethyl acetate. The organic layer was extracted with water and a saturated sodium chloride solution successively and dried over anhydrous sodium sulfate, and the solid resulted after evaporating the solvent was crystallized from hexane-ether-acetone to provide 327 mg (yield 87%) of 2-[4-[(3-hydroxypropyl)homopiperazin-1-yl]-N-(2,6-diisopropylphenyl)acetamide as pale red needles.

To a solution of the resulting alcohol (130 mg, 0.34 mmol) in methylene chloride (3 ml) were added triethylamine (52 mg, 0.52 mmol) and 4-dimethylaminopyridine (6 mg, 0.05 mmol) and then methanesulfonyl chloride (59 mg, 0.52 mmol) was gradually dropped thereinto with ice-cooling and stirring. The mixture was stirred at room temperature for 30 minutes and then the reaction solution was extracted with ethyl acetate. The organic layer was washed with water and a saturated sodium chloride solution successively and dried over anhydrous sodium sulfate and the solvent was evaporated therefrom.

The resulting residue was dissolved in DMF (2 ml), then 2-mercaptobenzooxazole (51 mg, 0.34 ml), potassium carbonate (51 mg, 0.37 mmol) and 18-crown-6 (11 mg, 0.04 mmol) were added thereto and the mixture was stirred at 80° C. for 2 hours. The reaction solution was diluted with water and extracted with ethyl acetate. The organic layer was successively washed with water and a saturated sodium chloride solution and dried over anhydrous sodium sulfate and the residue obtained by evaporating of the solvent was purified by a preparative thin layer chromatography (developing solvent, hexane:acetone=1:1) followed by recrystallizing from hexane-acetone to provide 140 mg (yield 81%) of the desired compound as colorless needles.

Melting point: 109–111° C. IR (KBr) cm$^{-1}$: 3429, 3275, 1661, 1500, 1453. 1H-NMR (CDCl$_3$) δ: 1.21 (12H, d, J=6.8 Hz), 1.89 (2H, quint, J=5.8 Hz), 2.00 (2H, quint, J=6.8 Hz), 2.67 (2H, t, J=6.8 Hz), 2.73–2.78 (4H, m), 2.91–2.96 (4H, m), 3.03 (2H, sept, J=6.8 Hz), 3.35 (2H, s), 3.37 (2H, t, J=6.8 Hz), 7.18 (2H, d, J=7.6 Hz), 7.21–7.31 (3H, m), 7.43 (1H, m), 7.58 (1H, m), 8.77 (1H, br s).

EIMS m/z (relative intensity): 508 (M$^+$, 100). Elementary analysis as C$_{29}$H$_{40}$N$_4$O$_2$S. Calculated: C, 68.47; H, 7.92; N, 11.01; S, 6.30. Found: C, 68.19; H, 8.03; N, 10.79; S, 6.28.

Example 14

Preparation of 2-[4-[3-(7-methoxycarbonylbenzoxazol-2-ylthio)propyl]homopiperazin-1-yl]-N-(2,6-diisopropylphenyl)acetamide:

The same reaction and treatment as in Example 13 were conducted using 2-mercapto-7-methoxycarbonylbenzoxazole instead of 2-mercaptobenzooxazole to provide the desired compound as colorless needles.

Melting point: 83–85° C. IR (KBr) cm$^{-1}$: 3425, 3250, 1735, 1719, 1660. 1H-NMR (CDCl$_3$) δ: 1.21 (12H, d, J=6.8 Hz), 1.89 (2H, quint, J=5.8 Hz), 2.02 (2H, quint, J=6.8 Hz), 2.68 (2H, t, J=6.8 Hz), 2.73–2.79 (4H, m), 2.91–2.96 (4H, m), 3.02 (2H, sept, J=6.8 Hz), 3.35 (2H, s), 3.40 (2H, t, J=6.8 Hz), 4.00 (3H, s) 7.18 (2H, d, J=7.6 Hz), 7.28 (1H, t, J=7.6 Hz), 7.34 (1H, t, J=7.8 Hz), 7.76 (1H, dd, J=7.8, 1.2 Hz), 7.87 (1H, dd, J=7.8, 1.2 Hz), 8.77 (1H, br s).

EIMS m/z (relative intensity): 566 (M$^+$), 153 (100). Elementary analysis as C$_{31}$H$_{42}$N$_4$O$_4$S Calculated: C, 65.70; H, 7.47; N, 9.89; S, 5.66. Found: C, 65.81; H, 7.56, N, 9.79; S, 5.65.

Example 15

Preparation of 2-[4-[3-(oxazolo[4,5-b]pyridin-2-ylthio)propyl]homopiperazin-1-yl]-N-(2,6-diisopropylphenyl)acetamide:

The same reaction and treatment as in Example 13 were conducted using 2-mercaptooxazolo[4,5-b]pyridine instead of 2-mercaptobenzooxazole to provide the desired compound as colorless needles.

Melting point: 73–75° C. IR (KBr) cm$^-$: 3435, 3240, 1660, 1497, 1403. 1H-NMR (CDCl$_3$) δ: 1.21 (12H, d, J=6.8 Hz), 1.87–1.95 (2H, m), 2.01–2.10 (2H, m), 2.67–2.73 (2H, m), 2.75–2.82 (4H,m ), 2.92–2.96 (4H, m), 3.03 (2H, sept, J=6.8 Hz), 3.36 (2H, s), 3.43 (2H, t, J=6.8 Hz), 7.18 (1H, dd, J=8.0, 5.0 Hz), 7.18 (2H, d, J=7.6 Hz), 7.28 (1H, t, J=7.6 Hz), 7.69 (1H, dd, J=8.0, 1.5 Hz), 8.45 (1H, dd, J=5.0, 1.5 Hz), 8.78 (1H, br s).

EIMS m/z (relative intensity): 509 (M$^+$), 316 (100). Elementary analysis as C$_{28}$H$_{39}$N$_5$O$_2$S.0.2H$_2$O Calculated: C, 65.52; H, 7.74; N, 13.64; S, 6.25. Found: C, 65.52; H, 7.71, N, 13.44; S, 6.31.

Example 16

Preparation of N-[2-[4-[2-(benzoxazol-2-ylthio)ethyl]piperazin-1-yl]ethyl]-N'-(2,6-diisopropylphenyl)-N-heptylurea:

To a solution of n-heptylamine (2.30 g, 20 mmol) in THF (20 ml) was dropped a solution of bromoacetyl bromide (2.02 g, 10 mmol) in THF (10 ml) with ice-cooling and stirring and the mixture was stirred at 0° C. for 1 hour. The reaction solution was concentrated in vacuo, water was added to the residue and the mixture was extracted with ether. The organic layer was washed with water and a saturated sodium chloride solution successively and dried over anhydrous sodium sulfate and the solvent was evaporated therefrom to provide 2.36 g (yield 99%) of crude 2-bromo-N-heptylacetamide as oil.

Potassium carbonate (1.52 g, 11 mmol) was added to a solution of this amide (2.36 g, 10 mmol) and 1-(2-hydroxyethyl)piperazine (1.30 g, 10 mmol) in acetonitrile (40 ml) and the mixture was stirred at room temperature for 12 hours. The reaction solution was concentrated and the residue was extracted with ethyl acetate. The organic layer was washed with water and a saturated sodium chloride solution successively and dried over anhydrous sodium sulfate and the residue obtained by evaporation of the solvent was purified by a silica gel column chromatography (75 g of silica gel; developing solvent, ammonia-saturated methanol:chloroform=1:20) to provide 2.39 g (yield 83%) of N-heptyl-2-[4-(2-hydroxyethyl)piperazin-1-yl]acetamide as colorless oil.

Lithium aluminum hydride (380 mg, 10 mmol) was added to a solution of this amide (1.69 g, 5.92 mmol) in THF (40 ml) with ice-cooling and stirring and the mixture was stirred for 15 minutes after returning to room temperature and heated to reflux for 2 hours. Saturated aqueous solution of ammonium chloride was added gradually thereto with ice-cooling and stirring until the reaction solution became turbid, the separated matters were filtered off with celite, the filtrate was dried over anhydrous sodium carbonate and the solvent was evaporated therefrom. The resulting residue was purified by a silica gel column chromatography (75 g of silica gel; developing solvent, ammonia-saturated methanol:chloroform=1:20) to provide 694 mg (yield 43%) of 2-[4-(2-heptylaminoethyl)-piperazin-1-yl]ethanol as colorless oil.

To a solution of this aminoalcohol (271 mg, 1 mmol) in chloroform (5 ml) was added 2,6-diisopropylphenyl isocyanate (204 mg, 1 mmol) and the mixture was stirred for 15 minutes. The reaction solution was concentrated, the residue was purified by a silica gel column chromatography (10 g of silica gel; developing solvent being ammonia-saturated methanol:chloroform=3:97) and the resulting crystals were recrystallized from acetone-hexane to provide 340 mg (yield 71%) of N'-(2,6-diisopropylphenyl)-N-heptyl-N-[2-[4-(2-hydroxyethyl)piperazin-1-yl]ethyl]urea as colorless needles.

To a solution of this alcohol (338 mg, 0.71 mmol) in THF (5 ml) were added triethylamine (93 mg, 0.92 mmol) and 4-dimethylaminopyridine (9 mg, 0.07 mmol), then methanesulfonyl chloride (89 mg, 0.78 mmol) was dropped there into with ice-cooling and stirring and the mixture was stirred for 30 minutes. After that, triethylamine (93 mg, 0.92 mmol) was added thereto, methanesulfonyl chloride (89 mg, 0.78 mmol) was dropped there into with ice-cooling and stirring and the mixture was stirred for 20 minutes. The reaction solution was diluted with water and extracted with ethyl acetate. The organic layer was washed with water, aqueous solution of sodium bicarbonate and saturated sodium chloride solution successively and dried over anhydrous sodium sulfate and the solvent was evaporated therefrom.

The resulting residue was dissolved in DMF (3 ml), then 2-mercaptobenzooxazole (91 mg, 0.6 mmol), potassium carbonate (104 mg, 0.75 mmol) and 18-crown-6 (16 mg, 0.06 mmol) were added thereto and the mixture was stirred at 80° C. for 1 hour. The reaction solution was diluted with water and extracted with ethyl acetate. The organic layer was washed with water and saturated sodium chloride solution successively and the solvent was evaporated therefrom. The residue was purified by a silica gel column chromatography (40 g of silica gel; developing solvent, hexane:acetone=5:1~10:3) and the resulting crystals were recrystallized from acetone-hexane to provide 243 mg (yield 57%) of the desired compound as colorless needles.

Melting point: 110–111° C. IR (KBr) cm$^{-1}$: 3326, 2956, 1627, 1498, 1130. 1H-NMR (CDCl$_3$) δ: 0.88 (3H, t, J=7.1 Hz), 1.14–1.36 (22H, m), 2.39–2.61 (8H, m), 2.63 (2H, t, J=5.1 Hz), 2.69 (2H, t, J=6.8 Hz), 3.16 (2H, sept, J=7.1 Hz), 3.34 (2H, t, J=7.1 Hz), 3.39 (2H, t, J=6.8 Hz), 3.46 (2H, t, J=5.1 Hz), 7.13 (1H, d, J=8.3 Hz), 7.13 (1H, d, J=7.1 Hz), 7.19–7.30 (3H, m), 7.41 (1H, dd, J=7.6, 1.4 Hz), 7.56 (1H, dd, J=7.6, 1.4 Hz), 8.10 (1H, br s).

EIMSm/z (relative intensity): 607 (M$^+$), 254 (100). Elementary analysis as $C_{35}H_{53}N_5O_2S$ Calculated: C, 69.15; H, 8.79, N, 11.52; S, 5.27. Found: C, 69.27; H, 8.93; N, 11.29; S, 5.32.

Example 17

Preparation of N'-(2,6-diisopropylphenyl)-N-heptyl-N-[2-[4-[2-(7-methoxycarbonylbenzoxazol-2-ylthio)-ethyl]piperazin-1-yl]ethyl]urea:

The same reaction and treatment as in Example 16 were conducted using 7-methoxycarbonyl-2-mercaptobenzooxazole instead of 2-mercaptobenzooxazole to provide the desired compound as colorless crystals.

Melting point: 125–126° C. IR (KBr) cm$^{-1}$: 3425, 3304, 2957, 1725, 1628. 1H-NMR (CDCl$_3$) δ: 0.88 (3H, t, J=6.7 Hz), 1.20 (12H, d, J=6.8 Hz), 1.25–1.33 (8H, m), 1.51–1.59 (2H, m), 2.43–2.51 (4H, m), 2.54–2.65 (6H, m), 2.71 (2H, t, J=6.8 Hz), 3.16 (2H, sept, J=6.8 Hz), 3.34 (2H, t, J=7.3 Hz), 3.40–3.47 (4H, m), 3.98 (3H, s), 7.13 (1H, d, J=8.8 Hz), 7.13 (1H, d, J=6.4 Hz), 7.23 (1H, dd, J=8.8, 6.4 Hz), 7.34 (1H, t, J=7.8 Hz), 7.74 (1H, dd, J=7.8, 1.2 Hz), 7.87 (1H, dd, J=7.8, 1.2 Hz), 8.10 (1H, br s).

EIMSm/z (relative intensity): 665 (M$^+$), 265 (100). Elementary analysis as $C_{37}H_{55}N_5O_4S$ Calculated: C, 66.73; H, 8.32; N, 10.52; S, 4.81. Found: C, 66.77; H, 8.24, N, 10.45; S, 4.79.

Example 18

Preparation of N'-(2,6-diisopropylphenyl)-N-heptyl-N-[2-[4-[2-(oxazolo[4,5-b]pyridin)-2-ylthio)ethyl]piperazin-1-yl]ethyl]urea:

The same reaction and treatment as in Example 16 were conducted using 2-mercaptooxazolo[4,5-b]pyridine instead of 2-mercaptobenzooxazole to provide the desired compound as colorless crystals.

Melting point: 106–108° C. IR (KBr) cm$^{-1}$: 3420, 3331, 2958, 1628, 1495. 1H-NMR (CDCl$_3$) δ: 0.88 (3H, t, J=6.9 Hz), 1.20 (12H, d, J=6.9 Hz), 1.26–1.33 (8H, m), 1.53–1.59 (2H, m), 2.43–2.51 (4H, m), 2.55–2.66 (6H, m), 2.73 (2H, t, J=6.7 Hz), 3.16 (2H, sept, J=6.9 Hz), 3.34 (2H, t, J=7.3 Hz), 3.44–3.50 (4H, m), 7.13 (1H, d, J=8.5 Hz), 7.13 (1H, d, J=6.4 Hz), 7.17 (1H, dd, J=8.1, 4.9 Hz), 7.23 (1H, dd, J=8.5, 6.4 Hz), 7.68 (1H, dd, J=8.1, 1.5 Hz), 8.06 (1H, br s), 8.44 (1H, dd, J=4.9, 1.5 Hz).

EIMSm/z (relative intensity): 608 (M$^+$), 188 (100). Elementary analysis as $C_{34}H_{52}N_6O_2S$ Calculated: C, 67.07; H, 8.61; N, 13.80; S, 5.27. Found: C, 67.06; H, 8.52, N, 13.66; S, 5.27.

Example 19

Preparation of N-[2-[4-[3-(benzoxazol-2-ylthio)propyl]piperazin-1-yl]ethyl]-N'-(2,6-diisopropylphenyl)-N-(heptylurea:

Potassium carbonate (2.49 g, 18 mmol) was added to a solution of 2-bromo-N-heptylacetamide (3.30 g, 15 mmol) obtained in Example 16 and 1-(3-hydroxypropyl)piperazine (2.16 g, 15 mmol) in acetonitrile (60 ml) and the mixture was stirred at room temperature for 15 hours. The reaction solution was concentrated and the residue was extracted with ethyl acetate. The organic layer was washed with water and saturated sodium chloride solution successively and dried over anhydrous sodium carbonate and the residue obtained after evaporation of the solvent was purified by a silica gel column chromatography (75 g of silica gel; developing solvent, ammonia-saturated methanol:chloroform=1:20) to provide 4.38 g (yield 97%) of N-heptyl-2-[4-[3-hydroxypropyl]piperazin-1-yl]acetamide as colorless oil.

Lithium aluminum hydride (380 mg, 10 mmol) was added to a solution of this amide (1.50 g, 5.0 mmol) in THF (50 ml) with ice-cooling and stirring and the mixture was returned to room temperature and stirred for 15 minutes and then heated to reflux for 2 hours. Under ice-cooling and stirring, a saturated ammonium chloride solution was gradually added thereto until the reaction solution became turbid, the separated matters were filtered off through celite, the filtrate was dried over anhydrous sodium carbonate and the solvent was evaporated therefrom. The resulting residue was purified by a silica gel column chromatography (75 g of silica gel; developing solvent, ammonia-saturated methanol:chloroform=1:20) to provide 586 mg (yield 41%) of 3-[4-(2-heptylaminoethyl)piperazin-1-yl]propanol as colorless oil.

To a solution of this aminoalcohol (586 mg, 2.05 mmol) in chloroform (5 ml) was added 2,6-diisopropylphenyl isocyanate (408 mg, 2 mmol) and the mixture was stirred for 15 minutes. The reaction solution was concentrated, the residue was purified by a silica gel column chromatography (20 g of silica gel; developing solvent, ammonia-saturated methanol:chloroform=3:97) and the resulting crystals were recrystallized from acetone-hexane to provide 340 mg (yield 71%) of N'-(2,6-diisopropylphenyl)-N-heptyl-N-[2-[4-(3-hydroxypropyl)-piperazin-1-yl]ethyl]urea as colorless needles.

To a solution of this alcohol (147 mg, 0.3 mmol) in THF (3 ml) were added triethylamine (39 mg, 0.39 mmol) and 4-dimethylaminopyridine (3.7 mg, 0.03 mmol), then methanesulfonyl chloride (38 mg, 0.33 mmol) was dropped thereino with ice-cooling and stirring and the mixture was stirred for 30 minutes. Then triethylamine (39 mg, 0.39 mmol) was added thereto, methanesulfonyl chloride (38 mg, 0.33 mmol) was dropped thereinto and the mixture was stirred for 30 minutes. The reaction solution was diluted with water and extracted with ethyl acetate. The organic layer was washed with water, aqueous solution of sodium bicarbonate and saturated sodium chloride solution successively and dried over anhydrous sodium sulfate and the solvent was evaporated therefrom. The resulting residue was dissolved in DMF (3 ml), then 2-mercaptobenzooxazole (45 mg, 0.3 mol), potassium carbonate (62 mg, 0.45 mmol) and 18-crown-6 (8 mg, 0.03 mmol) were added thereto, and the mixture was stirred at 80° C. for 1 hour. The reaction solution was diluted with water and extracted with ethyl acetate. The organic layer was washed with water and saturated sodium chloride solution successively and dried over anhydrous sodium sulfate and the solvent was evaporated therefrom. The residue was purified by a silica gel column chromatography (25 g of silica gel; developing solvent, hexane:acetone=5:1~5:2) and the resulting crystals were recrystallized from ether-pentane to provide 78 mg (yield 42%) of the desired compound as colorless crystals.

Melting point: 93–94° C. IR (KBr) cm$^{-1}$: 3430, 3313, 2959, 2931, 1627, 1502. 1H-NMR (CDCl$_3$) δ: 0.88 (3H, t, J=6.7 Hz), 1.20 (12H, d, J=6.8 Hz), 1.25–1.35 (8H, m), 1.53–1.59 (2H, m), 1.95 (2H, quint, J=7.0 Hz), 2.34–2.42 (6H, m), 2.54–2.66 (6H, m), 3.16 (2H, sept, J=6.8 Hz), 3.31 (2H, t, J=7.0 Hz), 3.34 (2H, t, J=7.0 Hz), 3.46 (2H, t, J=5.0 Hz), 7.13 (1H, d, J=8.5 Hz), 7.13 (1H, d, J=6.8 Hz), 7.20–7.31 (3H, m), 7.42 (1H, m), 7.57 (1H, m), 8.17 (1H, br s).

EIMSm/z (relative intensity): 621 (M$^+$), 188 (100). Elementary analysis as $C_{36}H_{55}N_5O_2S$ Calculated: C, 69.53; H, 8.91; N, 11.26. Found: C, 69.51; H, 9.02; N, 11.12.

Example 20

Preparation of N'-(2,6-diisopropylphenyl)-N-heptyl-N-[2-[4-[3-(7-methoxycarbonylbenzoxazol-2-ylthio)propyl] piperazin-1-yl]ethyl]urea:

The same reaction and treatment as in Example 19 were conducted using 7-methoxycarbonyl-2-mercaptobenzooxazole instead of 2-mercaptobenzooxazole to provide the desired compound as colorless crystals.

Melting point: 97–99° C. IR (KBr) cm$^{-1}$: 3428, 3318, 2958, 1728, 1628. 1H-NMR (CDCl$_3$) δ: 0.88 (3H, t, J=6.7 Hz), 1.20 (12H, d, J=6.8 Hz), 1.25–1.34 (8H, m), 1.54–1.59 (2H, m), 1.97 (2H, quint, J=7.1 Hz), 2.35–2.43 (6H, m), 2.55–2.66 (6H, m), 3.16 (2H, sept, J=6.8 Hz), 3.33 (2H, t, J=7.1 Hz), 3.34 (2H, t, J=7.1 Hz), 3.34 (2H, t, J=4.9 Hz), 3.99 (3H, s), 7.13 (1H, d, J=8.8 Hz), 7.13 (1H, d, J=6.6 Hz), 7.23 (1H, dd, J=8.8, 6.6 Hz), 7.14 (1H, t, J=7.8 Hz), 7.75 (1H, dd, J=7.8, 1.2 Hz), 7.87 (1H, dd, J=7.8, 1.2 Hz), 8.17 (1H, br s).

EIMSm/z (relative intensity): 476 (M$^+$–203), 97 (100). Elementary analysis as $C_{39}H_{57}N_5O_4S$ Calculated: C, 67.12; H, 8.45; N, 10.30. Found: C, 66.90; H, 8.48, N, 10.12.

Example 21

Preparation of N'-(2,6-diisopropylphenyl)-N-heptyl N-[2-[4-[3-(oxazolo[4,5-b]pyridin)-2-ylthio)propyl]piperazin-1-yl]ethyl]urea:

The same reaction and treatment as in Example 19 were conducted using 2-mercaptooxazolo[4,5-b]pyridine instead of 2-mercaptobenzooxazole to provide the desired compound as colorless crystals.

Melting point: 90–92° C. IR (KBr) cm$^{-1}$: 3434, 3310, 2958, 1626, 1515. 1H-NMR (CDCl$_3$) δ: 0.88 (3H, t, J=6.8 Hz), 1.20 (12H, d, J=6.8 Hz), 1.25–1.34 (8H, m), 1.54–1.59 (2H, m), 1.98 (2H, quint, J=7.1 Hz), 2.34–2.42 (6H, m), 2.55–2.66 (6H, m), 3.16 (2H, sept, J=6.8 Hz), 3.34 (2H, t, J=7.1 Hz), 3.37 (2H, t, J=7.1 Hz), 3.46 (2H, t, J=4.9 Hz), 7.13 (1H, d, J=8.8 Hz), 7.13 (1H, d, J=6.6 Hz), 7.17 (1H, dd, J=8.3, 5.1 Hz), 7.23 (1H, dd, J=8.8, 6.6 Hz), 7.68 (1H, dd, J=8.3, 1.5 Hz), 8.16 (1H, br s), 8.46 (1H, dd, J=5.1, 1.5 Hz).

EIMSm/z (relative intensity): 622 (M$^+$), 98 (100). Elementary analysis as $C_{35}H_{14}N_6O_2S$ Calculated: C, 67.49; H, 8.74; N, 13.49. Found: C, 67.36; H, 8.76, N, 13.25.

Example 22

Preparation of 3-[4-[2-(benzoxazol-2-ylthio)ethyl] piperazin-1-yl]-N-(2,6-iisopropylphenyl)propanamide:

Di-tert-butyl dicarbonate (5.2 g, 2.4 mmol) was added to a solution of 1-(2-hydroxyethyl)piperazine (2.6 g, 20 mmol) in methylene chloride (50 ml) with ice-cooling and the mixture was stirred for 3 hours. The reaction solution was concentrated and the resulting residue was purified by a silica gel column chromatography (75 g of silica gel; developing solvent, chloroform:methanol=20:1) to provide 5.5 g (yield 100%) of 1-tert-butoxycarbonyl-4-(2-hydroxyethyl) piperazine as colorless needles.

To a solution of 1-tert-butoxycarbonyl-4-(2hydroxyethyl) piperazine (1.15 g, 5 mmol) in THF (20 ml) were added triethylamine (607 mg, 6 mmol) and 4-dimethylaminopyridine (73 mg, 0.6 mmol), then methanesulfonyl chloride (687 mg, 6 mmol) was gradually dropped thereinto with ice-cooling and the mixture was stirred for 30 minutes. The reaction solution was filtered to remove triethylamine hydrochloride and the filtrate was concentrated.

To a solution of the resulting residue in DMF (30 ml) were added 2-mercaptobenzooxazole (756 mg, 5 mmol), potassium carbonate (760 mg, 5.5 mmol) and 18-crown-6 (132 mg, 0.5 mmol) and the mixture was stirred at 80° C. for 2 hours. The reaction solution was diluted with water and extracted with ethyl acetate. The organic layer was washed with water and saturated sodium chloride solution successively and dried over anhydrous sodium sulfate and the solvent was evaporated therefrom. The residue was purified by a silica gel column chromatography (75 g of silica gel; developing solvent, hexane:acetone=8:1) and the resulting crystals were recrystallized from hexane-ether to provide 1.02 g (yield 56%) of 1-tert-butoxycarbonyl-4-[2-(benzoxazol-2-ylthio)ethyl]piperazine as colorless needles.

To this tert-butoxy carbonyl compound (364 mg, 1 mmol) was added trifluoroacetic acid (1.8 ml), the mixture was stirred for 5 minutes and the reaction solution was concentrated. Crystallization from ether gave 492 mg (yield 100%) of 1-[2-(benzoxazol-2-ylthio)ethyl]piperazine ditrifluoroacetate.

To a solution of 2,6-diisopropylaniline (1.77 g, 10 mmol) in chloroform (30 ml) was added triethylamine (1.11 g, 11 mmol), then acryloyl acid chloride (905 mg, 10 mmol) was gradually dropped thereinto with ice-cooling and the mixture was stirred for 1 hour. The reaction solution was concentrated, diluted with water and extracted with ethyl acetate. The organic layer was washed with diluted hydrochloric acid, saturated aqueous solution of sodium bicarbonate, water and saturated sodium chloride solution successively and dried over anhydrous sodium sulfate, the solvent was evaporated therefrom and the resulting crystals were recrystallized from hexane-ether to provide 1.9 g (yield 82%) of N-(2,6-diisopropylphenyl)acrylamide as colorless needles.

Triethylamine (142 mg, 1.4 mmol) was added to a solution of 1-[2-(benzoxazol-2-ylthio)ethyl]-piperazine ditrifluoroacetate (344 mg, 0.7 mmol) as prepared in the above into ethanol (10 ml), then N-(2,6-diisopropylphenyl) acrylamide (162 mg, 0.7 mmol) was added thereto and the mixture was heated to reflux for 3 days. The reaction solution was concentrated, diluted with water and extracted with ethylacetate. The organic layer was washed with aqueous solution of sodium bicarbonate, water and saturated sodium chloride solution successively and dried over anhydrous sodium sulfate and the solvent was evaporated therefrom. The residue was purified by a silica gel column chromatography (25 g of silica gel; developing solvent, hexane:acetone=5:1~1:1) and the resulting crystals were recrystallized from hexane-ether-acetone to provide 165 mg (yield 48%) of the desired compound as colorless needles.

Melting point: 125–127° C. IR (KBr) cm$^{-1}$: 3433, 3253, 1647, 1500, 1455. 1H-NMR (d$_6$-DMSO) δ: 1.12 (12H, d, J=6.8 Hz), 2.40–2.55 (10H, m), 2.65 (2H, t, J=6.8 Hz), 2.76 (2H, t, J=6.8 Hz), 3.13 (2H, sept, J=6.8 Hz), 3.46 (2H, t, J=6.8 Hz), 7.10 (2H, d, J=7.8 Hz), 7.20 (1H, t, J=7.8 Hz), 7.25–7.32 (2H, m), 7.54–7.59 (2H, m), 8.88 (1H, br s).

EIMSm/z (relative intensity): 494 (M$^+$), 344 (100). Elementary analysis as $C_{28}H_{38}N_4O_2S$ Calculated: C, 67.98; H, 7.74; N, 11.33; S, 6.48. Found: C, 68.05; H, 7.69; N, 11.23; S, 6.45.

Example 23

Preparation of 3-[4-[3-(benzoxazol-2-ylthio)propyl]piperazin-1-yl]-N-(2,6-diisopropylphenyl)propanamide:

The same reaction and treatment as in Example 22 were conducted using 1-(3-hydroxypropyl)piperazine instead of 1-(2-hydroxyethyl)piperazine to provide the desired compound as colorless needles.

Melting point: 93–95° C. IR (KBr) cm$^{-1}$: 3418, 3229, 1645, 1504, 1454. 1H-NMR (d$_6$-DMSO) δ: 1.12 (12H, d, J=6.8 Hz), 1.95 (2H, quint, J=6.8 Hz), 2.40–2.51 (12H, m), 2.67 (2H, t, J=6.8 Hz), 3.13 (2H, sept, J=6.8 Hz), 3.36 (2H, t, J=6.8 Hz), 7.10 (2H, d, J=7.6 Hz), 7.20 (1H, t, J=7.6 Hz), 7.25–7.33 (2H, m), 7.54–7.59 (2H, m), 8.90 (1H, br s).

EIMSm/z (relative intensity): 508 (M$^+$, 100). Elementary analysis as C$_{29}$H$_{40}$N$_4$O$_2$S Calculated: C, 68.47; H, 7.92; N, 11.01; S, 6.30. Found: C, 68.51; H, 7.90, N, 10.85; S, 6.30.

Example 24

Preparation of 2-[4-[2-(benzoxazol-2-ylthio)ethyl]piperazin-1-yl]-N-(2,4-bis(methylthio)-6-methyl-3-pyridyl)acetamide.

To a solution of N-[2,4-bis(methylthio)-6methyl-pyridin-3-yl]-2-bromoacetamide (synthesized by a method according the description in U.S. Pat. No. 5,583,147) (130 mg, 0.40 mmol) in DMF (2.5 ml) were added 1-[2-(benzoxazol-2-ylthio)ethyl]piperazine ditrifluoroacetate (199 mg, 0.40 mmol), potassium carbonate (224 mg, 1.62 mmol) and 18-crown-6 (53 mg, 0.20 mmol) and the mixture was stirred at 80° C. for 4 hours. The reaction solution was diluted with water and extracted with ethyl acetate. The organic layer was washed with water and dried over anhydrous magnesium sulfate and the solvent was evaporated therefrom. The residue was purified by a preparative thin layer chromatography (developing solvent, chloroform:methanol=20:1) and the resulting crystals were recrystallized from ethyl acetate-hexane to provide 169 mg (yield 83%) of the desired compound as colorless needles.

Melting point: 140–141° C. IR (KBr) cm$^{-1}$: 3440, 3308, 2824, 1695, 1480. 1H-NMR (d$_6$-DMSO) δ: 2.34 (3H, s), 2.36 (3H, s), 2.38 (3H,s), 2.50–2.58 (8H, m), 2.72 (2H, t, J=6.8 Hz), 3.00 (2H, s), 3.40 (2H, t, J=6.8 Hz), 6.80 (1H,s), 7.19–7.26 (2H, m), 7.46–7.54 (2H, m), 8.66 (1H, br s).

EIMSm/z (relative intensity): 504 (M$^+$), 179 (100). Elementary analysis as C$_{23}$H$_{29}$N$_1$O$_2$S$_3$ Calculated: C, 54.85; H, 5.80; N, 13.90. Found: C, 54.92; H, 5.83; N, 13.64.

Example 25

Preparation of N-[2,4-bis(methylthio)-6-methyl-3-pyridyl]-2-[4-[2-(oxazolo[4,5-b]pyridin-2-ylthio)ethyl]piperazin-1-yl]acetamide:

The same reaction and treatment as in Example 24 were conducted using 1-[2-(oxazolo[4,5-b]pyridin-2-ylthio)ethyl]piperazine ditrifluoroacetate instead of 1-[2-(benzoxazol-2-ylthio)ethyl]piperazine ditrifluoroacetate to provide the desired compound as colorless amorphous. IR (KBr) cm$^{-1}$: 3448, 3274, 2816, 1699, 1493. 1H-NMR (d$_6$-DMSO) δ: 2.47 (3H, s), 2.49 (3H, s), 2.50 (3H, s), 2.64–2.72 (8H, m), 2.87 (2H, t, J=6.7 Hz), 3.13 (2H, s), 3.58 (2H, t, J=6.7 Hz), 6.93 (1H, s), 7.34 (1H, dt, J=8.1, 4.9 Hz), 8.01 (1H, dt, J=8.1, 1.5 Hz), 8.46 (1H, dt, J=4.9, 1.5 Hz), 8.81 (1H, br s).

EIMSm/z (relative intensity): 503 (M$^+$), 97 (100). Elementary analysis as C$_{22}$H$_{28}$N$_6$O$_2$S$_3$ Calculated: C, 52.36; H, 5.59; N, 16.65. Found: C, 52.34; H, 5.73, N, 16.39.

Example 26

Preparation of N-[2,4-bis(methylthio)-6-methyl-3pyridyl]-2-[4–2-[7-methoxycarbonylbenzoxazol-2-ylthio)ethyl]piperazin-1-yl]acetamide:

The same reaction and treatment as in Example 24 were conducted using 1-[2-(7-methoxycarbonyrbenzoxazol-2-ylthio)ethyl]piperazine ditrifluoroacetate instead of 1-[2-(benzoxazol-2-ylthio)ethyl]piperazine ditrifluoroacetate to provide the desired compound as colorless crystals.

Melting point: 125–127° C. IR (KBr) cm$^{-1}$: 3434, 3303, 1724, 1702, 1482. 1H-NMR (CDCl$_3$) δ: 2.42 (3H, s), 2.50 (3H, s), 2.52 (3H, s), 2.63–2.85 (8H, m), 2.87 (2H, t, J=6.8 Hz), 3.20 (2H, s), 3.52 (2H, t, J=6.8 Hz), 4.00 (3H, s), 6.67 (1H, s), 7.35 (1H, t, J=7.8 Hz), 7.77 (1H, dd, J=7.8, 1.2 Hz), 7.88 (1H, dd, J=7.8, 1.2 Hz), 8.55 (1H, br s).

EIMSm/z (relative intensity): 561 (M$^+$), 334 (100). Elementary analysis as C$_{25}$H$_{31}$N$_5$O$_4$S$_3$ Calculated: C, 53.46; H, 5.56; N, 12.47. Found: C, 53.41; H, 5.49, N, 12.32.

Example 27

Preparation of 3-[4-[2-(benzoxazol-2-ylthio)ethyl]piperazin-1-yl]-N-[2,4-bis(methylthio)-6-methyl-3pyridyl]propanamide:

The same reaction and treatment as in Example 22 were conducted using 3-amino-2,4-bis(methylthio)-6-methylpyridine instead of 2,6-diisopropylaniline to provide the desired compound as colorless powdery crystals.

Melting point: 110–112° C. IR (KBr) cm$^{-1}$: 3439, 3242, 2814, 1648, 1500. 1H-NMR (CDCl$_3$) δ: 1.54–1.64 (2H, m), 2.40 (3H, s), 2.50 (3H, s), 2.51 (3H, s), 2.46–2.82 (12H, m), 3.47 (2H, t, J=6.8 Hz), 6.65 (1H, s), 7.21–7.30 (2H, m), 7.42 (1H, dd, J=7.6, 1.0 Hz), 7.57 (1H, dd, J=7.0, 0.8 Hz), 10.35 (1H, br s). Elementary analysis as C$_{24}$H$_{31}$N$_5$O$_2$S$_3$ Calculated: C, 55.68; H, 6.04; N, 13.53. Found: C, 55.76; H, 5.99, N, 13.39.

Example 28

Preparation of 2-[4-[3-(benzoxazol-2-ylthio)propyl]piperazin-1-yl]-N-[2,4-bis(methylthio)-6-methyl-3-pyridyl]acetamide:

The same reaction and treatment as in Example 24 were conducted using 1-[3-(benzoxazol-2-ylthio)propyl]piperazine ditrifluoroacetate instead of 1-[2-(benzoxazol-2-ylthio)ethyl]piperazine ditrifluoroacetate to provide the desired compound as colorless powdery crystals.

Melting point: 160–161° C. IR (KBr) cm$^{-1}$: 3441, 3312, 2809, 1699, 1482. 1H-NMR (d$_6$-DMSO) δ: 1.89 (2H, t, J=7.1 Hz), 2.33 (3H, s), 2.36 (3H, s), 2.38 (3H, s), 2.39–2.45 (6H, m), 2.54–2.60 (4H, m), 3.01 (2H, s), 3.29 (2H, t, J=7.1 Hz), 6.80 (1H, s), 7.19–7.25 (2H, m), 7.48–7.52 (2H, m), 8.67 (1H, br s). Elementary analysis as C$_{24}$H$_{31}$N$_5$O$_2$S$_3$ Calculated: C, 55.68; H, 6.04; N, 13.53. Found: C, 55.83; H, 6.10, N, 13.17.

Example 29

Preparation of N-[2,4-bis(methylthio)-6-methyl-3pyridyl]-2-[4-[3-(oxazolo[4,5-b]pyridin)-2-ylthio)-propyl]piperazin-1-yl]acetamide:

The same reaction and treatment as in Example 24 were conducted using 1-[3-(oxazolo[4,5-b]pyridin-2-ylthio)propyl]piperazine ditrifluoroacetate instead of 1-[2-(benzoxazol-2-ylthio)ethyl]piperazine ditrifluoroacetate to provide the desired compound as colorless powdery crystals.

Melting point: 79–82° C. IR (KBr) cm$^{-1}$: 3433, 3291, 2818, 1701, 1493. 1H-NMR (CDCl$_3$) δ: 2.07–2.17 (2H, m), 2.42 (3H, s), 2.49 (3H, s), 2.52 (3H, br s), 2.52–2.66 (8H, m), 2.72–2.87 (2H, m), 3.22 (2H, s), 3.44 (2H, t, J=7.1 Hz), 6.67 (1H, s), 7.18 (1H, dd, J=8.1, 5.1 Hz), 7.69 (1H, dd, J=8.1, 1.5 Hz), 8.46 (1H, dd, J=5.1, 1.5 Hz), 8.54 (1H, br s).

Example 30

Preparation of N-[2,4-bis(methylthio)-6-methyl-3pyridyl]-2-[4-[3-(7-methoxycarbonylbenzoxazol-2-ylthio)propyl]piperazin-1-yl]acetamide:

The same reaction and treatment as in Example 24 were conducted using 1-[3-(7-methoxycarbonylbenzoxazol-2-ylthio)propyl]piperazine ditrifluoroacetate instead of 1-[2-(benzoxazol-2-ylthio)ethyl]piperazine ditrifluoroacetate to provide the desired compound as colorless powdery crystals.

Melting point: 76–79° C. IR (KBr) cm$^{-1}$: 3430, 3305, 2819, 1725, 1694. 1H-NMR (d$_6$-DMSO) δ: 1.97–2.04 (2H, m), 2.42 (3H, s), 2.44 (3H, s), 2.46 (3H, s), 2.48–2.53 (6H, m), 2.61–2.69 (4H, m), 3.06–3.11 (2H, m), 3.41 (2H, t, J=7.1 Hz), 3.95 (3H, s), 6.89 (1H, s), 7.43 (1H, t, J=7.8 Hz), 7.81 (1H, dd, J=7.8, 1.2 Hz), 7.84 (1H, dd, J=7.8, 1.2 Hz), 8.72 (1H, br s). Elementary analysis as $C_{26}H_{33}N_5O_4S_3$ Calculated: C, 54.24; H, 5.78; N, 12.16. Found: C, 54.44; H, 6.01, N, 11.79.

Example 31

Preparation of 2-[4-[2-(benzothiazol-2-ylthio)ethyl]piperazin-1-yl]-N-(2,4-bis(methylthio)-6-methyl-3-pyridyl)acetamide:

The same reaction and treatment as in Example 24 were conducted using 1-[2-(benzothiazol-2-ylthio)ethyl]piperazine ditrifluoroacetate instead of 1-[2-(benzoxazol-2-ylthio)ethyl]piperazine ditrifluoroacetate to provide the desired compound as colorless powdery crystals.

Melting point: 136–139° C. IR (KBr) cm$^{-1}$: 3444, 2923, 1696, 1480, 1427. 1H-NMR (d$_6$—CDCl$_3$) δ: 2.42 (3H, s), 2.50 (3H, s), 2.52 (3H, s), 2.60–2.96 (10H, m), 3.18–3.27 (2H, m), 3.48–3.65 (2H, m), 6.67 (1H, s), 7.30 (1H, m), 7.41 (1H,m), 7.75 (1H, d, J=8.1 Hz), 7.84 (1H, d, J=8.1 Hz), 8.53 (1H, br s).

EIMSm/z (relative intensity): 519 (M$^+$), 352 (100). Elementary analysis as $C_{23}H_{29}N_5OS_4$ Calculated: C, 53.15; H, 5.62; N, 13.47; S, 24.67. Found: C, 53.17; H, 5.67, N, 13.24; S, 24.52.

Example 32

Preparation of 2-[4-[2-(benzimidazol-2-ylthio)ethyl]piperazin-1-yl]-N-[2,4-bis(methylthio)-6-methyl-3-pyridyl]acetamide dihydrochloride:

The same reaction and treatment as in Example 24 were conducted using 1-[2-(benzimidazol-2-ylthio)ethyl]piperazine ditrifluoroacetate instead of 1-[2-(benzoxazol-2-ylthio)ethyl]piperazine ditrifluoroacetate, and further reaction and treatment are performed to the obtained 2-[4-[2-(benzimidazol-2-ylthio)ethyl]piperazin-1-yl]-N-[2,4-bis(methylthio)-6-methyl-3-pyridyl]acetamide in order to provide dihydrochloride, then the compound as colorless powdery crystals was obtained.

Melting point: 214–218° C. IR (KBr) cm$^{-1}$: 3240, 2923, 1679, 1485, 1438. 1H-NMR (d$_6$-DMSO) δ: 2.40 (3H, s), 2.41 (3H, s), 2.45 (3H, s), 3.00–3.81 (15H, m), 6.93 (1H, s), 7.13–7.23 (2H, m), 7.46–7.57 (2H, m), 9.65 (1H, br s).

EIMSm/z (relative intensity): 519 (M$^+$), 352 (100).

Example 33

Preparation of N-[2,4-bis(methylthio)-6-methyl-3pyridyl]-3-[4-[3-(oxazolo[4,5-b]pyridin-2-ylthio)propyl]piperazin-1-yl]propaneamide dihydrochloride:

Triethylamine (277 mg, 2.75 mmol) was added to a solution of 3-amino-2,4-bis(methylthio)-6-methylpyridine (500 mg, 2.50 mmol) in THF (10 ml), then a solution of acryloyl acid chloride (225 mg, 2.50 mmol) in THF (3 ml) was gradually dropped thereinto and the mixture was stirred for 14 hours. The reaction solution was diluted with water and extracted with ethyl acetate. The organic layer was washed with a sodium chloride solution and dried over anhydrous sodium sulfate, the solvent was evaporated therefrom and the resulting crystals were recrystallized from chloroform-ethyl acetate-hexane to provide 276 mg (yield 44%) of N-[2,4-bis(methylthio)-6-methyl-3-pyridyl]acrylamide as colorless powdery crystals.

Triethylamine (79 mg, 0.78 mmol) was added to a solution of 1-[3-(oxazolo[4,5-b]pyridin-2-ylthio)propyl]piperazine ditrifluoroacetate (199 mg, 0.39 mmol) in ethanol (10 ml), then the above-prepared N-[2,4-bis(methylthio)-6-methyl-3-pyridyl]acrylamide (100 mg, 0.39 mmol) was added thereto and the mixture was heated to reflux for four days. The reaction solution was concentrated, diluted with water and extracted with ethyl acetate. The organic layer was washed with a saturated sodium chloride solution and dried over anhydrous sodium sulfate and the solvent was evaporated therefrom. The residue was purified by a silica gel column chromatography (developing solvent, chloroform:methanol=20:1) to provide N-[2,4-bis(methylthio)-6-methyl-3-pyridyl]-3-[4-[3-(oxazolo [4,5-b]pyridin-2-ylthio)propyl]piperazin-1-yl]propanamide. The resulting crystals were made into a dihydrochloride to provide 193 mg (yield 81%) of a desired compound as colorless powdery crystals.

Melting point: 224–227° C. IR (KBr) cm$^{-1}$: 3413, 2922, 2424, 1683, 1404. 1H-NMR (CD$_3$OD) δ: 2.38–2.47 (2H, m), 2.57 (3H, s), 2.63 (3H, s), 2.64 (3H, s), 3.05 (2H, t, J=7.1 Hz), 3.42 (2H, t, J=7.1 Hz), 3.47–3.74 (12H, m), 7.24 (1H, s), 7.40 (1H, dd, J=8.2, 5.1 Hz), 8.04 (1H, dd, J=8.2, 1.3 Hz), 8.44 (2H, dd, J=5.1, 1.3 Hz).

EIMSm/z (relative intensity): 532 (M$^+$), 55 (100).

Example 34

Preparation of 2-[4-[2-(benzoxazol-2-ylthio)ethyl]piperazin-1-yl]-N-[2,4-bis(ethylthio)-6-methyl-3-pyridyl]acetamide:

Ethanethiol (1.55 g, 25 mmol) was dropped into a solution of sodium ethoxide (1.27 g, 25 mmol) in ethanol (50 ml) with ice-cooling and the mixture was stirred for 30 minutes. With ice-cooling, a solution of 2,4-dichloro-6-methyl-3-nitropyridine (2.1 g, 10 mmol) in DMF (40 ml) was gradually dropped thereinto. After stirring for 2 hours, the reaction mixture was extracted with ethyl acetate. The organic layer was washed with water and a saturated sodium chloride solution successively and dried over anhydrous sodium sulfate and the solvent was evaporated therefrom to provide 2.45 g (yield 95%) of 2,4-bis(ethylthio)-6-methyl-3-nitropyridine as yellow needles. The nitropyridine (775 mg, 3 mmol) was dissolved in a mixed solvent of acetic acid (30 ml) and concentrated hydrochloric acid (1.5 ml) and zinc (4 g, 60 mmol) was added little by little thereto with ice-cooling. After stirring for 10 minutes, the reaction mixture was filtered off and the filtrate was neutralized with an aqueous solution of sodium hydroxide and extracted with ethyl acetate. The organic layer was washed with water and a saturated sodium chloride solution successively and dried over anhydrous sodium sulfate and the solvent was evaporated therefrom to provide 590 mg (yield 86%) of 3-amino-2,4-bis(ethylthio)-6-methylpyridine as yellow oil. Triethylamine (304 mg, 3 mmol) was added to a solution of the aminopyridine (590 mg, 2.6 mmol) in THF (10 ml), then bromoacetyl bromide (606 mg, 3 mmol) was gradually dropped thereinto with ice-cooling and the mixture was stirred at room temperature for 1 hour. The reaction mixture was filtered, the filtrate was concentrated and the residue was purified by a silica gel column chromatography (60 g of silica gel; developing solvent, hexane:acetone=10:1→5:1) to provide 410 mg (yield 45%) of 2-bromo-N-[2,4-bis(ethylthio)-6-methyl-3-pyridyl]-acetamide as pale brown needles. Potassium carbonate (166 mg, 1.2 mmol) was added to a solution of the amide (105 mg, 0.3 mmol) and 1-[2-(benzoxazol-2-ylthio)ethyl]piperazine ditrifluoroacetate (147 mg, 0.3 mmol) in acetonitrile (8 ml) and the mixture was stirred at room temperature for 3 hours. The reaction mixture was extracted with ethylacetate, the organic layer was washed with water and a saturated sodium chloride solution successively and dried over sodium sulfate and the solvent was evaporated therefrom. The residue was purified by a silica gel column chromatography (25g of silica gel; developing solvents, hexane:acetone= 3:1→chloroform:methanol=20:1) and the resulting crude crystals were recrystallized from acetone-hexane to provide 140 mg (yield 88%) of the desired compound as colorless crystals.

Melting point: 108–109° C. IR (KBr) cm$^{-1}$: 3433, 3304, 1697 1500, 1482. 1H-NMR (d$_6$-DMSO) δ: 1.32 (3H, t, J=7.3 Hz), 1.35 (3H, t, J=7.3 Hz), 2.47 (3H, s), 2.64–2.70 (4H, m), 2.74–2.81 (4H, m), 2.85 (2H, t, J=6.8 Hz), 2.93 (2H, q, J=7.3 Hz), 3.16 (2H, q, J=7.3 Hz), 3.20 (2H, s), 3.49 (2H, t, J=6.8 Hz), 6.70 (1H, s), 7.22–7.30 (2H, m), 7.44 (1H, m), 7.59 (1H, m), 8.53 (1H, br s).

EIMSm/z (relative intensity): 531 (M$^+$), 381 (100). Elementary analysis as C$_{25}$H$_{33}$N$_5$O$_2$S$_3$ Calculated: C, 56.47; H, 6.25; N, 13.17; S, 18.09. Found: C, 56.73; H, 6.23; N, 13.08; S, 18.20.

Example 35

Preparation of -2-[4-[2-(7-methoxycarbonylbenzoxazol-2-ylthio)ethyl]piperazin-1-yl]-N-[2,4-bis(ethylthio)-6methyl-3-pyridyl)acetamide:

The same reaction and treatment as in Example 34 were conducted using 1-[2-(7-methoxycarbonylbenzoxazol-2-ylthio)ethyl]piperazine ditrifluoroacetate instead of 1-[2-(benzoxazol-2-ylthio)ethyl]piperazine ditrifluoroacetate to provide the desired compound as colorless crystals.

Melting point: 118–119° C. IR (KBr) cm$^{-1}$: 3424, 3350, 1718, 1505. 1H-NMR (CDCl$_3$) δ: 1.32 (3H, t, J=7.4 Hz), 1.36 (3H, t, J=7.4 Hz), 2.47 (3H, s), 2.66–2.70 (4H, m), 2.74–2.78 (4H, m), 2.87 (2H, t, J=6.8 Hz), 2.93 (2H, q, J=7.4 Hz), 3.15 (2H, q, J=7.4 Hz), 3.19 (2H, s) 3.52 (2H, t, J=6.8 Hz), 4.00 (3H, s), 6.70 (1H, s), 7.34 (1H, dd, J=8.1, 7.8 Hz), 7.77 (1H, dd, J=8.1, 1.2 Hz), 7.88 (1H, dd, J=7.8, 1.2 Hz), 8.53 (1H, br s).

EIMSm/z (relative intensity): 589 (M$^+$), 380 (100). Elementary analysis as C$_{27}$H$_{35}$N$_5$O$_4$S$_3$ Calculated: C, 54.99; H, 5.98; N, 11.87; S, 16.31. Found: C, 54.98; H, 5.96, N, 11.75; S, 16.26.

Example 36

Preparation of 2-[4-[2-(benzoxazol-2-ylthio)ethyl]piperazin-1-yl]-N-[2,4-bis(isopropylthio)-6-methyl-3-pyridyl]acetamide dihydrochloride:

2-Propanethiol (1.90 g, 25 mmol) was dropped into a solution of sodium isopropoxide (2.05 g, 25 mmol) in 2-propanol (50 ml) with ice-cooling and the mixture was stirred for 30 minutes. With ice-cooling, a solution of 2,4-dichloro-6-methyl-3-nitropyridine (2.07 g, 10 mmol) in DMF (40 ml) was gradually dropped thereinto. After stirring for 2 hours, the reaction mixture was extracted with ethyl acetate. The organic layer was washed with water and a saturated sodium chloride solution successively and dried over sodium sulfate and the solvent was evaporated therefrom to provide 2.77 g (yield 97%) of 2,4-bis(isopropylthio)-6-methyl-3-nitropyridine as yellow needles. The nitropyridine (1.08 g, 3.77 mmol) was dissolved in a mixed solvent of acetic acid (35 ml) and concentrated hydrochloric acid (1.6 ml) and then zinc (2.96 g, 45.25 mmol) was added little by little thereto with ice-cooling. After stirring for 1 hour, the reaction mixture was filtered and the filtrate was neutralized with an aqueous solution of sodium bicarbonate and extracted with chloroform. The organic layer was washed with water and a saturated sodium chloride solution successively and the residue obtained by evaporation of the solvent therefrom was purified by a silica gel column chromatography (developing solvent, hexane-:ethyl acetate=30:1→10:1) to provide 774 mg (yield 80%) of 3-amino-2,4-bis(isopropylthio)-6-methylpyridine as yellow oil.

Triethylamine (336 mg, 3.32 mmol) was added to a solution of the aminopyridine (774 mg, 3.02 mmol) inn THF (10 ml), then bromoacetic acid bromide (732 mg, 3.62 mmol) was gradually dropped thereinto with ice-cooling and the mixture was stirred for 17 hours. The reaction mixture was filtered, the filtrate was concentrated and the residue was purified by a silica gel column chromatography (developing solvent, hexane:ethyl acetate=10:1) to provide 595 mg (yield 52%) of N-[2,4-bis(isopropylthio)-6-methyl-3-pyridyl]-2-bromoacetamide as colorless powdery crystals.

After that, the same reaction and treatment as in Example 24 were conducted using N-[2,4-bis(isopropylthio)-6-methyl-3-pyridyl]-2-bromoacetamide instead of N-[2,4-bis-(methylthio)-6-methyl-3-pyridyl]-2-bromoacetamide and the resulting 2-[4-[2-(benzoxazol-2-ylthio)-ethyl]piperazin-1-yl]-N-[2,4bis(isopropylthio)-6-methyl-3-pyridyl] acetamide was converted to a dihydrochloride to provide a desired compound as colorless powdery crystals.

Melting point: 159–164° C. IR (KBr) cm$^{-1}$: 3421, 2965, 1695, 1502, 1454. 1H-NMR (d$_6$-DMSO) δ: 1.29–1.35 (12H, m), 2.46 (3H, s), 2.93–3.33 (12H, m), 3.52 (2H, t, J=7.0 Hz), 3.61 (1H, m), 3.94 (1H, m), 7.00 (1H, m), 7.30–7.35 (2H, m), 7.57–7.63 (2H, m), 8.16 (1H, s).

EIMSm/z (relative intensity): 559 (M$^+$), 125 (100).

Example 37

Preparation of 2-[4-[2-(benzimidazol-2-ylthio)ethyl] piperazin-1-yl]-N-(2,4-bis(isopropylthio)-6-methyl-3-pyridyl)acetamide:

1-[2-(Benzimidazol-2-ylthio)ethyl]piperazine ditrifluoroacetate was obtained as colorless powdery crystals according to Example 22 using 2-mercaptobenzimidazole instead of 2-mercaptobenzooxazole.

Potassium carbonate (146 mg, 1.08 mmol) was added to a solution of the above-prepared 1-[2-(benzimidazol-2- ylthio)ethyl]piperazine ditrifluoroacetate (160 mg, 0.27 mmol) and N-[2,4-bis(isopropylthio)-6-methyl-3-pyridyl]-2-bromoacetamide (100 mg, 0.27 mmol) in acetonitrile (5 ml) and the mixture was stirred at room temperature for 3 hours. The reaction solution was diluted with water and extracted with ethyl acetate. The organic layer was washed with a sodium chloride solution and dried over anhydrous sodium sulfate and the solvent was evaporated therefrom. The residue was purified by a silica gel column chromatography (developing solvent, chloroform:methanol=20:1) and the resulting crystals were recrystallized from ether-hexane to provide 104 mg (yield 70%) of the desired compound as colorless powdery crystals.

Melting point: 186–188° C. IR (KBr) cm$^{-1}$: 3197, 2963, 2816, 1660, 1518, 1491. 1H-NMR (CDCl$_3$) δ: 1.35 (6H, d, J=6.8 Hz), 1.36 (6H, d, J=6.8 Hz), 2.47 (3H, s), 2.88–3.05 (8H, m), 3.07 (2H, t, J=5.4 Hz), 3.30 (2H, t, J=5.4 Hz), 3.34 (2H, s)., 3.51 (1H, sept, J=6.8 Hz), 4.04 (1H, sept, J=6.8 Hz), 6.76 (1H, s), 7.19–7.23 (2H, m), 7.51–7.56 (2H, m), 8.34 (1H, br s).

EIMSm/z (relative intensity): 558 (M$^+$), 125 (100).

Example 38

Preparation of 2-[4-[2-(benzothiazol-2-ylthio)ethyl]piperazin-1-yl]-N-[2,4-bis(isopropylthio)-6-methyl-3-pyridyl]acetamide dihydrochloride:

The same reaction and treatment as in Example 37 were conducted using 2-mercaptobenzothiazole instead of 2-mercaptobenzimidazole to provide the desired compound as colorless powdery crystals.

Melting point: 139–142° C. IR (KBr) cm$^{-1}$: 3424, 2962, 1690, 1456, 1428. 1H-NMR (d$_6$-DMSO) δ: 1.31 (6H, d, J=6.6 Hz), 1.34 (6H, d, J=6.6 Hz), 2.45 (3H, s), 3.05–3.37 (10H, m), 3.46–3.52 (2H, m), 3.61 (1H, sept, J=6.6 Hz), 3.74 (2H, t, J=7.2 Hz), 3.93 (1H, sept, J=6.6 Hz), 6.99 (1H,s), 7.37 (1H, m), 7.47 (1H, m), 7.86 (1H, d, J=8.4 Hz), 7.96 (1H, d, J=7.8 Hz), 8.53 (1H, br s).

EIMSm/z (relative intensity): 575 (M$^+$), 125 (100).

Example 39

Preparation of N-[2,4-bis(isopropylthio)-6-methyl-3-pyridyl]-2-[4-[2-(7-methoxycarbonylbenzoxazol-2-ylthio)ethyl]piperazin-1-yl]acetamide:

The same reaction and treatment as in Example 37 were conducted using 7-methoxycarbonyl-2-mercaptobenzooxazole instead of 2-mercaptobenzimidazole to provide the desired compound as colorless amorphous.

Melting point: 60–63° C. IR (KBr) cm$^{-1}$: 3302, 2960, 1726, 1702, 1482. 1H-NMR (CDCl$_3$) δ: 1.35 (6H, d, J=6.6 Hz), 1.36 (6H, d, J=6.6 Hz), 2.46 (3H,s), 2.62–2.93 (10H, m), 3.14–3.24 (2H, m), 3.46–3.57 (2H, m), 3.96–4.06 (2H, m), 4.00 (3H, s), 6.76 (1H, s), 7.35 (1H, m), 7.76 (1H, d, J=7.8 Hz), 7.88 (1H, d, J=7.5 Hz), 8.50 (1H, br s).

EIMSm/z (relative intensity): 617 (M$^+$), 334 (100). Elementary analysis as $C_{29}H_{39}N_5O_4S_3$ Calculated: C, 56.38; H, 6.36; N, 11.34; S, 15.57. Found: C, 56.30; H, 6.25; N, 11.21; S, 15.50.

Example 40

Preparation of N-[2,4-bis(isopropylthio)-6-methyl-3-pyridyl]-2-[4-[2-(oxazolo[4,5-b]pyridin-2-ylthio)ethyl]piperazin-1-yl]acetamide dihydrochloride:

The same reaction and treatment as in Example 37 were conducted using 2-mercaptooxazolo[4,5-b]pyridine instead of 2-mercaptobenzimidazole to provide the desired compound as pale yellow powdery crystals.

Melting point: 170–172° C. IR (KBr) cm$^{-1}$: 3416, 2967, 1699, 1615, 1496. 1H-NMR (d$_6$-DMSO) δ: 1.31 (6H, d, J=6.7 Hz), 1.34 (6H, d, J=6.7 Hz), 2.45 (3H,s), 3.00–3.38 (10H, m), 3.56–3.65 (3H, m), 3.74 (2H, t, J=7.1 Hz), 3.94 (1H, sept, J=6.7 Hz), 6.99 (1H, s), 7.33 (1H, dd, J=8.0, 4.9 Hz), 8.00 (1H, dd, J=8.0, 1.4 Hz), 8.44 (1H, dd, J=4.9, 1.4 Hz), 9.30 (1H, br s).

EIMSm/z (relative intensity): 560 (M$^+$), 277 (100).

Example 41

Preparation of 2-[4-[3-(benzoxazol-2-ylthio)propyl]piperazin-1-yl]-N-(2,4-bis(isopropylthio)-6-methyl-3-pyridyl)acetamide dihydrochloride:

Potassium carbonate (120 mg, 0.88 mmol) was added to a solution of 1-[3-(benzoxazol-2-ylthio)propyl]piperazine ditrifluoroacetate (110 mg, 0.22 mmol) and N-[2,4-bis(isopropylthio)-6-methyl-3-pyridyl]-2-bromoacetamide (82 mg, 0.22 mmol) in acetonitrile (4 ml) and the mixture was stirred for 3 hours. The reaction solution was diluted with water and extracted with ethyl acetate. The organic layer was washed with a sodium chloride solution and dried over anhydrous sodium sulfate and the solvent was evaporated therefrom. The residue was purified by a preparative thin layer chromatography (developing solvent, chloroform:methanol=20:1) and the resulting 2-[4-[3-(benzoxazol-2-ylthio)-propyl]piperazin-1-yl]-N-(2,4-bis(isopropylthio)-6-methyl-3-pyridyl)acetamide was converted to a dihydrochloride to provide 71 mg (yield 51%) of the desired compound as colorless powdery crystals.

Melting point: 178–181° C. IR (KBr) cm$^{-1}$: 3424, 2964, 1691, 1499, 1454. 1H-NMR (d$_6$-DMSO) δ: 1.22 (6H, d, J=6.6 Hz), 1.25 (6H, d, J=6.6 Hz), 2.17–2.25 (2H, m), 2.37 (3H, s), 2.83–3.30 (12H, m), 3.38 (2H, t, J=7.1 Hz), 3.51 (1H, sept, J=6.6 Hz), 3.84 (1H, sept, J=6.6 Hz), 6.90 (1H, s), 7.21–7.28 (2H, m), 7.49–7.54 (2H, m), 8.94 (1H, br s).

EIMSm/z (relative intensity): 573 (M$^+$), 111 (100).

Example 42

Preparation of 2-[4-[2-(benzoxazol-2-ylthio)ethyl]-piperazin-1-yl]-N-(2-methylthio-3-pyridyl)acetamide dihydrochloride:

Triethylamine (197 mg, 1.95 mmol) was added to a solution of 3-amino-2-(methylthio)pyridine (248 mg, 1.77 mmol) in THF (5 ml), then a solution of bromoacetyl bromide (428 mg, 2.12 mmol) in THF (1 ml) was dropped thereinto and the mixture was stirred for 17 hours. The reaction solution was diluted with water and extracted with ethyl acetate. The organic layer was washed with a saturated sodium chloride solution and dried over anhydrous sodium sulfate, the solvent was evaporated therefrom and the residue was purified by a silica gel column chromatography (developing solvent, hexane:ethyl acetate=5:1) to provide 104 mg (yield 22%) of N-(2-methylthio-3-pyridyl)-2-bromoacetamide as colorless powdery crystals.

Potassium carbonate (214 mg, 1.55 mmol) was added to a solution of 1-[2-(benzoxazol-2-ylthio)ethyl]piperazine ditrifluoroacetate (190 mg, 0.39 mmol) and N-(2-methylthio-3-pyridyl)-2-bromoacetamide (101 mg, 0.39 mmol) in acetonitrile (5 ml) and the mixture was stirred for 3 hours. The reaction solution was diluted with water and extracted with ethylacetate. The organic layer was washed with a saturated sodium chloride solution and dried over anhydrous sodium sulfate and the solvent was evaporated therefrom. The residue was purified by a preparative thin layer chromatography (developing solvent, chloroform:methanol=20:1) to provide 147 mg (yield 74%) of 2-[4-[2-(benzoxazol-2-ylthio)-ethyl]piperazin-1-yl]-N-(2-methylthio-3-pyridyl)acetamide. The resulting crystals were converted to a dihydrochloride to provide the desired compound as colorless powdery crystals.

Melting point: 186–189° C. IR (KBr) cm$^{-1}$: 3424, 2926, 2553, 1702, 1504, 1453. 1H-NMR (CD$_3$OD) δ: 2.65 (3H, s), 3.26–3.37 (5H, m), 3.60–3.80 (7H, m), 3.79 (2H, s), 7.31–7.38 (3H, m), 7.55 (1H, m), 7.61 (1H, m), 8.13 (1H, m), 8.38 (1H, m).

EIMSm/z (relative intensity): 443 (M$^+$), 125 (100).

Example 43

Preparation of 2-[4-[2-(benzoxazol-2-ylthio)ethyl]piperazin-1-yl]-N-(2-methyl-6-methylthio-3-pyridyl) acetamide:

The same reaction and treatment as in Example 42 were conducted using 3-amino-2-methyl-6-(methylthio)pyridine instead of 3-amino-2-(methylthio)pyridine to provide the desired compound as colorless powdery crystals.

Melting point: 116–117° C. IR (KBr) cm$^{-1}$: 3265, 2944, 1670, 1497, 1453. 1H-NMR (CDCl$_3$) δ: 2.49 (3H, s), 2.54 (3H, s), 2.60–2.80 (8H, s), 2.82–2.95 (8H, m), 3.12–3.24 (2H, m), 3.43–3.57 (2H, m), 7.04 (1H, d, J=8.6 Hz), 7.22–7.32 (2H, m), 7.44 (1H, d, J=7.3 Hz), 7.58 (1H, d, J=7.3 Hz), 8.30 (1H, d, J=8.6 Hz), 9.20 (1H, br s).

EIMSm/z (relative intensity): 457 (M$^+$), 125 (100). Elementary analysis as C$_{22}$H$_{27}$N$_5$O$_2$S$_2$·0.4H$_2$O Calculated: C, 56.85; H, 6.03; N, 15.07; S, 13.80. Found: C, 56.94; H, 5.90, N, 14.94; S, 13.65.

Example 44

Preparation of 2-[4-[2-(benzoxazol-2-ylthio)ethyl]piperazin-1-yl]-N-(6-methyl-2-methylthio-3-pyridyl) acetamide dihydrochloride:

The same reaction and treatment as in Example 42 were conducted using 3-amino-6-methyl-2-(methylthio)pyridine instead of 3-amino-2-(methylthio)pyridine to provide the desired compound as colorless powdery crystals.

Melting point: 200–203° C. IR (KBr) cm$^{-1}$: 3416, 2924, 1698, 1507, 1455. 1H-NMR (d$_6$-DMSO) δ: 2.42 (3H, s), 2.49 (3H, s), 3.05–3.13 (4H, m), 3.22–3.30 (4H, m), 3.38 (2H, t, J=7.4 Hz), 3.49 (2H, s), 3.70 (2H, t, J=7.4 Hz), 6.94 (1H, d, J=7.9 Hz), 7.25–7.31 (2H, m), 7.52–7.60 (2H, m), 7.68 (1H, d, J=7.9 Hz), 9.32 (1H, br s).

EIMSm/z (relative intensity): 457 (M$^+$), 125 (100).

Example 45

Preparation of 2-[4-[2-(benzoxazol-2-ylthio)ethyl]piperazin-1-yl]-N-[2,4-dimethoxy-6-methyl-3-pyridyl)acetamide:

The same reaction and treatment as in Example 42 were conducted using 3-amino-2,4-dimethoxy-6-methylpyridine instead of 3-amino-2-(methylthio)pyridine to provide the desired compound as colorless powdery crystalsy crystals.

Melting point: 113–115° C. IR (KBr) cm$^{-1}$: 3326, 2944, 1698, 1600, 1504. 1H-NMR (CDCl$_3$) δ: 2.42 (3H, s), 2.57–2.97 (10H, m), 3.13–3.22 (2H, m), 3.45–3.57 (2H,m), 3.84 (33H, s), 3.91 (3H, s), 6.42 (1H, s), 7.22–7.31 (2H, m), 7.44 (1H, m), 7.58 (1H, m), 8.22 (1H, br s).

EIMSm/z (relative intensity): 471 (M$^+$), 307 (100). Elementary analysis as C$_{23}$H$_{29}$N$_5$O$_4$S Calculated: C, 58.58; H, 6.20; N, 14.85; S, 6.80. Found: C, 58.54; H, 6.24, N, 14.88; S, 6.79.

Example 46

Preparation of 2-[4-[2-(benzoxazol-2-ylthio)ethyl]piperazin-1-yl]-N-[4,6-bis(methylthio)-5-pyrimidyl)acetamide:

Triethylamine (78 mg, 0.8 mmol) was added to a solution of 4,6-bis(methylthio)-5-aminopyrimidine (120 mg, 0.7 mmol) in THF (2 ml) at room temperature, then bromoacetyl bromide (141 mg, 0.7 mmol) was dropped thereinto and the mixture was stirred for 1 hour. Then the same amounts of triethylamine and bromoacetyl bromide were added followed by stirring for 1 hour. The reaction solution was diluted with water and extracted with ether. The organic layer was washed with water and a saturated sodium chloride solution successively and dried over magnesium sulfate and the solvent was evaporated therefrom. The residue was purified by a silica gel column chromatography (20 g of silica gel; developing solvent, hexane:acetone=5:1) to provide 78 mg (yield 40%) of N-[4,6-bis(methylthio)-5-pyrimidyl]-2-bromoacetamide as pale yellow crystals.

Potassium carbonate (104 mg, 0.75 mmol) was added to a solution of 1-[2-(benzoxazol-2-ylthio)ethyl]piperazine ditrifluoroacetate (123 mg, 0.25 mmol) in acetonitrile (3 ml), then the above-prepared amide (78 mg, 0.25 mmol) was added and the mixture was stirred at 50° C. for 1 hour. The reaction solution was extracted with ether. The organic layer was washed with water and a saturated sodium chloride solution successively and dried over sodium sulfate and the solvent was evaporated therefrom. The residue was purified by a preparative thin layer chromatography (developing solvent, chloroform:methanol=50:1) to provide 70 mg (yield 57%) of the desired compound as pale yellow needles.

Melting point: 171–172° C. IR (KBr) cm$^{-1}$: 3441, 3280, 1699, 1528, 1412. 1H-NMR (CDCl$_3$) δ: 2.54 (6H, s), 2.63–2.80 (8H, m), 2.86 (2H, t, J=6.8 Hz), 3.21 (2H, s), 3.49 (2H, t, J=6.8 Hz), 7.22–7.32 (2H, m), 7.44 (1H, m), 7.59 (1H, m), 8.67 (1H, s), 8.67 (1H, br s).

EIMSm/z (relative intensity): 489 (M$^+$-1), 339 (100). Elementary analysis as C$_{21}$H$_{26}$N$_6$O$_2$S$_3$ Calculated: C, 51.41; H, 5.34; N, 17.13; S, 19.60. Found: C, 51.42; H, 5.45; N, 16.90; S, 19.41.

Example 47

Preparation of 2-[4-[2-(benzoxazol-2-ylthio)ethyl]piperazin-1-yl]-N-(2,4,6-trimethyl-3-pyridyl)acetamide:

The same reaction and treatment as in Example 42 were conducted using 3-amino-2,4,6-trimethylpyridine instead of 3-amino-2-(methylthio)pyridine to provide the desired compound as colorless powdery crystals.

Melting point: 159–160° C. IR (KBr) cm$^{-1}$: 3262, 2943, 1666, 1500, 1453. 1H-NMR (CDCl$_3$) δ: 2.21 (3H, s), 2.46 (3H, s), 2.51 (3H,s), 2.65–2.80 (8H, m), 2.89 (2H, t, J=6.9 Hz), 3.22 (2H, s), 3.51 (2H, t, J=6.9 Hz), 6.94 (1H, s), 7.22–7.31 (2H, m), 7.44 (1H, m), 7.59 (1H, m), 8.66 (1H, br s).

EIMSm/z (relative intensity): 439 (M$^+$), 163 (100). Elementary analysis as C$_{23}$H$_{29}$N$_5$O$_2$S Calculated: C, 62.33; H, 6.69; N, 15.80; S, 7.24. Found: C, 62.26; H, 6.68; N, 15.62; S, 7.16.

Example 48

Preparation of 2-[4-[2-(benzoxazol-2-ylthio)ethyl]piperazin-1-yl]-N-(2,4,6-triisopropylphenyl)acetamide:

Triethylamine (111 mg, 1.1 mmol) was added to a solution of 2,4,6-triisopropylaniline (219 mg, 1.0 mmol) in chloroform (3 ml), then bromoacetyl bromide (222 mg, 1.1 mmol) was gradually dropped thereinto with ice-cooling and the mixture was stirred for 1 hour. The reaction mixture was concentrated and the residue was extracted with ethyl acetate. The organic layer was washed with diluted hydrochloric acid, an aqueous solution of sodium bicarbonate and a saturated sodium chloride solution successively and dried over magnesium sulfate and the solvent was evaporated therefrom. The residue was purified by a silica gel column chromatography (15 g of silica gel; developing solvent, hexane:acetone=5:1) followed by recrystallizing from hexane-ether to provide 275 mg (yield 81%) of 2-Bromo-N-(2,4,6-triisopropylphenyl)acetamide as colorless needles.

Potassium carbonate (124 mg, 0.9 mmol) was added to a solution of 1-[2-(benzoxazol-2-ylthio)ethyl]piperazine ditrifluoroacetate (147 mg, 0.3 mmol) in acetonitrile (5 ml) at room temperature, then the above-prepared anilide (102 mg, 0.3 mmol) was added and the mixture was stirred for 4 hours. The reaction solution was diluted with water and extracted with ethyl acetate. The organic layer was washed with water and a saturated sodium chloride solution successively and dried over sodium sulfate and the solvent was evaporated therefrom. The residue was purified by a silica gel column chromatography (12 g of silica gel; developing solvent, hexane:acetone=5:1) and then recrystallized from hexane-acetone to provide 75 mg (yield 48%) of the desired compound as colorless needles.

Melting point: 160–163° C. IR (KBr) cm$^{-1}$: 3433, 3239, 1666, 1498, 1455. 1H-NMR (CDCl$_3$) δ:1 1.21 (12H, d, J=6.8 Hz), 1.24 (6H, d, J=6.0 Hz), 2.60–2.76 (8H,m), 2.84 (2H, t, J=6.8 H), 2.89 (1H, sept, J=6.0 Hz), 2.98 (2H, sept, J=6.8 Hz), 3.21 (2H, s), 3.49 (2H, t, J=6.8 Hz), 7.03 (2H, s), 7.22–7.31 (2H, m), 7.44 (1H, m), 7.58 (1H, m), 8.67 (1H, br s).

EIMSm/z (relative intensity): 522 (M$^+$, 100). Elementary analysis as C$_{30}$H$_{42}$N$_4$O$_2$S Calculated: C, 68.93; H, 8.10; N, 10.72; S, 6.13. Found: C, 68.89; H, 8.05; N, 10.64; S, 6.11.

Example 49

Preparation of 2-[4-[2-(benzimidazol-2-ylthio)ethyl]piperazin-1-yl]-N-(2,4,6-triisopropylphenyl)acetamide:

The same reaction and treatment as in Example 48 were conducted using 2-mercaptobenzimidazole instead of 2-mercaptobenzooxazole to provide the desired compound as colorless crystals.

Melting point: 217–218° C. IR (KBr) cm$^{-1}$: 3440, 3292, 2959, 1670, 1498. 1H-NMR (CDCl$_3$) δ: 1.22 (12H, d, J=7.1 Hz), 1.25 (6H, d, J=7.1 Hz), 2.74–2.97 (11H, m), 2.99 (2H, sept, J=7.1 Hz), 3.24–3.27 (2H, m), 3.35 (2H, s), 7.04 (2H, s), 7.19–7.24 (2H, m), 7.37 (1H, m), 7.65 (1H, m), 8.43 (1H, br s).

EIMSm/z (relative intensity): 521 (M$^+$), 372 (100). Elementary analysis as C$_{30}$H$_{43}$N$_5$OS Calculated: C, 69.06; H, 8.31; N, 13.41; S, 6.14. Found: C, 69.18; H, 8.31; N, 13.16; S, 6.14.

Example 50

Preparation of 2-[4-[2-(benzothiazol-2-ylthio)ethyl]piperazin-1-yl]-N-(2,4-6-triisopropylphenyl)acetamide:

The same reaction and treatment as in Example 48 were conducted using 2-mercaptobenzothiazole instead of 2-mercaptobenoxazole to provide the desired compound as colorless crystals.

Melting point: 117–118° C. IR (KBr) cm$^{-1}$: 3435, 3263, 1683, 1668, 1493. 1H-NMR (CDCl$_3$) δ: 1.21 (12H, d, J=7.1 Hz), 2.24 (6H, d, J=7.1 Hz), 2.60–2.77 (8H, m), 2.83 (2H, t, J=7.3 Hz), 2.89 (1H, sept, J=7.1 Hz), 2.98 (2H, sept, J=7.1 Hz), 3.22 (2H, s), 3.54 (2H, t, J=7.3 Hz), 7.03 (2H, s), 7.29 (1H, m), 7.41 (1H, m), 7.76 (1H, m), 7.85 (1H, m), 8.56 (1H, br s).

EIMSm/z (relative intensity): 538 (M$^+$), 359 (100). Elementary analysis as C$_{30}$H$_{42}$N$_4$OS$_2$ Calculated: C, 66.88; H, 7.86; N, 10.40; S, 11.90. Found: C, 66.65; H, 7.79; N, 10.15; S, 11.79.

Example 51

Preparation of 2-[4-[2-(7-methoxycarbonylbenzoxazol-2-ylthio)ethyl]piperazin-1-yl]-N-(2,4-6-triisopropylphenyl)acetamide:

The same reaction and treatment as in Example 48 were conducted using 7-methoxycarbonyl-2-mercaptobenzooxazole instead of 2-mercaptobenzooxazole to provide the desired compound as colorless crystals.

Melting point: 153–155° C. IR (KBr) cm$^{-1}$: 3427, 3248, 1723, 1664, 1501. 1H-NMR (CDCl$_3$) δ: 1.21 (12H, d, J=6.8 Hz), 1.24 (6H, d, J=6.8 Hz), 2.60–2.74 (8H, m), 2.85 (2H, t, J=6.8 Hz), 2.86 (1H, sept, J=6.8 Hz), 2.98 (2H, sept, J=6.8 Hz), 3.21 (2H, s), 3.51 (2H, t, J=6.8 Hz), 4.00 (3H, s), 7.03 (2H, s), 7.35 (1H, t, J=7.8 Hz), 7.77 (1H, dd, J=7.8, 1.2 Hz), 7.88 (1H, dd, J=7.8, 1.2 Hz), 8.56 (1H, br s).

EIMSm/z (relative intensity): 580 (M$^+$), 373 (100). Elementary analysis as C$_{32}$H$_{44}$N$_4$O$_4$S Calculated: C, 66.18; H, 7.64; N, 9.65; S, 5.58. Found: C, 66.27; H, 7.63; N, 9.46; S, 5.52.

Example 52

Preparation of 2-[4-[2-(oxazolo[4,5-b]pyridin-2-ylthio)ethyl]piperazin-1-yl]-N-(2,4-6-triisopropylphenyl)acetamide:

The same reaction and treatment as in Example 48 were conducted using 2-mercaptooxazolo[4,5-b]pyridine instead of 2-mercaptobenzooxazole to provide the desired compound as colorless needles.

Melting point: 144–145° C. IR (KBr) cm$^{-1}$: 3434, 3247, 2959, 1668, 1490. 1H-NMR (CDCl$_3$) δ: 1.21 (12H, d, J=6.8 Hz), 1.24 (6H, d, J=6.8 Hz), 2.62–2.76 (8H, m), 2.84–2.94 (3H, m), 2.98 (2H, sept, J=6.8 Hz), 3.22 (2H, s), 3.56 (2H, t, J=6.7 Hz), 7.03 (2H, s), 7.19 (1H, dd, J=8.1, 4.9 Hz), 7.70 (1H, dd, J=8.1, 1.5 Hz), 8.46 (1H, dd, J=4.9, 1.5 Hz), 8.56 (1H, br s).

EIMSm/z (relative intensity): 523 (M$^+$), 372 (100). Elementary analysis as C$_{29}$H$_{41}$N$_5$O$_2$S Calculated: C, 66.51; H, 7.89; N, 13.37; S, 6.12. Found: C, 66.55; H, 7.94; N, 13.21; S, 6.13.

Example 53

Preparation of 2-[4-[3-(benzoxazol-2-ylthio)propyl]piperazin-1-yl]-N-(2,4-6-triisopropylphenyl)acetamide:

The manner according to Example 22 were conducted using 1-(3-hydroxypropyl)piperazine instead of 1-(2- hydroxyethyl) piperazine to provide 1-[3-(benzoxazol-2-ylthio)propyl]piperazine ditrifluoroacetate, and the same reaction and treatment as in Example 48 were conducted to provide the desired compound as colorless crystals.

Melting point: 125–127° C. IR (KBr) cm$^{-1}$: 3429, 3234, 2958, 1663, 1503. 1H-NMR (CDCl$_3$) δ: 1.21 (12H, d, J=6.8 Hz), 1.24 (6H, d, J=6.8 Hz), 2.04 (2H, quint, J=7.1 Hz), 2.51–2.56 (6H, m), 2.72–2.76 (4H, m), 2.89 (1H, sept, J=6.8 Hz), 2.98 (2H, sept, J=6.8 Hz), 3.22 (2H, s), 3.38 (2H, t, J=7.1 Hz), 7.03 (2H, s), 7.21–7.32 (2H, m), 7.44 (1H, m), 7.59 (1H, m), 8.58 (1H, br s).

EIMSm/z (relative intensity): 536 (M$^+$, 100). Elementary analysis as C$_{31}$H$_{44}$N$_4$O$_2$S Calculated: C, 69.37; H, 8.26; N, 10.44; S, 5.97. Found: C, 69.28; H, 8.28; N, 10.43; S, 5.98.

Example 54

Preparation of 2-[4-[3-(benzimidazol-2-ylthio)propyl]piperazin-1-yl]-N-(2,4-6-triisopropylphenyl)acetamide:

The same reaction and treatment as in Example 53 were conducted using 2-mercaptobenzimidazole instead of 2-mercaptobenzooxazole to provide the desired compound as colorless crystals.

Melting point: 229–231° C.(d) IR (KBr) cm$^{-1}$: 3433, 3261, 2961, 1654. 1H-NMR (CDCl$_3$) δ: 1.22 (12H, d, J=6.8 Hz), 1.25 (6H, d, J=6.8 Hz), 2.02 (2H, quint, J=6.5 Hz), 2.58–2.68 (6H, m), 2.84–2.92 (5H, m), 2.99 (2H, sept, J=6.8 Hz), 3.31 (2H, t, J=6.5 Hz), 3.32 (2H, s), 7.04 (2H, s), 7.17–7.24 (2H, m), 7.38 (1H, m), 7.65 (1H, m), 8.50 (1H, br s).

EIMSm/z (relative intensity): 535 (M$^+$), 139 (100). Elementary analysis as C$_{31}$H$_{45}$N$_5$OS Calculated: C, 69.49; H, 8.47; N, 13.07; S, 5.98. Found: C, 69.41; H, 8.44; N, 12.82; S, 5.90.

Example 55

Preparation of 2-[4-[3-(benzothiazol-2-ylthio)propyl]piperazin-1-yl]-N-(2,4,6-triisopropylphenyl)acetamide:

The same reaction and treatment as in Example 53 were conducted using 2-mercaptobenzothiazole instead of 2-mercaptobenzooxazole to provide the desired compound as colorless crystals.

Melting point: 107–108° C. IR (KBr) cm$^{-1}$: 3436, 3227, 2956, 1669. 1H-NMR (CDCl$_3$) δ: 1.21 (12H, d, J=6.8 Hz), 1.24 (6H, d, J=6.8 Hz), 2.03 (2H, quint, J=7.1 Hz), 2.50–2.55 (6H, m), 2.72–2.76 (4H, m), 2.89 (1H, sept, J=6.8 Hz), 2.99 (2H, sept, J=6.8 Hz), 3.22 (2H, s), 3.41 (2H, t, J=7.1 Hz), 7.03 (2H, s), 7.29 (1H, m), 7.41 (1H, m), 7.76 (1H, m), 7.85 (1H, m), 8.59 (1H, br s).

EIMSm/z (relative intensity): 552 (M$^+$), 385 (100). Elementary analysis as C$_{31}$H$_{44}$N$_4$OS$_2$ Calculated: C, 67.35; H, 8.02; N, 10.13; S, 11.60. Found: C, 67.20; H, 8.08; N, 10.01; S, 11.59.

Example 56

Preparation of 2-[4-[3-(7-methoxycarbonylbenzoxazol-2-ylthio)propyl]piperazin-1-yl]-N-(2,4-6-triisopropylphenyl)acetamide:

The same reaction and treatment as in Example 53 were conducted using 7-methoxycarbonyl-2-mercaptobenzooxazole instead of 2-mercaptobenzooxazole to provide the desired compound as colorless needles.

Melting point: 137–139° C. IR (KBr) cm$^{-1}$: 3433, 3260, 1727, 1661, 1505. 1H-NMR (CDCl$_3$) δ: 1.21 (12H, d, J=6.8 Hz), 1.24 (6H, d, J=6.8 Hz), 2.06 (2H, quint, J=7.1 Hz), 2.52–2.57 (6H, m), 2.73–2.76 (4H, m), 2.89 (1H, sept, J=6.8 Hz), 2.99 (2H, sept, J=6.8 Hz), 3.22 (2H, s), 3.40 (2H, t, J=7.1 Hz), 4.00 (3H, s), 7.03 (2H, s), 7.35 (1H, t, J=7.8 Hz), 7.77 (1H, dd, J=7.8, 1.2 Hz), 7.88 (1H, dd, J=7.8, 1.2 Hz), 8.58 (1H, br s).

EIMSm/z (relative intensity): 594 (M$^+$), 348 (100). Elementary analysis as C$_{33}$H$_{46}$N$_4$O$_4$S Calculated: C, 66.64; H, 7.79; N, 9.42; S, 5.39. Found: C, 66.49; H, 7.84; N, 9.12; S, 5.27.

Example 57

Preparation of 2-[4-[3-(oxazolo[4,5-b]pyridin-2-ylthio)propyl]piperazin-1-yl]-N-(2,4-6-triisopropylphenyl)acetamide:

The same reaction and treatment as in Example 53 were conducted using 2-mercaptooxazolo[4,5-b]pyridine instead of 2-mercaptobenzooxazole to provide the desired compound as colorless crystals.

Melting point: 156–157° C. IR (KBr) cm$^{-1}$: 3433, 3248, 2958, 1662, 1496. 1H-NMR (CDCl$_3$) δ: 1.21 (12H, d, J=7.1 Hz), 1.24 (6H, d, J=7.1 Hz), 2.08 (2H, quint, J=7.1 Hz), 2.50–2.56 (6H, m), 2.72–2.76 (4H, m), 2.89 (1H, sept, J=7.1 Hz), 2.99 (2H, sept, J=7.1 Hz), 3.22 (2H, s), 3.43 (2H, t, J=7.1 Hz), 7.03 (2H, s), 7.18 (1H, dd, J=8.1, 5.1 Hz), 7.69 (1H, dd, J=8.11.5 Hz), 8.45 (1H, dd, J=5.1, 1.5 Hz), 8.59 (1H, br s).

EIMSm/z (relative intensity): 537 (M$^+$), 139 (100). Elementary analysis as C$_{30}$H$_{43}$N$_5$O$_2$S Calculated: C, 67.01; H, 8.06; N, 13.02; S, 5.96. Found: C, 67.13; H, 8.12; N, 12.88; S, 6.02.

Example 58

Preparation of 2-[4-[2-(benzoxazol-2-ylthio)ethyl]piperazin-1-yl]-N-(2,6-diisopropyl-3-nitrophenyl)acetamide:

2-Bromo-N-(2,6-diisopropylphenyl)acetamide (5.96 g, 20 mmol) was dissolved in concentrated sulfuric acid (100 ml) with ice-cooling, a solution of fuming nitric acid (1.51 g, 24 mmol) dissolved in concentrated sulfuric acid (10 ml) was dropped thereinto and the mixture was stirred for 10 minutes. The reaction solution was poured onto ice water, the separated matters were filtered off and the extraction with ethyl acetate was conducted. The organic layer was washed with water and a saturated sodium chloride solution successively and dried over sodium sulfate and the solvent was evaporated therefrom. The residue was recrystallized from acetone-hexane to provide 6.52 g (yield 95%) of 2-bromo-N-(2,6-diisopropyl-3-nitrophenyl)acetamide as pale yellow needles.

The same reaction and treatment as in Example 1 were conducted using 2-bromo-N-(2,6-diisopropyl-3-nitrophenyl)acetamide instead of 2-bromo-N-(2,6-diisopropylphenyl)acetamide to provide the desired compound as colorless crystals.

Melting point: 143–145° C. IR (KBr) cm$^{-1}$: 3432, 3293, 1663, 1527, 1496. 1H-NMR (CDCl$_3$) δ: 1.21 (6H, d, J=6.9 Hz), 1.33 (6H, d, J=7.2 Hz), 2.63–2.70 (4H, m), 2.74–2.78 (4H, m), 2.85 (2H, t, J=6.8 Hz), 2.99 (1H, sept, J=6.9 Hz), 3.23 (2H, s), 3.25 (1H, sept, J=7.2 Hz), 3.49 (2H, t, J=6.8 Hz), 7.22–7.31 (2H, m), 7.30 (1H, d, J=8.5 Hz), 7.44 (1H, m), 7.48 (1H, d, J=8.5 Hz), 7.59 (1H, m), 8.81 (1H, br s).

EIMSm/z (relative intensity): 525 (M$^+$), 375 (100). Elementary analysis as C$_{27}$H$_{35}$N$_5$O$_4$S Calculated: C, 61.69; H, 6.71; N, 13.32; S, 6.10. Found: C, 61.62; H, 6.70; N, 13.15; S, 6.14.

Example 59

Preparation of 2-[4-[2-(benzoxazol-2-ylthio)ethyl] piperazin-1-yl]-N-(2,6-diisopropyl-3-dimethylaminophenyl)acetamide:

Zinc (8.37 g, 128 mmol) was added to a solution of 2-[4-[2-(benzoxazol-2-ylthio)ethyl]piperazin-1-yl]-N-(2, 6-d iisopropyl-3-nitrophenyl)acetamide (3.36 g, 6.4 mmol) in acetic acid (35 ml) with ice-cooling and the mixture was stirred at room temperature for 5 minutes. The reaction solution was diluted with ethyl acetate and filtered off through celite and the filtrate was concentrated. The residue was diluted with water, adjusted to pH, 10 with potassium carbonate and extracted with methylene chloride. The organic layer was washed with a saturated sodium chloride solution and dried over potassium carbonate, the solvent was evaporated therefrom and the resulting crude crystals were recrystallized from acetone-hexane to provide 2.90 g (yield 91%) of 2-[4-[2-(benzoxazol-2-ylthio)ethyl]piperazin-1-yl]-N-(3-amino-2,6-diisopropyl)acetamide as colorless needles.

To a solution of the acetamide (248 mg, 0.5 mmol) in acetonitrile (2 ml) were added at room temperature, a solution of a 37% aqueous solution of formaldehyde (405 mg, 5.0 mmol) in acetonitrile (1 ml), a solution of sodium cyanoborohydride (126 mg, 2.0 mmol) in acetonitrile (2 ml), and acetic acid (0.1 ml) successively followed by stirring for 1 hour. The reaction solution was concentrated, diluted with water and extracted with ethyl acetate. The organic layer was washed with water and a saturated sodium chloride solution successively and dried over sodium sulfate and the solvent was evaporated therefrom. The residue was purified by a preparative thin layer chromatography (developing solvent, chloroform:methanol=20:1) and the resulting crude crystals were recrystallized from acetone-hexane to provide 100 mg (yield 38%) of the desired compound as colorless needles.

Melting point: 159–161° C. IR (KBr) cm$^{-1}$: 3432, 3302, 2936, 1667, 1500. 1H-NMR (CDCl$_3$) δ: 1.18 (6H, d, J=6.8 Hz), 1.30 (6H, d, J=6.8 Hz), 2.61 (6H,s), 2.63–2.67 (4H, m), 2.74–2.78 (4H, m), 2.85-(2H, t, J=6.8 Hz), 2.92 (1H, sept, J=6.8 Hz), 3.21 (2H, s), 3.49 (2H, t, J=6.8 Hz), 3.77 (1H, sept, J=6.8 Hz), 7.16 (2H, s) 7.21–7.30 (2H, m),7.44 (1H, m), 7.59 (1H, m), 8.74 (1H, br s).

EIMSm/z (relative intensity): 523 (M$^+$), 323 (100). Elementary analysis as C$_{29}$H$_{41}$N$_5$O$_2$S Calculated: C, 66.51; H, 7.89; N, 13.37; S, 6.12. Found: C, 66.28; H, 7.95; N, 13.35; S, 6.11.

Example 60

Preparation of 2-[4-[2-(benzoxazol-2-ylthio)ethyl] piperazin-1-yl]-N-[2,6-diisopropyl-3-(methylthio)phenyl] acetamide:

Isoamyl nitrite (1 ml) was slowly dropped into a solution of N-[3-amino-2,6-diisopropylphenyl]-2-[4-(2-hydroxyethyl)piperazin-1-yl]acetamide (500 mg) in dimethyl disulfide (10 ml) with heating and stirring at 110° C. followed by stirring at the same temperature for 20 minutes. The reaction solution was allowed to cool and concentrated. The resulting residue was purified by a silica gel column chromatography (developing solvent, chloroform:methanol=20:1) to provide 370 mg (yield 68%) of N-[2,6-diisopropyl-3-(methylthio)phenyl]-2-[4-(2-hydroxyethyl)piperazin-1-yl]acetamide.

After that, the same reaction and treatment as in Example 1 were conducted using N-[2,6-diisopropyl-3-(methylthio) phenyl]-2-[4-(2-hydroxyethyl)piperazin-1-yl]acetamide instead of N-(2,6-diisopropylphenyl)-2-[4-(2-hydroxyethyl) piperazin-1yl]acetamide to provide a desired compound as pale yellow powdery crystals.

Melting point: 148–150° C. IR (KBr) cm$^{-1}$: 3286, 2960, 2817, 1664, 1499, 1455. 1H-NMR (CDCl$_3$) δ: 1.12–1.27 (6H, m), 1.28–1.44 (6H, m), 2.43 (3H, s), 2.59–2.79 (9H, m), 2.81–2.88 (2H, m), 2.92 (1H, sept, J=6.8 Hz), 3.21 (2H, s), 3.49 (2H, t, J=6.6 Hz), 7.16–7.30 (4H, m), 7.43 (1H, d, J=7.3 Hz), 7.58 (1H, d, J=7.3 Hz), 8.73 (1H, br s).

EIMSm/z (relative intensity): 526 (M$^+$), 56 (100). Elementary analysis as C$_{28}$H$_{31}$N$_4$O$_2$S$_2$.0.4H$_2$O Calculated: C, 62.98; H, 7.32; N, 10.49 Found: C, 62.79; H, 7.32; N, 10.76.

Example 61

Preparation of 2-[4-[2-(benzoxazol-2-ylthio)ethyl] piperazin-1-yl]-N-(2,6-diisopropyl-3-hydroxyphenyl) acetamide:

2-[4-[2-(Benzoxazol-2-ylthio)ethyl]piperazin-1-yl]-N-(3-amino-2,6-diisopropylphenyl)acetamide (198 mg, 0.4 mmol) was dissolved in 6% aqueous solution of sulfuric acid (3.4 ml), an aqueous solution (0.8 ml) of sodium nitrite (35 mg, 0.5 mmol) was added thereto at 0° C. and the mixture was stirred at that temperature for 30 minutes. The reaction solution was slowly dropped into a boiling water (40 ml) which was heating and stirring at an external temperature of 140° C. After 10 minutes from the dropping, the reaction solution was allowed to cool, neutralized with sodium bicarbonate and extracted with chloroform. The organic layer was washed with water and a saturated sodium chloride solution successively and dried over anhydrous magnesium sulfate and the solvent was evaporated. The residue was purified by a preparative thin layer chromatography (developing solvent, chloroform:ammonia-saturated methanol=20:1) to provide 178 mg (yield 89%) of the desired compound, which was recrystallized from ethanol-hexane to provide colorless needles.

Melting point: 96–98° C. IR (KBr) cm$^{-1}$: 3282, 2958, 1667, 1499, 1454. 1H-NMR (CDCl$_3$) δ: 1.16 (6H, d, J=7.1 Hz), 1.34 (6H, d, J=7.1 Hz), 2.60–2.78 (8H, m), 2.84 (2H, t, J=6.8 Hz), 2.89 (2H, sept, J=7.1 Hz), 3.14 (2H, t, J=6.8 Hz) 3.20 (2H, s), 3.49 (2H, t, J=6.8 Hz), 5.31 (1H, br s), 6.65 (1H, d, J=8.3 Hz), 6.99 (1H, d, J=8.3 Hz), 7.24 (1H, td, J=8.5, 1.4 Hz), 7.28 (1H, td, J=8.5, 1.4 Hz), 7.43 (1H, dd, J=8.5, 1.4 Hz), 7.58 (1H, dd, J=8.5, 1.4 Hz), 8.70 (1H, br s).

EIMSm/z (relative intensity): 496 (M$^+$), 125 (100). Elementary analysis as C$_{27}$H$_{36}$N$_4$O$_2$S Calculated: C, 65.29; N, 7.31; N, 11.28; S, 6.46. Found: C, 64.65; N, 7.32; N, 11.16; S, 6.36.

Example 62

Preparation of 2-[4-[2-(benzoxazol-2-ylthio)ethyl]-piperazin-1-yl]-N-(2,6-diisopropyl-3-mesyloxyphenyl) acetamide:

Methanesulfonyl chloride (103 mg, 0.9 mmol) was added to a solution of 2-[4-[2-(benzoxazol-2-ylthio)ethyl] piperazin-1-yl]-N-(2,6-diisopropyl-3-hydroxyphenyl) acetamide (149 mg, 0.3 mmol) and triethylamine (91 mg, 0.9 mmol) in THF (2 ml) with ice-cooling and the mixture was stirred for 30 minutes. Then triethylamine (46 mg, 0.45 mmol) and methanesulfonyl chloride (52 mg, 0.45 mmol) were further added thereto and the mixture was stirred for 20 minutes. The reaction solution was diluted with water and extracted with ethyl acetate. The organic layer was washed with water and a saturated sodium chloride solution successively and dried over sodium sulfate and the solvent was evaporated therefrom. The residue was purified by a silica gel column chromatography (20 g of silica gel; developing solvent, chloroform:methanol=20:1) and the resulting crude crystals were recrystallized from acetone and hexane to provide 120 mg (yield 70%) of the desired compound as colorless crystals.

Melting point: 164–166° C. (decomposition) IR (KBr) cm$^{-1}$: 3433, 3273, 1668, 1455, 1450. 1H-NMR (CDCl$_3$) δ: 1.19 (6H, d, J=6.8 Hz), 1.33 (6H, d, J=7.3 Hz), 2.65–2.81 (8H, m), 2.86–2.90 (2H, m), 2.94 (1H, sept, J=6.8 Hz), 3.22 (5H, s), 3.34 (1H, sept, J=7.3 Hz), 3.51 (2H, t, J=6.7 Hz), 7.21 (1H, d, J=8.5 Hz), 7.23–7.31 (2H, m), 7.39 (1H, d, J=8.5 Hz), 7.44 (1H, m), 7.58 (1H, m), 8.72 (1H, br s).

EIMSm/z (relative intensity): 574 (M$^+$), 410 (100). Elementary analysis as C$_{28}$H$_{38}$N$_4$O$_5$S$_2$.0.2H$_2$O Calculated: C, 58.15; H, 6.69; N, 9.69; S, 11.09. Found: C, 58.18; H, 6.63; N, 9.74; S, 11.05.

Example 63

Preparation of 2-[4-[2-(benzoxazol-2-ylthio)ethyl] piperazin-1-yl]-N-(2,6-diisopropyl-3-acetyloxyphenyl) acetamide:

Acetic anhydride (2 ml) was added to a solution of 2-[4-[2-(benzoxazol-2-ylthio)ethyl]piperazin-1-yl]-N-(2, 6-d iisopropyl-3-hydroxyphenyl)acetamide (176 mg, 0.354 mmol) in pyridine (1 ml) and the mixture was stirred at room temperature for 90 minutes. The reaction solution was neutralized with an aqueous solution of sodium bicarbonate and extracted with ethyl acetate. The organic layer was washed with water and a saturated sodium chloride solution successively and dried over sodium sulfate and the solvent was evaporated therefrom. The residue was purified by a silica gel column chromatography (20 g of silica gel; developing solvent, chloroform:methanol=30:1→20:1) and the resulting crude crystals were recrystallized from acetone-hexane to provide 140 mg (yield 73%) of the desired compound as colorless needles.

Melting point: 129–131° C. IR (KBr) cm$^-$: 3436, 3291, 1760, 1665, 1499. 1H-NMR (CDCl$_3$) δ: 1.20 (6H, d, J=6.8 Hz), 1.26 (6H, d, J=7.1 Hz), 2.32 (3H,s), 2.64–2.81 (8H, m), 2.86–2.92 (2H, m), 2.95 (1H, sept, J=6.8 Hz), 3.11 (1H, sept, J=7.1 Hz), 3.22 (2H, s), 3.51 (2H, t, J=7.0 Hz), 6.98 (1H, d, J=8.5 Hz), 7.18 (1H, d, J=8.5 Hz), 7.23–7.33 (2H, m), 7.44 (1H, m), 7.59 (1H, m), 8.60 (1H, br s).

EIMSm/z (relative intensity): 538 (M$^+$), 388 (100). Elementary analysis as C$_{29}$H$_{38}$N$_4$O$_2$S.0.4H$_2$O Calculated: C, 64.02; H, 7.15; N, 10.30; S, 5.89. Found: C, 63.64; H, 7.10; N, 10.23; S, 5.92.

Example 64

Preparation of 2-[4-[2-(benzoxazol-2-ylthio)ethyl] piperazin-1-yl]-N-(2,6-diisopropyl-3-methoxyphenyl) acetamide dihydrochloride:

Sodium hydride (21 mg, 0.48 mmol) was added to a solution of 2-[4-[2-(benzoxazol-2-ylthio)ethyl]piperazin-1-yl]-N-(2,6-diisopropyl-3-hydroxyphenyl)acetamide (200 mg, 0.40 mmol) in DMF (2 ml), the mixture was stirred at 40° C. for 10 minutes and iodomethane (68 mg, 0.48 mmol) was added thereto followed by stirring for 1 hour. The reaction solution was diluted with water and extracted with ethyl acetate. The organic layer was washed with a saturated sodium chloride solution and dried over sodium sulfate and the solvent was evaporated therefrom. The residue was purified by a silica gel column chromatography (developing solvent, chloroform:methanol=50:1) to provide 47 mg (yield 23%) of 2-[4-[2-(benzoxazol-2-ylthio)ethyl]-piperazin-1-yl]-N-(2,6diisopropyl-3-methoxyphenyl)acetamide. This was made into a dihydrochloride and recrystallized to provide the desired compound as colorless powdery crystals.

Melting point: 218–222° C. IR (KBr) cm$^{-1}$: 3432, 2963, 1669, 1506, 1454. 1H-NMR (CD$_3$OD) δ: 1.17 (6H, d, J=6.8 Hz), 1.29 (6H, d, J=6.8 Hz), 2.96 (1H, sept, J=6.8 Hz), 3.17 (1H, sept, J=6.8 Hz), 3.47–3.64 (10H, m), 3.67–3.75 (2H, m), 3.81 (2H, s), 4.11 (2H, s), 6.97 (1H, d, J=8.8 Hz), 7.17 (1H, d, J=8.8 Hz), 7.28–7.37 (2H, m), 7.53–7.63 (2H, m)

EIMSm/z (relative intensity): 510 (M$^+$), 360 (100). Elementary analysis as C$_{28}$H$_{38}$N$_4$O$_3$S$_2$.2HCl.0.6H$_2$O Calculated: C, 56.58; H, 6.99; N, 9.43; Cl 11.93. Found: C, 56.88; H, 6.94; N, 9.47; Cl 11.64.

Example 65

Preparation of 2-[4-[2-(benzoxazol-2-ylthio)ethyl] piperazin-1-yl]-N-[2,6-diisopropyl-3-(2-ethoxyethyloxy) phenyl)acetamide:

2-Bromoethyl ethyl ether (2 ml) and potassium fluoride catalyst carried on alumina (40 wt %, 225 mg, 1.51 mmol) were added to a solution of 2-[4-[2-(benzoxazol-2ylthio) ethyl]piperazin-1-yl]-N-(2,6-diisopropyl-3-hydroxyphenyl) acetamide (150 mg, 0.30 mmol) in acetonitrile (3 ml) followed by stirring for 41 hours. The catalyst was filtered off and the filtrate was diluted with water and extracted with ethyl acetate. The organic layer was washed with a sodium chloride solution and dried over anhydrous sodium sulfate and the solvent was evaporated therefrom. The residue was purified by a preparative thin layer chromatography (developing solvent, chloroform:ammonia-saturated methanol=20:1) and the resulting crude crystals were recrystallized from ethyl acetate-hexane to provide 120 mg (yield 70%) of the desired compound as colorless powdery crystals.

Melting point: 100–103° C. IR (KBr) cm$^{-1}$: 3282, 2960, 1661, 1498, 1454. 1H-NMR (CDCl$_3$) δ: 1.17 (6H, d, J=6.9 Hz), 1.23 (3H, t, J=7.0 Hz), 1.32 (6H, d, J=6.9 Hz), 2.62–2.79 (8H, m), 2.86 (2H, t, J=6.2 Hz), 2.93 (1H, sept, J=6.9 Hz), 3.19 (1H, sept, J=6.9 Hz), 3.21 (2H, s), 3.50 (2H, t, J=6.2 Hz), 3.59 (2H, q, J=7.0 Hz), 3.81 (2H, t, J=5.1 Hz), 4.09 (2H, t, J=5.9 Hz), 6.83 (1H, d, J=8.7 Hz), 7.09 (1H, d, J=8.7 Hz), 7.22–7.30 (2H, m), 7.43 (1H, m), 7.58 (1H, m), 8.56 (1H, br s).

EIMSm/z (relative intensity): 568 (M$^+$), 276 (100). Elementary analysis as C$_{31}$H$_{44}$N$_4$O$_4$S Calculated: C, 65.46; H, 7.80; N, 9.85; S, 5.64. Found: C, 65.16; H, 7.75; N, 9.81; S, 5.70.

Example 66

Preparation of 2-[4-[2-(benzoxazol-2-ylthio)ethyl] piperazin-1-yl]-N-(2,6-diisopropyl-3-hydroxy-4-nitrophenyl)acetamide:

Acetyl nitrate (145 mg, 0.75 mmol) was added to a solution of 2-[4-[2-(benzoxazol-2-ylthio)ethyl]piperazin-1-yl]-N-(2,6-diisopropyl-3-hydroxyphenyl)acetamide (107 mg, 0.22 mmol) in acetonitrile (3 ml) with ice cooling followed by stirring for 10 minutes. The reaction solution was diluted with water, made alkaline by adding an aqueous solution of sodium bicarbonate thereto and extracted with chloroform twice. The organic layer was washed with a saturated sodium chloride solution and dried over anhydrous sodium sulfate and the solvent was evaporated therefrom. The residue was purified by a preparative thin layer chromatography (developing solvent, chloroform:methanol=

20:1) and the resulting crude crystals were recrystallized from chloroform-ethyl acetate-hexane to provide 60 mg (yield 51%) of the desired compound as yellow powdery crystals.

Melting point: 139–141° C. IR (KBr) cm$^{-1}$: 3256, 2962, 1690, 1480, 1454. 1H-NMR (CDCl$_3$) δ: 1.21 (6H, d, J=7.0 Hz), 1.38 (6H, d, J=7.0 Hz), 2.63–2.73 (4H, m), 2.73–2.79 (4H, m), 2.87 (4H, t, J=6.9 Hz), 2.92 (1H, sept, J=7.0 Hz), 3.20 (1H, sept, J=7.0 Hz), 3.22 (2H, s), 3.50 (2H, t, J=6.9 Hz), 7.23–7.32 (2H, m), 7.44 (1H, m), 7.58 (1H, m), 7.93 (1H, s), 8.83 (1H, br s), 11.10 (1H, br s).

EIMSm/z (relative intensity): 541 (M$^+$), 377 (100). Elementary analysis as C$_{27}$H$_{35}$N$_5$O$_5$S Calculated: C, 59.87; H, 6.51; N, 12.93; S, 5.92. Found: C, 59.81; H, 6.64; N, 12.94; S, 5.84.

Example 67

Preparation of 2-[4-[3-(benzoxazol-2-ylthio)propyl] piperazin-1-yl]-N-(2,6-diisopropyl-3-nitrophenyl) acetamide:

Potassium carbonate (226 mg, 1.63 mmol) was added to a solution of 1-[3-(benzoxazol-2-ylthio)propyl]piperazine ditrifluoroacetate (206 mg, 0.41 mmol) and N-(2,6-diisopropyl-3-nitrophenyl)-2-bromoacetamide (140 mg, 0.41 mmol) in acetonitrile (5 ml) followed by stirring for 2 hours. The reaction solution was diluted with water and extracted with ethylacetate. The organic layer was washed with a saturated sodium chloride solution and dried over anhydrous sodium sulfate and the solvent was evaporated therefrom. The resulting crude crystals were recrystallized from ethyl acetate-hexane to provide 179 mg (yield 81%) of the desired product as colorless powdery crystals.

Melting point: 156–158° C. IR (KBr) cm$^{-1}$: 3277, 2936, 1665, 1499, 1455. 1H-NMR (CDCl$_3$) δ: 1.21 (6H, d, J=6.9 Hz), 1.32 (6H, d, J=6.9 Hz), 2.05 (2H, quint, J=6.9 Hz), 2.51–2.62 (4H, m), 2.55 (2H, t, J=6.9 Hz), 2.73–2.79 (4H, m), 2.99 (1H, sept, J=6.9 Hz), 3.24 (2H, s), 3.25 (1H, sept, J=6.9 Hz), 3.38 (2H, t, J=6.9 Hz), 7.24–7.31 (2H, m), 7.30 (1H, d, J=8.7 Hz), 7.43 (1H, m), 7.47 (1H, d, J=8.7 Hz), 7.58 (1H, m), 8.83 (1H, br s).

EIMSm/z (relative intensity): 539 (M$^+$), 193 (100). Elementary analysis as C$_{28}$H$_{37}$N$_5$O$_4$S Calculated: C, 62.31; H, 6.91; N, 12.98. Found: C, 62.23; H, 6.94; N, 12.85.

Example 68

Preparation of 2-[4-[3-(benzoxazol-2-ylthio)propyl] piperazin-1-yl]-N-[2,6-diisopropyl-3-(methylthio)phenyl] acetamide:

The same reaction and treatment as in Example 60 were conducted using N-[3-amino-2,6-diisopropylphenyl]-2-[4-(3hydroxypropyl)piperazin-1-yl]acetamide instead of N-[3-amino-2,6-diisopropylphenyl]-2-[4-(2-hydroxyethyl) piperazin-1-yl]acetamide to provide the desired compound as pale yellow powdery crystals.

Melting point: 126–127° C. IR (KBr) cm$^{-1}$: 3271, 2961, 1662, 1499, 1454. 1H-NMR (CDCl$_3$) δ: 1.13–1.22 (6H, m), 1.30–1.39 (6H, m), 2.04 (2H, quint, J=6.9 Hz), 2.43 (3H, s), 2.51–2.57 (4H, m), 2.54 (2H, t, J=6.9 Hz), 2.72–2.80 (5H, m), 2.93 (1H, sept, J=6.9 Hz), 3.21 (2H, s), 3.38 (2H, t, J=6.9 Hz), 7.16–7.31 (4H, m), 7.43 (1H, m), 7.59 (1H, m), 8.76 (1H, br s).

EIMSm/z (relative intensity): 540 (M$^+$), 70 (100). Elementary analysis as C$_{29}$H$_{40}$N$_4$O$_2$S$_2$ Calculated: C, 64.41; H, 7.46; N, 10.36. Found: C, 64.46; H, 7.48; N, 10.55.

Example 69

Preparation of 2-[4-[3-(benzoxazol-2-ylthio)propyl] piperazin-1-yl]-N-(2,6-diisopropyl-3-hydroxy)phenyl] acetamide:

The same reaction and treatment as in Example 61 were conducted using 2-[4-(3-benzoxazole-2-ylthio) propyl] piperazin-1-yl]-N-(2,6-diisopropyl-3-nitrophenyl) acetamide instead of 2-[4-[2-benzoxazole-2-ylthio)ethyl] piperazin-1-yl]-N-(2,6-diisopropyl-3-nitrophenyl] acetamide to provide the desired compound as colorless powdery crystals.

Melting point: 176–178° C. IR (KBr) cm$^{-1}$: 3263, 2960, 1665, 1496, 1454. 1H-NMR (CDCl$_3$) δ: 1.16 (6H, d, J=6.9 Hz), 1.34 (6H, d, J=6.9 Hz), 2.05 (2H, quint, J=6.9 Hz), 2.51–2.60 (4H, m), 2.54 (2H, t, J=6.9 Hz), 2.70–2.77 (4H, m), 2.91 (1H, sept, J=6.9 Hz), 3.16 (1H, sept, J=6.9 Hz), 3.21 (2H, s), 3.38 (2H, t, J=6.9 Hz), 4.80 (1H, br s), 6.66 (1H, d, J=8.4 Hz), 7.01 (1H, d, J=8.4 Hz), 7.22–7.30 (2H, m), 7.43 (1H, m), 7.59 (1H, m) 8.60 (1H, br s).

EIMSm/z (relative intensity): 510 (M$^+$), 70 (100). Elementary analysis as C$_{28}$H$_{38}$N$_4$O$_3$S Calculated: C, 65.85; H, 7.50; N, 10.97. Found: C, 65.66; H, 7.52; N, 10.80.

Example 70

Preparation of 2-[4-[3-(benzoxazol-2-ylthio)propyl] piperazin-1-yl]-N-(2,6-diisopropyl-3-methoxyphenyl) acetamide:

2-[4-[3-(Benzoxazol-2-ylthio)propyl]piperazin-1-yl]-N-(2,6-diisopropyl-3-hydroxyphenyl)acetamide (150 mg, 0.29 mmol) was dissolved in methanol (2 ml) and acetonitrile (3 ml), then N,N-diisopropylethylamine (227 mg, 1.76 mmol) and a solution of trimethylsilyl diazomethane in hexane (2.0M, 0.88 ml, 1.76 mmol) were added thereto and the mixture was stirred for 14 hours. The reaction solution was concentrated, made alkaline with an aqueous solution of sodium bicarbonate and extracted with ethyl acetate. The organic layer was washed with water and a saturated sodium chloride solution successively and dried over anhydrous sodium sulfate and the solvent was evaporated therefrom. The residue was purified by a silica gel column chromatography (developing solvent, hexane:acetone=7:3) and the resulting crude crystals were recrystallized from ethyl acetate and hexane to provide 31 mg (yield 20%) of the desired compound as colorless powdery crystals.

Melting point: 105–107° C. IR (KBr) cm$^{-1}$: 3289, 2959, 1663, 1501, 1454. 1H-NMR (CDCl$_3$) δ: 1.17 (6H, d, J=6.9 Hz), 1.29 (6H, d, J=6.9 Hz), 2.04 (2H, quint, J=6.9 Hz), 2.51–2.59 (4H, m), 2.54 (2H, t, J=6.9 Hz), 2.71–2.78 (4H, m), 2.92 (1H, sept, J=6.9 Hz), 3.19 (1H, sept, J=6.9 Hz), 3.21 (2H, s), 3.38 (2H, t, J=6.9 Hz), 3.80 (3H, s), 6.84 (1H, d, J=8.6 Hz), 7.12 (1H, d, J=8.6 Hz), 7.22–7.31 (2H, m), 7.43 (1H, m), 7.59 (1H, m), 8.60 (1H, br s).

EIMSm/z (relative intensity): 524 (M$^+$), 290 (100).

Example 71

Preparation of 2-[4-[3-(benzoxazol-2-ylthio)propyl] piperazin-1-yl]-N-[2,6-diisopropyl-3-(2-ethoxyethyloxy) phenyl]acetamide:

To a solution of N-(2,6-diisopropyl-3hydroxyphenyl)-2-[4-(3-hydroxypropyl) piperazin-1-yl]acetamide (180 mg, 0.61 mmol) in DMF (3 ml) were added 2-bromoethyl ethyl ether (2 ml) and potassium fluoride catalyst carried on alumina (40 wt %, 355 mg, 2.39 mmol) followed by stirring at 50° C. for 3 hours. After the catalyst was filtered off, the filtrate was diluted with water and extracted with ethyl acetate. The organic layer was washed with a saturated sodium chloride solution and dried over anhydrous sodium sulfate and the solvent was evaporated therefrom. The residue was purified by a silica gel column chromatography (developing solvent, chloroform:methanol=20:1) to provide 90 mg (yield 42%) of N-(2,6-diisopropyl-3-(2-ethoxyethyloxy)phenyl)-2-[4-(3-hydroxypropyl)piperazin-1-yl]acetamide as colorless powdery crystals.

After that, the same reaction and treatment as Example 1 were conducted using N-(2,6-diisopropyl-3-(2-ethoxyethyloxy)phenyl)-2-[4-(3-hydroxypropyl)piperazin-1-yl]acetamide instead of N-(2,6-diisopropylphenyl)-2[4-(2-hydroxyethyl)piperazin-1-yl]acetamide to provide a desired compound as colorless powdery crystals.

Melting point: 99–100° C. IR (KBr) cm$^{-1}$: 3267, 2962, 1664, 1501, 1455. 1H-NMR (CDCl$_3$) δ: 1.17 (6H, d, J=6.9 Hz), 1.23 (3H, t, J=7.0 Hz), 1.32 (6H, d, J=6.9 Hz), 2.04 (2H, quint, J=6.9 Hz), 2.51–2.59 (4H, m), 2.54 (2H, t, J=6.9 Hz), 2.70–2.77 (4H, m), 2.91 (1H, sept, J=6.9 Hz), 3.16 (1H, sept, J=6.9 Hz), 3.21 (2H, s), 3.38 (2H, t, J=7.0 Hz), 3.59 (2H, q, J=7.0 Hz), 3.81 (2H, t, J=5.1 Hz), 4.09 (2H, t, J=5.1 Hz), 6.83 (1H, d, J=8.8 Hz), 7.09 (1H, d, J=8.8 Hz), 7.22–7.31 (2H, m), 7.43 (1H, m), 7.59 (1H, m), 8.59 (1H, br s).

EIMSm/z (relative intensity): 582 (M$^+$), 139 (100).

Example 72

Preparation of 2-[4-[2-(benzoxazol-2-ylthio)ethyl]piperazin-1-yl]-N-(2,6-diisopropyl-4-hydroxyphenyl)acetamide:

To a solution of sodium carbonate (51 mg, 0.5 mmol) in water (1 ml) was added sulfanilic acid (167 mg, 1.0 mmol), the mixture was heated to dissolve, then sodium nitrite (73 mg, 1.1 mmol) was added with ice cooling and concentrated hydrochloric acid (0.25 ml) was dropped thereinto to provide a colorless suspension.

3,5-Diisopropylphenol (172 mg, 1.0 mmol) was added to a solution of sodium hydroxide (212 mg, 5.5 mmol) in water (1.2 ml), the mixture was heated to dissolve, the previously-prepared suspension was slowly dropped thereinto with ice cooling and the mixture was stirred at room temperature for 2 hours. Sodium hydrosulfite was added thereto at 50° C. until the red color of the reaction solution almost disappeared and stirred at 80° C. for 2 hours. The reaction mixture was allowed to cool and the separated matter was collected by filtration and dried by heating in vacuo to provide 107 mg (yield 58%) of 4-amino-3,5-diisopropylphenol as purple needles.

Then the same reaction and treatment as in Example 48 were conducted using 4-amino-3,5-diisopropylphenol instead of 2,4,6-triisopropylaniline to provide the desired compound as colorless needles.

Melting point: 162–164° C. IR (KBr) cm$^{-1}$: 3307, 2961, 1665, 1499, 1455. 1H-NMR (CDCl$_3$) δ: 1.17 (12H, d, J=6.8 Hz), 2.60–2.76 (8H, m), 2.85 (2H, t, J=6.8 Hz), 2.93 (2H, sept, J=6.8 Hz), 3.20 (2H,s), 3.49 (2H, t, J=6.8 Hz), 5.59 (1H, br s), 6.62 (2H, s), 7.22–7.31 (2H, m), 7.44 (1H, m), 7.58 (1H, m), 8.47 (1H, br s).

EIMSm/z (relative intensity): 496 (M$^+$), 97 (100). Elementary analysis as C$_{27}$H$_{36}$N$_4$O$_3$S Calculated: C, 65.29; H, 7.31; N, 11.28; S, 6.46. Found: C, 65.35; H, 7.42; N, 11.12; S, 6.41.

Example 73

Preparation of 2-[4-[2-(benzoxazol-2-ylthio)ethyl]piperazin-1-yl]-N-(4-acetoxy-2,6-diisopropylphenyl)acetamide:

Acetic anhydride (2 ml) was dropped into a solution of 2-[4-[2-(benzoxazol-2-ylthio)ethyl]piperazin-1-yl]-N-(2,6-diisopropyl-4-hydroxyphenyl)acetamide (149 mg, 0.3 mmol) in pyridine (1 ml) with ice cooling and the mixture was stirred at room temperature for 3 hours. The reaction solution was neutralized by adding a saturated aqueous solution of sodium bicarbonate thereto and extracted with ethyl acetate. The organic layer was washed with water and a saturated sodium chloride solution successively and dried over sodium sulfate and the solvent was evaporated therefrom. The residue was purified by a silica gel column chromatography (developing solvent, chloroform:methanol=20:1) to provide 166 mg (yield 100%) of the desired compound as colorless needles.

Melting point: 126–129° C. IR (KBr) cm$^{-1}$: 3440, 3275, 1762, 1664, 1498. 1H-NMR (CDCl$_3$) δ: 1.20 (12H, d, J=6.8 Hz), 2.30 (3H, s), 2.60–2.78 (8H, m), 2.86 (2H, t, J=6.8 Hz), 2.99 (2H, sept, J=6.8 Hz), 3.22 (2H, s), 3.49 (2H, t, J=6.8 Hz), 6.89 (2H, s), 7.22–7.31 (2H, m), 7.44 (1H, m), 7.59 (1H, m), 8.60 (1H, br s).

EIMSm/z (relative intensity): 538 (M$^+$), 276 (100). Elementary analysis as C$_{29}$H$_{38}$N$_4$O$_4$S.0.2H$_2$O Calculated: C, 64.23; H, 7.14; N, 10.33. Found: C, 64.22; H, 7.08; N, 10.27.

Example 74

Preparation of 2-[4-[2-(benzoxazol-2-ylthio)ethyl]piperazin-1-yl]-N-(2,6-diisopropyl-4-mesyloxyphenyl)acetamide:

Triethylamine (30 mg, 0.3 mmol) was added to a solution of 2-[4-[2-(benzoxazol-2-ylthio)ethyl]piperazin-1-yl]-N-(2,6-diisopropyl-4-hydroxyphenyl)acetamide (50 mg, 0.1 mmol) in THF (1 ml), then methanesulfonyl chloride (34 mg, 0.3 mmol) was dropped thereinto with ice cooling and the mixture was stirred at room temperature for 2 hours. The reaction solution was diluted with water and extracted with ethyl acetate. The organic layer was washed with water and a saturated sodium chloride solution successively and dried over sodium sulfate and the solvent was evaporated therefrom. The residue was purified by a preparative thin layer chromatography (developing solvent, chloroform:methanol=19:1) to provide 47 mg (yield 82%) of the desired compound as colorless needles.

Melting point: 115–117° C. IR (KBr) cm$^{-1}$: 3436, 3222, 1666, 1497, 1367. 1H-NMR (CDCl$_3$) δ: 1.21 (12H, d, J=6.8 Hz), 2.60–2.77 (8H, m), 2.85 (2H, t, J=6.8 Hz), 3.00 (2H, sept, J=6.8 Hz), 3.14 (3H, s), 3.22 (2H, s), 3.49 (2H, t, J=6.8 Hz), 7.08 (2H, s), 7.22–7.31 (2H, m), 7.44 (1H, m), 7.59 (1H, m), 8.63 (1H, br s).

EIMSm/z (relative intensity): 574 (M$^+$), 125 (100). Elementary analysis as C$_{21}$H$_{38}$N$_4$O$_5$S$_2$.0.3H$_2$O Calculated: C, 57.97; H, 6.71; N, 9.66. Found: C, 58.06; H, 6.63; N, 9.56.

Example 75

Preparation of 2-[4-[2-(benzoxazol-2-ylthio)ethyl]piperazin-1-yl]-N-(2,6-diisopropyl-4-methoxyphenyl)acetamide:

Sodium hydride (7 mg, 0.3 mmol) was added to a solution of 2-[4-[2-(benzoxazol-2-ylthio)ethyl]piperazin-1-yl]-N-(2, 6-diisopropyl-4-hydroxyphenyl)acetamide (99 mg, 0.2 mmol) in DMF (2 ml), the mixture was heated at 60° C. for 10 minutes, and iodomethane (43 mg, 0.3 mmol) was dropped thereinto followed stirring for 30 minutes. The reaction solution was diluted with water and extracted with ethyl acetate. The organic layer was washed with water and a saturated sodium chloride solution successively and dried over sodium sulfate and the solvent was evaporated therefrom. The residue was purified by a preparative thin layer chromatography (developing solvent, hexane:acetone 5:3) to provide 44 mg (yield 43%) of the desired compound as colorless needles.

Melting point: 115–117° C. IR (KBr) cm$^{-1}$: 3432, 3238, 1662, 1500, 1455. 1H-NMR (CDCl$_3$) δ: 1.20 (12H, d, J=6.8 Hz), 2.60–2.78 (8H, m), 2.86 (2H, t, J=6.8 Hz), 2.97 (2H, sept, J=6.8 Hz), 3.21 (2H, s), 3.50 (2H, t, J=6.8 Hz), 3.81 (3H, s), 6.71 (2H, s), 7.22–7.31 (2H, m), 7.44 (1H, m), 7.58 (1H, m), 8.45 (1H, br s).

EIMSm/z (relative intensity): 510 (M$^+$), 276 (100). Elementary analysis as C$_{21}$H$_{38}$N$_4$O$_3$S Calculated: C, 65.85; H, 7.50; N, 10.97; S, 6.28. Found: C, 65.80; H, 7.63; N, 10.71; S, 6.05.

Example 76

Preparation of 2-[4-[2-(benzoxazol-2-ylthio)ethyl]piperazin-1-yl]-N-(4-diethoxyphosphoryloxy-2,6-diisopropylphenyl)acetamide:

The same reaction and treatment as in Example 75 were conducted using diethylphosphoric chloride instead of iodomethane to provide the desired compound as colorless needles.

Melting point: 108–109° C. IR (KBr) cm$^{-1}$: 3440, 3276, 1673, 1497, 1455. 1H-NMR (CDCl$_3$) δ: 1.19 (12H, d, J=6.8 Hz), 1.36 (6H, m), 2.60–2.78 (8H, m), 2.85 (2H, t, J=6.8 Hz), 2.97,(2H, sept, J=6.8 Hz), 3.21 (2H, s), 3.49 (2H, t, J=6.8 Hz), 4.22 (4H, m), 7.02 (2H, s), 7.22–7.31 (2H, m), 7.44 (1H, m), 7.58 (1H, m), 8.53 (1H, br s).

EIMSm/z (relative intensity): 632 (M$^+$), 482 (100). Elementary analysis as C$_{31}$H$_{45}$N$_4$O$_6$PS Calculated: C, 58.84; H, 7.17; N, 8.85. Found: C, 59.00; H, 7.22; N, 8.79.

Example 77

Preparation of 2-[4-[2-(benzoxazol-2-ylthio)ethyl]piperazin-1-yl]-N-[2,6-diisopropyl-4-ethoxycarbonylmethyloxyphenyl)acetamide:

The same reaction and treatment as in Example 75 were conducted using bromoethylacetate instead of iodomethane to provide the desired compound as colorless needles.

Melting point: 118–120° C. IR (KBr) cm$^{-1}$: 3330, 2939, 1766, 1662, 1499. 1H-NMR (CDCl$_3$) δ: 1.18 (12H, d, J=6.8 Hz), 1.32 (3H, t, J=7.2 Hz), 2.60–2.78 (8H, m), 2.84 (2H, t, J=6.8 Hz), 2.97 (2H,sept, J=6.8 Hz), 3.20 (2H, s), 3.49 (2H, t, J=6.8 Hz), 4.29 (2H, q, J=7.2 Hz), 4.61 (2H, s), 6.73 (2H, s), 7.22–7.31 (2H, m), 7.44 (1H, m), 7.58 (1H, m), 8.48 (1H, br s).

EIMSm/z (relative intensity): 582 (M$^+$), 363 (100). Elementary analysis as C$_{31}$H$_{42}$N$_4$O$_5$S Calculated: C, 63.89; H, 7.26; N, 9.61;,S, 5.50. Found: C, 63.94; H, 7.33; N, 9.57; S, 5.54.

Example 78

Preparation of 2-[4-[2-(benzoxazol-2-ylthio)ethyl]piperazin-1-yl]-N-[2,6-diisopropyl-4-(2-ethoxyethyl)oxyphenyl)acetamide:

The same reaction and treatment as in Example 75 were conducted using chloroethyl ethyl ether instead of iodomethane to provide the desired compound as colorless needles.

Melting point: 92–95° C. IR (KBr) cm$^{-1}$: 3429, 3296, 1664, 1501, 1455. 1H-NMR (CDCl$_3$) δ: 1.18 (12H, d, J=6.8 Hz), 1.25 (3H, t, J=7.0 Hz), 2.60–2.78 (8H, m), 2.85 (2H, t, J=6.8 Hz), 2.96 (2H, sept, J=6.8 Hz), 3.20 (2H, s), 3.49 (2H, t, J=6.8 Hz), 3.61 (2H, q, J=7.0 Hz), 3.79 (2H, t, J=5.5 Hz), 4.13 (2H, t, J=5.5 Hz), 6.74 (2H, s), 7.22–7.31 (2H, m), 7.44 (1H, m), 7.58 (1H, m), 8.46 (1H, br s).

EIMSm/z (relative intensity): 568 (M$^+$), 405 (100). Elementary analysis as C$_{31}$H$_{44}$N$_4$O$_4$S Calculated: C, 65.46; H, 7.80; N, 9.85; S, 5.64. Found: C, 65.42; H, 7.75; N, 9.73; S, 5.68.

Example 79

Preparation of N-[2-[4-[2-(benzoxazol-2-ylthio)-ethyl]piperazin-1-yl]ethyl]-N'-(2,6-diisopropylphenyl)urea:

To a solution of 1-(2-hydroxyethyl)piperazine (2.60 g, 20 mmol) in acetonitrile (35 ml) was added potassium carbonate (3.04 g, 22 mmol) and chloroacetonitrile (1.51 g, 20 mmol) was dropped thereinto with ice cooling. The mixture was stirred at room temperature for 30 minutes and then stirred at 45° C. for 30 minutes. This reaction mixture was filtered off, the filtrate was concentrated in vacuo and the residue was purified by a silica gel column chromatography (100 g of silica gel; developing solvent, chloroform:ammonia-saturated methanol=20:1→10:1) to provide 3.20 g (yield 95%) of 4-(cyanomethyl)piperazine-1-ethanol.

A solution of 4-(cyanomethyl)piperazine-1-ethanol (1.69 g, 10 mmol) in THF (20 ml) was added to a solution of lithium aluminum hydride in THF (20 ml, 20 mmol) in an argon stream with ice cooling, the mixture was stirred at room temperature for 5 minutes and heated to reflux for 90 minutes. The reaction solution was allowed to cool, diluted with ethanol with ice cooling and stirred at room temperature for 15 minutes after adding an aqueous 1N sodium hydroxide solution thereto. This was filtered off through celite and the filtrate was concentrated in vacuo to provide 4-(aminoethyl)piperazine-1-ethanol.

Into a solution of 4-(aminoethyl)piperazine-1-ethanol in chloroform (20 ml) was dropped a solution of 2,6-diisopropylphenyl isocyanate (2.03 g, 10 mmol) in chloroform (20 ml) followed by stirring for 5 minutes. The reaction solution was concentrated in vacuo and the residue was purified by a silica gel column chromatography (100 g of silica gel; developing solvents, chloroform→chloroform:ammonia-saturated methanol =20:1) to provide 2.03 g (yield 54%) of N-[2-[4-(2-hydroxyethyl)piperazin-1-yl]ethyl]-N'-(2,6-diisopropylphenyl)urea.

Then the same reaction and treatment as in Example 1 were conducted using N-[2-[4-(2-hydroxyethyl)-piperazin-1-yl]ethyl]-N'-(2,6-diisopropylphenyl)urea instead of N-(2,6-diisopropylphenyl)-2-[4-(2-hydroxyethyl)-piperazin-1-yl]acetamide to provide the desired compound as colorless needles.

Melting point: 152–153° C. IR (KBr) cm$^{-1}$: 3345, 3276, 1633, 1500. 1H-NMR (CDCl$_3$) δ: 1.19 (12H, d, J=6.8 Hz), 2.22–2.38 (10H, m), 2.70 (2H, t, J=7.1 Hz), 3.25 (2H, q, J=5.6 Hz), 3.30 (2H, sept, J=6.8 Hz), 3.41 (2H, t, J=7.1 Hz), 4.90 (1H, t, J=5.6 Hz), 5.68 (1H, br s), 7.19–7.35 (5H, m), 7.43 (1H, m), 7.59 (1H, m).

EIMSm/z (relative intensity): 509 (M$^+$), 227 (100). Elementary analysis as $C_{21}H_{39}N_5O_2S$ Calculated: C, 65.98; H, 7.71; N, 13.74; S, 6.29. Found: C, 65.98; H, 7.63; N, 13.60; S, 6.24.

Example 80

Preparation of N-[2-[4-[2-(benzimidazol-2-ylthio)ethyl]piperazin-1-yl]ethyl]-N'-(2,6-diisopropylphenyl)urea:

The same reaction and treatment as in Example 79 were conducted using 2-mercaptobenzimidazole instead of 2-mercaptobenzooxazole to provide the desired compound as colorless crystals.

Melting point: 120–122° C. IR (KBr) cm$^{-1}$: 3329, 3280, 1632, 1567. 1H-NMR (CDCl$_3$) δ: 1.20 (12H, d, J=6.1 Hz), 2.49–2.53 (10H, m), 2.86–2.89 (2H, m), 3.11–3.15 (2H, m), 3.24–3.39 (4H, m), 4.81 (1H, t, J=5.0 Hz), 5.70 (1H, br s), 7.14–7.20 (2H, m), 7.23 (1H, d, J=8.6 Hz), 7.23 (1H, d, J=6.8 Hz), 7.35 (1H, dd, J=8.6, 6.8 Hz), 7.43–7.56 (2H, m).

EIMSm/z (relative intensity): 508 (M$^+$), 156 (100). Elementary analysis as $C_{28}H_{40}N_6OS$ Calculated: C, 66.11; H, 7.92; N, 16.52; S, 6.30. Found: C, 65.87; H, 8.02; N, 16.32; S, 6.26.

Example 81

Preparation of N-[2-[4-[2-(benzothiazole-2-ylthio)ethyl]piperazin-1-yl]ethyl]-N'-(2,6-diisopropylphenyl)urea:

The same reaction and treatment as in Example 79 were conducted using 2-mercaptobenzothiazole instead of 2-mercaptobenzooxazole to provide the desired compound as colorless needles.

Melting point: 147–149° C. IR (KBr) cm$^{-1}$: 3327, 3260, 1632, 1567. 1H-NMR (CDCl$_3$) δ: 1.18 (12H, d, J=6.8 Hz), 2.25–2.38 (10H, m), 2.70 (2H, d, J=7.1 Hz), 3.25 (2H, q, J=5.9 Hz), 3.30 (2H, sept, J=6.8 Hz), 3.46 (2H, t, J=7.1 Hz), 4.91 (1H, t, 5.9 Hz), 5.67 (1H, br s), 7.20 (1H, d, J=8.4 Hz), 7.20 (1H, d, J=7.3 Hz), 7.26–7.34 (2H, m), 7.42 (1H, td, J=8.1, 0.8 Hz), 7.76 (1H, dd, J=8.1, 0.8 Hz), 7.86 (1H, dd, J=8.1, 0.8 Hz).

EIMSm/z (relative intensity): 525 (M$^+$), 293 (100). Elementary analysis as $C_{28}H_{39}N_5OS_2$ Calculated: C, 63.96; H, 7.48; N, 13.32; S, 12.20. Found: C, 63.82; H, 7.51; N, 13.14; S, 12.27.

Example 82

Preparation of N-[2-[4-[2-(7-methoxycarbonylbenzoxazol-2-ylthio)ethyl]piperazin-1-yl]ethyl]-N'-(2,6-diisopropylphenyl)urea:

The same reaction and treatment as in Example 79 were conducted using 7-methoxycarbonyl-2-mercaptobenzooxazole instead of 2-mercaptobenzooxazole to provide the desired compound as colorless crystals.

Melting point: 186–188° C. IR (KBr) cm$^{-1}$: 3414, 3349, 1718, 1668, 1508. 1H-NMR (CDCl$_3$) δ: 1.18 (12H, d, J=6.8 Hz), 2.24–2.37 (10H, m), 2.72 (2H, t, J=7.0 Hz), 3.25 (2H, q, J=5.4 Hz), 3.30 (2H, sept, J=6.8 Hz), 3.44 (2H, t, J=7.0 Hz), 3.99 (3H, s), 4.88 (1H, t, J=5.4 Hz), 5.67 (1H, br s), 7.20 (1H, d, J=7.1 Hz), 7.20 (1H, d, J=8.3 Hz), 7.32 (1H, dd, J=8.3, 7.1 Hz), 7.35 (1H, t, J=7.8 Hz), 7.77 (1H, dd, J=7.8, 1.2 Hz), 7.88 (1H, dd, J=7.8, 1.2 Hz).

EIMSm/z (relative intensity): 567 (M$^+$), 146 (100). Elementary analysis as $C_{30}H_{41}N_5O_4S$ Calculated: C, 63.47; H, 7.28; N, 12.34; S, 5.65. Found: C, 63.53; H, 7.25; N, 12.10; S, 5.59.

Example 83

Preparation of N-[2-[4-[2-(oxazolo[4,5-b]pyridine-2-ylthio)ethyl]piperazin-1-yl]ethyl]-N'-(2,6-diisopropylphenyl)urea:

The same reaction and treatment as in Example 79 were conducted using 2-mercaptooxazolo[4,5-b]pyridine instead of 2-mercaptobenzooxazole to provide the desired compound as colorless needles.

Melting point: 175–176° C. IR (KBr) cm$^{-1}$: 3385, 3313, 1660, 1541. 1H-NMR (CDCl$_3$) δ: 1.19 (12H, d, J=6.8 Hz), 2.25–2.38 (10H, m), 2.73 (2H, t, J=7.1 Hz), 3.25 (2H, q, J=6.1 Hz), 3.30 (2H, sept, J=6.08 Hz), 3.49 (2H, t, J=7.1 Hz), 4.90 (1H, t, J=6.1 Hz), 5.69 (1H, br s), 7.18 (1H, dd, J=8.1, 4.9 Hz), 7.21 (1H, d, J=8.6 Hz), 7.21 (1H, d, J=6.8 Hz), 7.33 (1H, dd, J=8.6, 6.8 Hz), 7.69 (1H, dd, J=8.1, 1.5 Hz), 8.46 (1H, dd, J=4.9, 1.5 Hz).

EIMSm/z (relative intensity): 510 (M$^+$), 97 (100). Elementary analysis as $C_{27}H_{31}N_6O_2S$ Calculated: C, 63.50; H, 7.50; N, 16.46; S, 6.28. Found: C, 63.63; H, 7.50; N, 16.16; S, 6.21.

Example 84

Preparation of 4-[4-[2-(benzoxazol-2-ylthio)ethyl]piperazin-1-yl]ethyl]-N-(2,6-diisopropylphenyl)butyramide:

To a solution of 2,6-diisopropylaniline (1.77 g, 10 mmol) in chloroform (30 ml) was added triethylamine (1.11 g, 11 mmole), then 4-bromobutyryl bromide (1.95 mg, 10.5 mmol) was slowly dropped thereinto with ice cooling and the mixture was made to react for 20 minutes. The reaction solution was diluted with water and extracted with chloroform. The organic layer was washed with 0.5N HCl, water, aqueous solution of sodium bicarbonate and saturated sodium chloride solution successively and dried over magnesium sulfate and the solvent was evaporated therefrom. The residue was purified by a silica gel column chromatography (120 g of silica gel; developing solvent, hexane:acetone=7:1→5:1) and the resulting crude crystals were recrystallized from hexane-acetone to provide 2.06 g (yield 63%) of 4-bromo-N-(2,6-diisopropylphenyl)butyramide as colorless needles.

Potassium carbonate (1.11 g, 8 mmol) was added to a solution of the amide (655 mg, 2 mmol) and 1-[2-(benzoxazol-2-ylthio)ethyl]piperazine ditrifluoroacetate (983 mg, 2 mmol) in acetonitrile (15 ml) and the mixture was stirred at room temperature for 7 hours. The reaction solution was filtered and the filtrate was concentrated in vacuo. The residue was diluted with ethylacetate. The organic layer was washed with water and a saturated sodium chloride solution successively and dried over sodium sulfate and the solvent was evaporated therefrom. The residue was purified by a silica gel column chromatography (75 g of silica gel; developing solvents, chloroform:methanol=25:1→chloroform:ammonia-saturated methanol=10:1) and the resulting crude crystals were recrystallized from acetone-ether-hexane to provide 117 mg (yield 12%) of the desired compound as colorless crystals.

Melting point: 134–136° C. IR (KBr) cm$^{-1}$: 3432, 3290, 1652, 1500. 1H-NMR (CDCl$_3$) δ: 1.12 (12H, d, J=6.8 Hz), 1.77–1.82 (2H, m), 2.34–2.41 (6H, m), 2.50–2.52 (6H, m), 2.75 (2H, t, J=6.8 Hz), 3.08 (2H, sept, J=6.8 Hz), 3.46 (2H, t, J=6.8 Hz), 7.10 (2H, d, J=7.6 Hz), 7.20 (1H, t, J=7.6 Hz), 7.25–7.32 (2H, m), 7.53–7.58 (2H, m), 8.72 (1H, br s).

EIMSm/z (relative intensity): 508 (M⁺, 100). Elementary analysis as $C_{29}H_{40}N_4O_2S$ Calculated: C, 68.47; H, 7.92; N, 11.01; S, 6.30. Found: C, 68.31; H, 8.03; N, 11.25; S, 6.26.

Example 85

Preparation of 2-[4-[2-(7-trifluoromethylbenzoxazol-2-ylthio)ethyl]piperazin-1-yl]-N-(2,6-diisopropylphenyl)acetamide:

Acetyl nitrate obtained mixing acetyl anhydride (3.30 g, 33 mmol) with fuming nitric acid (2.05 g, 33 mmol) at 0° C. was dropped into a solution of 2-trifluoromethylphenol (4.86 mg, 30 mmol) in acetonitrile (60 ml) at 0° C. followed by stirring for 10 minutes. The reaction solution was diluted with water and extracted with ether. The organic layer was washed with water and a saturated sodium chloride solution successively and dried and the solvent was evaporated therefrom. The residue was purified by a silica gel column chromatography (60 g of silica gel; developing solvent, hexane:methylene chloride=5:1) to provide 2.1 g (yield 33%) of 2-nitro-6-trifluoromethylphenol as pale yellow crystals.

A 10% palladium carbon catalyst (1.0 g) was added to a solution of the resulting nitro compound (2.0 g, 9.65 mmol) in ethanol (60 ml) and the mixture was stirred under hydrogen atmosphere at room temperature for 5 hours. After completion of the reaction, the reaction solution was filtered off through celite and the filtrate was concentrated to provide 1.70 g (yield 99%) of 2-amino-6-trifluoromethylphenol as pale yellow crystals.

O-Ethyl potassium dithiocarbonate (1.68 g, 11 mmol) was added to a solution of the aminophenol (1.70 g, 11 mmol) in ethanol (30 ml), the mixture was heated to reflux for 16 hours and the solvent was evaporated therefrom. The residue was dissolved in water, the solution was adjusted to pH, 3–4 by adding 2N hydrochloric acid thereto and extracted with ethyl acetate. The organic layer was washed with water and a saturated sodium chloride solution successively and dried over anhydrous magnesium sulfate and the solvent was evaporated therefrom. The residue was purified by a silica gel column chromatography (60 g of silica gel; developing solvents, hexane:acetone=5:1) to provide 1.78 g (yield 81%) of 2-mercapto-7-trifluoromethylbenzoxazole as pale brown crystals.

The same reaction and treatment as in Example 1 were conducted using 2-mercapto-7-trifluoromethylbenzoxazole instead of 2-mercaptobenzooxazole to provide the desired compound as colorless needles.

Melting point: 135–137° C. (decomposition) IR (KBr) cm⁻¹: 3433, 3229, 1664, 1505. 1H-NMR (CDCl₃) δ: 1.21 (12H, d, J=6.8 Hz), 2.64–2.68 (4H, m), 2.71–2.75 (4H, m), 2.86 (2H, t, J=6.8 Hz), 3.00 (2H, sept, J=6.8 Hz), 3.21 (2H, s), 3.50 (2H, t, J=6.8 Hz), 7.18 (1H, d, J=8.3 Hz), 7.18 (1H, d, J=7.1 Hz), 7.29 (1H, dd, J=8.3, 7.1 Hz), 7.38 (1H, t, J=7.8 Hz), 7.48 (1H, d, J=7.8 Hz), 7.76 (1H, d, J=7.8 Hz), 8.59 (1H, br s).

EIMSm/z (relative intensity): 548 (M⁺), 261 (100). Elementary analysis as $C_{28}H_{31}F_3N_4O_2S$ Calculated: C, 61.30; H, 6.43; N, 10.21; F, 10.39. Found: C, 61.31; H, 6.41; N, 10.15; F, 10.16.

Example 86

Preparation of 2-[4-[2-(7-trifluoromethylbenzoxazol-2-ylthio)ethyl]piperazin-1-yl]-N-(2,6-diisopropyl-4-methoxyphenyl)acetamide:

Potassium carbonate (1.52 g, 11 mmol) was added to a solution of 1-(2-hydroxyethyl)piperazine (1.43 g, 11 mmol) and 2-bromo-N-(2,6-diisopropyl-4-hydroxyphenyl)acetamide in acetonitrile (50 ml) and the mixture was stirred at room temperature for 12 hours. The reaction solution was diluted with water and extracted with chloroform. The organic layer was washed with water and a saturated sodium chloride solution successively and dried oven anhydrous sodium sulfate and the solvent was evaporated therefrom. The crude crystals were recrystallized from acetone-hexane to provide 2.5 g (yield 69%) of 2-[4-(2-hydroxyethyl)piperazin-1-yl]-N-(2,6-diisopropyl-4-hydroxyphenyl)acetamide as colorless needles.

Into a solution of the acetamide (640 mg, 1.76 mmol) in a mixed solvent (10 ml) of methanol and acetonitrile (1:4) were dropped N,N-diisopropylethylamine (0.43 ml, 2.46 mmol) and trimethylsilyl diazomethane (1.23 ml, 2.46 mmol) and the mixture was stirred for 12 hours. The residue obtained by evaporation of the solvent was made alkaline by adding 2N sodium hydroxide and then extracted with chloroform. The organic layer was washed with water and a saturated sodium chloride solution successively and dried over anhydrous sodium sulfate and the solvent was evaporated therefrom to provide 550 mg (yield 83%) of 2-[4-(2-hydroxyethyl)piperazin-1-yl]-N-(2,6-diisopropyl-4-methoxyphenyl)acetamide as colorless crystals.

The same reaction and treatment as in Example 85 were conducted using the acetamide instead of 2-[4-(2-hydroxyethyl)piperazin-1-yl]-N-(2,6-diisopropylphenyl)-acetamide to provide the desired compound as colorless needles.

Melting point: 122–123° C. IR (KBr) cm⁻¹: 3471, 3266, 2961, 1633, 1603. 1H-NMR (CDCl₃) δ: 1.18 (12H, d, J=7.0 Hz), 2.64–2.69 (4H, m), 2.69–2.74 (4H, m), 2.86 (2H, t, J=7.0 Hz), 2.97 (2H, sept, J=7.0 Hz), 3.19 (2H, s), 3.50 (2H, t, J=7.0 Hz), 3.81 (3H, s), 6.71 (2H, s), 7.38 (1H, t, J=7.8 Hz), 7.47 (1H, d, J=7.8 Hz), 7.75 (1H, d, J=7.8 Hz), 8.45 (1H, br s).

EIMSm/z (relative intensity): 578 (M⁺), 111 (100). Elementary analysis as $C_{29}H_{37}F_3N_4O_3S$ Calculated: C, 60.19; H, 6.44; N, 9.68; F, 9.85. Found: C, 60.43; H, 6.49; N, 9.63; F, 9.57.

Example 87

Preparation of 2-[4-[2-(7-trifluoromethylbenzoxazol-2-ylthio)ethyl]piperazin-1-yl]-N-(2,6-diisopropyl-3-nitrophenyl)acetamide:

The same reaction and treatment as in Example 85 were conducted using 2-bromo-N-(2,6-diisopropyl-3-nitrophenyl)acetamide instead of 2-bromo-N-(2,6-diisopropylphenyl) acetamide to provide the desired compound as colorless needles.

Melting point: 115–117° C. IR (KBr) cm⁻¹: 3441, 3294, 1665, 1526, 1506. 1H-NMR (CDCl₃) δ: 1.21 (6H, d, J=6.9 Hz), 1.33 (6H, d, J=7.1 Hz), 2.46–2.69 (4H, s), 2.72–2.76 (4H, m), 2.86 (2H, t, J=6.8 Hz), 2.99 (1H, sept, J=6.9 Hz), 3.22 (2H, s), 3.25 (1H, sept, J=7.1 Hz), 3.50 (2H, t, J=6.8 Hz), 7.30 (1H, d, J=8.5 Hz), 7.38 (1H, t, J=7.8 Hz), 7.47 (1H, d, J=8.5 Hz), 7.48 (1H, d, J=7.8 Hz), 7.76 (1H, d, J=7.8 Hz), 8.80 (1H, br s).

EIMSm/z (relative intensity): 593 (M⁺), 375 (100). Elementary analysis as $C_{28}H_{34}F_3N_5O_4S$ Calculated: C, 56.65; H, 5.77; N, 11.80. Found: C, 56.66; H, 5.85; N, 11.75.

Example 88

Preparation of 2-[4-[2-(7-trifluoromethylbenzoxazol-2-ylthio)ethyl]piperazin-1-yl]-N-(2,4-bis(methylthio-6-methyl-3-pyridyl)acetamide:

The same reaction and treatment as in Example 85 were conducted using 2-bromo-N-[2,4-bis(methylthio)-6-methylpyridine-3-yl]acetamide instead of 2-bromo-N-(2,6-diisopropylphenyl)acetamide to provide the desired compound as colorless needles.

Melting point: 153–155° C. IR (KBr) cm$^{-1}$: 3437, 3280, 1653, 1505. 1H-NMR (CDCl$_3$) δ: 2.42 (3H, s), 2.50 (3H, m), 2.52 (3H, s), 2.65–2.70 (4H, m), 2.73–2.78 (4H, m), 2.86 (2H, t, J=7.0 Hz), 3.19 (2H, s), 3.50 (2H, t, J=7.0 Hz), 6.67 (1H, s), 7.37 (1H, t, J=7.8 Hz), 7.47 (1H, d, J=7.8 Hz), 7.76 (1H, d, J=7.8 Hz), 8.55 (1H, br s).

EIMSm/z (relative intensity): 571 (M$^+$), 354 (100). Elementary analysis as C$_{24}$H$_{28}$F$_3$N$_5$O$_2$S$_3$ Calculated: C, 50.42; H, 4.94; N, 12.25. Found: C, 50.49; H, 4.98; N, 12.14.

Example 89

Preparation of 2-[4-[2-(7-trifluoromethylbenzoxazol-2-ylthio)ethyl]piperazin-1-yl]-N-[2,4-bis(ethylthio)-6-methyl-3-pyridyl]acetamide:

The same reaction and treatment as in Example 85 were conducted using 2-bromo-N-[2,4-bis(ethylthio)-6-methyl-3-pyridyl]acetamide instead of 2-bromo-N-(2,6-diisopropylphenyl)acetamide to provide the desired compound as colorless needles.

Melting point: 107–108° C. IR (KBr) cm$^{-1}$: 3438, 3298, 1702, 1505. 1H-NMR (CDCl$_3$) δ: 1.32 (3H, t, J=7.3 Hz), 1.35 (3H, t, J=7.3 Hz), 2.47 (3H,s), 2.64–2.71 (4H, m), 2.73–2.79 (4H, m), 2.86 (2H, t, J=6.8 Hz), 2.93 (2H, q, J=7.3 Hz), 3.16 (2H, q, J=7.3 Hz), 3.19 (2H, s), 3.51 (2H, t, J=6.8 Hz), 6.70 (1H, s), 7.37 (1H, t, J=7.8 Hz), 7.47 (1H, d, J=7.8 Hz), 7.76 (1H, d, J=7.8 Hz), 8.52 (1H, br s).

EIMSm/z (relative intensity): 599 (M$^+$), 538 (100). Elementary analysis as C$_{26}$H$_{32}$F$_3$N$_5$O$_2$S$_3$ Calculated: C, 52.07; H, 5.38; N, 11.68. Found: C, 52.16; H, 5.43; N, 11.59.

Example 90

Preparation of 2-[4-[2-(7-trifluoromethylbenzoxazol-2-ylthio)ethyl]piperazin-1-yl]-N-[2,4-bis(isopropylthio)-6-methyl-3-pyridyl]acetamide:

The same reaction and treatment as in Example 85 were conducted using 2-bromo-N-[2,4-bis(isopropylthio)-6-methyl-3-pyridyl]acetamide instead of 2-bromo-N-(2,6-isopropylphenyl)acetamide to provide the desired compound as pale amorphous. IR (KBr) cm$^{-1}$: 3434, 3312, 1702, 1506. 1H-NMR (CDCl$_3$) δ: 1.35 (6H, d, J=6.8 Hz), 1.36 (6H, d, J=6.8 Hz), 2.46 (3H, s), 2.65–2.71 (4H, m), 2.73–2.80 (4H, m), 2.87 (2H, t, J=7.0 Hz), 3.18 (2H, s), 3.50(1H, sept, J=6.8 Hz), 3.51 (2H, t, J=7.0 Hz), 4.02 (1H, sept, J=6.8 Hz), 6.75 (1H, s), 7.37 (1H, t, J=7.8 Hz), 7.47 (1H, d, J=7.8 Hz), 7.76 (1H, d, J=7.8 Hz), 8.51 (1H, br s).

EIMSm/z (relative intensity): 627 (M$^+$), 111 (100).

Example 91

Preparation of 2-[4-[3-(7-trifluoromethylbenzoxazol-2-ylthio)propyl]homopiperazin-1-yl]-N-(2,6-diisopropylphenyl)acetamide:

The same reaction and treatment as in Example 13 were conducted using 2-mercapto-7-trifuluorobenzoxazole instead of 2-mercaptobenzooxazole to provide the desired compound as pale yellow crystals.

Melting point: 77–79° C. IR (KBr) cm$^{-1}$: 3447, 3276, 1661, 1503. 1H-NMR (CDCl$_3$) δ: 1.21 (12H, d, J=6.8 Hz), 1.89 (2H, quint, J=5.9 Hz), 2.02 (2H, quint, J=6.8 Hz), 2.68 (2H, t, J=6.8 Hz), 2.74–2.78 (4H, m), 2.92–2.96 (4H, m), 3.02 (2H, sept, J=6.8 Hz), 3.35 (2H, s), 3.39 (2H, t, J=6.8 Hz), 7.18 (2H, d, J=8.1 Hz), 7.28 (1H, t, J=8.1 Hz), 7.37 (1H, t, J=7.8 Hz), 7.47 (1H, d, J=7.8 Hz), 7.75 (1H, d, J=7.8 Hz), 8.77 (1H, br s).

EIMSm/z (relative intensity): 576 (M$^+$), 153 (100). Elementary analysis as C$_{30}$H$_{39}$F$_3$N$_4$O$_2$S Calculated: C, 62.48; H, 6.82; N, 9.71; F, 9.88. Found: C, 62.56; H, 6.85; N, 9.69; F, 9.71.

Example 92

Preparation of 2-[4-[2-(7-acetylbenzoxazol-2-ylthio)-ethyl]piperazin-1-yl]ethyl]-N-(2,6-diisopropylphenyl) acetamide:

Potassium O-ethyl dithiocarbonate (241 mg, 1.5 mmol) was added to a solution of 3-amino-2-hydroxyacetophenone (113 mg, 0.75 mmol) in ethanol (10 ml) and the mixture was heated to reflux for 16 hours. The reaction was concentrated, water (20 ml) was added thereto and the mixture was adjusted to pH, 3–4 with diluted hydrochloric acid. The separated matter was collected by filtration and dried by heating in vacuo to provide 134 mg (yield 92%) of 7-acetyl-2-mercaptobenzooxazole as a dark solid.

After that, the same reaction and treatment as in Example 1 were conducted using 7-acetyl-2-mercaptobenzooxazole instead of 2-mercaptobenzooxazole to provide the desired compound as colorless needles.

Melting point: 137–139° C. IR (KBr) cm$^{-1}$: 3432, 3291, 2961, 1688, 1505. 1H-NMR (CDCl$_3$) δ: 1.21 (12H, d, J=6.8 Hz), 2.64–2.69 (4H, m), 2.73–2.77 (4H, m), 2.78 (3H, s), 2.87 (2H, t, J=6.8 Hz), 3.01 (2H, sept, J=6.8 Hz), 3.23 (2H, s), 3.53 (2H, t, J=6.8 Hz), 7.19 (2H, d, J=7.8 Hz), 7.29 (1H, t, J=7.8 Hz), 7.37 (1H, t, J=7.8 Hz), 7.77 (1H, dd, J=7.8, 1.2 Hz), 7.82 (1H, dd, J=7.8, 1.2 Hz), 8.60 (1H, br s).

EIMSm/z (relative intensity): 522 (M$^+$), 314 (100). Elementary analysis as C$_{29}$H$_{38}$N$_4$O$_3$S Calculated: C, 66.64; H, 7.33; N, 10.72; S, 6.13. Found: C, 66.57; H, 7.34; N, 10.70; S, 6.19.

Example 93

Preparation of 2-[4-[2-(7-acetylbenzoxazol-2-ylthio) ethyl]piperazin-1-yl]-N-(2,6-diisopropyl-4-methoxyphenyl) acetamide:

The same reaction and treatment as in Example 92 were conducted using 2-[4-(2-hydroxyethyl)piperazin-1-yl]-N-(2, 6-diisopropyl-4-methoxyphenyl)acetamide instead of 2-[4-(2-hydroxyethyl)piperazin-1-yl]-N-(2,6-diisopropylphenyl) acetamide to provide the desired compound as pale yellow needles.

Melting point: 185–186° C. IR (KBr) cm$^{-1}$: 3454, 3270, 2961, 1686, 1657. 1H-NMR (CDCl$_3$) δ: 1.19 (12H, d, J=7.0 Hz), 1.43 (3H, s), 2.65–2.69 (4H, m), 2.72–2.77 (4H, m), 2.87 (2H, t, J=6.7 Hz), 2.98 (2H, sept, J=7.0 Hz), 3.21 (2H, s), 3.53 (2H, t, J=6.7 Hz), 3.81 (3H, s), 6.71 (2H, s), 7.37 (1H, dd, J=8.0, 7.8 Hz), 7.77 (1H, d, J=8.0 Hz), 7.82 (1H, d, J=7.8 Hz), 8.46 (1H, br s).

EIMSm/z (relative intensity): 552 (M$^+$), 318 (100).

Example 94

Preparation of 2-[4-[3-(7-acetylbenzoxazol-2-ylthio)propyl]homopiperazin-1-yl]-N-(2,6-diisopropylphenyl)acetamide:

The same reaction and treatment as in Example 13 were conducted using 7-acetyl-2-mercaptobenzooxazole instead of 2-mercaptobenzooxazole to provide the desired compound as colorless crystals.

Melting point: 86–88° C. IR (KBr) cm$^{-1}$: 3425, 3303, 2960, 1687, 1658. 1H-NMR (CDCl$_3$) δ: 1.21 (12H, d, J=6.8 Hz), 1.87–1.93 (2H, m), 2.00–2.06 (2H, m), 2.67–2.70 (2H, m), 2.46–2.78 (7H, m), 2.92–2.96 (4H, m), 3.03 (2H, sept, J=6.8 Hz), 3.35 (2H, s), 3.41 (2H, t, J=7.0 Hz), 7.18 (2H, d, J=7.6 Hz), 7.28 (1H, t, J=7.6 Hz), 7.37 (1H, t, J=7.8 Hz), 7.77 (1H, dd, J=7.8, 1.2 Hz), 7.82 (1H, dd, J=7.8, 1.2 Hz), 8.75 (1H, br s).

EIMSm/z (relative intensity): 550 (M$^+$), 84 (100). Elementary analysis as C$_{31}$H$_{42}$N$_4$O$_3$S Calculated: C, 67.61; H, 7.69; N, 10.17; S, 5.82. Found: C, 67.37; H, 7.62; N, 10.18; S, 5.73.

Example 95

Preparation of 2-[4-[2-(7-tert-butylbenzoxazol-2-ylthio)ethyl]piperazin-1-yl]-N-(2,6-diisopropylphenyl)acetamide:

Acetyl nitrate obtained by mixing acetyl anhydride (1.35 g, 13.3 mmol) with fuming nitric acid (13.3 mmol) at 0° C. was dropped into a solution of 2-tert-butylphenol (2.00 g, 13.3 mmol) in acetonitrile (30 ml) at −20° C. followed by stirring for 5 minutes. The reaction solution was diluted with water and extracted with ether. The organic layer was washed with water and a saturated sodium chloride solution successively and dried over anhydrous magnesium sulfate and the solvent was evaporated therefrom. The residue was purified by a silica gel column chromatography (60 g of silica gel; developing solvent, hexane:acetone=3:1) to provide 600 mg (yield 23%) of 2-tert-butyl-6-nitrophenol as yellow crystals.

A 10% palladium carbon catalyst (250 mg) was added to a solution of the nitrophenol (316 mg, 1.62 mmol) in ethanol (20 ml) and stirred under hydrogen atmosphere at room temperature for 12 hours. The reaction solution was filtered off through celite and the filtrate was evaporated in vacuo to provide 260 mg (yield 97%) of 2-amino-6-tert-butylphenol as red crystals. Potassium O-ethyl dithiocarbonate (242 mg, 1.51 mmol) was added to a solution of the aminophenol (227 mg, 1.37 mmol) in ethanol (10 ml) followed by heating to reflux for eight hours. After allowing to cool, the solvent was evaporated in vacuo and the resulting residue was dissolved in water, acidified with concentrated hydrochloric acid and extracted with ethyl acetate. The organic layer was washed with water and a saturated sodium chloride solution successively and dried over an hydrous sodium sulfate and the solvent was evaporated therefrom. The residue was purified by a silica gel column chromatography (20 g of silica gel; developing solvent, hexane:acetone=4:1) to provide 124 mg (yield 44%) of 7-tert-butyl-2-mercaptobenzooxazole as colorless crystals.

After that, the same reaction and treatment as in Example 1 were conducted using 7-tert-butyl-2-mercaptobenzooxazole instead of 2-mercaptobenzooxazole to provide the desired compound as colorless needles.

Melting point: 138–140° C. IR (KBr) cm$^{-1}$: 3431, 3286, 2961, 1664, 1503. 1H-NMR (CDCl$_3$) δ: 1.21 (12H, d, J=6.8 Hz), 1.46 (9H, s), 2.63–2.68 (4H, m), 2.73–2.77 (4H, m), 2.86 (2H, t, J=7.0 Hz), 3.00 (2H, sept, J=6.8 Hz), 3.22 (2H, s), 3.49 (2H, t, J=7.0 Hz), 7.14 (1H, dd, J=7.8, 1.2 Hz), 7.18–7.23 (3H, m), 7.29 (1H, t, J=7.7 Hz), 7.44 (1H, dd, J=7.8, 1.2 Hz), 8.61 (1H, br s).

EIMSm/z (relative intensity): 536 (M$^+$), 263 (100). Elementary analysis as C$_{31}$H$_{44}$N$_4$O$_2$S Calculated: C, 69.37; H, 8.26; N, 10.44. Found: C, 60.53; H, 8.21; N, 10.41.

Example 96

Preparation of 2-[4-[2-(7-tert-buthylbenzoxazol-2-ylthio)ethyl]piperazin-1-yl]-N-(2,4-bis(ethylthio)-6-methyl-3-pyridyl)acetamide:

The same reaction and treatment as in Example 89 were conducted using 7-tert-buthyl-2-mercaptobenzooxazole instead of 2-mercapto-7-trifluoromethylbenzoxazole to provide the desired compound as colorless needles.

Melting point: 115–117° C. IR (KBr) cm$^{-1}$: 3430, 3327, 1699, 1504, 1479. 1H-NMR (CDCl$_3$) δ: 1.32 (3H, t, J=7.3 Hz), 1.35 (3H, t, J=7.3 Hz), 1.46 (9H, s), 2.47 (3H, s), 2.65–2.70 (4H, m), 2.76–2.81 (4H, m), 2.87 (2H, t, J=7.0 Hz), 2.93 (2H, q, J=7.3 Hz), 3.16 (2H, q, J=7.3 Hz), 3.20 (2H, s), 3.50 (2H, t, J=7.0 Hz), 6.70 (1H, s), 7.16 (1H, dd, J=7.8, 1.2 Hz), 7.21 (1H, t, J=7.8 Hz), 7.44 (1H, dd, J=7.8, 1.2 Hz), 8.54 (1H, br s).

EIMSm/z (relative intensity): 587 (M$^+$), 381 (100).

Example 97

Preparation of 2-[4-[2-(5-chloro-7-isopropyl-4-methylbenzoxazol-2-ylthio)ethyl]piperazin-1-yl]-N-(2,6-diisopropylphenyl)acetamide:

Acetyl nitrate obtained by mixing acetyl anhydride (1.12 g, 11 mmol) with fuming nitric acid (693 mg, 11 mmol) at 0° C. was dropped into a solution of 4-chloro-2-isopropyl-5-methylphenol (1.84 g, 10 mmol) in acetonitrile (20 ml) at 0° C. followed by stirring for 50 minutes. The reaction solution was diluted with water and extracted with ether. The organic layer was washed with water and a saturated sodium chloride solution successively and dried over anhydrous magnesium sulfate and the solvent was evaporated therefrom. The residue was purified by a silica gel column chromatography (80 g of silica gel; developing solvent, hexane:methylene chloride=30:1→10:1) to provide 1.88 g (yield 83%) of 4-chloro-6-isopropyl-3-methyl-2-nitrophenol as pale yellow crystals.

Zinc (6.4 g, 98 mmol) was added little by little to a solution of the nitro compound (1.88 g, 8.18 mmol) in acetic acid (30 ml) with ice cooling. After stirring for 1 hour, the reaction solution was diluted by adding ethyl acetate thereto and the mixture was filtered off. The filtrate was neutralized with an aqueous solution of sodium carbonate and extracted with ethyl acetate. The organic layer was washed with water and a saturated sodium chloride solution successively and dried over magnesium sulfate and the solvent was evaporated therefrom to provide 1.63 g (yield 99%) of 2-amino-4-chloro-6-isopropyl-3-methylphenol as pale yellow oil.

Potassium O-ethyl dithiocarbonate (1.60 g, 10 mmol) was added to a solution of the aminophenol (1.60 g, 8.0 mmol) in ethanol (30 ml), the mixture was heated to reflux for 16 hours and the solvent was evaporated. The resulting residue was dissolved in water, acidified to pH 3–4 by adding 2N hydrochloric acid and extracted with ethyl acetate. The organic layer was washed with water and a saturated sodium chloride solution successively and dried over anhydrous magnesium sulfate and the solvent was evaporated therefrom. The residue was purified by a silica gel column chromatography (70 g of silica gel; developing solvent, hexane:acetone=7:1) to provide 1.28 g (yield 66%) of 5-chloro-7-isopropyl-2-mercapto-4-methyl-benzoxazole as colorless needles.

After that, the same reaction and treatment as in Example 1 were conducted using 5-chloro-7-isopropyl-2-mercapto-4-methylbenzoxazole instead of 2-mercaptobenzooxazole to provide the desired compound as colorless needles.

Melting point: 162–163° C. IR (KBr) cm$^{-1}$: 3436, 3290, 2963, 1660, 1505. 1H-NMR (CDCl$_3$) δ: 1.21 (12H, d, J=6.9 Hz), 1.33 (6H, d, J=6.9 Hz), 2.52 (3H, s), 2.64–2.70 (4H, m), 2.73–2.77 (4H, m), 2.85 (2H, t, J=7.1 Hz), 3.01 (2H, sept, J=6.9 Hz), 3.22 (1H, sept, J=6.9 Hz), 3.23 (2H, s), 3.48 (2H, t, J=7.1 Hz), 7.07 (1H, s), 7.19 (2H, d, J=7.8 Hz), 7.29 (1H, t, J=7.8 Hz), 8.61 (1H, br s).

EIMSm/z (relative intensity): 570 (M$^+$), 330 (100). Elementary analysis as $C_{31-43}ClN_4O_2S$ Calculated: C, 65.18; H, 7.59; N, 9.81. Found: C, 65.19; H, 7.59; N, 9.83.

Example 98

Preparation of 2-[4-[2-(4,5,6-trimethoxybenzoxazol-2-ylthio)ethyl]piperazin-1-yl]-N-(2,6-diisopropylphenyl)acetamide:

Sulfanilic acid (1.0 g, 6.0 mmol) was added to a solution of sodium carbonate (318 mg, 3.0 mmol) in water (5 ml) and dissolved by heating, a solution of sodium nitrite (414 mg, 6.0 mmol) in water (1 ml) was added thereto with ice cooling and concentrated hydrochloric acid (1.25 ml) was dropped thereinto to prepare a colorless suspension.

3,4,5-Trimethoxyphenol (921 mg, 6.0 mmol) was added to a solution of sodium hydroxide (1.1 g, 27.5 mmol) in water (6 ml) and dissolved by heating, then the above-prepared suspension was slowly dropped thereinto with ice cooling and the mixture was stirred at room temperature for 1.5 hours. Sodium hydrosulfite was added thereto at 50° C. until the red color of the reaction solution almost disappeared. The reaction solution was allowed to cool and extracted with ether three times and with ethyl acetate once. The organic layer was washed with water and a saturated sodium chloride solution successively and dried over magnesium sulfate and the solvent was evaporated therefrom to provide 640 mg (yield 64%) of crude 2-amino-3,4,5-trimethoxyphenol.

Potassium O-ethyl dithiocarbonate (321 mg, 2.0 mmol) was added to a solution of the aminophenol (199 mg, 1.0 mmol) in ethanol (5 ml) and the mixture was heated to reflux for 16 hours. The reaction solution was concentrated, water (30 ml) was added thereto and the mixture was adjusted to pH, 3–4 with diluted hydrochloric acid the separated matter was collected by filtration, dried by heating in vacuo and recrystallized from methanol, ether and hexane to provide 155 mg (yield 64%) of 2-mercapto-4,5,6-trimethoxybenzoxazole as reddish-purple needles.

After that, the same reaction and treatment as in Example 1 were conducted using 2-mercapto-4,5,6-trimethoxybenzoxazole instead of 2-mercaptobenzooxazole to provide the desired compound as colorless crystals.

Melting point: 126–129° C. (decomposition) IR (KBr) cm$^{-1}$: 3433, 3254, 2960, 1663, 1486. 1H-NMR (CDCl$_3$) δ: 1.21 (12H, d, J=6.8 Hz), 2.62–2.67 (4H, m), 2.72–2.77 (4H, m), 2.83 (2H, t, J=7.0 Hz), 3.00 (2H, sept, J=6.8 Hz), 3.22 (2H, s), 3.43 (2H, t, J=7.0 Hz), 3.84 (3H, s), 3.88 (3H, s), 4.32 (3H, s), 6.71 (1H, s), 7.18 (2H, d, J=7.6 Hz), 7.29 (1H, t, J=7.6 Hz), 8.59 (1H, br s).

EIMSm/z (relative intensity): 570 (M$^+$), 126 (100). Elementary analysis as $C_{30}H_{42}N_4O_5S$ Calculated: C, 63.13; H, 7.42; N, 9.82; S, 5.62. Found: C, 63.01; H, 7.35; N, 9.64; S, 5.51.

Example 99

Preparation of 2-[4-[2-(6,7-bis(methoxycarbonyl)benzoxazol-2-ylthio)ethyl]piperazin-1-yl]-N-(2,6-diisopropylphenyl)acetamide:

Acetyl nitrate obtained by mixing acetic anhydride (3.6 g, 36 mmol) with fuming nitric acid (2.16 g, 36 mmol) at 0° C. was dropped into a solution of dimethyl 3-hydroxyphthalate (3.8 g, 18 mmol) in acetonitrile (60 ml) at 0° C. followed by stirring for 40 minutes. The reaction solution was diluted with water and extracted with ether. The organic layer was washed with water and a saturated sodium chloride solution successively and dried over anhydrous magnesium sulfate and the solvent was evaporated therefrom. A 3:2 mixture (4.34 g; yield 94%) of dimethyl 3-hydroxy-4-nitrophthalate and dimethyl 3-hydroxy-6-nitrophthalatewas obtained as a yellow solid. This was used in the next reaction without separation and purification.

A 10% palladium carbon catalyst (2.5 g) was added to a solution of the nitro compound mixture (4.3 g, 16.8 mmol) in ethyl acetate (60 ml) and stirred under hydrogen atmosphere at room temperature for 3 hours. The reaction solution was filtered off through celite and the filtrate was concentrated. The residue was dissolved in methanol (50 ml), potassium O-ethyl dithiocarbonate (1.76 g, 11.0 mmol) was added thereto and the mixture was heated to reflux for 16 hours. After cooling, the solvent was evaporated in vacuo. The residue was diluted and acidified with 2N hydrochloric acid and extracted with ethyl acetate. The organic layer was washed with water and a saturated sodium chloride solution successively and dried over anhydrous magnesium sulfate and the solvent was evaporated therefrom. The residue was crystallized from ether to provide 1.61 g (yield 60%) of 6,7-bis(methoxycarbonyl)-2-mercaptobenzooxazole as yellow crystals.

After that, the same reaction and treatment as in Example 1 were conducted using 6,7-bis(methoxycarbonyl)-2-mercaptobenzooxazole instead of 2-mercaptobenzooxazole to provide the desired compound as colorless needles.

Melting point: 186–187° C. IR (KBr) cm$^{-1}$: 3312, 2963, 1733, 1718, 1660. 1H-NMR (CDCl$_3$) δ: 1.21 (12H, d, J=6.8 Hz), 2.60–2.78 (8H, m), 2.84 (2H, t, J=6.8 Hz), 3.00 (2H, sept, J=6.8 Hz), 3.21 (2H, s), 3.50 (2H, t, J=6.8 Hz), 3.92 (3H, s), 4.01 (3H, s), 7.18 (2H, d, J=7.8 Hz), 7.28 (1H, t, J=8.3 Hz), 7.63 (1H, d, J=8.3 Hz), 7.89 (1H, d, J=8.3 Hz), 8.59 (1H, br s).

EIMSm/z (relative intensity): 596 (M$^+$), 330 (100). Elementary analysis as $C_{31}H_{40}N_4O_6S$ Calculated: C, 62.40; H, 6.76; N, 9.39; S, 5.37. Found: C, 62.21; H, 6.76; N, 9.37; S, 5.40.

Example 100

Preparation of 2-[4-[2-(6,7-bis(methoxymethyl)benzoxazol-2-ylthio)ethyl]piperazin-1-yl]-N-(2,6-diisopropylphenyl)acetamide:

N,N-Diisopropylethylamine (4.39 g, 34.0 mmol) was added to a solution of 3-hydroxyphthalic anhydride (5.0 g, 30.5 mmol) in dichloroethane (60 ml), then chloromethyl methyl ether (2.57 g, 32.0 mmol) was dropped thereinto under cooling with ice water and the mixture was returned to room temperature and stirred for 1 hour. Then N,N-diisopropylethylamine (2.20 g, 17.0 mmol) and chloromethyl methyl ether (1.28 g, 16.0 mmol) were further added thereto followed by stirring for 1 hour. After the reaction, the solvent was evaporated and the residue was diluted with water followed by extracting with ether. The organic layer was washed with water and a saturated sodium chloride solution successively and dried over anhydrous magnesium sulfate and the solvent was evaporated therefrom to provide 6.3 g (yield 99%) of 3-methoxymethyloxyphthalic anhydride as colorless oil.

After that, lithium aluminum hydride (1.14 g, 30.0 mmol) was added little by little to a solution of 3-methoxymethyloxyphthalic anhydride (3.0 g, 14.4 mmol) in anhydrous tetrahydrofuran (100 ml) under cooling with ice water and the mixture was returned to room temperature followed by stirring for 12 hours. The reaction solution was diluted with ether (300 ml) and a saturated aqueous solution (3 ml) of ammonium chloride was added thereto followed by stirring for 1 hour. The reaction solution was dried over anhydrous magnesium sulfate, filtered off through celite and the filtrate was concentrated to provide 1.71 g (yield 60%) of 3-methoxymethyloxy-1,2-benzenedimethanol as colorless oil.

Sodium hydride (384 mg, 8.0 mmol) was added to a solution of the above-prepared diol (714 mg, 3.6 mmol) indimethyl formamide (10 ml) under cooling with ice water followed by stirring for 15 minutes. Then iodomethane (1.13 g, 8.0 mmol) was added thereto and the mixture was returned to room temperature and stirred for 1 hour. The reaction solution was diluted with a saturated ammonium chloride solution and extracted with ether. The organic layer was washed with water and a saturated sodium chloride solution successively and dried over anhydrous magnesium sulfate and the solvent was evaporated therefrom to provide 810 mg (yield 99%) of 1,2-bis(methoxymethyl)-3-methoxymethyloxybenzene as colorless oil.

Then 2N hydrochloric acid (8 ml) was added to a solution of the above-prepared methoxymethyl ether (810 mg) in tetrahydrofuran (12 ml) and stirred at room temperature for 12 hours. The reaction solution was diluted with water and extracted with ether. The organic layer was washed with a saturated sodium chloride solution and dried over anhydrous magnesium sulfate and the solvent was evaporated therefrom. The residue was purified by a silica gel column chromatography (20 g of silica gel; developing solvent, hexane:acetone=10:1) to provide 480 mg (yield 73%) of 2,3-bis(methoxymethyl)phenol as colorless oil.

Acetyl nitrate obtained by mixing acetic anhydride (306 mg, 3.0 mmol) with fuming nitric acid (189 mg, 3.0 mmol) at 0° C. was dropped into a solution of 2,3-bis (methoxymethyl)phenol (483 mg, 2.65 mmol) in acetonitrile (5 ml) at 0° C. followed by stirring for 40 minutes. The reaction solution was diluted with water and extracted with ether. The organic layer was washed with water and a saturated sodium chloride solution successively and dried over anhydrous magnesium sulfate and the solvent was evaporated therefrom to provide a 2:1 mixture (329 mg; yield 54%) of 2,3-bis(methoxymethyl)-6-nitrophenol and 2,3-bis(methoxymethyl)-4-nitrophenol as yellow solid. This was used in the next reaction without separation and purification.

Zinc (1.13 g, 17 mmol) was added little by little to a solution of the nitro compound (329 mg, 1.44 mmol) in acetic acid (5 ml) under cooling with water. After stirring for 40 minutes, the reaction solution was diluted by adding ethyl acetate thereto and the mixture was filtered. The filtrate was neutralized with an aqueous solution of sodium carbonate and extracted with ethyl acetate. The organic layer was washed with water and a saturated sodium chloride solution successively and dried over magnesium sulfate and the solvent was evaporated therefrom to provide 276 mg (yield 89%) of a 2:1 mixture of 2-amino-5,6-bis(methoxymethyl) phenol and 4-amino-2,3-bis(methoxymethyl)phenol as oil. This was used to the next reaction without separation and purification.

Thus, the aminophenol (276 mg, 1.29 mmol) was dissolved in ethanol (10 ml) and potassium O-ethyl dithiocarbonate (228 mg, 1.42 mmol) was added thereto followed by heating to reflux for 16 hours. After cooling, the solvent was evaporated therefrom in vacuo. The residue was acidified by adding 2N hydrochloric acid thereto and extracted with ethyl acetate. The organic layer was washed with water and a saturated sodium chloride solution successively and dried over anhydrous magnesium sulfate and the solvent was evaporated therefrom. The residue was purified by a preparative thin layer chromatography (developing solvent, hexane:acetone=5:3) to provide 182 mg (yield 59%) of 6,7-bis(methoxymethyl)-2-mercaptobenzooxazole as pale brown solid.

After that, the same reaction and treatment as in Example 1 were conducted using the above-prepared 6,7-bis (methoxymethyl)-2-mercaptobenzooxazole instead of 2-mercaptobenzooxazole to provide the desired compound as colorless needles.

Melting point: 96–97° C. IR (KBr) cm$^{-1}$: 3290, 2961, 1662, 1506, 1125. 1H-NMR (CDCl$_3$) δ: 1.20 (12H, d, J=6.8 Hz), 2.60–2.78 (8H, m), 2.84 (2H, t, J=6.8 Hz), 3.00 (2H, sept, J=6.8 Hz), 3.22 (2H, s), 3.40 (6H, s), 3.48 (2H, t, J=6.8 Hz), 4.63 (2H, s), 4.74 (2H, s), 7.18 (2H, d, J=7.6 Hz), 7.29 (1H, d, J=7.6 Hz), 7.34 (1H, d, J=8.0 Hz), 7.49 (1H, d, J=8.0 Hz), 8.60 (1H, br s).

EIMSm/z (relative intensity): 568 (M$^+$), 330 (100). Elementary analysis as $C_{31}H_{44}N_4O_4S$ Calculated: C, 65.46; H, 7.80; N, 9.85. Found: C, 65.41; H, 7.75; N, 9.71.

Example 101

Preparation of 2-[4-[2-(6,7-bis(methoxymethyl) benzoxazol-2-ylthio)ethyl]piperazin-1-yl]-N-(2,4-bis (ethylthio)-6-methyl-3-pyridyl)acetamide:

The same reaction and treatment as in Example 89 were conducted using 6,7-bis(methoxyxethyl)-2-mercaptobenzooxazole instead of 2-mercapto-7-trifluoromethylbenzoxazole to provide the desired compound as colorless needles.

Melting point: 118–120° C. IR (KBr) cm$^{-1}$: 3334, 2926, 1699, 1561, 1501. 1H-NMR (CDCl$_3$) δ: 1.32 (3H, t, J=7.4 Hz), 1.35 (3H, t, J=7.4 Hz), 2.47 (3H, s), 2.64–2.69 (4H, m), 2.75–2.88 (4H, m), 2.85 (2H, t, J=7.0 Hz), 2.93 (2H, q, J=7.4 Hz), 3.15 (2H, q, J=7.4 Hz), 3.20 (2H, s), 3.40 (3H, s), 3.41 (3H, s), 3.49 (2H, t, J=7.0 Hz), 4.64 (2H, s), 4.77 (2H, s), 6.70 (1H, s), 7.34 (1H, d, J=8.3 Hz), 7.50 (1H, d, J=8.3 Hz), 8.53 (1H, br s).

EIMSm/z (relative intensity): 619 (M$^+$), 381 (100). Elementary analysis as $C_{29}H_{41}N_5O_4S_3$ Calculated: C, 56.19; H, 6.67; N, 11.30. Found: C, 56.27; H, 6.67; N, 11.19.

Example 102

Preparation of 2-[4-[2-(7-hydroxymethylbenzoxazol-2-ylthio]ethyl]piperazin-1-yl]-N-(2,6-diisopropylphenyl) acetamide:

A 1.0M solution of diisobutyl aluminum hydride in toluene (10 ml) was slowly dropped, under argon atmosphere at −78° C., into a solution of 2-mercapto-7-methoxycarbonylbenzoxazole (1.1 g, 5.0 mmol) in THF (20 ml) followed by stirring for 30 minutes. At that temperature, a 1.0M solution of diisobutyl aluminum hydride in toluene (5 ml) was slowly dropped thereinto followed by stirring for 30 minutes. After cooling, diluted hydrochloric acid was added to the reaction mixture to decompose the excessive diisobutyl aluminum hydride, after then extracted with ethyl acetate. The organic layer was washed with diluted hydrochloric acid solution and a saturated sodium chloride solution, dried over sodium sulfate and the solvent was evaporated therefrom. The resulting crude product was recrystallized from hexane-acetone-methanol to provide 848 mg (yield 94%) of 7-hydroxymethyl-2-mercaptobenzooxazole as colorless needles.

After that, the same reaction and treatment as in Example 1 were conducted using 7-hydroxymethyl-2-mercaptobenzooxazole instead of 2-mercaptobenzooxazole to provide the desired compound as colorless crystals.

Melting point: 138–139° C. IR (KBR) cm$^{-1}$: 3331, 2962, 1657, 1507, 1427. 1H-NMR (d$_6$-DMSO) δ: 1.13 (12H, d, J=6.8 Hz), 2.55–2.65 (8H, m), 2.79 (2H, t, J=6.8 Hz), 3.05 (2H, sept, J=6.8 Hz), 3.11 (2H, s), 3.47 (2H, t, J=6.8 Hz), 4.74 (2H, d, J=5.5 Hz), 4.90 (1H, t, J=5.5 Hz), 7.12 (2H, d, J=7.6 Hz), 7.22 (1H, t, J=7.6 Hz), 7.26 (1H, t, J=7.2 Hz), 7.29 (1H, dd, J=7.2, 2.0 Hz), 7.45 (1H, dd, J=7.2, 2.0 Hz), 8.77 (1H, br s), EIMSm/z (relative intensity): 510 (M$^+$), 316 (100). Elementary analysis as $C_{28}H_{38}N_4O_3S$ Calculated: C, 65.85; H, 7.50; N, 10.97. Found: C, 65.77; H, 7.64; N, 10.84.

Example 103

Preparation of 2-[4-[2-[7-(pyrazol-3-yl)benzoxazol-2-ylthio]ethyl]piperazin-1-yl]-N-(2,6-diisopropylphenyl)acetamide:

Dimethylformamide dimethylacetal (146 mg, 1.2 mmol) was dropped into a solution of 2-[4-[2-(7-acetylbenzoxazol-2-ylthio)ethyl]piperazin-1-yl]-N-(2,6-diisopropylphenyl)acetamide (214 mg, 0.4 mmol) in DMF (15 ml), followed by stirring at 80° C. for 4 hours. The reaction solution was allowed to cool and extracted with ethyl acetate. The organic layer was washed with water and diluted hydrochloric acid solution successively and dried over sodium sulfate to provide 245 mg of crude 2-[4-[2-[7-(3-dimethylaminoacryloyl)benzoxazol-2-ylthio]ethyl]piperazin-1-yl]-N-(2,6-diisopropylphenyl)acetamide.

To a solution of the enamine (245 mg, 0.4 mmol) in methanol (6 ml) were added acetic acid (123 mg, 2.05 mmol) and hydrazine monohydrate (102 mg, 2.05 mmol) followed by stirring at room temperature for 15 hours. The reaction solution was concentrated and extracted with ethyl acetate. The organic layer was washed with water and a saturated sodium chloride solution, dried over sodium sulfate and the solvent was evaporated therefrom. The residue was purified by a preparative thin layer chromatography (developing solvent, hexane:acetone=5:3) to provide 129 mg (yield 58%) of the desired compound as colorless needles.

Melting point: 181–183° C. IR (KBR) cm$^{-1}$: 3262, 2960, 2360, 1655, 1500. 1H-NMR (CDCl$_3$) δ: 1.21 (12H, d, J=6.8 Hz), 2.60–2.76 (8H, m), 2.87 (2H, t, J=6.8 Hz), 3.01 (2H, sept, J=6.8 Hz), 3.23 (2H, s), 3.53 (2H, t, J=6.8 Hz), 6.89 (1H, d, J=2.2 Hz), 7.19 (2H, d, J=7.6 Hz), 7.29 (1H, t, J=7.6 Hz), 7.34 (1H, t, J=8.0 Hz), 7.55 (1H, dd, J=8.0, 1.2 Hz), 7.68 (1H, d, J=2.2 Hz), 7.71 (1H, dd, J=8.0, 1.2 Hz), 8.62 (1H, br s).

EIMSm/z (relative intensity): 546 (M$^+$), 342 (100). Elementary analysis as $C_{30}H_{38}N_6O_2S$ Calculated: C, 65.91; H, 7.01; N, 15.37. Found: C, 65.89; H, 7.06; N, 15.22.

Example 104

Preparation of 2-[4-[2-(7-nitrobenzoxazol-2-ylthio)ethyl]-piperazin-1-yl]-N-(2,6-diisopropylphenyl)acetamide:

Potassium carbonate (16.6 g, 120.1 mmol) was added to a solution of 3-nitrosalicylic acid (10 g, 54.6 mmol) in DMF (100 ml) and benzyl bromide (14.3 ml, 120.1 mmol) was dropped thereinto. The mixture was stirred at 80° C. for 12 hours and the reaction solution was diluted with water and extracted with ether. The organic layer was washed with water and a saturated sodium chloride solution successively, dried over anhydrous sodium sulfate and the solvent was evaporated therefrom to provide 16.1 g (yield 81%) of benzyl 2-benzyloxy-3-nitrobenzoate as brown oil.

To a suspension of the benzyl ester compound (4.42 g, 12.2 mmol) in ethanol (30 ml) was added an aqueous solution (30 ml) of potassium hydroxide (1.37 g, 24.4 mmol) followed by stirring at 50° C. for 2 hours. The reaction solution was diluted with water, washed with ether, acidified with 2N hydrochloric acid and extracted with ether. The organic layer was washed with water and a saturated sodium chloride solution successively, dried over anhydrous sodium sulfate and the solvent was evaporated therefrom. The residue was purified by a silica gel column chromatography (90 g of silica gel; developing solvent, hexane:acetone:acetic acid=25:25:1) and the resulting crude crystals were recrystallized from acetone-hexane to provide 2.1 g (yield 63%) of 2-benzyloxy-3-nitrobenzoic acid as colorless crystals.

Into a solution of the benzoic acid (2.1 g, 7.69 mmol) in tert-butanol (70 ml) were dropped triethylamine (3.2 ml, 23.1 mmol) and diphenylphosphoryl azide (1.7 ml, 7.69 mmol) with ice cooling and the mixture was heated to reflux for 1 hour. The reaction solution was diluted with water and extracted with ethyl acetate. The organic layer was successively washed with a 2N aqueous solution of sodium hydroxide, 2N hydrochloric acid, water and a saturated sodium chloride solution, dried over anhydrous sodium sulfate and the solvent was evaporated therefrom. The residue was purified by a silica gel column chromatography (90 g of silica gel; developing solvent, hexane:acetone=5:1) to provide 1.61 g (yield 61%) of N-tert-butoxycarbonyl-2-benzyloxy-3-nitroaniline as pale yellow oil.

Into a solution of the aniline compound (1.41 g, 4.1 mmol) in trifuoroacetic acid (30 ml) was dropped thioanisole (4.8 ml, 4 mmol) and the mixture was stirred at room temperature for 15 minutes. The reaction solution was diluted with water, neutralized with a 2N aqueous solution of sodium hydroxide and a saturated sodium bicarbonate solution and extracted with ethyl acetate. The organic layer was washed with water and a saturated sodium chloride solution successively, dried over anhydrous sodium sulfate and the solvent was evaporated therefrom. The residue was purified by a silica gel column chromatography (30 g of silica gel; developing solvent, hexane:acetone=3:1) to provide 430 mg (yield 68%) of 2-amino-6-nitrophenol as reddish purple crystals.

To a solution of the phenol compound (430 mg, 2.8 mmol) in ethanol (30 ml) was added potassium O-ethyl dithiocarbonate (497 mg, 3.1 mmol) and the mixture was heated to reflux for 12 hours. The reaction mixture was diluted with water, acidified with 2N hydrochloric acid and extracted with ether. The organic layer was washed with water and a saturated sodium chloride solution successively, dried over anhydrous sodium sulfate and the solvent was evaporated therefrom. The residue was purified by a silica gel column chromatography (30 g of silica gel; developing solvent, chloroform:methanol=10:1) to provide 381 mg (yield 69%) of 2-mercapto-7-nitrobenzoxazole as yellow crystals.

The same reaction and treatment as in Example 1 were conducted using 2-mercapto-7-nitrobenzoxazole instead of 2-mercaptobenzooxazole to provide the desired compound as pale yellow needles.

Melting point: 153–155° C. IR (KBr) cm$^{-1}$: 3437, 3226, 1662, 1532, 1505. 1H-NMR (CDCl$_3$) δ: 1.21 (12H, d, J=6.8 Hz), 2.65–2.70 (4H, m), 2.72–2.76 (4H, m), 2.88 (2H, t, J=6.8 Hz), 3.00 (2H, sept, J=6.8 Hz), 3.22 (2H, s), 3.54 (2H, t, J=6.8 Hz), 7.19 (2H, d, J=7.8 Hz), 7.29 (1H, t, J=7.8 Hz), 7.43 (1H, t, J=8.3 Hz), 7.88 (1H, dd, J=8.3, 1.0 Hz), 8.07 (1H, dd, J=8.3, 1.0 Hz), 8.60 (1H, br s).

EIMSm/z (relative intensity): 525 (M$^+$), 125 (100). Elementary analysis as C$_{27}$H$_{35}$N$_5$O$_4$S Calculated: C, 61.69; H, 6.71; N, 13.32. Found: C, 61.77, H, 6.79; N, 13.16.

Example 105

Preparation of 2-[4-[2-(7-nitrobenzoxazol-2-ylthio) ethyl]-piperazin-1-yl]-N-(2,6-diisopropyl-4-methoxyphenyl)acetamide:

The same reaction and treatment as in Example 104 were conducted using 2-[4-(2-hydroxyethyl)piperazin-1-yl]-N-(2,6-diisopropyl-4-methoxyphenyl)acetamide instead of 2-[4-(2-hydroxyethyl)piperazin-1-yl]-N-(2,6-diisopropylphenyl)acetamide to provide the desired compound as pale yellow needles.

Melting point: 165–166° C. IR (KBr) cm$^{-1}$: 3271, 2963, 1659, 1600, 1534. 1H-NMR (CDCl$_3$) δ: 1.19 (12H, d, J=6.8 Hz), 2.65–2.71 (4H, m), 2.71–2.76 (4H, m), 2.88 (2H, t, J=6.8 Hz), 2.97 (2H, sept, J=6.8 Hz), 3.20 (2H, s), 3.54 (2H, t, J=6.8 Hz), 3.81 (3H, s), 6.71 (2H, s), 7.43 (1H, dd, J=8.3, 7.9 Hz), 7.88 (1H, d, J=7.9 Hz), 8.07 (1H, d, J=8.3 Hz), 8.45 (1H, br s).

EIMSm/z (relative intensity): 555 (M$^+$), 70 (100). Elementary analysis as C$_{28}$H$_{37}$N$_5$O$_5$S Calculated: C, 60.52; H, 6.71; N, 12.60. Found: C, 60.49; H, 6.71; N, 12.58.

Example 106

Preparation of 2-[4-[2-(7-nitrobenzoxazol-2-ylthio) ethyl]-piperazin-1-yl]-N-[2,4-bis(ethylthio)-6-methyl-3-pyridyl]acetamide:

The same reaction and treatment as in Example 104 were conducted using 2-[4-(2-hydroxyethyl)piperazin-1-yl]-N-[2,4-bis(ethylthio)-6-methyl-3-pyridyl]acetamide instead of 2-[4-(2-hydroxyethyl)piperazin-1-yl]-N-(2,6-diisopropylphenyl)acetamide to provide the desired compound as pale yellow amorphous.

Melting point: 50–52° C. IR (KBr) cm$^{-1}$: 3292, 2929, 2817, 1699, 1532. 1H-NMR (CDCl$_3$) δ: 1.33 (3H, t, J=7.3 Hz), 1.36 (3H, t, J=7.4 Hz), 2.47 (3H, s), 2.64–2.70 (4H, m), 2.72–2.77 (4H, m), 2.88 (2H, t, J=6.8 Hz), 2.93 (2H, q, J=7.3 Hz), 3.54 (2H, t, J=6.8 Hz), 3.16 (2H, q, J=7.4 Hz), 3.19 (2H, s), 6.70 (1H, s), 7.43 (1H, dd, J=8.4, 7.9 Hz), 7.88 (1H, d, J=7.9 Hz), 8.06 (1H, d, J=8.4 Hz), 8.52 (1H, br s).

Example 107

Preparation of 2-[4-[2-(7-nitrobenzoxazol-2-ylthio) ethyl]-piperazin-1-yl]-N-[2,4-bis(isopropylthio)-6-methyl-3-pyridyl]acetamide:

The same reaction and treatment as in Example 104 were conducted using 2-[4-(2-hydroxyethyl)piperazin-1-yl]-N-[2,4-bis(isopropylthio)-6-methyl-3-pyridyl]acetamide instead of 2-[4-(2-hydroxyethyl)piperazin-1-yl]-N-(2,6-diisopropylphenyl)acetamide to provide the desired compound as pale yellow amorphous.

Melting point: 57–59° C. IR (KBr) cm$^{-1}$: 3299, 2962, 2818, 1702, 1559. 1H-NMR (CDCl$_3$) δ: 1.35 (6H, d, J=6.7 Hz), 1.36 (6H, d, J=6.8 Hz), 2.46 (3H, s), 2.64–2.69 (4H, m), 2.72–2.76 (4H, m), 2.89 (2H, t, J=6.9 Hz), 3.18 (2H, s), 3.50 (1H, sept, J=6.7 Hz), 3.55 (2H, t, J=6.9 Hz), 4.02 (1H, sept, J=6.8 Hz), 6.75 (1H, s), 7.43 (1H, dd, J=8.3, 7.9 Hz), 7.88 (1H, d, J=7.9 Hz), 8.06 (1H, d, J=8.3 Hz), 8.50 (1H, br s).

EIMSm/z (relative intensity): 604 (M$^+$), 409 (100).

Example 108

Preparation of 2-[4-[2-(7-nitrobenzoxazol-2-ylthio) ethyl]-piperazin-1-yl]-N-(2,6-diisopropylphenyl-3-nitrophenyl)acetamide:

The same reaction and treatment as in Example 104 were conducted using 2-[4-(2-hydroxyethyl)piperazin-1-yl]-N-(2,6-diisopropyl-3-nitrophenyl)acetamide instead of 2-[4-(2-hydroxyethyl)piperazin-1-yl]-N-(2,6-diisopropylphenyl)acetamide to provide the desired compound as pale yellow amorphous.

Melting point: 70–72° C. IR (KBr) cm$^{-1}$: 3290, 2966, 2820, 1683, 1530. 1H-NMR (CDCl$_3$) δ: 1.22 (6H, d, J=6.5 Hz), 1.32 (6H, d, J=7.2 Hz), 2.60–2.85 (8H, m), 2.89 (2H, t, J=6.8 Hz), 2.99 (1H, sept, J=6.5 Hz), 3.23 (2H, s), 3.26 (1H, sept, J=7.2 Hz), 3.54 (2H, t, J=6.8 Hz), 7.30 (1H, d, J=8.5 Hz), 7.44 (1H, dd, J=8.3, 8.0 Hz), 7.48 (1H, d, J=8.5 Hz), 7.88 (1H, d, J=8.0 Hz), 8.07 (1H, d, J=8.3 Hz), 8.79 (1H, br s).

EIMSm/z (relative intensity): 570 (M$^+$), 321 (100).

Example 109

Preparation of 2-[4-[2-(5-chloro-7-isopropyl-4-methylbenzoxazol-2-ylthio)ethyl]piperazin-1-yl]-N-[2,6-bis(ethylthio)-6-methyl-3-pyridyl]acetamide:

The same reaction and treatment as in Example 97 were conducted using 2-[4-(2-hydroxyethyl)piperazin-1-yl]-N-[2,4-bis(ethylthio)-6-methyl-3-pyridyl]instead of 2-[4-(2-hydroxyethyl)piperazin-1-yl]-N-(2,6-diisopropylphenyl)acetamide to provide the desired compound as colorless needles.

Melting point: 120–122° C. IR (KBr) cm$^{-1}$: 3301, 2968, 1690, 1481, 1216. 1H-NMR (CDCl$_3$) δ: 1.32 (3H, t, J=7.3 Hz), 1.33 (6H, d, J=6.8 Hz), 1.35 (3H, t, J=7.3 Hz), 2.47 (3H, s), 2.66–2.71 (4H, m), 2.75–2.81 (4H, m), 2.86 (2H, t, J=7.1 Hz), 2.93 (2H, q, J=7.3 Hz), 3.15 (2H, q, J=7.3 Hz), 3.20 (2H, s), 3.22 (1H, sept, J=6.8 Hz), 3.49 (2H, t, J=7.1 Hz), 6.70 (1H, s), 7.07 (1H, s), 8.53 (1H, br s).

EIMSm/z (relative intensity): 621 (M$^+$), 368 (100). Elementary analysis as C$_{29}$H$_{40}$ClN$_5$O$_2$S$_3$ Calculated: C, 55.97; H, 6.48; N, 11.25. Found: C, 56.26; H, 6.40; N, 11.17.

Example 110

Preparation of 2-[4-[3-(5-chloro-7-isopropyl-4-methylbenzoxazol-2-ylthio)propyl]piperazin-1-yl]-N-(2,6-diisopropyl-3-methoxyphenyl)acetamide:

N,N-Diisopropylethylamine (513 mg, 3.97 mmol) and a solution of trimethylsilyl diazomethane in hexane (2.0 M, 2.0 ml, 3.97 mmol) were added to a solution of N-(2,6-diisopropyl-3-hydroxyphenyl)-2-[4-(3-hydroxypropyl) piperazin-1-yl]acetamide (500 mg, 1.32 mmol) in a mixed solvent of methanol (8 ml) and acetonitrile (12 ml) and the mixture was stirred for four days. After the reaction, the solvent was evaporated. The residue was made basic by adding an aqueous solution of sodium bicarbonate and extracted with chloroform. The organic layer was washed with a saturated sodium chloride solution, dried over anhydrous sodium sulfate and the solvent was evaporated therefrom. The residue was purified by a silica gel column chromatography (developing solvent, chloroform methanol=10:1) to provide 449 mg (yield 87%) of N-(2,6-diisopropyl-3-methoxyphenyl)-2-[4-(3-hydroxypropyl) piperazin-1-yl]acetamide.

To a solution of the alcohol (150 mg, 0.38 mmol) in THF (3 ml) were added triethylamine (50 mg, 0.50 mmol) and 4-dimethylaminopyridine (5 mg, 0.04 mmol), then methanesulfonyl chloride (53 mg, 0.46 mmol) was dropped thereinto with ice cooling and stirring, the mixture was stirred for 30 minutes. After the reaction, the reaction solution was diluted with water and extracted with ethyl acetate. The organic layer was washed with a saturated sodium chloride solution, dried over anhydrous sodium sulfate and the solvent was evaporated. The resulting residue was dissolved in DMF (5 ml), then 5-chloro-7-isopropyl-2-mercapto-4-methylbenzoxazole (93 mg, 0.38 mmol), potassium carbonate (64 mg, 0.46 mmol) and 18-crown-6 (10 mg, 0.04 mmol) were added thereto and the mixture was stirred at 80° C. for 1 hour. The reaction solution was diluted with water and extracted with ethyl acetate. The organic layer was washed with water and a saturated sodium chloride solution successively, dried over anhydrous sodium sulfate and the solvent was evaporated. The resulting residue was purified by a silica gel column chromatography (developing solvent, chloroform:methanol=50:1) and the resulting crystals were recrystallized from ethyl acetate-hexane to provide 91 mg (yield 39%) of the desired compound as colorless powdery crystals.

Melting point: 126–127° C. IR (KBr) cm$^{-1}$: 3288, 2962, 1663, 1501, 1491. 1H-NMR (CDCl$_3$) δ: 1.18 (6H, d, J=6.9 Hz), 1.30 (6H, d, J=6.9 Hz), 1.33 (6H, d, J=6.9 Hz), 2.92 (2H, quint, J=7.0 Hz), 2.50–2.60 (4H, m), 2.52 (3H, s), 2.54 (2H, t, J=7.0 Hz), 2.70–2.79 (4H, m), 2.92 (1H, sept, J=6.9 Hz), 3.13–3.26 (2H, m), 3.21 (2H, s), 3.36 (2H, t, J=7.0 Hz), 3.80 (3H, s), 6.84 (1H, d, J=8.7 Hz), 7.07 (1H, s) 7.12 (1H, d, J=8.7 Hz), 8.59 (1H, br s).

EIMSm/z (relative intensity): 616 (M$^+$+1), 139 (100).

Example 111

Preparation of N-(2,6-diisopropyl-3-methoxyphenyl)-2-[4-[3-(7-trifuluoromethylbenzoxazol-2-ylthio)propyl] piperazin-1-yl]acetamide:

The same reaction and treatment as in Example 110 were conducted using 2-mercapto-7-trifluoromethylbenzoxazole instead of 5-chloro-7-isopropyl-2-mercapto-4-methylbenzoxazole to provide the desired compound as colorless powdery crystals.

Melting point: 139–141° C. IR (KBr) cm$^{-1}$: 3278, 2960, 1664, 1506, 1332. 1H-NMR (CDCl$_3$) δ: 1.17 (6H, d, J=6.9 Hz), 1.30 (6H, d, J=6.9 Hz), 2.06 (2H, quint, J=6.9 Hz), 2.50–2.60 (4H, m), 2.55 (2H, t, J=6.9 Hz), 2.71–2.78 (4H, m), 2.92 (1H, sept, J=6.9 Hz), 3.18 (1H, sept, J=6.9 Hz), 3.21 (2H, s), 3.39 (2H, t, J=6.9 Hz), 3.80 (3H, s), 6.84 (1H, d, J=8.6 Hz), 7.12 (1H, d, J=8.6 Hz), 7.38 (1H, m), 7.47 (1H, d, J=7.8 Hz), 7.75 (1H, d, J=7.8 Hz), 8.60 (1H, br s).

Example 112

Preparation of 2-[4-[2-(7-methylthiobenzoxazol-2-ylthio) ethyl]piperazin-1-yl]-N-(2,6-diisopropylphenyl)acetamide:

N-tert-Butoxycarbonyl-2-benzyloxy-3-nitroaniline (9.37 g, 27.2 mmol) was dissolved in methanol (150 ml), p-toluenesulfonic acid monohydrate (7.84 g, 45.5 mmol) was added thereto and the mixture was stirred at 50° C. for 12 hours. The reaction solution was neutralized with a saturated aqueous solution of sodium bicarbonate and extracted with chloroform. The organic layer was washed with water and a saturated sodium chloride solution successively and dried over anhydrous sodium sulfate and the solvent was evaporated. The residue was purified by a silica gel column chromatography (50 g of silica gel; developing solvent, hexane:ethyl acetate=6:1) to provide 6.44 g (yield 96.9%) of 2-benzyloxy-3-nitroaniline as pale yellowish brown oil.

To the resulting nitroaniline (5.80 g, 23.7 mmol) was added concentrated hydrochloric acid (10 ml) with ice cooling and, with stirring, a solution of sodium nitrite (4.27 g, 61.9 mmol) in water (5 ml) was dropped into the resulting suspension during 10 minutes. The mixture was stirred for 1 hour in an ice bath, adjusted to pH, 7 with a saturated aqueous solution of sodium bicarbonate, then sodium thiomethoxide (2.00 g, 28.5 mmol) was added thereto, and the mixture was stirred for 5 minutes. This was stirred at 80° C. for 10 minutes more, the reaction solution was allowed to cool to room temperature, extracted with chloroform, the organic layer was washed with water and a saturated sodium chloride solution successively and dried over anhydrous sodium sulfate and the solvent was evaporated. The residue was purified by a silica gel column chromatography (150 g of silica gel; developing solvent, hexane:benzene=2:1) and the resulting crude crystals were recrystallized from ethyl acetate-hexane to provide 0.87 g (yield 19.8%) of 2-methylthio-6-nitrophenol as pale yellowish brown needles.

The nitrophenol (290 mg, 1.57 mmol) was dissolved in acetic acid (13 ml) and concentrated hydrochloric acid (0.3 ml) and, under cooling with water, zinc powder (411 mg, 6.28 mmol) was added thereto. The mixture was stirred at room temperature for 15 minutes, the reaction solution was filtered off and the filtrate was neutralized with 2N sodium hydroxide and a saturated aqueous solution of sodium bicarbonate and extracted with ethyl acetate. The organic layer was washed with water and a saturated sodium chloride solution successively and dried over anhydrous sodium sulfate and the solvent was evaporated. The residue was purified by a silica gel column chromatography (20 g of silica gel; developing solvent, hexane:ethyl acetate=1:1) to provide 230 mg (yield 94%) of 2-amino-6-methylthiophenol as pale brown needles.

To a solution of the phenol compound (230 mg, 1.48 mmol) in ethanol (30 ml) was added potassium O-ethyldithiocarbonate (285 mg, 1.78 mmol) and the mixture was heated to reflux for 12 hours. The reaction solution was diluted with water, acidified with 2N hydrochloric acid and extracted with ethyl acetate. The organic layer was washed with water and a saturated sodium chloride solution successively and dried over anhydrous sodium sulfate and the solvent was evaporated. The residue was purified by a silica gel column chromatography (25 g of silica gel; developing solvent, hexane:ethyl acetate=2:1) to provide 224 mg (yield 77%) of 2-mercapto-7-methylthiobenzoxazole as yellow crystals.

The same reaction and treatment as in Example 1 were conducted using 2-mercapto-7-methylthiobenzoxazole instead of 2-mercaptobenzooxazole to provide the desired compound as colorless needles.

Melting point: 120–121° C. IR (KBr) cm$^{-1}$: 3247, 2960, 1660, 1499, 1414. 1H-NMR (CDCl$_3$) δ: 1.20 (12H, d, J=7.0

Hz), 2.59 (3H, s), 2.60–2.78 (8H, m), 2.85 (2H, t, J=6.8 Hz), 3.00 (2H, sept, J=7.0 Hz), 3.21 (2H, s), 3.49 (2H, t, J=6.8 Hz), 7.13–7.31 (5H, m), 7.40 (1H, d, J=7.8 Hz), 8.61 (1H, br s).

EIMSm/z (relative intensity): 526 (M$^+$), 125 (100).

Example 113

Preparation of 2-[4-[2-(7-methanesulfonylbenzoxazol-2-ylthio)ethyl]piperazin-1-yl]-N-(2,6-diisopropylphenyl)acetamide:

Sodium perborate tetrahydrate (640 mg, 4.16 mmol) was added to a solution of 2-methylthio-6-nitrophenol (120 mg, 0.648 mmol) in acetic acid (6 ml) and the mixture was stirred at 55° C. for 4 hours. The residue obtained by concentrating the reaction solution was purified by a silica gel column chromatography (50 g of silica gel; developing solvent, chloroform→chloroform:methanol=50:1→chloroform:methanol=4:1), the resulting residue was suspended in acetic acid (12 ml), under cooling with ice water then zinc (450 mg, 6.88 mmol) and concentrated hydrochloric acid (0.2 ml) were added thereto and the mixture was returned to room temperature and stirred for 20 minutes. The reaction solution was neutralized by adding a saturated sodium bicarbonate solution thereto and extracted with chloroform. The organic layer was washed with a saturated sodium chloride solution and dried over anhydrous sodium sulfate and the solvent was evaporated. The residue was purified by a preparative thin layer chromatography (developing solvent, chloroform:methanol=10:1) to provide 26 mg (yield 21%) of 2-amino-6-methanesulfonylphenol as brown oil.

Potassium O-ethyldithiocarbonate (67.3 mg, 0.420 mmol) was added to a solution of the phenol compound (25.5 mg, 0.136 mmol) in ethanol (8 ml) and the mixture was heated to reflux with stirring for 9 hours. The reaction solution was concentrated, 1N hydrochloric acid was added to the residue until pH became 4 and the mixture was extracted with chloroform. The organic layer was washed with a saturated sodium chloride solution and dried over anhydrous sodium sulfate and the solvent was evaporated. The residue was purified by a silica gel column chromatography (2.5 g of silica gel; developing solvent, chloroform:methanol=10:1) to provide 29.4 mg (yield 94.4%) of 2-mercapto-7-methanesulfonylbenzoxazole as brown solid. This was recrystallized from methanol-chloroform-ether to provide pale brown crystals.

The same reaction and treatment as in Example 1 were conducted using 2-mercapto-7-methanesulfonylbenzoxazole instead of 2-mercaptobenzooxazole to provide the desired compound as colorless crystals.

Melting point: 125–128° C. IR (KBr) cm$^{-1}$: 3449, 1660, 1503, 1426, 1322. 1H-NMR (CDCl$_3$) δ: 1.21 (12H, d, J=6.8 Hz), 2.66–2.71 (4H, m), 2.74–2.81 (4H, m), 2.86 (2H, t, J=6.8 Hz), 3.00 (2H, sept, J=6.8 Hz), 3.22 (2H, s), 3.26 (3H, s), 3.53 (2H, t, J=6.8 Hz), 7.18 (1H, d, J=8.3 Hz), 7.19 (1H, d, J=7.3 Hz), 7.29 (1H, dd, J=8.3, 7.3 Hz), 7.45 (1H, t, J=7.8 Hz), 7.78 (1H, dd, J=7.8, 1.2 Hz), 7.84 (1H, dd, J=7.8, 1.2 Hz), 8.60 (1H, br s).

Example 114

Preparation of 2-[4-[2-(7-trifluoromethylbenzoxazol-2-ylthio)ethyl]piperazin-1-yl]-N-(2,6-diisopropyl-4-hydroxyphenyl)acetamide:

The same reaction and treatment as in Example 22 were conducted using 2-mercapto-7-trifluoromethylbenzoxazole instead of 2-mercaptobenzoxazole to provide 1-[2-(7-trifluoromethylbenzoxazol-2-ylthio)ethyl]piperazine ditrifluoroacetate.

The same reaction and treatment as in Example 48 were conducted using 4-amino-3,5-diisopropylphenol instead of 2,4,6-triisopropylaniline, and using 1-[2-(7-trifluoromethylbenzoxazol-2-ylthio)ethyl]piperazine ditrifluoroacetate instead of 1-[2-(benzoxazol-2-ylthio)ethyl]piperazine ditrifluoroacetate to provide the desired compound as colorless powdery crystals.

Melting point: 258–259° C. IR (KBr) cm$^{-1}$: 3440, 2967, 1661, 1609, 1594. 1H-NMR (d$_6$-DMSO, 120° C.) δ: 1.12 (12H, d, J=6.8 Hz), 2.97 (2H, sept, J=6.8 Hz), 3.05–3.24 (10H, m), 3.66 (2H, t, J=6.8 Hz), 3.78 (2H, s), 6.57 (2H, s), 7.54 (1H, t, J=7.8 Hz), 7.63 (1H, d, J=7.8 Hz), 7.92 (1H, d, J=7.8 Hz), 9.10 (1H, br s). Elementary analysis as: C$_{28}$H$_{36}$ClF$_3$N$_4$O$_3$S Calculated: C, 55.95; H, 6.04; N, 9.32; Cl, 5.90; F, 9.48. Found: C, 55.80; H, 6.01; N, 9.23; Cl, 5.92; F, 9.31.

Example 115

Preparation of N'-(2,6-diisopropyl-4-hydroxyphenyl)-N-heptyl-N-[2-[4-[2-(7-trifluoromethylbenzoxazol-2-ylthio)ethyl]piperazin-1-yl]ethyl]urea hydrochloride:

To a solution of 4-amino-3,5-diisopropylphenol (1.02 g, 5.27 mmol) in dichloromethane (10 ml) was added N,N-dimethylaniline (770 mg, 6.34 mmol), then a solution of phenyl chloroformate (910 mg, 5.81 mmol) in dichloromethane (2 ml) was dropped thereinto with ice-cooling and stirring, and the mixture was stirred for 30 minutes. The reaction solution was diluted with water and extracted with dichloromethane. The organic layer was washed with a saturated sodium chloride solution, dried over anhydrous sodium sulfate, and concentrated in vacuo. The resulting residue was purified by a silica gel column chromatography (silica gel 34 g, developing solvent; hexane:acetone=5:1) to provide 1.27 g (77%) of phenyl N-(2,6-diisopropyl-4-hydroxyphenyl)carbamate as colorless oil.

To a solution of 2-[4-(2-heptylaminoethyl)piperazin-1-yl]ethanol (4.67 g, 17.2 mmol) prepared in Example 16 in chloroform (50 ml) was added a solution of di-tert-butyl dicarbonate (3.80 g, 17.4 mmol) in chloroform (20 ml) at 0° C. and stirred for 1 hour. The reaction solution was concentrated in vacuo, and the resulting residue was purified by a silica gel column chromatography (silica gel 140 g, developing solvent; chloroform:methanol=100:1 30:1) to provide 3.88 g (yield 61%) of tert-butyl N-heptyl-N-[2-[4-(2-hydroxyethyl)piperazin-1-yl]ethyl]carbamate as pale yellow oil.

To a solution of this alcohol (500 mg, 1.35 mmol) in THF (10 ml) were added triethylamine (180 mg, 1.78 mmol) and 4-(dimethylamino) pyridine (16 mg, 0.13 mmol), and then methanesulfonyl chloride (190 mg, 1.66 mmol) was dropped there into with ice-cooling and stirred for 20 minutes. Further, to the same solution were added triethylamine (45 mg, 0.44 mmol) and methanesulfonyl chloride (45 mg, 0.39 mmol) was dropped thereinto with ice-cooling and stirred for 1 hour. The reaction solution was filtered and the filtrate was concentrated in vacuo. The resulting residue was dissolved in DMF (3 ml), and the resulting solution was dropped into a solution of 2-mercapto-7-trifluoromethylbenzoxazole (310 mg, 1.41 mmol) and potassium carbonate (280 mg, 2.03 mmol) in DMF (7 ml) and stirred at 80° C. for 90 minutes. The reaction solution was concentrated in vacuo and the resulting residue was filtered off with ether. The filtrate was concentrated in vacuo and the resulting residue was purified by a silica gel column chromatography (silica gel 35 g, developing solvent; hexane:acetone=10:1) to provide 283 mg (yield 37%) of tert-butyl N-heptyl-N-[2-[4-[2-(7-trifluoromethylbenzoxazol-2-ylthio)ethyl]piperazin-1-yl]ethyl]carbamate as pale yellow oil.

This tert-butylcarbamate (250 mg, 0.44 mmol) was dissolved in trifluoroacetic acid (0.75 ml) and stirred at room temperature for 1 hour. The reaction solution was concentrated in vacuo. To the resulting residue was added 2 N sodium hydroxide and extracted with chloroform. The organic layer was washed with water and a saturated sodium chloride solution successively, dried over anhydrous sodium sulfate and concentrated in vacuo to provide 206 mg (yield 100%) of crude N-heptyl-N-[2-[4-[2-(7-trifluoromethylbenzoxazol-2-ylthio)ethyl]piperazin-1-yl]ethyl]amine as pale brown oil.

To a solution of this amine (206 mg, 0.44 mmol) solution in toluene (2 ml) was added triethylamine (68 mg, 0.67 mmol), and phenyl N-(2,6-diisopropyl-4-hydroxyphenyl) carbamate (140 mg, 0.45 mmol) was dropped thereinto and stirred at 80° C. for 30 minutes. Further, to the same solution was added phenyl N-(2,6-diisopropyl-4-hydroxyphenyl) carbamate (28 mg, 0.089 mmol) and stirred at 80° C. for 30 minutes. The reaction solution was diluted with water and toluene. The organic layer was washed with a saturated sodium chloride solution, dried over anhydrous sodium sulfate and concentrated in vacuo. The resulting residue was purified by a silica gel column chromatography (silica gel 4 g, developing solvent; ether) to provide 222 mg (yield 72%) of N'-(2,6-diisopropyl-4-hydroxyphenyl)-N-heptyl-N-[2-[4-[2-(7-trifluoromethylbenzoxazol-2-ylthio)ethyl]piperazin-1-yl]ethyl]urea as colorless amorphous.

This urea compound was then converted into its salt with hydrochloride according to a conventional way and recrystallized from chloroform-hexane to provide the desired compound as colorless needles.

Melting point: 95–97° C. IR (KBr) cm$^{-1}$: 3255, 2961, 1632, 1608, 1591. 1H-NMR (d$_6$-DMSO) δ: 0.88 (3H, t, J=6.1 Hz), 1.05 (6H, d, J=6.8 Hz), 1.12 (6H, d, J=6.8 Hz), 1.21–1.36 (8H, m), 1.50–1.62 (2H, m), 3.00 (2H, sept, J=6.8 Hz), 3.12–3.78 (18H, m), 6.50 (2H, s), 7.56 (1H, t, J=8.1 Hz), 7.69 (2H, d, J=8.1 Hz), 7.98 (1H, d, J=8.1 Hz), 9.13 (1H, br s). Elementary analysis as: $C_{36}H_{52}F_3N_5O_3S \cdot 1.5HCl \cdot H_2O$ Calculated: C, 56.55; H, 7.32; N, 9.16; Cl, 6.96; F, 7.45. Found: C, 56.83; H, 7.13; N, 9.16; Cl, 6.86; F, 7.30.

Example 116

Preparation of N-[2-[4-[2-(5-chloro-7-isopropyl-4-methylbenzoxazol-2-ylthio)ethyl]piperazin-1-yl]ethyl]-N'-(2,6-diisopropyl-4-hydroxyphenyl)-N-heptylurea:

The same reaction and treatment as in Example 115 were conducted using 5-chloro-7-isopropyl-2-mercapto-4-methylbenzoxazole instead of 2-mercapto-7-trifluoromethylbenzoxazole to provide the desired compound as colorless powdery crystals.

Melting point: 138–140°IR (KBr) cm$^{-1}$: 3317, 2958, 1621, 1591, 1499. 1H-NMR (CDCl$_3$) δ: 0.88 (3H, t, J=7.1 Hz), 1.11 (6H, d, J=6.1 Hz), 1.17 (6H, d, J=6.1 Hz), 1.22–1.34 (16H, m), 1.50–1.63 (2H, m), 2.38–2.67 (13H, m), 2.71 (2H, t, J=7.1 Hz), 3.06 (2H, sept, J=6.1 Hz), 3.19 (1H, sept, J=6.8 Hz), 3.33 (2H, t, J=7.1 Hz), 3.40 (2H, t, J=7.1 Hz), 3.44 (2H, br s), 6.49 (2H, s), 7.06 (1H, s). Elementary analysis as: $C_{39}H_{60}ClN_5O_3S$ Calculated: C, 65.56; H, 8.46; N, 9.80; Cl, 4.96; S, 4.49. Found: C, 65.56; H, 8.30; N, 9.80; Cl, 4.85; S, 4.41.

Example 117

Preparation of 2-[4-[3-(5-chloro-7-isopropyl-4-methylbenzoxazol-2-ylthio)propyl]piperazin-1-yl]ethyl]-N-[2,6-diisopropyl-3-(2-ethoxyethyloxy)phenyl]acetamide:

The same reaction and treatment as in Example 1 were conducted using N-[2,6-diisopropyl-3-(2-ethoxyethyloxy)phenyl]-2-[4-(3-hydroxypropyl)piperazin-1-yl]acetamide prepared in Example 71 instead of N-(2,6-diisopropylphenyl)-2-[4-(2-hydroxyethyl) piperazin-1-yl] acetamide and using 5-chloro-7-isopropyl-2-mercapto-4-methylbenzoxazole instead of 2-mercaptobenzoxazole to provide the desired compound as colorless, powdery crystals.

Melting Point: 137–139° C. IR (KBr) cm$^{-1}$: 3281, 2964, 1664, 1505, 1145. 1H-NMR (CDCl$_3$) δ: 1.17 (6H, d, J=6.9 Hz), 1.23 (3H, t, J=7.0 Hz), 1.32 (6H, d, J=6.9 Hz), 1.33 (6H, d, J=6.9 Hz), 2.05 (2H, quint, J=7.0 Hz), 2.50–2.62 (4H, m), 2.52 (3H, s), 2.55 (2H, t, J=7.0 Hz), 2.69–2.80 (4H, m), 2.91 (1H, sept, J=6.9 Hz), 3.18 (1H, sept, J=6.9 Hz ), 3.20 (1H, sept, J=6.9 Hz), 3.21 (2H, s), 3.36 (2H, t, J=7.0 Hz), 3.59 (2H, q, J=7.0 Hz), 3.81 (2H, t, J=5.1 Hz), 4.09 (2H, t, J=5.1 Hz), 6.83 (1H, d, J=8.7 Hz), 7.07 (1H, s), 7.10 (1H, d, J=8.7 Hz), 8.59 (1H, br s).

EIMSm/z (relative intensity): 672 (M$^+$), 139 (100). Elementary analysis as: $C_{36}H_{53}ClN_4O_4S$ Calculated: C, 64.22; H, 7.93; N, 8.32; S, 4.76. Found: C, 64.17; H, 7.94; N, 8.23; S, 4.64.

Example 118

Preparation of 2-[4-[3-(benzoxazol-2-ylthio)propyl]piperazin-1-yl]-N-(2,6-diisopropyl-4-hydroxyphenyl)acetamide:

The same reaction and treatment as in Example 48 were conducted using 4-amino-3,5-diisopropylphenol instead of 2,4,6-triisopropylaniline, and using 1-[3-(benzoxazol-2-ylthio)propyl]piperazine ditrifluoroacetate instead of 1-[2-(benzoxazol-2-ylthio)ethyl]piperazine ditrifluoroacetate to provide the desired compound as colorless powdery crystals.

Melting point: 201–203° C. IR (KBr) cm$^{-1}$: 3292, 2960, 1663, 1497, 1456. 1H-NMR (CDCl$_3$) δ: 1.17 (12H, d, J=6.8 Hz), 2.05 (2H, quint, J=7.0 Hz), 2.48–2.63 (4H, m), 2.54 (2H, t, J=7.0 Hz), 2.68–2.78 (4H, m), 2.95 (2H, sept, J=6.8 Hz), 3.20 (2H, s), 3.38 (2H, t, J=7.0 Hz), 4.96 (1H, br s), 6.63 (2H, s), 7.22–7.31 (2H, m), 7.43 (1H, m), 7.58 (1H, m), 8.47 (1H, br s)

EIMSm/z (relative intensity): 510 (M$^+$), 139 (100). Elementary analysis as: $C_{28}H_{38}N_4O_3S$ Calculated: C, 65.85; H, 7.50; N, 10.97; S, 6.28. Found: C, 65.75; H, 7.58; N, 10.81; S, 6.21.

Example 119

Preparation of 2-[4-[3-(benzoxazol-2-ylthio)propyl]piperazin-1-yl]-N-(2,6-diisopropyl-4-methoxyphenyl)acetamide:

The same reaction and treatment as in Example 86 were conducted using 1-(3-hydroxypropyl)piperazine instead of 1-(2-hydroxyethyl)piperazine to provide 2-[4-(3-hydroxypropyl)piperazin-1-yl]-N-(2,6-diisopropyl-4-methoxyphenyl)acetamide.

The same reaction and treatment as in Example 1 were conducted using this acetamide instead of N-(2,16-diisopropylphenyl)-2-[4-(2-hydroxyethyl)piperazin-1-yl] acetamide to provide the desired compound as colorless powdery crystals.

Melting point: 129–130° C. IR (KBr) cm$^{-1}$: 3301, 2959, 1668, 1499, 1453. 1H-NMR (CDCl$_3$) δ: 1.19 (12H, d, J=6.8 Hz), 2.40 (2H, quint, J=7.1 Hz), 2.48–2.62 (4H, m), 2.54 (2H, t, J=7.1 Hz), 2.68–2.77 (4H, m), 2.98 (2H, sept, J=6.8 Hz), 3.21 (2H, s), 3.38 (2H, t, J=7.1 Hz), 3.81 (3H, s), 6.71 (2H, s), 7.20–7.32 (2H, m), 7.43 (1H, m), 7.59 (1H, m), 8.49 (1H, br s).

EIMSm/z (relative intensity): 524 (M$^+$), 290 (100). Elementary analysis as: C$_{29}$H$_{40}$N$_4$O$_3$S Calculated: C, 66.38; H, 7.68; N, 10.68; S, 6.11. Found: C, 65.57; H, 7.68; N, 10.63; S, 6.26.

Example 120

Preparation of 2-[4-[3-(benzoxazol-2-ylthio)propyl]piperazin-1-yl]-N-[2,6-diisopropyl-4-(2-ethoxyethyloxy)phenyl]acetamide:

To a solution of 1-(3-hydroxypropyl)piperazine (700 mg, 4.88 mmol) in acetonitrile (15 ml) were added potassium carbonate (805 mg, 5.82 mmol) and 2-bromo-N-(2,6-diisopropyl-4-hydroxyphenyl)acetamide (1.53 g, 4.88 mmol), and the mixture was stirred at room temperature for 1 hour. To the reaction solution was added a saturated ammonium chloride solution and the mixture was extracted with chloroform-methanol mixture solvent. The organic layer was washed with water and a saturated sodium chloride successively and dried over anhydrous sodium sulfate, and the solvent was evaporated therefrom. The resulting residue was recrystallized from chloroform-methanol-hexane to provide 1.13 g (yield 62%) of 2-[4-(3-hydroxypropyl)piperazin-1-yl]-N-[2,6-diisopropyl-4-hydroxyphenyl]acetamide as colorless powdery crystals.

To a solution of this acetamide (500 mg, 1.32 mmol) solution in DMF (12 ml) were added 2-bromoethyl ethyl ether (7 ml) and potassium fluoride 40 wt. % on alumina (40 wt. %, 1.96 g, 13.2 mmol), and the mixture was stirred at room temperature for 5 days. After the catalyst was filtered off, the filtrate was diluted with water and extracted with ethylacetate. The organic layer was washed with a saturated sodium chloride solution and dried over anhydrous sodium sulfate, and the solvent was evaporated therefrom. The resulting residue was purified by a silica gel column chromatography (developing solvent; chloroform:methanol=30:1) to provide 448 mg (yield 78%) of N-[2,6-diisopropyl-4-(2-ethoxyethyloxy)phenyl]-2-[4-(3-hydroxypropyl)piperazin-1-yl]acetamide as colorless powdery crystals.

The same reaction and treatment as in Example 1 were conducted using N-[2,6-diisopropyl-4-(2-ethoxyethyloxy)phenyl]-2-[4-(3-hydroxypropyl)piperazin-1-yl]acetamide instead of N-(2,6-diisopropylphenyl)-2-[4-(2-hydroxyethyl)piperazin-1-yl]acetamide to provide the desired compound as colorless powdery crystals.

Melting point: 115–117° C. IR (neat) cm$^{-1}$: 3278, 2960, 1662, 1500, 1455. 1H-NMR (CDCl$_3$) δ: 1.18 (12H, d, J=6.8 Hz), 1.25 (3H, t, J=7.0 Hz), 2.04 (2H, quint, J=7.1 Hz), 2.45–2.63 (4H, m), 2.54 (2H, t, J=7.1 Hz), 2.65–2.78 (4H, m), 2.97 (2H, sept, J=6.8 Hz), 3.20 (2H, s), 3.38 (2H, t, J=7.1 Hz), 3.61 (2H, q, J=7.0 Hz), 3.79 (2H, t, J=4.9 Hz), 4.13 (2H, t, J=4.9 Hz), 6.74 (2H, s), 7.22–7.31 (2H, m), 7.43 (1H, m), 7.58 (1H, m), 8.48 (1H, br s).

EIMSm/z (relative intensity): 582 (M$^+$), 290 (100). Elementary analysis as: C$_{32}$H$_{46}$N$_4$O$_4$S Calculated: C, 65.95; H, 7.96; N, 9.61; S, 5.50. Found: C, 65.90; H, 7.89; N, 9.73; S, 5.60.

Example 121

Preparation of 2-[4-[2-(7-methanesulfinylbenzoxazol-2-ylthio)ethyl]piperazin-1-yl]-N-(2,6-diisopropylphenyl)acetamide:

To a solution of 2-methylthio-6-nitrophenol (410 mg, 2.21 mmol) in acetic acid (15 ml) was added sodium perborate tetrahydrate (1.00 g, 6.50 mmol) and the mixture was stirred at room temperature for 2 hours. To the reaction solution was then added zinc powder (7 g, 0.107 mmol) with ice-cooling, and the mixture was stirred at room temperature for 1 hour. The reaction mixture was neutralized with a saturated sodium bicarbonate solution and extracted with chloroform. The organic layer was washed with a saturated sodium chloride solution, dried over anhydrous sodium sulfate and concentrated in vacuo. The resulting residue was purified by a silica gel column chromatography (silica gel 50 g, developing solvent; chloroform) to provide 234 mg (yield 62%) of 2-amino-6-methanesulfinylphenol as colorless amorphous.

To a solution of this aminophenol. (233 mg, 1.36 mmol) in ethanol (10 ml) was added potassium O-ethyl dithiocarbonate (300 mg, 1.87 mmol) and the mixture was stirred under heating to reflux for 9 hours. The reaction solution was acidified to pH, 4 with 1 N hydrochloric acid and extracted with chloroform. The organic layer was washed with a saturated sodium chloride solution, dried over anhydrous sodium sulfate and concentraed in vacuo. The resulting residue was purified by a silica gel preparative thin layer chromatography (developing solvent; chloroform:methanol=10:1) and recrystallized from chloroform-ether to provide 223 mg (yield 77%) of 2-mercapto-7-methansulfinylbenzoxazole as pale brown powdery crystals.

The same reaction and treatment as in Example 1 were conducted using 2-mercapto-7-methansulfinylbenzoxazole instead of 2-mercaptobenzoxazole to provide the desired compound as colorless powdery crystals.

Melting point: 119–120° C. IR (KBr) cm$^{-1}$: 3435, 3246, 1661, 1591, 1501. 1H-NMR (CDCl$_3$) δ: 1.22 (12H, d, J=6.8 Hz), 2.59–2.81 (8H, m), 2.86 (2H, t, J=6.8 Hz), 2.94 (3H, s), 3.00 (2H, sept, J=6.8 Hz), 3.23 (2H, s), 3.52 (2H, t, J=6.8 Hz), 7.19 (2H, d, J=7.6 Hz), 7.30 (1H, t, J=7.6 Hz), 7.49 (1H, t, J=7.6 Hz), 7.70 (2H, d, J=7.6 Hz), 8.60 (1H, br s).

EIMSm/z (relative intensity): 542 (M$^+$), 330 (100). HRMS: C$_{28}$H$_{38}$N$_4$O$_3$S$_2$ Calculated: 542.23850. Found: 542.23851.

Example 122

Preparation of 2-[4-[2-(7-isopropyl-4-methylbenzoxazol-2-ylthio)ethyl]piperazin-1-yl]-N-(2,6-diisopropylphenyl)acetamide:

To a solution of 4-chloro-6-isopropyl-3-methyl-2-nitrophenol (1.82 g, 7.92 mmol) obtained in Example 97 in ethanol (40 ml) was added 10% palladium carbon catalyst (1.8 g) and the mixture was stirred under hydrogen atmosphere at 60° C. for 3 hours. After the reaction was over, the reaction solution was filtered with celite and the filtrate was concentrated to provide 1.60 g of 2-amino-6-isopropyl-3-methylphenol (yield 99%) as pale brown solid. To a solution of this aminophenol (1.65 g, 7.92 mmol) in ethanol (25 ml) was added potassium O-ethyl dithiocarbonate (1.52 g, 9.50 mmol) and the mixture was heated to reflux for 8 hours and the solvent was evaporated. The resulting residue was dissolved in water, acidified to pH, 3–4 with 2 N hydrochloric acid and extracted with ethyl acetate. The organic layer was washed with water, a saturated sodium chloride solution successively, dried over anhydrous magnesium sulfate and concentrated in vacuo. The resulting residue was crystallized from ethyl acetate-hexane to provide 0.99 g (yield 60%) of 7-isopropyl-2-mercapto-4-methylbenzoxazole as pale yellow needles.

The same reaction and treatment as in Example 1 were conducted using 7-isopropyl-2-mercapto-4-methylbenzoxazole instead of 2-mercaptobenzoxazole to provide the desired compound as colorless needles.

Melting point: 133–134° C. IR (KBr) cm$^{-1}$: 3433, 3282, 1661, 1497. 1H-NMR (CDCl$_3$) δ: 1.20 (12H, d, J=6.8 Hz), 1.34 (6H, d, J=6.8 Hz), 2.51 (3H, s), 2.61–2.78 (8H, m), 2.85 (2H, t, J=7.2 Hz), 3.00 (2H, sept, J=6.8 Hz), 3.21 (2H, s), 3.24 (1H, sept, J=6.8 Hz), 3.47 (2H, t, J=7.2 Hz), 6.97 (1H, d, J=7.8 Hz), 7.01 (1H, d, J=7.8 Hz), 7.18 (2H, d, J=7.8 Hz), 7.29 (1H, t, J=7.8 Hz), 8.61 (1H, br s).

EIMSm/z (relative intensity): 536 (M$^+$), 192 (100). Elementary analysis as: C$_{31}$H$_{44}$N$_4$O$_2$S Calculated: C, 69.37; H, 8.26; N, 10.44; S, 5.97. Found: C, 69.37; H, 8.22; N, 10.30; S, 5.86.

Example 123

Preparation of N-[2-[4-[3-(benzoxazol-2-ylthio)propyl]piperazin-1-yl]ethyl]-N'-[2,4-bis(methylthio)-6-methyl-3-pyridyl]-N-heptylurea dihydrochloride:

The same reaction and treatment as in Example 115 were conducted using 3-amino-2,4-bis(methylthio)-6-methylpyridine instead of 4-amino-3,5-diisopropylphenol to provide phenyl N-[2,4-bis(methylthio)-6-methylpyridyl]carbamate.

To a solution of this phenyl carbamate (188 mg, 0.59 mmol) in toluene (3 ml) were added triethylamine (72 mg, 0.71 mmol) and 3-[4-(2-heptylaminoethyl)piperazin-1-yl]propanol (168 mg, 0.59 mmol) and the mixture was stirred at 80° C. for 3 hours. The reaction solution was diluted with water and extracted with chloroform. The organic layer was washed with water and a saturated sodium chloride solution successively, dried over anhydrous sodium sulfate and concentrated in vacuo. The resulting residue was purified by a silica gel column chromatography (silica gel 15 g, developing solvent; chloroform:methanol=40:1 10:1) to provide 249 mg (yield 83%) of N'-[2,4-bis(methylthio)-6-methyl-3-pyridyl]-N-heptyl-N-[2-[4-(3-hydroxypropyl)piperazin-1-yl]ethyl]urea as colorless oil.

The same reaction and treatment as in Example 19 were conducted using this urea compound instead of N'-(2,6-diisopropylphenyl)-N-heptyl-N-[2-[4-(3-hydroxypropyl)piperazin-1-yl]ethyl]urea, and the resulting compound was converted into its salt with hydrochloride in a conventional manner to provide the desired compound as colorless powdery crystals.

Melting point: 208–210° C. IR (KBr) cm$^{-1}$: 3421, 3258, 1658, 1562, 1494. 1H-NMR (d$_6$-DMSO) δ: 0.87 (3H, t, J=6.8 Hz), 1.21–1.35 (8H, m), 1.50–1.66 (2H, m), 2.28 (2H, quint, J=6.6 Hz), 3.39 (6H, s), 2.45 (3H, s), 2.75–4.01 (18H, m), 6.88 (1H, s), 7.30–7.37 (2H, m), 7.63–7.68 (2H, m), 8.34 (1H, br s). Elementary analysis as: C$_{32}$H$_{48}$N$_6$O$_2$S$_3$.2HCl Calculated: C, 53.54; H, 7.02; N, 11.71; S, 13.40; Cl, 9.88. Found: C, 53.35; H, 7.01; N, 11.63; S, 13.37; Cl, 9.88.

Example 124

Preparation of N-[2-[4-[2-(benzoxazol-2-ylthio)ethyl]piperazin-1-yl]ethyl]-N'-[2,4-bis(ethylthio)-6-methyl-3-pyridyl]-N-heptylurea dihydrochloride:

The same reaction and treatment as in Example 115 were conducted using 3-amino-2,4-bis(ethylthio)-6-methylpyridine instead of 4-amino-3,5-diisopropylphenol to provide phenyl N-[2,4-bis(ethylthio)-6-methylpyridyl]carbamate.

To a solution of this phenyl carbamate (1.46 g, 4.19 mmol) in toluene (20 ml) were added triethylamine (509 mg, 5.03 mmol) and 2-[4-(2-heptylaminoethyl)piperazin-1-yl]ethanol (1.14 g, 4.20 mmol) obtained in Example 16 and the mixture was stirred at 80° C. for 2 hours. The reaction solution was diluted with water and extracted with chloroform. The organic layer was washed with water and a saturated sodium chloride solution successively, dried over anhydrous sodium sulfate and concentrated in vacuo. The resulting residue was purified by a silica gel column chromatography (silica gel 100 g, developing solvent; chloroform:methanol=40:1 20:1) to provide 1.95 g (yield 88%) of N'-[2,4-bis(ethylthio)-6-methyl-3-pyridyl]-N-heptyl-N-[2-[4-(2-hydroxyethyl)piperazin-1-yl]ethyl]urea as pale yellow oil.

The same reaction and treatment as in Example 16 were conducted using this urea compound instead of N'-(2,6-diisopropylphenyl)-N-heptyl-2-[4-(2-hydroxyethyl)piperazin-1-yl]ethyl]urea, and the resulting compound was converted into its salt with hydrochloride in a conventional manner to provide the desired compound as colorless crystals.

Melting point: 124–127° C. IR (KBr) cm$^{-1}$: 3413, 2928, 1636, 1500, 1453. 1H-NMR (CD$_3$OD) δ: 0.91 (3H, t, J=6.8 Hz), 1.32 (3H, t, J=7.4 Hz), 1.39 (3H, t, J=7.4 Hz), 1.24–1.46 (8H, m), 1.68–1.82 (2H, m), 2.64 (3H, s), 3.13 (2H, q, J=7.4 Hz), 3.18–3.60 (14H, m), 3.45 (2H, t, J=7.4 Hz), 3.63 (2H, t, J=7.2 Hz), 3.70–3.80 (2H, m), 7.26–7.34 (3H, m), 7.50–7.61 (2H, m).

EIMSm/z (relative intensity): 659 (M$^+$), 136 (100). Elementary analysis as: C$_{33}$H$_{50}$N$_6$O$_2$S$_3$.2HCl.0.4H$_2$O Calculated: C, 53.62; H, 7.20; N, 11.37; S, 13.02. Found: C, 53.91; H, 7.36; N, 11.19; S, 13.23.

Example 125

Preparation of N-[2-[4-[2-(benzothiazol-2-ylthio)ethyl]piperazin-1-yl]ethyl]-N'-[2,4-bis(ethylthio)-6-methyl-3-pyridyl]-N-heptylurea dihydrochloride:

The same reaction and treatment as in Example 124 were conducted using 2-mercaptobenzothiazole instead of 2-mercaptobenzoxazole, and the resulting compound was converted into its salt with hydrochloride in a conventional manner to provide the desired compound as colorless powdery crystals.

Melting point: 136–138° C. IR (KBr) cm$^{-1}$: 3407, 2926, 1643, 1612, 1494. 1H-NMR (CD$_3$OD) δ: 0.91 (3H, t, J=6.8 Hz), 1.32 (3H, t, J=7.4 Hz), 1.40 (3H, t, J=7.4 Hz), 1.28–1.44 (8H, m), 1.70–1.82 (2H, m), 2.66 (3H, s), 3.13 (2H, q, J=7.4 Hz), 3.20–3.85 (20H, m), 7.35 (1H, td, J=7.3, 1.1 Hz), 7.40 (1H, s), 7.46 (1H, td, J=7.3, 1.1 Hz), 7.86 (1H, dd, J=7.3, 1.1 Hz), 7.88 (1H, dd, J=7.3, 1.1 Hz).

EIMSm/z (relative intensity): 675 (M$^+$), 154 (100). Elementary analysis as: C$_{33}$H$_{50}$N$_6$OS$_4$.2HCl.0.5H$_2$O Calculated: C, 52.36; H, 7.06; N, 11.10; S, 16.94; Cl, 9.37. Found: C, 52.16; H, 7.13; N, 10.91; S, 17.02; Cl, 9.67.

Example 126

Preparation of N-[2-[4-[2-(benzimidazol-2-ylthio)ethyl] piperazin-1-yl]ethyl]-N'-[2,4-bis(ethylthio)-6-methyl-3-pyridyl]-N-heptylurea dihydrochloride:

The same reaction and treatment as in Example 124 were conducted using 2-mercaptobenzimidazole instead of 2-mercaptobenzoxazole to provide the desired compound as colorless powdery crystals.

Melting point: 134–137° C. IR (KBr) cm$^{-1}$: 3407, 2956, 1625, 1501, 1456. 1H-NMR (CD$_3$OD) δ: 0.91 (3H, t, J=6.7 Hz), 1.31 (3H, t, J=7.4 Hz), 1.37 (3H, t, J=7.4 Hz), 1.25–1.42 (8H, m), 1.69–1.81 (2H, m), 2.57 (3H, s), 3.00 (2H, t, J=6.1 Hz), 3.07 (4H, q, J=7.4 Hz), 3.10–3.25 (16H, m), 3.43 (2H, t, J=7.4 Hz), 7.16 (1H, s), 7.53 (2H, dt, J=9.3, 3.2 Hz), 7.68 (2H, dt, J=9.3, 3.2 Hz).

EIMSm/z (relative intensity): 658 (M$^+$), 154 (100).

Example 127

Preparation of 2-[4-[2-(oxazolo[4,5-b]pyridine-2-ylthio)ethyl]piperazin-1-yl]-N-[2,4-bis(ethylthio)-6-methyl-3-pyridyl]acetamide dimaleate:

The same reaction and tratment as in Example 34 were conducted using 1-[2-(oxazolo[4,5-b]pyridin-2-ylthio)ethyl] piperazine ditrifluoroacetate instead of 1-[2-(benzoxazol-2-ylthio)ethyl]piperazine ditrifluoroacetate to provide the desired compound as colorless crystals.

Melting point: 148–149° C. IR (KBr) cm$^{-1}$: 3432, 2967, 1694, 1496. 1H-NMR (d$_6$-DMSO) δ: 1.23 (3H, t, J=7.3 Hz), 1.25 (3H, t, J=7.3 Hz), 2.43 (3H, s), 2.70–3.50 (12H, m), 2.97 (2H, q, J=7.3 Hz), 3.05 (2H, q, J=7.3 Hz), 3.63 (2H, br s), 6.13 (4H, s), 6.96 (1H, s), 7.36 (1H, dd, J=8.3, 5.2 Hz), 8.09 (1H, dd, J=8.3, 1.4 Hz), 8.43 (1H, dd, J=5.2, 1.4 Hz), 8.61 (1H, br s).

EIMSm/z (relative intensity): 536 (M$^+$), 192 (100). Elementary analysis as: C$_{24}$H$_{32}$N$_6$O$_2$S$_3$.2C$_4$H$_4$O$_4$.0.6 H$_2$O Calculated: C, 50.25; H, 5.27; N, 10.99; S, 12.57. Found: C, 49.99; H, 5.26; N, 10.93; S, 12.56.

Example 128

Preparation of [2-[4-[2-(benzoxazol-2-ylthio)ethyl] piperazin-1-yl]-N-(2,6-diisopropyl-3-methanesulfonylaminophenyl)acetamide dimaleate:

To a solution of [2-[4-[2-(benzoxazol-2-ylthio)ethyl] piperazin-1-yl]-N-(3-amino-2,6-diisopropylphenyl) acetamide (114 mg, 0.23 mmol) obtained in Example 59 in chloroform (1 ml) was added triethylamine (81 mg, 0.81 mmol), then methanesulfonyl chloride (79 mg, 0.69 mmol) was dropped thereinto with ice-cooling and stirring, and the mixture was stirred for 8 hours. To the mixture was added triethylamine (81 mg, 0.81 mmol), then methanesulfonyl chloride (79 mg, 0.69 mmol) was dropped thereinto with ice-cooling and stirring and the mixture was stirred for 12 hours. The reaction solution was concentrated in vacuo. The resulting residue was dissolved in methanol (1 ml) and 4N sodium hydroxide solution (0.5 ml) was added. The resulting solution stirred at room temperature for 1 hour. The reaction solution was neutralized with dil. hydrochloric acid and concentrated in vacuo. The resulting residue was purified a by a silica gel preparative thin layer chromatography (developing solvent; chloroform:sat. ammonia methanol= 10:1) and the resulting crystal was recrystallized from acetone-hexane to provide 41 mg (yield 31%) of the desired compound as colorless crystals.

Melting point: 176–177° C. IR (KBr) cm$^{-1}$: 3429, 1695, 1622, 1578, 1505. 1H-NMR (d$_6$-DMSO) δ: 1.11–1.31 (12H, m), 2.87 (2H, sept, J=6.8 Hz), 3.02 (3H, s), 2.60–3.70 (14H, m), 6.14 (4H, s), 7.18–7.27 (2H, m), 7.28–7.36 (2H, m), 7.59–7.68 (2H, m), 8.95 (1H, br s).

EIMSm/z (relative intensity): 573 (M$^+$), 125 (100). Elementary analysis as: C$_{28}$H$_{39}$N$_5$O$_4$S$_2$.2C$_4$H$_4$O$_4$.0.5 H$_2$O Calculated: C, 53.06; H, 5.94; N, 8.59; S, 7.87. Found: C, 53.09; H, 5.90; N, 8.53; S, 7.95.

Example 129

Preparation of 2-[4-[2-(7-trifluoromethylbenzoxazol-2-ylthio)ethyl]piperazin-1-yl]-N-(2,6-diisopropyl-3-methanesulfonylaminophenyl)acetamide dimaleate:

The same reaction and treatment as in Example of 128 were conducted using 2-[4-[2-(7-trifluoromethylbenzoxazol-2-ylthio)ethyl]piperazin-1-yl]-N-(3-amino-2,6-diisopropylphenyl)acetamide that had been obtained by the reduction according to the method in Example 59 instead of 2-[4-[2-(7-trifluoromethylbenzoxazol-2-ylthio)ethyl]piperazin-1-yl]-N-(2,6-diisopropyl-3-nitrophenyl)acetamide obtained in Example 87 to provide the desired compound as colorless crystals.

Melting point: 172–174° C. IR (KBr) cm$^{-1}$: 3434, 1689, 1625, 1508. 1H-NMR (d$_6$-DMSO) δ: 1.13–1.38 (12H, m), 2.94 (2H, sept, J=6.8 Hz), 3.09 (3H, s), 2.70–4.20 (14H, m), 6.21 (4H, s), 7.28 (1H, d, J=7.8 Hz), 7.32 (1H, d, J=7.8 Hz), 7.62 (1H, dd, J=8.0, 7.8 Hz), 7.75 (1H, d, J=7.8 Hz), 8.03 (1H, dd, J=8.0 Hz), 9.03 (1H, br s).

EIMSm/z (relative intensity): 641 (M$^+$), 344 (100). Elementary analysis as: C$_{29}$H$_{38}$F$_3$N$_5$O$_4$S$_2$.2C$_4$H$_4$O$_4$ Calculated: C, 50.85; H, 5.31; N, 8.01. Found: C, 50.88; H, 5.49; N, 8.09.

Example 130

Preparation of 2-[4-[2-(7-trifluoromethylbenzoxazol-2-ylthio)ethyl]piperazin-1-yl]-N-(2,6-diisopropyl-3-hydroxyphenyl)acetamide:

The same reaction and treatment as in Example 61 were conducted using 2-[4-[2-(7-trifluoromethylbenzoxazol-2-ylthio)ethyl]piperazin-1-yl]-N-(3-amino-2,6-diisopropylphenyl)acetamide obtained in Example 129 instead of 2-[4-[2-(benzoxazol-2-ylthio)ethyl]piperazin-1-yl]-N-(3-amino-2,6-diisopropylphenyl)acetamide to provide the desired compound as colorless crystals.

Melting point: 82–84° C. IR (KBr) cm$^{-1}$: 3314, 1667, 1595, 1505, 1330. 1H-NMR (CDCl$_3$) δ: 1.16 (6H, d, J=6.8 Hz), 1.34 (6H, d, J=6.8 Hz), 2.60–2.77 (8H, m), 2.85 (2H, t, J=6.8 Hz), 2.89 (1H, sept, J=6.8 Hz), 3.14 (1H, sept, J=6.8 Hz), 3.20 (2H, s), 3.50 (2H, t, J=6.8 Hz), 5.82 (1H, br s), 6.65 (1H, d, J=8.5 Hz), 6.99 (1H, d, J=8.5 Hz), 7.34 (1H, t, J=7.8 Hz), 7.47 (1H, d, J=7.8 Hz), 7.75 (1H, d, J=7.8 Hz), 8.58 (1H, br s).

EIMSm/z (relative intensity): 564 (M$^+$), 346 (100).

Example 131

Preparation of 2-[4-[2-(benzoxazol-2-ylthio)ethyl] piperazin-1-yl]-[-N-(2-(2-hydroxyethylthio)-6-methyl-4-methylthio-3-pyridyl]-acetamide:

To a solution of 3-amino-2-(2-tert-butyldimethylsilyloxyethylthio)-6-methyl-4-methylthiopyridine (synthesized by the method disclosed in Example 30 in WO96/26925) (1.50 g, 4.35 mmol) in dichloromethane (30 ml) were added N,N-dimethylaniline (0.63 g, 5.22 mmol) and bromoacetyl bromide (1.05 g, 5.22 mmol)

with ice-cooling and stirring, and the mixture was stirred at room temperature for 1 hour. The reaction solution was mixed with a saturated ammonium chloride solution and extracted with chloroform. The organic layer was washed with water and a saturated sodium chloride solution successively, dried over anhydrous sodium sulfate and concentrated in vacuo. The resulting residue was purified by a silica gel column chromatography (silica gel 100 g, developing solvent; hexane:ethyl acetate=3:1) to provide 1.57 g (yield 78%) of 2-bromo-N-[2-(2-tert-butyldimethylsilyloxyethylthio)-6-methyl-4-methylthio-3-pyridyl]acetamide as colorless powdery crystals.

To a solution of 1-[2-(benzoxazol-2-ylthio)ethyl]piperazine ditrifluoroacetate (246 mg, 0.50 mmol) obtained in Example 22 in acetonitrile (4 ml) were added potassium carbonate (235 mg, 1.70 mmol) and 2-bromo-N-2-(2-tert-butyldimethylsilyloxyethylthio)-6-methyl-4-methylthio3-pyridyl]acteamide (233 mg, 0.50 mmol), and the mixture was stirred at room temperature for 3 hours. The reaction mixture was diluted with water and extracted with ethyl acetate. The organic layer was washed with water and a saturated sodium chloride solution successively, dried over anhydrous sodium sulfate and concentrated in vacuo. The resulting residue was purified by a silica gel column chromatography (silica gel 15 g, developing solvent; hexane:acetone=2:1) to provide 280 mg (yield 86%) of 2-[4-[2-(benzoxazol-2-ylthio)ethyl]piperazin-1-yl]-N-[2-(2-tert-butyldimethylsilyloxyethylthio)-6-methyl-4-methylthio-3-pyridyl]acetamide as colorless amorphous.

To a solution of this silyl ether (255 mg, 0.39 mmol) in THF (5 ml) was added tetrabutylammonium fluoride (1.0 M THF soluton 0.78 ml, 0.78 mmol) with ice-cooling and stirring, W1 is lower alkyl group which may be substituted with and the mixture was stirred at room temperature for 2 hours. The reaction mixture was concentrated in vacuo. The resulting residue was purified by a silica gel column chromatography (silica gel 20 g, developing solvent; chloroform:methanol=30:1) to provide 177 mg (yield 85%) of the desired compound as pale yellow amorphous.

IR (KBr) cm$^{-1}$: 3276, 2923, 2819, 1686, 1564, 1497. 1H-NMR (CDCl$_3$) δ: 2.42 (3H, s), 2.49 (3H, s), 2.58–2.82 (8H, m), 2.85 (2H, t, J=6.9 Hz), 3.20 (2H, s), 3.29 (2H, t, J=4.9 Hz), 3.49 (2H, t, J=6.9 Hz), 3.95 (2H, t, J=4.9 Hz), 5.31 (1H, br s), 6.72 (1H, s), 7.19–7.32 (2H, m), 7.43 (1H, d, J=7.3 Hz), 7.58 (1H, d, J=7.3 Hz), 8.62 (1H, br s).

EIMSm/z (relative intensity): 533 (M$^+$), 125 (100).

Example 132

Preparation of 2-[4-[2-(oxazolo[4,5-b]pyridin-2-ylthio)ethyl]piperazin-1-yl]-N-[2-(2-hydroxyethylthio)-6-methyl-4-methylthio-3-pyridyl]acetamide:

The same reaction and treatment as in Example 131 were conducted using 1-[2-(oxazolo[4,5-b]pyridin-2-ylthio)ethyl]piperazine ditrifluoroacetate instead of 1-[2-(benzoxazol-2-ylthio)ethyl]piperazine ditrifluoroacetate to provide the desired compound as pale yellow amorphorus.

IR (KBr) cm$^{-1}$: 3402,3236,2923, 1648, 1562, 1415. 1H-NMR (CDCl$_3$) δ: 2.43 (3H, s), 2.50 (3H, s), 2.63 (4H, t, J=5.0 Hz), 2.79 (2H, t, J=6.4 Hz), 2.94 (2H, t, J=6.4 Hz), 3.31 (2H, t, J=5.1 Hz), 3.49 (2H, s), 3.69 (4H, t, J=5.0 Hz), 3.93 (2H, t, J=5.1 Hz), 5.05 (1H, br s), 6.72 (1H, S), 6.91 (1H, dd, J=7.8, 5.3 Hz), 7.41 (1H, dd, J=7.8, 1.4 Hz), 8.23 (1H, dd, J=5.3, 1.4 Hz), 9.15 (1H, br s).

EIMSm/z (relative intensity): 488 (M$^+$–46), 217 (100).

Example 133

Preparation of 2-[4-[2-(benzoxazol-2-ylthio)ethyl]piperazin-1-yl]-N-[2,6-diisopropyl-4-(β-D-glucopyranos)oxphenyl]acetamide:

To a solution of 2-[4-[2-(benzoxazol-2-ylthio)ethyl]piperazin-1-yl]-N-(2,6-diisopropyl-4-hydroxyphenyl)acetamide (374 mg, 0.753 mmol) obtained in Example 72 in 1,2-dichloroethane (20 ml) were added pentaacetyl-β-D-glucopyranoside (735 mg, 1.88 mmol) and molecular sieves 4A (powder, 215 mg) with ice-cooling, and the mixture was stirred for 30 minutes. A solution of tin(IV) chloride in 1,2-dichloroethane (2 M, 4 ml, 8.00 mmol) was dropped into the mixture with ice-cooling and stirred at 50° C. for 14 hours. After a saturated sodium bicarbonate solution was added with ice-cooling to the reaction solution in order to inactivate tin(IV) chloride, the reaction solution was filtered and the filtrate was extracted with chloroform. The organic layer-was washed with a saturated sodium chloride solution, dried over anhydrous sodium sulfate and concentrated in vacuo. The resulting residue was purified by a silica gel preparative thin layer chromatography (developing solvent; chloroform:methanol=15:1) to provide 205 mg (yield 33%) of 2-[4-[2-(benzoxazol-2-ylthio)ethyl]piperazin-1-yl]-N-[2,6-diisopropyl-4-(β-D-pentaacetylglucopyranosyl)oxyphenyl]acetamide as colorless amorphous.

This pentaacetylglucopyranoside (199 mg, 0.241 mmol) was dissolved in a saturated ammonia methanol solution (15 ml) with ice-cooling and the mixture was stirred at room temperature for 3 hours. The reaction solution was concentrated in vacuo, and the resulting residue was dissolved into chloroform. The organic layer was washed with water and a saturated sodium chloride solution, dried over anhydrous sodium sulfate and concentrated in vacuo. The resulting residue was purified by a silica gel preparative thin layer chromatography (developing solvent; chloroform:methanol=6:1) and recrystallized from chloroform-ether-hexane to provide 57 mg (yield 36%) of the desired compound as colorless powdery crystals.

$[\alpha]_D^{25}$: –39.05 (c. 0.770, CHCl$_3$).

Melting point: 127–129° C. IR (KBr) cm$^{-1}$: 3446, 1652, 1603, 1501, 1455. 1H-NMR (CDCl$_3$) δ: 1.18 (6H, d, J=6.8 Hz), 1.20 (6H, d, J=6.8 Hz), 2.68–2.81(8H, m), 2.85 (2H, d, J=6.8 Hz), 2.93 (2H, sept, J=6.8 Hz), 3.20 (2H, s), 3.21 (1H, t, J=7.6 Hz), 3.30 (1H, t, J=7.6 Hz), 3.39 (1H, m), 3.45 (1H, t, J=7.6 Hz), 3.49 (2H, t, J=6.8 Hz), 3.72 (1H, dd, J=5.8, 12.4 Hz), 3.85 (1H, dd, J=2.4, 12.4 Hz), 4.90 (1H, d, 7.6 Hz), 6.87 (2H, s), 7.24 (1H, td, J=7.6, 1.5 Hz), 7.28 (1H, td, J=7.6, 1.5 Hz), 7.43 (1H, dd, J=7.6, 1.5 Hz), 7.58 (1H, dd, J=7.6, 1.5 Hz), 8.64 (1H, br s).

FABMS m/z (relative intensity): 659 (M$^+$+1), 106 (100).

Example 134

Preparation of 2-[4-[2-(7-trifluoromethylbenzoxazol-2-ylthio)ethyl]piperazin-1-yl]-N-[2,6-diisopropyl-4-(β-D-glucopyranosyl)oxyphenyl]acetamide:

The same reaction and treatment as in Example 133 were conducted using 2-[4-[2-(7-trifluoromethylbenzoxazol-2-ylthio)ethyl]piperazin-1-yl]-N-(2,6-diisoproyl-4-hydroxyphenyl)acetamide obtained in Example 114 instead of 2-[4-[2-(benzoxazol-2-ylthio)ethyl]piperazin-1-yl]-N-(2,6-diisopropyl-4-hydroxyphenyl)acetamide to provide the desired compound as colorless powdery crystals.

$[\alpha]_D^{25}$: –30.18 (c. 0.315, CHCl$_3$).

Melting point: 130–133° C. IR (KBr) cm$^{-1}$: 3409, 1668, 1603, 1507, 1493. 1H-NMR (CDCl$_3$) δ: 1.18 (6H, d, J=6.8

Hz), 1.21 (6H, d, J=6.8 Hz), 2.60–2.77(8H, m), 2.86 (2H, d, J=6.8 Hz), 2.93 (2H, sept, J=6.8 Hz), 3.17 (1H, t, J=7.8 Hz), 3.20 (2H, s), 3.26 (1H, t, J=7.8 Hz), 3.39 (1H, m), 3.42 (1H, t, J=7.8 Hz), 3.50 (2H, t, J=6.8 Hz), 3.71 (1H, dd, J=5.8, 12.0 Hz), 3.85 (1H, br. d, J=12.0 Hz), 4.90 (1H, d, 7.8 Hz), 6.87 (2H, s), 7.38 (1H, t, J=7.8 Hz), 7.48 (1H, d, J=7.8 Hz), 7.76 (1H, d, J=7.8 Hz), 8.64 (1H, br s).

EIMSm/z (relative intensity): 727 (M$^+$+1), 97 (100). HRMSas: $C_{34}H_{45}F_3N_4O_8S$ Calculated: 726.29097. Found: 726.29120.

Example 135

Preparation of 2-[4-[2-(benzoxazol-2-ylthio)ethyl] piperazin-1-yl]-N-[(S)-4-(2-aminopropionyl)oxy-2,6-diisopropylphenyl]acetamide tritrifluoroacetate:

To a solution of 2-[4-[2-(benzoxazol-2-ylthio)ethyl] piperazin-1-yl]-N-(2,6-diisopropyl-4-hydroxyphenyl) acetamide (70 mg, 0.141 mmol) in chloroform (2 ml) were added N-(tert-butoxycarbonyl)-L-alanine (27 mg, 0.143 mmol), 4-(dimethylamino)pyridine (20 mg, 0.164 mmol) and 1-ethyl-3-(3-dimethylaminopropyl)carbodiimide hydrochloride (32 mg, 0.169 mmol) successively, and the mixture was stirred for 4 days. The reaction solution was mixed with 2 N hydrochloric acid and extracted with chloroform. The organic layer was washed with a saturated sodium chloride solution, dried over anhydrous sodium sulfate and concentrated in vacuo. The resulting residue was purified by a silica gel preparative thin layer chromatography (developing solvent; chloroform:methanol=15:1) to provide 84 mg (yield 90%) of 2-[4-[2-(benzoxazol-2-ylthio)ethyl]piperazin-1-yl]-N-[(S)-4-[2-(tert-butoxycarbonylamino) propionyl]oxy-2,6-diisopropylphenyl]acetamide as colorless oil.

To a solution of this tert-butyl carbamate (84 mg, 0.126 mmol) in chloroform (2 ml) was dropped trifluoroacetic acid (1 ml, 13.0 mmol) with ice-cooling, and the mixture was stirred at room temperature for 3 hours. The reaction solution was concentrated in vacuo, and the resulting residue was recrystallized from THF-hexane to provide 100 mg (yield 87%) of the desired compound as colorless powdery crystals.

$[\alpha]_D^{25}$: −2.60 (c. 0.200, THF).

Melting point: 183–184° C. IR (KBr) cm$^{-1}$: 3432, 2969, 1772, 1675, 1598. 1H-NMR (d$_6$-DMSO, 120° C.) δ: 1.14 (12H, d, J=6.8 Hz), 1.60 (3H, d, J=7.3 Hz), 2.90–3.00 (8H, m), 3.07 (2H, sept, J=6.8 Hz), 3.08 (2H, t, J=7.3 Hz), 3.54 (2H, s), 3.56 (2H, t, J=7.3 Hz), 4.33 (1H, q, J=7.3 Hz), 6.95 (2H, s), 7.28–7.28 (2H, m), 7.57–7.60 (2H, m), 9.14 (1H, br s).

EIMSm/z (relative intensity): 567 (M$^+$), 125 (100). HRMSas: $C_{30}H_{41}N_5O_4S$ Calculated: 567.28788. Found: 567.28589.

Example 136

Preparation of 2-[4-[2-(7-trifluoromethylbenzoxazol-2-ylthio)ethyl]piperazin-1-yl]-N-[(S)-4-(2-aminopropionyl) oxy-2,6-diisopropylphenyl]acetamide tritrifluoroacetate:

The same reaction and treatment as in Example 135 using 2-[4-[2-(7-trifluoromethylbenzoxazol-2-ylthio)ethyl] piperazin-1-yl]-N-[2,6-diisopropyl-4-hydroxyphenyl] acetamide instead of 2-[4-[2-(benzoxazol-2-ylthio)ethyl] piperazin-1-yl]-N-[2,6-diisopropyl-4-hydroxyphenyl] acetamide to provide the desired compound as colorless powdery crystals.

$[\alpha]_D^{25}$: +0.30 (c. 0.200, THF).

Melting point: 124–126° C. IR (KBr) cm$^{-1}$: 3433, 1764, 1674, 1601, 1509. 1H-NMR (d$_6$-DMSO, 120° C.) δ: 1.14 (12H, d, J=6.6 Hz), 1.60 (3H, d, J=7.3 Hz), 2.85–2.95 (8H, m), 3.05 (2H, t, J=6.8 Hz), 3.07 (2H, sept, J=6.6 Hz), 3.53 (2H, s), 3.58 (2H, t, J=6.8 Hz), 4.33 (1H, q, J=7.3 Hz), 6.95 (2H, s), 7.52 (1H, t, J=7.8 Hz), 7.61 (1H, d, J=7.8 Hz), 7.89 (1H, d, J=7.8 Hz), 9.13 (1H, br s).

EIMSm/z (relative intensity): 635 (M$^+$), 344 (100). HRMSas: $C_{31}H_{40}F_3N_5O_4S$ Calculated: 635.27526. Found: 635.27698.

Example 137

Preparation of N'-(2,6-diisopropyl-4-hydroxyphenyl)-N-[2-[4-[2-(benzoxazol-2-ylthio)ethyl]piperazin-1-yl]ethyl]-N-heptylurea:

The same reaction and treatment as in Example 115 were conducted using 2-mercaptobenzoxazole instead of 2-mercapto-7-trifluoromethylbenzoxazole to provide the desired compound as colorless amorphous. 1H-NMR (CDCl$_3$) δ: 0.88 (3H, t, J=7.1 Hz), 1.00–1.36 (20H, m), 1.50–1.70 (2H, m), 2.20–2.85 (12H, m), 3.07 (2H, sept, J=6.8 Hz), 3.33 (2H, t, J=6.8 Hz), 3.41 (2H, t, J=6.8 Hz), 3.35–3.55 (2H, m), 5.28 (1H, br s), 6.53 (2H, s), 7.15–7.30 (2H, m), 7.41 (1H, d, J=8.1 Hz), 7.56 (1H, d, J=8.1 Hz), 8.00 (1H, br s).

FABMS m/z (relative intensity): 624 (M$^+$+1, 100).

Example 138

Preparation of N-[2-[4-[3-(benzoxazol-2-ylthio)propyl] piperazin-1-yl]ethyl]-N'-[4,6-bis(methylthio)-2-methyl-5-pyrimidyl]-N-heptylurea dihydrochloride monohydrate:

4,6-Dihydroxy-2-methylpyrimidine (1.00 g, 7.93 mmol) was added gradually to fuming nitric acid (3 ml) with ice-cooling, and the mixture was stirred at that temperature for 2 hours and then at room temperature for 1 hour. The reaction solution was poured into ice, and the precipitated crystal was filtered off and dried to provide 207 mg (yield 15%) of 4,6-dihydroxy-2-methyl-5-nitropyrimidine.

4,6-Dihydroxy-2-methyl-5-nitropyrimidine (205 mg, 1.20 mmol) was dissolved in phosphoryl chloride (1 ml). After adding N,N-diethylaniline (281 mg, 1.88 mmol), the mixture was stirred at 100° C. for 1 hour and then at 120° C. for 1 hour. The reaction solution was poured into ice and extracted with ethyl acetate. The organic layer was washed with a saturated sodium chloride solution, dried over magnesium sulfate and concentrated in vacuo. The resulting residue was purified by a silica gel column chromatography (developing solvent; hexane:ethylacetate=20:1) to provide 194 mg (yield 77%) of 4,6-dichloro-2-methyl-5-nitropyrimidine as colorless needles.

To a solution of sodium thiomethoxide (780 mg, 10.6 mmol) in methanol (10 ml) was dropped a solution of 4,6-dichloro-2-methyl-5-nitropyrimidine (1.00 g, 4.78 mmol) in methanol (10 ml) with ice-cooling, and the mixture was stirred at that temperature for 1 hour. The reaction solution was diluted with water and extracted with ethyl acetate. The organic layer was washed with a saturated sodium chloride solution, dried over anhydrous magnesium sulfate and concentrated in vacuo. The resulting residue was recrystallized from ethyl acetate-hexane to provide 609 mg (yield 55%) of 4,6-bis(methylthio)-2-methyl-5-nitropyrimidine.

Then, to a suspension of this nitropyrimidine (200 mg, 0.865 mmol) in ethanol (5 ml) was added 10% palladium carbon catalyst (50% wet, 300 mg), and the mixture was stirred under hydrogen atmosphere at 80° C. for 1 hour. The reaction solution was filtered, and then the filtrate was concentrated in vacuo and subjected to azeotropy treatment with toluene to provide 154 mg (yield 88%) of 5-amino-4,6-bis(methylthio)-2-methylpyrimidine as colorless crystals.

Then, to a solution of this aminopyrimidine (154 mg, 0.765 mmol) in dichloromethane (2 ml) were added N,N-dimethylaniline (112 mg, 0.924 mmol) and phenyl chloroformate (132 mg, 0.843 mmol) successively and the mixture was stirred at room temperature for 1 hour. To the mixture were added N,N-dimethylaniline (19 mg, 0.157 mmol) and phenyl chloroformate (24 mg, 0.153 mmol) and the mixture was stirred for 1.5 hours, and then stirred at 40° C. for 4 hours. N,N-dimethylaniline (40 mg, 0.330 mmol) and phenyl chloroformate (35 mg, 0.224 mmol) were further added to the mixture and stirred at 40° C. for 3.5 hours. After being let to stand at room temperature for 10 hours, the mixture was concentrated in vacuo. The resulting residue was suspended in a mixed solvent of ethyl acetate-hexane (1:4) and filtered off. The filtered-off solid was extracted with ethyl acetate. The organic layer was washed with water and a saturated sodium chloride solution successively, dried over anhydrous sodium sulfate and concentrated in vacuo. The resulting residue was crystallized from hexane to provide 187 mg (yield 76%) of phenyl N-[4,6-bis(methylthio)-2-methyl-5-pyrimidyl]carbamate as pale yellow powdery crystals.

The same reaction and treatment as in Example 115 were conducted using 3-[4-(2-heptylaminoethyl)piperazin-1-yl]propanol obtained in Example 19 instead of 2-[4-(2-heptylaminoethyl)piperazin-1-yl]ethanol, and using 2-mercaptobenzoxazole instead of 2-mercapto-7-trifluoromethylbenzoxazole to provide N-[2-[4-[3-benzoxazol-2-ylthio)propyl]piperazin-1-yl]ethyl]-N-heptylamine.

To a solution of this amine (150 mg, 0.358 mmol) in toluene (2 ml) was added phenyl N-[4,6-bis(methylthio)-2-methyl-5-pyrimidyl]carbamate (115 mg, 0.358 mmol) with stirring at room temperature, and was dropped a solution of triethylamine (44 mg, 0.435 mmol) in toluene (1 ml). The mixture was stirred at room temperature for 1 hour. The reaction solution was washed with water and a saturated sodium chloride solution, dried over anhydrous sodium sulfate and concentrated in vacuo. The resulting residue was purified by a silica gel column chromatography (developing solvent; chloroform:methanol=100:1 20:1) to provide 187 mg (yield 81%) of N-[2-[4-[3-(benzoxazol-2-ylthio)propyl]piperazin-1-yl]ethyl]-N'-[4,6-bis(methylthio)-2-methyl-5pyrimidyl]-N-heptylurea as pale brown oil.

This urea compound was converted into its salt with hydrochloride according to a conventional manner to provide 41 mg (yield 36%) of the desired compound as pale brown needles.

Melting point: 105–109° C. IR (KBr) cm$^{-1}$: 3421, 3289, 1637, 1521, 1500. 1H-NMR (d$_6$-DMSO) δ: 0.87 (3H, t, J=7.1 Hz), 1.21–1.35 (8H, m), 1.53–1.63 (2H, m), 2.43 (6H, s), 2.56 (3H, s), 3.00–3.80 (18H, m), 7.30–7.37 (2H, m), 7.63–7.68 (2H, m), 8.15 (1H, br s). Elementary analysis as: $C_{31}H_{51}Cl_2N_7O_3S_3$ Calculated: C, 50.53; H, 6.98; N, 13.31; Cl, 9.62; S, 13.05. Found: C, 50.47; H, 6.85; N, 13.45; Cl, 9.34; S, 13.21.

Example 139

Preparation of N'-(2,6-diisopropyl-4-hydroxyphenyl)-N-heptyl-N-[2-[4-[2-(oxazolo[4,5-b]pyridin-2-ylthio)ethyl]piperazin-1-yl]ethyl]urea:

The same reaction and treatment as in Example 115 were conducted using 2-mercaptooxazolo[4,5-b]pyridine instead of 2-mercapto-7-trifluoromethylbenzoxazole to provide the desired compound as colorless needles.

Melting point: 100–102° C. IR (KBr) cm$^{-1}$: 3207, 1644, 1611, 1594, 1492. 1H-NMR (d$_6$-DMSO) δ: 0.88 (3H, t, J=7.1 Hz), 1.11 (6H, d, J=6.4 Hz), 1.17 (6H, d, =6.4 Hz), 1.22–1.35 (8H, m), 1.51–1.61 (2H, m), 2.35–2.70 (10H, m), 2.75 (2H, t, J=6.8 Hz), 3.06 (2H, sept, J=6.4 Hz), 3.34 (2H, t, J=7.3 Hz), 3.42–3.48 (4H, m), 6.54 (2H, s), 7.18 (1H, dd, J=8.3, 5.1 Hz), 7.69 (1H, dd, J=8.3, 1.5 Hz), 8.45 (1H, dd, J=5.1, 1.5 Hz). Elementary analysis as: $C_{34}H_{52}N_6O_3S$ Calculated: C, 65.35; H, 8.39; N, 13.45; S, 5.13. Found: C, 65.33; H, 8.29; N, 13.39; S, 5.24.

Example 140

Preparation of 2-[4-[2-(7-trifluoromethylbenzoxazol-2-ylthio)ethyl]piperazin-1-yl]-N-[2,6-diisopropyl-4-hydroxymethylphenyl]acetamide:

To a solution of 2,6-diisopropylaniline (10.0 g, 56.4 mmol) in acetic acid (160 ml) were added water (40 ml) and hexamethylenetetramine (15.8 g, 0.113 mol) and stirred at 120° C. for 3 hours. The reaction solution was diluted with water and extracted with chloroform. The organic layer was washed with a saturated sodium chloride solution, dried over anhydrous sodium sulfate and concentrated in vacuo. The resulting residue was purified by a silica gel column chromatography (silica gel 200 g, developing solvent; hexane:ethyl acetate=10:1) to provide 10.6 g (yield 92%) of 4-amino-3,5-diisopropylbenzaldehyde as yellow solid.

To a mixed solution of this aldehyde (745 mg, 3.63 mmol) in dichloromethane (5 ml) and methanol (10 ml) was added sodium borohydride (280 mg, 7.40 mmol) with ice-cooling and stirred at room temperature for 1 hour. The reaction solution was diluted with water and extracted with chloroform. The organic layer was washed with a saturated sodium hydrochloride solution, dried over anhydrous sodium sulfate and concentrated in vacuo. The resulting residue was purified by a silica gel column chromatography (silica gel 50 g, developing solvent; hexane:ethyl acetate=6:1 2:1) to provide 736 mg (yield 98%) of 4-amino-3,5-diisopropylbenzenemethanol as colorless oil.

To a solution of this aniline (610 mg, 2.94 mmol) and N,N-dimethylaniline (430 mg, 3.55 mmol) in dichloromethane (5 ml) was dropped a solution of bromoacetyl bromide (556 mg, 2.75 mmol) in dichloromethane (0.5 ml) with ice-cooling, and the mixture was stirred at room temperature for 1 hour. The reaction solution was diluted with water and extracted with chloroform. The organic layer was washed with a saturated sodium chloride solution, dried over anhydrous sodium sulfate and concentrated in vacuo. The resulting residue was recrystallized from chloroform-ether-hexane to provide 584 mg (yield 60%) of 2-bromo-N-(2,6-diisopropyl-4-hydroxymethylphenyl)acetamide as colorless powdery crystals.

The same reaction and treatment as in Example 85 were conducted using 2-bromo-N-(2,6-diisopropyl-4hydroxymethylphenyl)acetamide instead of 2-bromo-N(2,6-diisopropylphenyl)acetamide to provide the desired compound as colorless powdery crystals.

Melting point: 146–148° C. IR (KBr) cm$^{-1}$: 3298, 1674, 1651, 1606, 1493. 1H-NMR (d$_6$-DMSO) δ: 1.09 (12H, d, J=6.8 Hz), 2.40–2.55 (8H, m), 2.76 (2H, t, J=6.8 Hz), 2.98 (2H, sept, J=6.8 Hz), 3.07 (2H, s), 3.53 (1H, t, J=6.8 Hz), 4.45 (2H, d, J=5.6 Hz), 5.12 (1H, t, J=5.6 Hz), 7.07 (2H, s), 7.53 (1H, t, J=8.2 Hz), 7.66 (1H, d, J=8.2 Hz), 7.95 (1H, d, J=8.2 Hz), 9.06 (1H, br s). Elementary analysis as: $C_{29}H_{37}F_3N_4O_3S$ Calculated: C, 60.19; H, 6.44; N, 9.68; F, 9.85. Found: C, 60.18; H, 6.53; N, 9.49; F, 9.98.

Example 141

Preparation of 2-[4-[2-(4chloro-6-trifluoromethylbenzimidazol-2-ylthio)ethyl]piperazin-1-yl]-N-(2,6-diisopropylphenyl)acetamide:

The same reaction and treatment as in Example 1 were conducted using 4-chloro-2-mercapto-6trifluoromethylbenzimidazole instead of 2-mercaptobenzoxazole to provide the desired compound as colorless powdery crystals. IR (KBr) cm$^{-1}$: 2967, 1670, 1589, 1500, 1331. 1H-NMR (CDCl$_3$) δ: 1.19 (12H, d, J=6.8 Hz), 2.60–3.18 (10H, m), 3.22 (2H, br.), 3.36 (2H, s), 3.53 (2H, br's), 7.18 (2H, d, J=7.7 Hz), 7.29 (1H, t, J=7.7 Hz), 7.44 (1H, s), 7.65 (1H, s), 8.27 (1H, br s).

EIMSm/z (relative intensity): 583/581(M$^+$), 125 (100).

Example 142

Preparation of 2-[4-[2-(5-chloro-7-isopropyl-4-methylbenzoxazol-2-ylthio)ethyl]piperazin-1-yl]-N-(26,-diisopropyl-4-hydroxyphenyl)acetamide:

The same reaction and treatment as in Example 114 were conducted using 5-chloro-7-isopropyl-2-mercapto-4-methylbenzoxazole instead of 2-mercapto-7-trifluoromethylbenzoxazole to provide the desired compound as pale yellow powdery crystals. IR (KBr) cm$^{-1}$: 3272, 2963, 1657, 1592, 1507. 1H-NMR (CDCl$_3$) δ: 1.14 (12H, d, J=6.8 Hz), 1.30 (6H, d, J=6.8 Hz), 2.49 (3H, s), 2.62–2.98 (12H, m) 3.13–3.23 (3H, m), 3.41–3.58 (2H, m), 6.62 (2H, s), 7.06 (1H, s), 8.41 (1H, br s).

Example 143

Preparation of 2-[4-[2-(benzimidazol-2-ylthio)ethyl]piperazin-1-yl]-N-[2-methanesulfinyl-6-methyl-4-(methylthio)-3-pyridyl]-acetamide:

To a solution of 2-[4-[2-(benzimidazol-2-ylthio)ethyl]piperazin-1-yl]-N-[2,4-bis(methylthio)-6-methyl-3-pyridyl] acetamide (4.58 g, 9.11 mmol) obtained in Example 32 in ethanol (170 ml) was added maleic acid (2.11 g, 18.2 mmol) with ice-cooling. The mixture was homogenized by adding chloroform (20 ml) and concentrated in vacuo. The resulting reside was crystallized from ethanol-ether to provide 5.27 g (yield 77%) of 2-[4-[2-(benzimidazol-2-ylthio)ethyl]piperazin-1-yl]-N-[2,4-bis(methylthio)-6-methyl-3-pyridyl] acetamide dimaleate.

To a mixed solution of this amide (500 mg, 0.664 mmol) in chloroform (10 ml) and methanol (2 ml) was added m-chloroperbenzoic acid (213 mg, 1.23 mmol) with ice-cooling, and stirred at room temperature for 26 hours. The reaction solution was diluted with chloroform. The organic layer was washed with a saturated sodium bicarbonate solution and a saturated sodium chloride solution successively, dried over anhydrous sodium sulfate and concentrated in vacuo. The resulting residue was purified by a silica gel preparative thin layer chromatography (developing solvent; chloroform:sat. ammonia methanol=10:1) to provide 138 mg (yield 40%) of the desired compound as colorless amorphous. IR (neat) cm$^{-1}$: 3424, 3155, 1695, 1571, 1481. 1H-NMR (d$_6$-DMSO, 120° C.) δ: 2.51 (3H, s), 2.56 (3H, s), 2.73,(3H, s), 2.59–2.68 (6H, m), 2.77 (2H, t, J=7.1 Hz), 2.81–2.92 (2H, br s), 3.11 (1H, d, J=15.8 Hz), 3.17 (1H, d, J=15.8 Hz), 3.41 (2H, t, J=7.1 Hz), 7.07–7.13 (2H, m), 7.30 (1H, S), 7.38–7.44 (2H, m), 9.26 (1H, br s).

EIMSm/z (relative intensity): 519 (M$^+$+1), 154 (100).

Example 144

Preparation of 2-[4-[2-(benzimidazol-2-ylthio)ethyl]piperazin-1-yl]-N-[4-methanesulfinyl-6-methyl-2-(methylthio)-3-pyridyl]-acetamide:

To a solution of 2-[4-[2-(benzimidazol-2ylthio)ethyl]piperazin-1-yl]-N-[2,4-bis(methylthio)-6-methyl-3-pyridyl] acetamide (1.00 g, 1.99 mmol) in acetic acid (20 ml) was dropped a solution of sodium perborate tetrahydrate (321 mg, 2.09 mmol) in acetic acid (30 ml), and the mixture was stirred for 3 hours. The reaction solution was concentrated in vacuo and the resulting residue was purified by a silica gel preparative thin layer chromatography (developing solvent; chloroform:sat. ammonia methanol 15:1) to provide 73 mg (yield 7%) of 2-[4-[2-(benzimidazol-2-ylthio)ethyl]piperazin-1-yl]-N-[4-methanesulfinyl-6-methyl-2-(methylthio)-3-pyridyl]acetamide as pale yellow oil. IR (KBr) cm$^{-1}$: 3375, 2496, 1672, 1553, 1122. 1H-NMR (CD$_3$OD) δ: 2.45 (3H, s), 2.51 (3H, s), 2.52–2.64 (8H,m), 2.70 (2H, t, J=6.8 Hz), 2.72 (3H, s), 3.04 (1H, d, J=16.1 Hz), 3.13 (1H, d, J=16.1 Hz), 3.30 (2H, t, J=6.8 Hz), 7.04–7.10 (2H, m), 7.32 (1H, s), 7.33–7.38 (2H, m), 7.78 (1H, s).

Example 145

Preparation of 2-[4-[2-(benzimidazol-2-ylthio)ethyl]piperazin-1-yl]-N-[2,4-bis(methanesulfinyl)-6-methyl-3-pyridyl]acetamide:

The same reaction and treatment as in Example 144 were conducted to provide 139 mg (yield 13%) of 2-[4-[2-(benzimidazol-2-ylthio)ethyl]piperazin-1-yl]-N-[2,4-bis(methanesulfinyl)-6-methyl-3-pyridyl]acetamide as colorless amorphous. IR (neat) cm$^{-1}$: 3165, 1687, 1580, 1475, 1440. 1H-NMR (CD$_3$OD) δ: 2.52–2.64 (8H, m), 2.65 (3H, s), 2.69 (3H, s), 2.71 (2H, t, J=6.8 Hz), 2.82 (3H, s), 3.13 (2H, s), 3.31 (2H, t, J=6.8 Hz), 7.06–7.11 (2H, m), 7.34–7.39 (2H, m), 7.83 (1H, s).

Example 146

Preparation of 2-[4-[2-(benzimidazol-2-ylsulfonyl)ethyl]piperazin-1-yl]-N-[2,4-bis(methylthio)-6-methyl-3-pyridyl] acetamide:

To a solution of 1-[2-(benzimidazol-2-ylthio)ethyl]piperazine ditrifluoroacetate (100 mg, 0.219 mmol) in acetic acid (4 ml) was added a solution of sodium perborate tetrahydrate (35 mg, 0.230 mmol) in acetic acid (1 ml) and the mixture was stirred for 5 hours. The reaction solution was concentrated in vacuo, and the resulting residue was purified by a silica gel preparative thin layer chromatography (developing solvent; chloroform:sat. ammonia methanol=4:1) to provide 5.6 mg (yield 9.2%) of 1-[2-(benzimidazol-2-ylsulfinyl)ethyl]piperazine and 17.4 mg (yield 27%) of 1-[2-(benzimidazol-2-ylsulfonyl)ethyl] piperazine.

To a solution of 1-[2-(benzimidazol-2-ylsulfonyl)ethyl] piperazine (17 mg, 0.058 mmol) in DMF (0.1 ml) were added potassium carbonate (16.0 mg, 0.116 mmol) and 2-bromo-N-[2,4-bis(methylthio)-6-methyl-3-pyridyl] acetamide (18.6 mg, 0.058 mmol), and the mixture was stirred at room temperature for 6 hours. The reaction solution was diluted with water and extracted with ethyl acetate. The organic layer was washed with water and a saturated sodium chloride solution, dried over anhydrous sodium sulfate and concentrated in vacuo. The resulting residue was purified by a silica gel preparative thin layer chromatography (developing solvent; chloroform:sat. ammonia methanol=5:1) to provide 19.8 mg (yield 64%) of the desired compound as pale yellow oil. IR (neat) cm$^{-1}$: 3345, 1672, 1565, 1420, 1124. 1H-NMR (CD$_3$OD) δ: 2.43 (3H, s), 2.47 (3H, s), 2.48 (3H, s), 3.00 (2H, br. d, J=12.9 Hz), 3.12 (2H, t, J=10.7 Hz), 3.34 (2H, s), 3.58–3.78 (8H, m), 6.85 (1H, s), 7.12–7.18 (2H, m), 7.43–7.48 (2H, m).

Example 147

Preparation of 2-[4-[2-(benzimidazol-2-ylsulfinyl)ethyl]piperazin-1-yl]-N-[2,4-bis(methylthio)-6-methyl-3-pyridyl]acetamide:

The same reaction and treatment as in Example 146 were conducted using 1-[2-(benzimidazol-2-ylsulfinyl)ethyl]piperazine instead of 1-[2-(benzimidazol-2-ylsulfonyl)ethyl]piperazine to provide the desired compound as pale yellow oil. IR (KBr) cm$^{-1}$: 3420, 1675, 1564, 1482, 1435. 1H-NMR (CD$_3$OD) δ: 2.25–2.56 (17H, m), 2.82 (1H, dt, J=13.6, 6.8 Hz), 2.92 (1H, dt, J=13.6, 6.8 Hz), 2.95 (2H,s), 3.45 (1H, dt, J=13.6, 6.8 Hz), 3.52 (1H, dt, J=13.6, 6.8 Hz), 6.83 (1H, s), 7.33–7.37 (2H, m), 7.63–7.69 (2H, m).

Example 148

Preparation of 2-[4-[2-(benzimidazol-2-ylsulfinyl)ethyl]piperazin-1-yl]-N-[2-(methanesulfinyl)-6-methyl-4-(methylthio)-3-pyridyl]acetamide:

To a solution of 2-bromo-N-[2,4-bis(methylthio)-6-methyl-3-pyridyl]acetamide (100 mg, 0.311 mmol) in chloroform (2 ml) was added a solution of m-chloroperbenzoic acid (50 mg, 0.327 mmol) in chloroform (0.5 ml), and stirred at room temperature for 17 hours. The reaction solution was diluted with water and extracted with ethyl acetate. The organic layer was washed with a saturated sodium bicarbonate solution, water and a saturated sodium chloride solution successively, dried over anhydrous sodium sulfate and concentrated in vacuo. The resulting residue was purified by a silica gel preparative thin layer chromatography (developing solvent; chloroform:acetone=1:1) to provide 21.4 mg (yield 20%) of 2-bromo-N-[2(methanesulfinyl)-6-methyl-4-(methylthio)-3-pyridyl]acetamide.

To a solution of this sulfoxide (21.4 mg, 0.063 mmol) in DMF (1 ml) were added 1-[2-(benzimidazol-2-ylsulfinyl)ethyl]piperazine (17.6 mg, 0.063 mmol) obtained in Example 146 and potassium carbonate (17.5 mg, 0.127 mmol), and stirred for 12 hours. The reaction solution was diluted with water and extracted with ethyl acetate. The organic layer was washed with water and a saturated sodium chloride solution successively, dried over anhydrous sodium sulfate and concentrated in vacuo. The resulting residue was purified by a silica gel preparative thin layer chromatography (developing solvent; chloroform:sat. ammonia methanol=5:1) to provide 16.7 mg (yield 49%) of the desired compound as pale yellow oil. IR (KBr) cm$^{-1}$: 3190, 2993, 1674, 1571, 1484. 1H-NMR (CD$_3$OD) δ: 2.15–2.65 (14H, m), 2.63–2.84 (5H, m), 2.89 (2H, s), 3.34 (1H, dt, J=12.0, 6.0 Hz), 3.43 (1H, dt, J=12.0, 6.0 Hz), 7.22 (1H, s), 7.23–7.28 (2H, m), 7.55–7.59 (2H, m).

Example 149

Preparation of 2-[4-[2-(imidazolo[4,5-b]pyridin-2-ylthio)ethyl]piperazin-1-yl]-N-[2,4-bis(methylthio)-6-methyl-3-pyridyl]acetamide:

To a solution of 2-bromo-N-[2,4-bis(methylthio)-6-methyl-3-pyridyl]acetamide (6.41 g, 0.02 mol) in acetonitrile (120 ml) was added 1-(2-hydroxyethyl)piperazine (3.53 g, 0.027 mol), and then added potassium carbonate (3.75 g, 0.027 mol) with ice-cooling and the mixture was stirred at room temperature for 23 hours. The reaction solution was diluted with water and extracted with chloroform. The organic layer was washed with a saturated sodium chloride solution, dried over anhydrous sodium sulfate and concentrated in vacuo. The resulting residue was recrystallized from ethanol-ether to provide 7.19 g (yield 97%) of 2-[4-(2-hydroxyethyl)piperazin-1-yl]-N-[2,4-bis(methylthio)-6-methyl-3-pyridyl]acetamide as colorless needles.

To a solution of 2,3-diaminopyridine (286 mg, 2.62 mmol) in THF (10 ml) were added thiophosgene (300 mg, 2.62 mmol) and triethylamine (265 mg, 2.62 mmol), and the mixture was stirred at room temperature for 20 hours. The reaction mixture was concentrated in vacuo, and the resulting residue was purified by a silica gel preparative thin layer chromatography (developing solvent; chloroform:sat. ammonia methanol=10:1) to provide 39 mg (yield 10%) of 2-mercaptoimidazolo[4,5-b]pyridine.

To a solution of 2-[4-(2-hydroxyethyl)piperazin-1-yl]-N-[2,4-bis(methylthio)-6-methyl-3-pyridyl]acetamide (93 mg, 0.251 mmol) in THF (2 ml) were added triethylamine (51 mg, 0.502 mmol) and 4-(dimethylamino)pyridine (3 mg, 0.025 mmol), and then dropped methanesulfonyl chloride (43 mg, 0.377 mmol) with ice-cooling. The mixture was stirred for 45 minutes. The reaction solution was concentrated in vacuo to provide crude 2-[4-(2-methanesulfonyloxyethyl)piperazin-1-yl]-N-[2,4-bis(methylthio)-6-methyl-3-pyridyl]acetamide.

To a solution of 2-mercaptoimidazolo[4,5-b]pyridine (38.1 mg, 0.252 mmol) in DMF (0.5 ml) were added 18-crown-6 (6.6 mg, 0.025 mmol) and potassium carbonate (63 mg, 0.454 mmol) and the mixture was stirred. Then to the mixture was dropped a solution of crude 2-[4-(2-methanesulfonyloxyethyl)piperazin-1-yl]-N-[2,4-bis(methylthio)-6-methyl-3-pyridyl]acetamide in DMF (1 ml) and stirred at 80° C. for 2 hours. The reaction mixture was diluted with water and extracted with ethyl acetate. The organic layer was washed with water and a saturated sodium chloride solution successively, dried over anhydrous sodium sulfate and concentrated in vacuo. The resulting residue was purified by a silica gel preparative thin layer chromatography (developing solvent; chloroform:methanol=10:1) to provide 51 mg (yield 40%) of the desired compound as colorless powdery crystals. IR (KBr) cm$^{-1}$: 3140, 1688, 1600, 1564, 1485. 1H-NMR (CDCl$_3$) δ: 2.38 (3H, s), 2.46 (3H, s), 2.49 (3H, s), 2.72–3.00 (10H, m), 3.29 (2H, s), 3.37 (2H, t, J=5.8 Hz), 6.63 (1H, s), 7.12 (1H, dd. J=7.8, 4.9 Hz), 7.82 (1H, d. J=7.8 Hz), 8.25 (1H, d. J=4.9 Hz), 8.49 (1H, br s).

Example 150

Preparation of 2-[4-[2-(5-benzyloxybenzimidazol-2-ylthio)ethyl]piperazin-1-yl]-N-[2,4-bis(methylthio)-6-methyl-3-pyridyl]acetamide:

To a solution of 4-benzyloxy-2-nitroaniline (2.31 g, 9.46 mmol) in acetic acid (50 ml) was added conc. hydrochloric acid (1 ml), and gradually added zinc powder (2.16 g, 0.330 mmol) with ice-cooling and the mixture was stirred for 15 minutes, and further added gradually zinc powder (2.16 g, 0.33 mmol) and stirred for 20 minutes. The reaction solution was filtered with celite, and the filtrate was concentrated in vacuo. The resulting residue was dissolved in chloroform and neutralized with a saturated sodium bicarbonate solution. The organic layer was washed with water and a saturated sodium chloride solution successively, dried over anhydrous sodium sulfate and concentrated in vacuo to provide 2.01 g (yield 99%) of crude 4-benzyloxy-1,2-phenylenediamine.

To a solution of this diamine (2.01 g, 9.38 mmol) in ethanol (50 ml) was added O-ethyl potassium dithiocarbonate (3.03 g, 19.9 mmol) and the mixture was heated to reflux for 19 hours. The reaction solution was concentrated in vacuo, and the resulting residue was dissolved in water (200 ml). To the mixture was added gradually conc. hydrochloric acid with ice-cooling to acidify it to pH3. The resulting pale yellow precipitate was filtered off and washed with water and hexane. The precipitate was purified by a silica gel column chromatography (developing solvent; chloroform:methanol=10:1) to provide 1.57 g (yield 65%) of 5-benzyloxy-2-mercaptobenzimidazole as pale yellow crystals.

The same reaction and treatment as in Example 149 were conducted using 5-benzyloxy-2-mercaptobenzimidazole instead of 2-mercaptoimidazolo[4,5-b]pyridine to provide the desired compound as yellow amorphous. IR (KBr) cm$^{-1}$: 3232, 2925, 1674, 1564, 1485. 1H-NMR (CDCl$_3$) δ: 2.37 (3H, s), 2.45 (3H, s), 2.49 (3H, s), 2.68–2.94 (10H, m), 3.22 (2H, t, J=5.6 Hz), 3.27 (2H, s), 5.06 (2H, s), 6.62 (1H, s), 6.88 (1H, dd. J=8.8, 2.2 Hz), 7.03 (1H, d, J=2.2 Hz), 7.28 (1H, t, J=7.6 Hz), 7.35 (2H, t, J=7.6 Hz), 7.37 (1H, d, J=8.8 Hz), 7.42 (2H, d, J=7.6 Hz), 8.43 (1H, br s).

Example 151

Preparation of 2-[4-[2-(5-hydroxybenzimidazol-2-ylthio) ethyl]piperazin-1-yl]-N-[2,4-bis(methylthio)-6-methyl-3-pyridyl]acetamide:

2-[4-[2-(5-benzyloxybenzimidazol-2-ylthio)ethyl] piperazin-1-yl]-N-[2,4-bis(methylthio)-6-methyl-3-pyridyl] acetamide (115 mg, 0.189 mmol) obtained in Example 150 was dissolved into trifluoroacetic acid (2 ml) and stirred at room temperature for 23 hours. The reaction solution was concentrated in vacuo, and the resulting residue was purified by a silica gel preparative thin layer chromatography (developing solvent; chloroform:sat. ammonia methanol= 10:1) to provide 75 mg (yield 76%) of the desired compound as colorless powdery crystals. IR (KBr) cm$^{-1}$: 3227, 1675, 1600, 1564, 1486. 1H-NMR (CDCl$_3$) δ: 2.36 (3H, s), 2.45 (3H, s), 2.47 (3H, s), 2.50–3.00 (10H, m), 3.10 (2H, s), 3.14 (2H, br s), 6.61 (1H, s), 6.74 (1H, d, J=8.8 Hz), 7.00 (1H, s), 7.29 (1H, d, J=8.8 Hz), 8.41 (1H, s).

Example 152

Preparation of 2-[4-[2-(5-methoxybenzimidazol-2-ylthio) ethyl]piperazin-1-yl]-N-[2,4-bis(mthylthio)-6-methyl-3-pyridyl]acetamide:

The same reaction and treatment as in Example 149 were conducted using 2-mercapto-5-methoxybenzimidazole instead of 2-mercaptoimidazolo[4,5-b]pyridine to provide the desired compound as yellow amorphous. IR (neat) cm$^{-1}$: 3250, 2942, 2824, 1683, 1487, 1435. 1H-NMR (CDCl$_3$) δ: 2.43 (3Hf s), 2.46 (3H, s), 2.48 (3H, s), 2.58–2.77 (8H, m), 2.79 (2H, t, J=7.0 Hz), 3.18 (2H, s), 3.35 (3H, t, J=7.0 Hz), 3.80 (3H, s), 6.82 (1H, dd, J=8.8, 2.5 Hz), 6.85 (1H, s), 6.99 (1H, d, J=2.5 Hz), 7.34 (1H, d, J=8.8 Hz).

EIMSm/z (relative intensity): 532 (M$^+$), 107 (100).

Example 153

Preparation of 2-[4-[2-(benzimidazol-2-yloxy)ethyl] piperazin-1-yl]-N-[2,4-bis(methylthio)-6-methyl-3-pyridyl] acetamide:

To a solution of tert-butyl 4-(2-hydroxyethyl)-1-piperazinecarboxylate (230 mg, 1.00 mmol) in DMF (2 ml) was added sodium hydride (55%, 52 mg, 1.19 mmol) with ice-cooling and stirred at 75° C. for 30 minutes, and then added 1-benzyl-2-chlorobenzimidazole (243 mg, 1.00 mmol) and stirred at 75° C. for 24 hours. The reaction solution was concentrated in vacuo, and the resulting residue was dissolved in chloroform. The organic layer was washed with water and a saturated sodium chloride solution successively, dried over anhydrous sodium sulfate and concentrated in vacuo. The resulting residue was purified by a silica gel column chromatography (silica gel 25 g, developing solvent; hexane:ethyl acetate=5:1 1:1) to provide 369 mg (yield 85%) of tert-butyl [4-[2-(benzimidazol-2-yloxy) ethyl]piperazin-1-yl]carboxylate as colorless solid.

To a solution of this tert-butyl carboxylate (326 mg, 0.747 mmol) in ethanol (10 ml) were added conc. hydrochloric acid (0.5 ml, 16.3 mmol) and 10% palladium carbon catalyst (328 mg), and stirred under hydrogen atmosphere at 55° C. for 17 hours. The reaction solution was filtered through celite, and the filtrate was concentrated in vacuo. The resulting residue was purified by a silica gel preparative thin layer chromatography (developing solvent; chloroform:sat. ammonia methanol=10:1) to provide 121 mg (yield 66%) of 1-[2-(benzimidazol-2-yloxy)ethyl]piperazine as colorless amorphous.

To a solution of this piperazine compound (119 mg, 0.483 mmol) in acetonitrile (2 ml) were added 2-bromo-N-[2,4-bis(methylthio)-6-methylpyridin-3-yl]acetamide (156 mg, 0.486 mmol) and potassium carbonate (80 mg, 0.579 mmol) successively with ice-cooling, and stirred at room temperature for 20 hours. The reaction solution was diluted with water and extracted with chloroform. The organic layer was washed with a saturated sodium chloride solution, dried over anhydrous sodium sulfate and concentrated in vacuo. The resulting residue was purified by a silica gel preparative thin layer chromatography (developing solvent; chloroform:sat. ammonia methanol=10:1) to provide 145 mg (yield 62%) of the desired compound as colorless oil. IR (neat) cm$^{-1}$: 3260, 1683, 1630, 1558, 1486. 1H-NMR (CDCl$_3$) δ: 2.39 (3H, s), 2.48 (3H, s), 2.51 (3H, s), 2.65–2.85 (8H, m), 2.89 (2H, t, J=5.4 Hz), 3.21 (2H, s), 4.65 (2H, t, J=5.4 Hz), 6.63 (2H, s), 7.09–7.15 (2H, m), 7.31–7.38 (1H, m), 8.54 (1H, br s).

EIMSm/z (relative intensity): 486 (M$^+$+1), 134 (100).

Example 154

Preparation of 2-[4-[2-(benzimidazol-2-yloxy)ethyl] piperazin-1-yl]-N-(2,6-diisopropylphenyl)acetamide:

The same reaction and treatment as in Example 153 were conducted using 2-bromo-N-(2,6-diisopropylphenyl) acetamide instead of 2-bromo-N-[2,4-bis(methylthio)-6-methyl-3-pyridyl]acetamide to provide the desired compound as colorless powdery crystals.

Melting point: 205–206° C. IR (KBr) cm$^{-1}$: 3302, 2962, 1662, 1630, 1552, 1501. 1H-NMR (CD$_3$OD) δ: 1.18 (12H, d, J=7.0 Hz), 2.60–2.82 (8H, m), 2.91 (2H, t, J=5.3 Hz), 3.03 (2H, sept, J=7.0 Hz), 3.24 (2H, s), 4.61 (2H, t, J=5.3 Hz), 7.04–7.12 (2H, m), 7.18 (2H, d, J=7.3 Hz), 7.28 (1H, t, J=7.3 Hz), 7.24–7.40 (2H, m).

EIMSm/z (relative intensity): 463 (M$^+$), 125 (100). Elementary analysis as: C$_{27}$H$_{37}$N$_5$O$_2$ Calculated: C, 69.95; H, 8.04; N, 15.11. Found: C, 69.92; H, 7.96; N, 15.15.

Example 155

Preparation of 2-[4-[2-(benzoxazol-2-ylthio)ethyl] piperazin-1-yl]-N-(2,6-diisopropyl-3-fluorophenyl) acetamide:

To a solution of 2,6-diisopropyl-3-fluoroaniline (synthesized by the method described in the Japanese Patent Application Laid open No. Sho. 63-208556) (550 mg, 2.82 mmol) indichloromethane (20 ml) were added N,N-diethylaniline (478 mg, 3.94 mmol) and bromoacetyl bromide (649 mg, 3.22 mmol) successively with ice-cooling, and stirred at room temperature for 2 hours. The reaction solution was diluted with water and extracted with chloroform. The organic layer was washed with a saturated sodium chloride solution, dried over anhydrous sodium sulfate and concentrated in vacuo. The resulting residue was purified by a silica gel column chromatography (silica gel 50 g, developing solvent; hexane:ethyl acetate=7:1 3:1) to provide 730 mg (yield 82%) of 2-bromo-N-(2,6-diisopropyl-3-fluorophenyl)acetamide as colorless prisms.

To a solution of this acetamide (498 mg, 1.57 mmol) in acetonitrile (10 ml) were added 1-(2-hydroxyethyl)piperazine (371 mg, 2.85 mmol) and potassium carbonate (469 mg, 3.39 mmol) successively with ice-cooling, and stirred at room temperature for 12 hours. The reaction solution was diluted with water and extracted with chloroform. The organic layer was washed with a saturated sodium chloride solution, dried over anhydrous sodium sulfate and concentrated in vacuo. The resulting reside was purified by a silica gel column chromatography (silica gel 50 g, developing solvent; chloroform:methanol=25:1 10:1) and recrystallized from ether-hexane to provide 575 mg (yield 99%) of 2-[4-(2-hydroxyethyl)piperazin-1-yl]-N-(2,6-diisopropyl-3-fluorophenyl)acetamide as colorless needles.

The same reaction and treatment as in Example 1 were conducted using 2-[4-(2-hydroxyethyl)piperazin-1-yl]-N-(2.6-diisopropyl-3-fluorophenyl)acetamide instead of 2-[4-(2-hydroxyethyl)piperazin-1-yl]-N-(2,6-diisopropylphenyl)acetamide to provide the desired compound as colorless powdery crystals.

Melting point: 142–144° C. IR (KBr) cm$^{-1}$: 3440, 3310, 1668, 1495, 1454. 1H-NMR (CDCl$_3$) δ: 1.19 (6H, d, J=6.8 Hz), 1.32 (3H, d, J=6.8 Hz), 1.33 (3H, d, J=6.8 Hz), 2.59–2.80 (8H, m), 2.85 (2H, t, J=6.8 Hz), 2.94 (1H, sept, J=6.8 Hz), 3.03 (1H, sept, J=6.8 Hz), 3.21 (2H, s), 3.49 (2H, t, J=6.8 Hz), 6.97 (1H, dd, J=8.8, 11.0 Hz), 7.12 (1H, dd, J=5.6, 8.8 Hz), 7.24 (1H, td, J=7.6, 1.5 Hz), 7.29 (1H, td, J=7.6, 1.5 Hz), 7.44 (1H, dd, J=7.6, 1.5 Hz), 7.59 (1H, d, J=7.6, 1.5 Hz), 8.61 (1H, br s). Elementary analysis as: C$_{27}$H$_{35}$FN$_4$O$_2$S Calculated: C, 65.03; H, 7.07; N, 11.24; F, 3.81. Found: C, 64.94; H, 7.08; N, 11.19; F, 3.69.

Example 156

Preparation of 2-[4-[2-(benzimidazol-2-ylthio)ethyl]piperazin-1-yl]-N-(2,6-diisopropyl-4-hydroxyphenyl)acetamide:

The same raction and treatment as in Example 72 were conducted using 1-[2-(benzimidazol-2-ylthio)ethyl]piperazine ditrifluoroacetate instead of 1-[2-(benzoxazol-2-ylthio)ethyl]piperazine ditrifluoroacetate to provide the desired compound as colorless powdery crystals.

Melting point: 241–242° C. IR (KBr) cm$^{-1}$: 3331, 2960, 1655, 1588, 1503, 1446. 1H-NMR (CD$_3$OD) δ: 1.14 (12H, d, J=6.9 Hz), 2.55–2.75 (8H, m), 2.80 (2H, t, J=7.0 Hz), 2.94 (2H, sept, J=6.9 Hz), 3.19 (2H, s), 3.40 (2H, t, J=7.0 Hz), 6.60 (2H, s), 7.13–7.21 (2H, m), 7.39–7.51 (2H, m).

EIMSm/z (relative intensity): 495 (M$^+$), 125 (100).

Example 157

Preparation of 2-[4-[2-(7-trifluoromethylbenzoxazol-2-ylthio)ethyl]piperazin-1-yl]-N-(2,6-diisopropyl-4-methanesulfonyloxyphenyl)acetamide:

The same reaction and treatment as in Example 62 were conducted using 2-[4-[2-(7-trifluoromethylbenzoxazol-2-ylthio)ethyl]piperazin-1-yl]-N-(2,6-diisopropyl-4-hydroxyphenyl)actamide obtained in Example 114 instead of 2-[4-[2-(benzoxazol-2-ylthio)ethyl]piperazin-1-yl]-N-(2,6-diisopropyl-3-hydroxyphenyl)acetamide to provide the desired compound as colorless oil. IR (neat) cm$^{-1}$: 3290, 2965, 1683, 1593, 1506. 1H-NMR (CDCl$_3$) δ: 1.21 (12H, d, J=6.8 Hz), 2.52–2.80 (8H, m), 2.86 (2H, t, J=6.8 Hz), 3.00 (2H, sept, J=6.8 Hz), 3.14 (3H, s), 3.21 (2H, s), 3.50 (2H, t, J=6.8 Hz), 7.08 (2H, s), 7.38 (1H, t, J=7.8 Hz), 7.48 (1H, d, J=7.8 Hz), 7.75 (1H, d, J=7.8 Hz), 8.62 (1H, br s).

EIMSm/z (relative intensity): 642 (M$^+$), 125 (100).

Example 158

Preparation of 2-[4-[2-(benzimidazol-2-ylthio)ethyl]piperazin-1-yl]-N-(2,6-diisopropyl-4-methanesulfonyloxyphenyl)acetamide:

The same reaction and treatment as in Example 62 were conducted using [2-[4-[2-(benzimidazol-2-ylthio)ethyl]piperazin-1-yl]-N-(4-hydroxy-2,6-diisopropylphenyl)acetamide obtained in Example 156 instead of 2-[4-[2-(benzoxazol-2-ylthio)ethyl]piperazin-1-yl]-N-(2,6-diisopropyl-3-hydroxyphenyl)acetamide to provide the desired compound as colorless oil. IR (neat) cm$^{-1}$: 3267, 2966, 1674, 0.1592, 1495. 1H-NMR (CDCl$_3$) δ: 1.22 (12H, d, J=6.8 Hz), 2.70–2.95 (8H, m), 2.97 (2H, t, J=5.4 Hz), 3.01 (2H, sept, J=6.8 Hz), 3.15 (3H, s), 3.29 (2H, t, J=5.4 Hz), 3.34 (2H, s), 7.09 (2H, s), 7.19–7.23 (2H, m), 7.38–7.65 (2H, m), 8.51 (1H, br s).

Example 159

Hydrate

Preparation of 2-[4-[2-(benzimidazol-2-ylthio)ethyl]piperazin-1-yl]-N-[2,4-bis(methylthio)-6-methylpyridin-3-yl]acetamide.H$_2$SO$_4$.4H$_2$O:

2-[4-[2-(benzimidazol-2-ylthio)ethyl]piperazin-1-yl]-N-[2,4-bis(methylthio)-6-methylpyridin-3-yl]acetamide (3.00 g, 5.86 mmol) was dissolved in 1 mol/L aqueous sulfuric acid (6 mL, 6.00 mmol) at 80° C. and left as it was at room temperature for three days to precipitate crystals, and then, the solution was removed by decantation to separate the resulting crystals. After water (15 mL) was added to the residue, the crystals were separated by filtration, and sequentially washed with water (15 mL) and isopropanol (10 mL+5 mL). The crystals were dried at room temperature under atmosphere for a day, to give 2-[4-[2-(benzimidazol-2-ylthio)ethyl]piperazin-1-yl]-N-[2,4-bis(methylthio)-6-methylpyridin-3-yl]acetamide.H$_2$SO$_4$.4H$_2$O (3.71 g at a yield of 94.1%) as colorless prisms.

Melting Point: unclear IR (KBr) cm$^{-1}$: 3431, 1674, 1625, 1564, 1520.
$^1$HNMR (DMSO d$_6$) δ: 2.40 (6H, s), 2.45 (3H, s), 2.80–3.72 (14H, m), 6.92 (1H, m), 7.11–7.18 (2H, m), 7.43–7.53 (2H, m), 9.38 (1H, br.s). Elementary Analysis: C$_{23}$H$_{30}$N$_6$OS$_3$.H$_2$SO$_4$.4H$_2$O Required: C, 41.06; H, 5.99; N, 12.49; S, 19.06. Found: C, 40.92; H, 5.85; N, 12.35; S, 19.07.

Example 160

Alcohol Solvate

Preparation of 2-[4-[2-(benzimidazol-2-ylthio)ethyl]piperazin-1-yl]-N-[2,4-bis(methylthio)-6-methylpyridin-3yl]acetamide.0.5 CH$_3$OH:

2-[4-[2-(benzimidazol-2-ylthio)ethyl]piperazin-1yl]-N-[2,4-bis(methylthio)-6-methylpyridin-3-yl]acetamide (134.31 g) was dissolved in methanol (500m) by heating, and then, cooled. The precipitated crystals were separated by filtration, washed with diethylether (300 mL) and dried at room temperature under atmosphere for a day, to give 2-[4-[2-(benzimidazol-2-ylthio)ethyl]piperazin-1-yl]-N-[2,4-bis(methylthio)-6-methylpyridin-3-yl] acetamide.0.5CH$_3$OH (61.54 g at a yield of 44%) as colorless needles.

Melting Point: 102–104° C. IR (KBr) cm$^{-1}$: 3269, 1672, 1618, 1563, 1533, 1488. $^1$H-NMR (DMSO d-$_6$) δ: 2.38 (3H, s), 2.39 (3H, s), 2.44 (3H, s), 2.50–2.64 (8H, m), 2.69 (2H, t, J=6.8 Hz), 3.07 (2H, s), 3.46 (1.5H, d, J=5.4 Hz, MeOH), 3.41 (2H, t, J=6.8 Hz), 4.08 (0.5H, q, J=5.4 Hz, MeOH), 6.89 (1H, s), 7.06–7.12 (2H, m), 7.35 (1H, m), 7.47 (1H, m), 9.13, (1H, br.s), 12.57 (1H, br.s). Elementary Analysis: C$_{23}$H$_{30}$N$_6$OS$_3$.0.5CH$_3$OH Required: C, 54.41; H, 6.22; N, 16.20; S, 18.54. Found: C, 54.36; H, 6.12; N, 16.28; S, 18.69.

Industrial Applicability

The present invention offers an ACAT inhibitor, an agent for inhibiting the transportation of intracellular cholesterol, an agent for lowering the cholesterol in blood or an agent for suppressing the foaming of macrophage containing the compound represented by the above formula (I) or salt(s) or solvate(s) thereof and a pharmaceutically acceptable carrier. Thus, the present invention offers a pharmaceutical composition for therapy and prevention, an agent for therapy and prevention and a method for therapy and prevention of the diseases such as hyperlipemia, arteriosclerosis, cervical and cerebral arteriosclerosis, cerebrovascular disorder, ischemic cardiopathy, coronary arteriosclerosis, nephrosclerosis, arteriosclerotic nephrosclerosis, arteriocapillary sclerotic nephrosclerosis, malignant nephrosclerosis, ischemic entheropathy, acute occlusion of mesenteric vessel, chronic mesenteric angina, ischemic colitis, aortic aneurysm and arteriosclerosis obliterans (ASO).

What is claimed is:

1. A compound represented by the formula (I), salt(s) thereof, or solvate(s) thereof where the solvate(s) are water and/or alcohol(s):

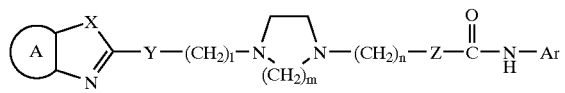

(I)

wherein

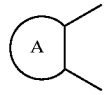

is a divalent residue of benzene, pyridine, cyclohexane or naphthalene each of which may be substituted with from one to four group(s) selected from W1;
or wherein the formula

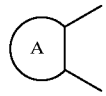

represents a group

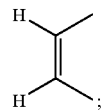

wherein

Ar is an aryl group which may be substituted with group(s) selected from W5;

X is —NH—, oxygen atom or sulfur atom;

Y is —NR$_1$—, oxygen atom, sulfur atom, sulfoxide or sulfone;

Z is a single bond or —NR$_2$—;

R$_1$ is hydrogen atom, lower alkyl group which may be substituted with group(s) selected from W2, aryl group which may be substituted with group(s) selected from W5 or silyl lower alkyl group which may be substituted with group(s) selected from W4;

R$_2$ is hydrogen atom, lower alkyl group which may be substituted with group(s) selected from W2, aryl group which maybe substituted with group(s) selected from W5 or silyl lower alkyl group which may be substituted with group(s) selected from W4;

W1 is lower alkyl group which may be substituted with group(s) selected from W2, lower alkoxy group which may be substituted with group(s) selected from W2, lower alkylcarbonyl group which may be substituted with group(s) selected from W2, lower alkylthio group, lower alkylsulfinyl group, lower alkylsulfonyl group, halogen atom, hydroxyl group, carboxyl group, alkoxycarbonyl group, phosphoric acid group, cyano group, nitro group, sulfonamide group, amino group which may be substituted with group(s) selected from W3, aminoalkyl group which may be substituted with group(s) selected from W3, silyl lower alkyl group which may be substituted with group(s) selected from W4 or heterocyclic residue; and alkylenedioxy group;

W2 is hydroxyl group, lower alkoxy group, lower alkylthio group, lower alkoxycarbonyl group, lower alkylcarbonyloxy group, aryl group, halogen atom, amino group, nitro group, hydroxy lower alkoxy group, lower alkoxy lower alkoxy group, lower alkoxycarbonyl lower alkoxy group and halogenated lower alkoxy group;

W3 is lower alkyl group, aryl group which may be substituted with lower alkyl group or lower alkoxy group and an aralkyl group which may be substituted with lower alkyl group or lower alkoxy group;

W4 is lower alkyl group, aryl groups and an aralkyl group;

W5 is lower alkyl group which may be substituted with group(s) selected from W2, lower alkoxy group which may be substituted with group(s) selected from W2, lower alkylthio group which may be substituted with group(s) selected from W2, lower alkylsulfinyl group which may be substituted with group(s) selected from W2, lower alkylsulfonyl group which may be substituted with group(s) selected from W2, lower alkylsulfonyloxy group which may be substituted with group(s) selected from W2, hydroxy lower alkylthio group, lower alkylcarbonyl group which may be substituted with group(s) selected from W2, lower alkylcarbonyloxy group which may be substituted with group(s)

selected from W2, halogen atom, hydroxyl group, nitro group, phosphoric acid group, di-(lower alkoxy)-phosphoryloxy group, sulfonamide group, amino group which may be substituted with group(s) selected from W3, pyranosyloxy group and alkylenedioxy group;

l is an integer of from 1 to 15;

m is an integer of 2 or 3; and n is an integer of from 1 to 3.

2. A compound represented by the formula (II), salt(s) thereof, or solvate(s) thereof where the solvate(s) are water and/or alcohol(s):

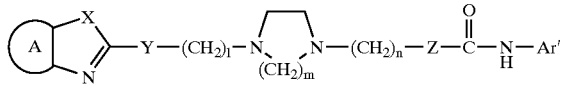
(II)

wherein

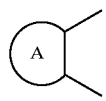

is a divalent residue of benzene, pyridine, cyclohexane or naphthalene each of which may be substituted with from one to four group(s) selected from W1; or the formula

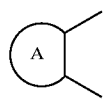

represents a group

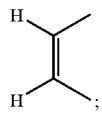

wherein

X is —NH—, oxygen atom or sulfur atom;

Y is —NR$_1$—, oxygen atom, sulfur atom, sulfoxide or sulfone;

Z is a single bond or —NR$_2$—;

Ar' is phenyl, pyridyl or pyrimidyl group which may be substituted with from one to four group(s) selected from lower alkyl group which may be substituted with group(s) selected from W2, lower alkoxy group which may be substituted with group(s) selected from W2, lower alkylthio group, lower alkylsulfinyl group, lower alkylsulfonyl group, lower alkylsulfonyloxy group, hydroxy lower alkylthio group, lower alkylcarbonyl group which may be substituted with group(s) selected from W2, halogen atom, hydroxyl group, lower alkylcarbonyloxy group which may be substituted with group(s) selected from W2, nitro group, phosphoric acid group, di-(lower alkoxy)-phosphoryloxy group, sulfonamide group, amino group which may be substituted with group(s) selected from W3, pyranosyloxy group and alkylenedioxy group;

R$_1$ is hydrogen atom, lower alkyl group which may be substituted with group(s) selected from W2, aryl group which may be substituted with group(s) selected from W5 or silyl lower alkyl group which may be substituted with group(s) selected from W4;

R$_2$ is hydrogen atom, lower alkyl group which may be substituted with group(s) selected from W2, aryl group which may be substituted with group(s) selected from W5, or silyl lower alkyl group which may be substituted with group(s) selected from W4;

W1 is lower alkyl group which may be substituted with group(s) selected from W2, lower alkoxy group which may be substituted with group(s) selected from W2, lower alkylcarbonyl group which may be substituted with group(s) selected from W2, lower alkylthio group, lower alkylsulfinyl group, lower alkylsulfonyl group, halogen atom, hydroxyl group, carboxyl group, alkoxycarbonyl group, phosphoric acid group, cyano group, nitro group, sulfonamide group, amino group which may be substituted with group(s) selected from W3, aminoalkyl group which may be substituted with group(s) selected from W3, silyl lower alkyl group which may be substituted with group(s) selected from W4 or heterocyclic residue; and alkylenedioxy group;

W2 is hydroxyl group, lower alkoxy group, lower alkylthio group, lower alkoxycarbonyl group, lower alkylcarbonyloxy group, aryl group, halogen atom, amino group, nitro group, hydroxy lower alkoxy group, lower alkoxy lower alkoxy group, lower alkoxycarbonyl lower alkoxy group and halogenated lower alkoxy group;

W3 is lower alkyl group, aryl group which may be substituted with lower alkyl group or lower alkoxy group and an aralkyl group which may be substituted with lower alkyl group or lower alkoxy group;

W4 is lower alkyl group, aryl groups and an aralkyl group;

W5 is lower alkyl group which may be substituted with group(s) selected from W2, lower alkoxy group which may be substituted with group(s) selected from W2, lower alkylthio group which may be substituted with group(s) selected from W2, lower alkyl sulfinyl group which may be substituted with group(s) selected from W2, lower alkylsulfonyl group which may be substituted with group(s) selected from W2, lower alkylsulfonyloxy group which may be substituted with group(s) selected from W2, lower alkylcarbonyl group which may be substituted with group(s) selected from W2, lower alkylcarbonyloxy group, halogen atom, hydroxyl group, nitro group, phosphoric acid group, di-(lower alkoxy)-phosphoryloxy group, sulfonamide group, amino group which may be substituted with group(s) selected from W3 and alkylenedioxy group;

l is an integer of from 1 to 15;

m is an integer of 2 or 3; and n is an integer of from 1 to 3.

3. A compound represented by the following formula (III), salt(s) thereof, or solvate(s) thereof where the solvate(s) are water and/or alcohol(s):

(III)

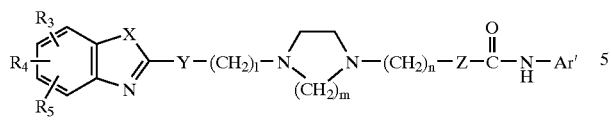

wherein

X is —NH—, oxygen atom or sulfur atom;

Y is —NR$_1$—, oxygen atom, sulfur atom, sulfoxide or sulfone;

Z is a single bond or —NR$_2$—;

Ar' is phenyl, pyridyl or pyrimidyl group which may be substituted with from one to four group(s) selected from lower alkyl group which may be substituted with group(s) selected from W2, lower alkoxy group which may be substituted with group(s) selected from W2, lower alkylthio group, lower alkylsulfinyl group, lower alkylsulfonyl group, lower alkylsulfonyloxy group, hydroxy lower alkylthio group, lower alkylcarbonyl group which may be substituted with group(s) selected from W2, halogen atom, hydroxyl group, lower alkylcarbonyloxy group which may be substituted with group(s) selected from W2, nitro group, phosphoric acid group, di-(lower alkoxy)-phosphoxyloxy group, sulfonamide group, amino group which may be substituted with group(s) selected from W3, pyranosyloxy group and alkylenedioxy group;

R$_1$ is hydrogen atom, lower alkyl group which may be substituted with group(s) selected from W2, aryl group which may be substituted with group(s) selected from W5, or silyl lower alkyl group which may be substituted with group(s) selected from W4;

R$_2$ is hydrogen atom, lower alkyl group which may be substituted with group(s) selected from W2, aryl group which may be substituted with group(s) selected from W5, or silyl lower alkyl group which may be substituted with group(s) selected from W4;

R$_3$, R$_4$ and R$_5$ are same or different and are hydrogen atom, lower alkyl group which may be substituted with group(s) selected from W2, lower alkoxy group which may be substituted with group(s) selected from W2, lower alkylcarbonyl group which may be substituted with group(s) selected from W2, lower alkylthio group, lower alkylsulfinyl group, lower alkylsulfonyl group, halogen atom, hydroxyl group, carbaxyl group, alkoxycarbonyl group, phosphoric acid group, cyano group, nitro group, sulfonamide group, amino group which may be substituted with group(s) selected from W3, aminoalkyl group which may be substituted with group(s) selected from W3, silyl lower alkyl group which may be substituted with group(s) selected from W4, or heterocyclic residue; or any of two of R$_3$, R$_4$ and R$_5$ form an alkylenedioxy group together;

W2 is hydroxyl group, lower alkoxy group, lower alkylthio group, lower alkoxycarbonyl group, lower alkylcarbonyloxy group, aryl group, halogen atom, amino group, nitro group, hydroxy lower alkoxy group, lower alkoxy lower alkoxy group, lower alkoxycarbonyl lower alkoxy group and halogenated lower alkoxy group;

W3 is lower alkyl group, aryl group which may be substituted with lower alkyl group or lower alkoxy group and an aralkyl group which may be substituted with lower alkyl group or lower alkoxy group;

W4 is lower alkyl group, aryl groups and an aralkyl group;

W5 is lower alkyl group which may be substituted with group(s) selected from W2, lower alkoxy group which may be substituted with group(s) selected from W2, lower alkylthio group which may be substituted with group(s) selected from W2, lower alkylsulfinyl group which may be substituted with group(s) selected from W2, lower alkylsulfonyl group which may be substituted with group(s) selected from W2, lower alkylsulfonyloxy group which may be substituted with group(s) selected from W2, lower alkylcarbonyl group which may be substituted with group(s) selected from W2, lower alkylcarbonyloxy group, halogen atom, hydroxyl group, nitro group, phosphoric acid group, di-(lower alkoxy)-phosphoryloxy group, sulfonamide group, amino group which may be substituted with group(s) selected from W3 and alkylenedioxy group;

l is an integer of from 1 to 15;

m is an integer of 2 or 3; and n is an integer of from 1 to 3.

4. A compound represented by the formula (IV), salt(s) thereof, or solvate(s) thereof where the solvate(s) are water and/or alcohol(s):

(II)

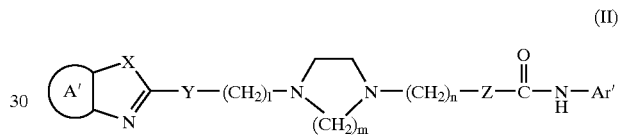

wherein

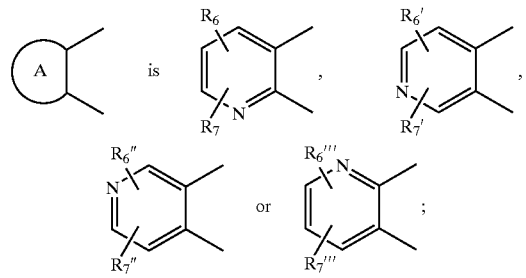

X is —NH—, oxygen atom or sulfur atom;

Y is —NR$_1$—, oxygen atom, sulfur atom, sulfoxide or sulfone;

Z is a single bond or —NR$_2$—;

Ar' is phenyl, pyridyl or pyrimidyl group which may be substituted with from one to four group(s) selected from lower alkyl group which may be substituted with group(s) selected from W2, lower alkoxy group which may be substituted with group(s) selected from W2, lower alkylthio group, lower alkylsulfinyl group, lower alkylsulfonyl group, lower alkylsulfonyloxy group, hydroxy lower alkylthio group, lower alkylcarbonyl group which may be substituted with group(s) selected from W2, halogen atom, hydroxyl group, lower alkylcarbonyloxy group which may be substituted with group(s) selected from W2, nitro group, phosphoric acid group, di-(lower alkoxy)-phosphoryloxy group, sulfonamide group, amino group which may be substituted with group(s) selected from W3, pyranosyloxy group and alkylenedioxy group;

R₁ is hydrogen atom, lower alkyl group which may be substituted with group(s) selected from W2, aryl group which may be substituted with group(s) selected from W5, or silyl lower alkyl group which may be substituted with group(s) selected from W4;

R₂ is hydrogen atom, lower alkyl group which may be substituted with group(s) selected from W2, aryl group which may be substituted with group(s) selected from W5, or silyl lower alkyl group which may be substituted with group(s) selected from W4;

$R_6$, $R_7$, $R_6'$, $R_7'$, $R_6''$, $R_7''$, $R_6'''$ and $R_7'''$ are same or different and are hydrogen atom, lower alkyl group which may be substituted with group(s) selected from W2, lower alkoxy group which may be substituted with group(s) selected from W2, halogen atom, hydroxyl group, carboxyl group, alkoxycarbonyl group, phosphoric acid group, sulfonamide group, amino group which may be substituted with group(s) selected from W3, amino alkyl group which may be substituted with group(s) selected from W3, silyl lower alkyl group which may be substituted with group(s) selected from W4, or heterocyclic residue; or any two of $R_6$, $R_7$, $R_6'$, $R_7'$, $R_6''$, $R_7''$, $R_6'''$ and $R_7'''$ may form an alkylenedioxy group;

W2 is hydroxyl group, lower alkoxy group, lower alkylthio group, lower alkoxycarbonyl group, lower alkylcarbonyloxy group, aryl group, halogen atom, amino group, nitro group, hydroxy lower alkoxy group, lower alkoxy lower alkoxy group, lower alkoxycarbonyl lower alkoxy group and halogenated lower alkoxy group;

W3 is lower alkyl group, aryl group which may be substituted with lower alkyl group or lower alkoxy group and an aralkyl group which may be substituted with lower alkyl group or lower alkoxy group;

W4 is lower alkyl group, aryl groups and an aralkyl group;

W5 is lower alkyl group which may be substituted with group(s) selected from W2, lower alkoxy group which may be substituted with group(s) selected from W2, lower alkyithia group which may be substituted with group(s) selected from W2, lower alkylsulfinyl group which may be substituted with group(s) selected from W2, lower alkylsulfonyl group which may be substituted with group(s) selected from W2, lower alkylsulfonyloxy group which may be substituted with group(s) selected from W2, lower alkylcarbonyl group which may be substituted with group(s) selected from W2, lower alkylcarbonyloxy group, halogen atom, hydroxyl group, nitro group, phosphoric acid group, di-(lower alkoxy)-phosphoryloxy group, sulfonamide group, amino group which may be substituted with group(s) selected from W3 and alkylenedioxy group;

1 is an integer of from 1 to 15;

m is an integer of 2 or 3; and n is an integer of from 1 to 3.

5. A pharmaceutical composition containing an effective amount of one or more of the compound(s) mentioned in any of claims 1 to 4, salt(s) thereof, or solvate(s) thereof where the solvate(s) are water and/or alcohol(s) and a pharmaceutically acceptable carrier.

6. A method for therapy of hyperlipemia, arteriosclerosis, cerebrovascular disorder, ischemic cardiopathy, ischemic entheropathy or aortic aneurysm by administering an effective amount of a compound mentioned in any of claims 1 to 4 or salt(s) thereof, or solvate(s) thereof where the solvate(s) are water and/or alcohol(s) to a patient suffering from hyperlipemia, arteriosclerosis, cerebrovascular disorder, isehemic cardiopathy, ischemic entheropathy or aortic aneurysm.

7. A method of therapy according to claim 6 where an effective amount is admimstered as an ACAT inhibitor, an agent for inhibiting the transportation of intracellular cholesterol, an agent for lowering the cholesterol in blood or an agent for suppressing the storage of cholesterol in macrophage as fat droplets.

\* \* \* \* \*

UNITED STATES PATENT AND TRADEMARK OFFICE
CERTIFICATE OF CORRECTION

PATENT NO. : 6,969,711 B2
APPLICATION NO. : 10/371234
DATED : November 29, 2005
INVENTOR(S) : K. Shibuya et al.

It is certified that error appears in the above-identified patent and that said Letters Patent is hereby corrected as shown below:

Column 2, line 64

Please correct:

"formula. (A)"

to

-- formula (A) --

Column 9, line 28

Please correct:

"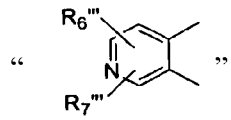"

to

-- 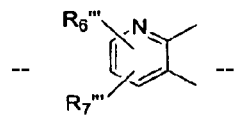 --

Column 14, line 43

Please correct:

"group upon"

to

-- group. Upon --

UNITED STATES PATENT AND TRADEMARK OFFICE
CERTIFICATE OF CORRECTION

PATENT NO.       : 6,969,711 B2
APPLICATION NO. : 10/371234
DATED            : November 29, 2005
INVENTOR(S)      : K. Shibuya et al.

It is certified that error appears in the above-identified patent and that said Letters Patent is hereby corrected as shown below:

Column 20, line 65

Please correct:

" —$(CH_2)_{n-1}$—N—
              $R_2$ "

to

-- —$(CH_2)_n$—N—
              $R_2$ --

Column 21, line 5

Please correct:

" —$(CH_2)_{n-1}$—N—
              $R_2$ "

to

-- —$(CH_2)_n$—N—
              $R_2$ --

Column 22, line 10

Please correct:

" —$(CH_2)_{n-1}$—N—
              $R_2$ "

to

-- —$(CH_2)_n$—N—
              $R_2$ --

UNITED STATES PATENT AND TRADEMARK OFFICE
CERTIFICATE OF CORRECTION

PATENT NO.      : 6,969,711 B2
APPLICATION NO. : 10/371234
DATED           : November 29, 2005
INVENTOR(S)     : K. Shibuya et al.

It is certified that error appears in the above-identified patent and that said Letters Patent is hereby corrected as shown below:

Column 67, entry 138

Please correct:

"2 2 2"

to

-- 3 2 2 --

Column 81, line 46

Please correct:

"$C_{26}H_{35}N_1O_2S$"

to

-- $C_{26}H_{35}N_5O_2S$ --

Column 89, line 25

Please correct:

"$C_{39}H_{57}N_5O_4S$"

to

-- $C_{38}H_{57}N_5O_4S$ --

Column 89, line 47

Please correct:

"$C_{35}H_{14}N_6O_2S$"

to

-- $C_{35}H_{54}N_6O_2S$ --

UNITED STATES PATENT AND TRADEMARK OFFICE
CERTIFICATE OF CORRECTION

PATENT NO. : 6,969,711 B2
APPLICATION NO. : 10/371234
DATED : November 29, 2005
INVENTOR(S) : K. Shibuya et al.

It is certified that error appears in the above-identified patent and that said Letters Patent is hereby corrected as shown below:

Column 91, line 47

Please correct:

"$C_{23}H_{29}N_1O_2S_3$"

to

-- $C_{23}H_{29}N_5O_2S_3$ --

Column 99, line 64

Please correct:

"3.84 (33H, s)"

to

-- 3.84 (3H, s) --

Column 105, line 39

Please correct:

"2.85-(2H, t, J=6.8 Hz)"

to

-- 2.85 (2H, t, J=6.8 Hz) --

Column 106, line 10

Please correct:

"$C_{28}H_{31}N_4O_2S_2.0.4H_2O$"

to

-- $C_{28}H_{38}N_4O_2S_2.0.4H_2O$ --

UNITED STATES PATENT AND TRADEMARK OFFICE
CERTIFICATE OF CORRECTION

PATENT NO.       : 6,969,711 B2
APPLICATION NO.  : 10/371234
DATED            : November 29, 2005
INVENTOR(S)      : K. Shibuya et al.

It is certified that error appears in the above-identified patent and that said Letters Patent is hereby corrected as shown below:

Column 112, line 57

Please correct:

" $C_{21}H_{38}N_4O_5S_2.0.3H_2O$ "

to

-- $C_{28}H_{38}N_4O_5S_2.0.3H_2O$ --

Column 113, line 22

Please correct:

" $C_{21}H_{38}N_4O_3S$ "

to

-- $C_{28}H_{38}N_4O_3S$ --

Column 115, line 6

Please correct:

" $C_{21}H_{39}H_5O_2S$ "

to

-- $C_{28}H_{39}N_5O_2S$ --

Column 116, line 22

Please correct:

" $C_{27}H_{31}N_6O_2S$ "

to

-- $C_{27}H_{38}N_6O_2S$ --

UNITED STATES PATENT AND TRADEMARK OFFICE
CERTIFICATE OF CORRECTION

PATENT NO.       : 6,969,711 B2
APPLICATION NO.  : 10/371234
DATED            : November 29, 2005
INVENTOR(S)      : K. Shibuya et al.

It is certified that error appears in the above-identified patent and that said Letters Patent is hereby corrected as shown below:

Column 117, line 58

Please correct:

" $C_{28}H_{31}F_3N_4O_2S$ "

to

-- $C_{28}H_{35}F_3N_4O_2S$ --

Column 123, line 16

Please correct:

" $C_{31-43}ClN_4O_2S$ "

to

-- $C_{31}H_{43}ClN_4O_2S$ --

Column 130, line 40

Please correct:

" 3-pyridyl]instead"

to

-- 3-pyridyl]acetamide instead --

Column 136, line 64

Please correct:

"instead of N-(2,16-"

to

-- instead of N-(2,6- --

UNITED STATES PATENT AND TRADEMARK OFFICE
CERTIFICATE OF CORRECTION

PATENT NO. : 6,969,711 B2
APPLICATION NO. : 10/371234
DATED : November 29, 2005
INVENTOR(S) : K. Shibuya et al.

It is certified that error appears in the above-identified patent and that said Letters Patent is hereby corrected as shown below:

Column 143, line 35

Please delete:

"W1 is lower alkyl group which may be substituted with"

Column 144, lines 4-5

Please correct:

"glucopyranos)oxphenyl]"

to

-- glucopyranosyl)oxyphenyl] --

Column 153, line 49

Please correct:

" 2.43 (3Hf s)"

to

-- 2.43 (3H, s) --

Column 156, line 23

Please correct:

"1674, 0.1592,"

to

-- 1674, 1592, --

UNITED STATES PATENT AND TRADEMARK OFFICE
CERTIFICATE OF CORRECTION

PATENT NO. : 6,969,711 B2
APPLICATION NO. : 10/371234
DATED : November 29, 2005
INVENTOR(S) : K. Shibuya et al.

It is certified that error appears in the above-identified patent and that said Letters Patent is hereby corrected as shown below:

Column 164, line 2

Please correct:

"alkyithia"

to

-- alkylthio --

Signed and Sealed this

First Day of July, 2008

JON W. DUDAS
*Director of the United States Patent and Trademark Office*